United States Patent
Maus et al.

(10) Patent No.: US 11,578,115 B2
(45) Date of Patent: Feb. 14, 2023

(54) CHIMERIC ANTIGEN RECEPTORS BASED ON ALTERNATIVE SIGNAL 1 DOMAINS

(71) Applicant: The General Hospital Corporation, Boston, MA (US)

(72) Inventors: Marcela V. Maus, Lexington, MA (US); Mark Cobbold, Winchester, MA (US); Irene Scarfo, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 318 days.

(21) Appl. No.: 16/476,588

(22) PCT Filed: Jan. 10, 2018

(86) PCT No.: PCT/US2018/013213
§ 371 (c)(1),
(2) Date: Jul. 9, 2019

(87) PCT Pub. No.: WO2018/132506
PCT Pub. Date: Jul. 19, 2018

(65) Prior Publication Data
US 2019/0330302 A1    Oct. 31, 2019

Related U.S. Application Data

(60) Provisional application No. 62/584,060, filed on Nov. 9, 2017, provisional application No. 62/580,243, filed on Nov. 1, 2017, provisional application No. 62/472,275, filed on Mar. 16, 2017, provisional application No. 62/444,605, filed on Jan. 10, 2017.

(51) Int. Cl.

| | |
|---|---|
| *A61K 35/17* | (2015.01) |
| *C07K 14/725* | (2006.01) |
| *A61P 37/06* | (2006.01) |
| *A61P 35/02* | (2006.01) |
| *A61P 35/00* | (2006.01) |
| *C07K 14/705* | (2006.01) |
| *C07K 16/28* | (2006.01) |
| *C12N 5/0783* | (2010.01) |
| *A61K 38/00* | (2006.01) |
| *A61K 39/00* | (2006.01) |

(52) U.S. Cl.
CPC .......... *C07K 14/7051* (2013.01); *A61K 35/17* (2013.01); *A61P 35/00* (2018.01); *A61P 35/02* (2018.01); *A61P 37/06* (2018.01); *C07K 14/70517* (2013.01); *C07K 14/70578* (2013.01); *C07K 16/2896* (2013.01); *C12N 5/0636* (2013.01); *A61K 38/00* (2013.01); *A61K 2039/505* (2013.01); *C07K 2317/622* (2013.01); *C07K 2317/73* (2013.01); *C07K 2317/76* (2013.01); *C07K 2317/92* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | |
|---|---|---|
| 11,352,434 B2 | 6/2022 | Maus et al. |
| 2008/0279850 A1 | 11/2008 | Brady et al. |
| 2009/0148447 A1 | 6/2009 | Ledbetter et al. |
| 2009/0175867 A1 | 7/2009 | Thompson et al. |
| 2009/0274692 A1 | 11/2009 | Tan et al. |
| 2010/0189722 A1 | 7/2010 | Heider et al. |
| 2013/0071414 A1 | 3/2013 | Dotti et al. |
| 2014/0072562 A1 | 3/2014 | Grosmaire et al. |
| 2015/0038684 A1 | 2/2015 | Jensen |
| 2015/0283178 A1 | 10/2015 | June et al. |
| 2015/0329640 A1 | 11/2015 | Finer |
| 2016/0046724 A1 | 2/2016 | Brogdon et al. |
| 2018/0057609 A1 | 3/2018 | June et al. |
| 2020/0079870 A1 | 3/2020 | Maus et al. |
| 2021/0268027 A1 | 9/2021 | Maus |

FOREIGN PATENT DOCUMENTS

| | | |
|---|---|---|
| WO | WO 2012/007576 A1 | 1/2012 |
| WO | WO-2014/099671 A1 | 6/2014 |
| WO | WO-2016/040441 A1 | 3/2016 |

(Continued)

OTHER PUBLICATIONS

Jain et al., Targeted therapies for CLL: Practical issues with the changing treatment paradigm. Blood Rev. May 2016;30(3):233-44. doi: 10.1016/j.blre.2015.12.002. Epub Dec. 24, 2015.

(Continued)

*Primary Examiner* — Phillip Gambel
(74) *Attorney, Agent, or Firm* — Wolf, Greenfield & Sacks, P.C.

(57) ABSTRACT

Described herein are methods for producing and utilizing an alternative signal 1 domain to construct an optimally signaling CAR. Alternative signal 1 domains of the present technology are based on alternatives to CD3ζ, including mutated ITAMs from CD3ζ (which contains 3 ITAM motifs), truncations of CD3ζ, and alternative splice variants known as CD3s, CD3 theta, and artificial constructs engineered to express fusions between CD3s or CD3θ and CD3ζ. CAR polypeptides comprising alternative signal 1 domains are utilized to engineer CAR T cells. Further, this technology related to methods of treating cancer by administering to a subject in need thereof CAR T cells comprising alternative signal 1 domains.

28 Claims, 87 Drawing Sheets
Specification includes a Sequence Listing.

(56) References Cited

FOREIGN PATENT DOCUMENTS

| WO | WO-2016/054520 A2 | 4/2016 |
| WO | WO 2016/164731 A2 | 10/2016 |
| WO | WO 2016/200676 A1 | 12/2016 |
| WO | WO 2017/029511 A1 | 2/2017 |
| WO | WO 2017/114497 A1 | 7/2017 |
| WO | WO-2017/118745 A1 | 7/2017 |
| WO | WO 2018/132506 A1 | 7/2018 |
| WO | WO 2018/170458 A1 | 9/2018 |
| WO | WO 2019/246546 A1 | 12/2019 |

OTHER PUBLICATIONS

Morabito et al., Promising therapies for the treatment of chronic lymphocytic leukemia. Expert Opin Investig Drugs. Jun. 2015;24(6):795-807. doi: 10.1517/13543784.2015.1021920. Epub Mar. 1, 2015.

Scarfo et al., Anti-CD37 chimeric antigen receptor T cells are active against B- and T-cell lymphomas. Blood. Oct. 4, 2018;132(14):1495-1506. doi: 10.1182/blood-2018-04-842708. Epub Aug. 8, 2018.

International Search Report and Written Opinion for International Application No. PCT/US18/13213, dated May 15, 2018 (16 pages).

International Preliminary Report on Patentability for International Application No. PCT/US2018/013213 dated Jul. 16, 2019 (7 pages).

Kochenderfer et al., Adoptive transfer of syngeneic T cells transduced with a chimeric antigen receptor that recognizes murine CD19 can eradicate lymphoma and normal B cells. Blood. 2010;116(19):3875-3886.

Zhao et al., A herceptin-based chimeric antigen receptor with modified signaling domains leads to enhanced survival of transduced T lymphocytes and antitumor activity. J Immunol. 2009;183(9):5563-5574.

De Munter et al., Nanobody Based Dual Specific CARs. Int J Mol Sci. Jan. 30, 2018;19(2):403. doi: 10.3390/ijms19020403.

Fry et al., CD22-targeted CAR T cells induce remission in B-ALL that is naive or resistant to CD19-targeted CAR immunotherapy. Nat Med. Jan. 2018;24(1):20-28. doi: 10.1038/nm.4441. Epub Nov. 20, 2017. Supplemental information included. 15 pages total.

Grada et al., TanCAR: A Novel Bispecific Chimeric Antigen Receptor for Cancer Immunotherapy. Mol Ther Nucleic Acids. Jul. 9, 2013;2(7):e105. doi: 10.1038/mtna.2013.32.

Kulemzin et al., Engineering Chimeric Antigen Receptors. Acta Naturae. Jan.-Mar. 2017;9(1):6-14.

Martyniszyn et al., CD20-CD19 Bispecific CAR T Cells for the Treatment of B-Cell Malignancies. Hum Gene Ther. Dec. 2017;28(12):1147-1157. doi: 10.1089/hum.2017.126.

Zah et al., T Cells Expressing CD19/CD20 Bispecific Chimeric Antigen Receptors Prevent Antigen Escape by Malignant B Cells. Cancer Immunol Res. Jun. 2016;4(6):498-508. doi: 10.1158/2326-6066.CIR-15-0231. Epub Apr. 8, 2016. Author manuscript provided. 22 pages.

(A) CD37 protein expression on normal cells is restricted to lymphoid tissues.

(B) CD37 expression on tumor cell lines. CD37 is highly expressed in non-Hodgkin lymphomas (NHL), including mantle cell lymphoma (JEKO-1), Burkitt lymphoma (RAJI), and B-cell chronic lymphocytic leukemia (OSU-CLL) but it is absent in acute lymphoblastic leukemia cell line (NALM6)

Design of anti-CD37 second-generation CAR, encoded by a lentiviral vector and bearing a 4-1BB costimulatory domain. Two different orientations of a humanized murine antibody-derived single-chain variable fragment $V_L$-$V_H$ (CAR-37 L-H, top) or $V_H$-$V_L$ (CAR-37 H-L, bottom)

(A) Representative flow plots of primary human T cells transduction efficiency after 10 days of activation with of CD3/CD28 beads.

(B) Expanded T cells included variable CAR-37 expression with a mean of 38% (L-H) and 75% (H-L) (N=3)

(C) Ex-vivo enrichment/expansion of CD3/CD28 bead activated T-cells using static culture conditions in 3 healthy donors for 38 days.

(D) Activation of Jurkat reporter (NFAT-Luc) T-cells transduced with different CAR constructs and co cultured with tumor cells. Luciferase activity was measure after 16 hours. (CD3-CD28 beads: positive control)

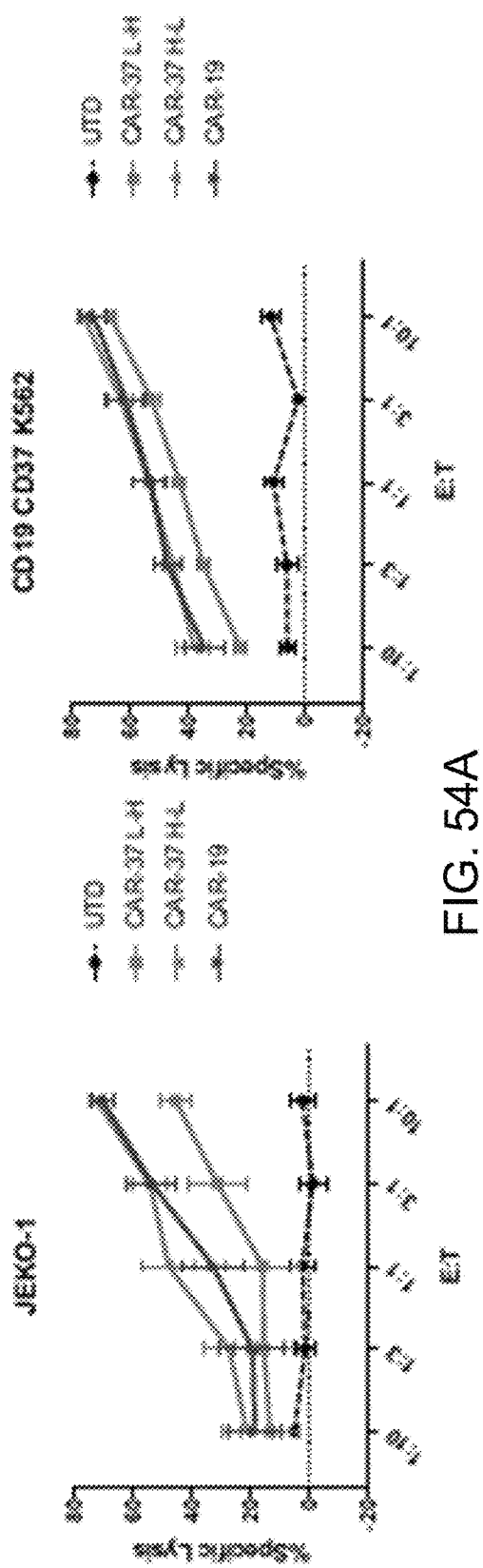
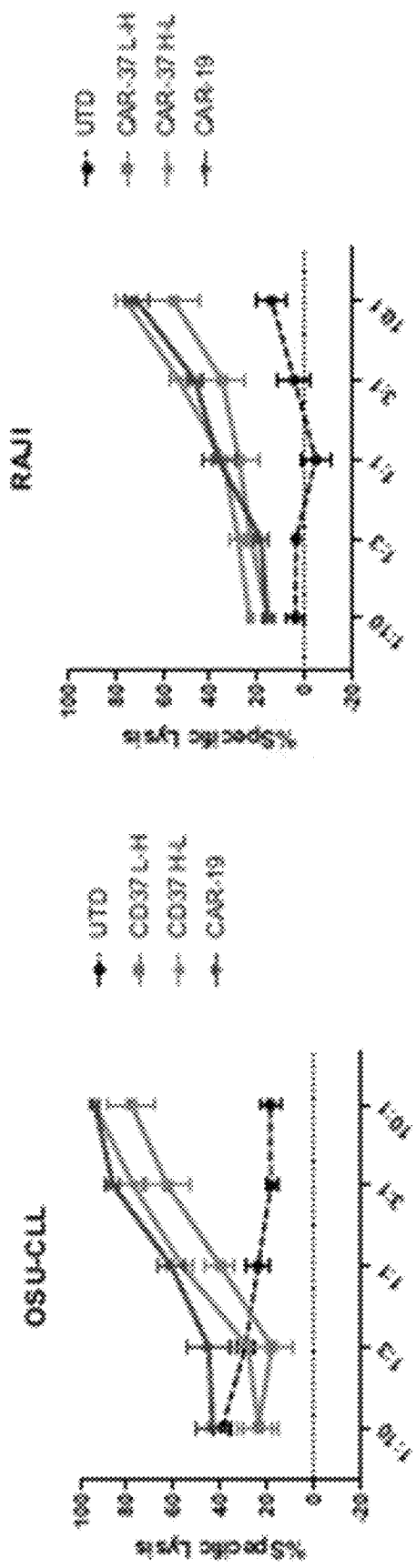
Cytotoxicity at 16 hours of CAR T cells co-cultured at indicated E:T ratios with JEKO-1, K562 expressing CD19 and CD37 (A) OSU-CLL (B) and RAJI (C). Increasing concentration of CAR-37 and CAR-19 T cells led to specific killing while no killing was observed in the control group (UTD)
FIG. 54A
FIG. 54B
FIG. 54C Cytokine production by CAR-37, CAR-19, or UTD T cells incubated with JEKO-1 (A), RAJI Cytokine production by CAR-37, CAR-19, or UTD T cells incubated with JEKO-1 (B), OSU-CLL Cytokine production by CAR-37, CAR-19, or UTD T cells incubated with JEKO-1 (C),cells for 24 hours at 1:1 E:T ratio was analyzed in the culture supernatant by Luminex assay.

(A) Experiment schematic: female NSG mice were injected i.v. with 1x106 JEKO-1 cells (CBG-GFP+). At day 7, mice were randomized based on tumor burden (BLI) to receive 2x106 control T cells (UTD), CAR-37 or CAR-19 (2 normal donors, N=10)

(B) Representative bioluminescent images of JEKO-1 growth over time (C) Tumor growth curve from each treatment group is displayed over time. Statistical analysis: two way anova (P>0.001).

CHIMERIC ANTIGEN RECEPTORS BASED ON ALTERNATIVE SIGNAL 1 DOMAINS

CROSS-REFERENCE TO RELATED APPLICATIONS

This application is a national stage filing under 35 U.S.C. § 371 of international PCT application PCT/US2018/013213, filed Jan. 10, 2018, which claims benefit under 35 U.S.C. § 119(e) of U.S. Provisional Application Nos. 62/444,605, filed Jan. 10, 2017, 62/472,275, filed Mar. 16, 2017, 62/580,243, filed Nov. 1, 2017, and 62/584,060, filed Nov. 9, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created Jun. 18, 2019, is named 51295-004004_Sequence_Listing_6.18.19_ST25 and is 76,888 bytes in size.

TECHNICAL FIELD

The technology described herein relates to immunotherapy.

BACKGROUND

Chimeric antigen receptor (CARs) provide a way to direct a cytotoxic T cell response to target cells expressing a selected target antigen, most often a tumor antigen or tumor-associated antigen. CARs are an adaptation of the T cell receptor, where the antigen binding domain is replaced with the antigen binding domain of an antibody that specifically binds the derived target antigen. Engagement of the target antigen on the surface of a target cell by a CAR expressed on a T cell ("CAR T cell" or "CAR-T") promotes killing of the target cell.

SUMMARY

Chimeric antigen receptors (CARs) generally include the full length CD3ζ (CD zeta) signaling domain. CD3ζ is thought to mediate "signal 1" in T cell activation. However, these signaling domains are phosphorylated upon T cell activation and have been associated with proliferation, cytokine secretion, cytotoxicity, and activation-induced cell death. As described herein, the present technology utilizes alternative signaling domains that decouple the cytotoxic signal from the activation-induced cell death signal which is mediated by engagement of the CAR and activation of CD3ζ. This change provides CAR-alternative T cells which display unexpectedly higher potency as compared to CAR-original T cells. The technology described herein is directed in part to the surprising finding that alternative signal 1 domains result in more efficient signaling of a CAR T cell.

Accordingly, one aspect of the technology described herein relates to a chimeric antigen receptor (CAR) polypeptide comprising; an extracellular domain comprising a target-binding sequence, a transmembrane domain, an intracellular domain of a co-stimulatory molecule, and a T cell intracellular signaling domain that lacks a functional ITAM3 sequence.

Another aspect of the technology described herein relates to a CAR polypeptide comprising an extracellular domain comprising a B cell maturation antigen (BCMA)-binding sequence, a transmembrane domain of CD8, an intracellular domain of 4-1BB, and a T cell intracellular signaling domain that lacks a functional ITAM3 sequence.

Another aspect of the technology described herein relates to a CAR polypeptide comprising an extracellular domain comprising a CD37-binding sequence, a transmembrane domain of CD8, an intracellular domain of 4-1BB, and a T cell intracellular signaling domain that lacks a functional ITAM3 sequence.

In one embodiment of any aspect, the transmembrane domain is the transmembrane domain of CD8 or 4-1BB.

In one embodiment of any aspect, the intracellular signaling domain comprises a CD3 ITAM3 sequence selected from SEQ ID NOs: 13, 14, 33, or 34.

In one embodiment of any aspect, the intracellular signaling domain comprises a CD3 ITAM3 sequence comprising a deletion relative to the CD3ζ ITAM3 sequence of SEQ ID NO: 13.

In one embodiment of any aspect, the T-cell intracellular signaling domain is the intracellular signaling domain of CD3eta (CD3ε) or CD3 theta (CD3θ).

In one embodiment of any aspect, the target-binding sequence comprises a ligand of the target or an antibody reagent that specifically binds the target. In one embodiment, the target is BCMA. In one embodiment, the target is CD37.

In one embodiment of any aspect, the antibody reagent comprises an scFv.

In one embodiment, the antibody reagent has a sequence selected from SEQ ID NOS: 1, 5, or 9.

In one embodiment of any aspect, the BCMA-binding sequence comprises a ligand of BCMA or an antibody reagent that specifically binds BCMA. In one embodiment, the CD37-binding sequence comprises a ligand of CD37 or an antibody reagent that specifically binds BCMA.

Another aspect of the technology described herein relates to a mammalian cell comprising any of the CAR polypeptides described herein, or a nucleic acid encoding any of the CAR polypeptides as described herein.

In one embodiment of any aspect, the cell is a T cell. In one embodiment, the cell is a human cell. In one embodiment, the cell is obtained from an individual having or diagnosed as having cancer, a plasma cell disorder, or autoimmune disease.

Another aspect of the technology described herein relates to a method of treating cancer, a plasma cell disorder, or an autoimmune disease in a subject in need thereof, the method comprising: engineering a T cell to express any of the CAR polypeptides described herein on the T cell surface; and administering the engineered CAR T cell to the subject.

Another aspect of the technology described herein relates to a method of treating cancer, a plasma cell disorder, or an autoimmune disease in a subject in need thereof, the method comprising administering a mammalian cell comprising a CAR polypeptide as described herein.

In one embodiment of any aspect, the cancer is a CD37+ or BCMA+ cancer. In one embodiment, the CD37+ cancer is lymphoma or leukemia. In one embodiment, lymphoma is B-cell Non-Hodgkin Lymphoma (NHL), mantle cell lymphoma, Burkitt's lymphoma, B cell lymphoblastic lymphoma or T cell lymphoma (e.g., peripheral T cell lymphoma (PTCL), including cutaneous T-cell lymphoma (CTCL) and anaplastic large cell lymphoma (ALCL)). In one embodiment, the leukemia is acute myeloid leukemia (AML).

Another aspect of the technology described herein relates to a method of treating cancer, a plasma cell disorder, or an autoimmune disease in a subject in need thereof, the method comprising: engineering a T cell to comprise a CAR polypeptide as described herein on the T cell surface, and administering the engineered CAR T cell to the subject, wherein the subject is non-responsive to anti-CD19 and/or anti-CD20 therapy.

Another aspect of the technology described herein relates to a method of treating cancer, a plasma cell disorder, or an autoimmune disease in a subject in need thereof, the method comprising administering a mammalian cells comprising a CAR polypeptide as described herein to the subject, wherein the cell comprises a CAR polypeptide comprising an extracellular domain comprising a CD37-binding sequences, and wherein the subject is non-responsive to anti-CD19 and/or anti-CD20 therapy.

Another aspect of the technology described herein relates to a method of treating cancer, a plasma cell disorder, or an autoimmune disease in a subject in need thereof, the method comprising selecting a subject who is non-responsive to anti-CD19 and/or anti-CD20 therapy, engineering a T cell to comprise a CAR polypeptide as described herein on the T cell surface, and administering the engineered CAR T cell to the subject.

Another aspect of the technology described herein relates to a method of treating cancer, a plasma cell disorder, or an autoimmune disease in a subject in need thereof, the method comprising selecting a subject who is non-responsive to anti-CD19 and/or anti-CD20 therapy, administering a mammalian cell comprising a CAR polypeptide as described herein to the subject, wherein the cell comprises a CAR polypeptide comprises an extracellular domain comprising a CD37-binding sequence.

Another aspect of the technology described herein relates to a method of treating cancer, a plasma cell disorder, or an autoimmune disease in a subject in need thereof, the method comprising engineering a T cell to comprise a CAR polypeptide as described herein on the T cell surface, administering the engineered CAR T cell to the subject, wherein the subject is concurrently administered an anti-CD19 and/or anti-CD20 therapy.

Another aspect of the technology described herein relates to a method of treating cancer, a plasma cell disorder, or an autoimmune disease in a subject in need thereof, the method comprising administering a mammalian cell comprising a CAR polypeptide as described herein to the subject, wherein the cell comprises a CAR polypeptide comprising an extracellular domain comprising a CD37-binding sequence, and wherein the subject is concurrently administered an anti-CD19 and/or anti-CD20 therapy.

Another aspect of the technology described herein relates to a composition comprising a CAR T cell as described herein, formulated for the treatment of cancer. In one embodiment, the composition further comprises a pharmaceutically acceptable carrier.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female.

A subject can be one who has been previously diagnosed with or identified as suffering from or having a condition in need of treatment (e.g. leukemia or another type of cancer, among others) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

A "disease" is a state of health of an animal, for example a human, wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

As used herein, the term "chimeric" refers to the product of the fusion of portions of at least two or more different polynucleotide molecules. In one embodiment, the term "chimeric" refers to a gene expression element produced through the manipulation of known elements or other polynucleotide molecules In some embodiments, "activation" can refer to the state of a T cell that has been sufficiently stimulated to induce detectable cellular proliferation. In some embodiments activation can refer to induced cytokine production. In other embodiments, activation can refer to detectable effector functions. At a minimum, an "activated T cell" as used herein is a proliferative T cell.

As used herein, the terms "specific binding" and "specifically binds" refer to a physical interaction between two molecules, compounds, cells and/or particles wherein the first entity binds to the second, target, entity with greater specificity and affinity than it binds to a third entity which is a non-target. In some embodiments, specific binding can refer to an affinity of the first entity for the second target, entity, which is at least 10 times, at least 50 times, at least 100 times, at least 500 times, at least 1000 times or more greater than the affinity for the third nontarget entity under the same conditions. A reagent specific for a given target is one that exhibits specific binding for that target under the conditions of the assay being utilized. A non-limiting example includes an antibody, or a ligand, which recognizes and binds with a cognate binding partner (for example, a stimulatory and/or costimulatory molecule present on a T cell) protein.

A "stimulatory ligand," as used herein, refers to a ligand that when present on an antigen presenting cell (APC e.g., a macrophage, a dendritic cell, a B-cell, an artificial APC, and the like) can specifically bind with a cognate binding partner (referred to herein as a "stimulatory molecule" or "co-stimulatory molecule") on a T cell, thereby mediating a primary response by the T cell, including, but not limited to, proliferation, activation, initiation of an immune response, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell.

"Co-stimulatory ligand," as the term is used herein, includes a molecule on an APC that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, 4-1BBL, OX40L, CD7, B7-1 (CD80), B7-2 (CD86), PD-L1, PD-L2, inducible COStimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll-like receptor and a ligand that specifically binds with B7-H3. A co-stimulatory ligand also can include, but is not limited to, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA, a Toll-like receptor, CD27, CD28, 4-1BB, OX40, CD30, CD40, PD-1, ICOS, lymphocyte function-associated antigen-1 (LFA-1), CD2, CD7, LIGHT, NKG2C, B7-H3, and CD83.

In one embodiment, the term "engineered" and its grammatical equivalents as used herein can refer to one or more human-designed alterations of a nucleic acid, e.g., the nucleic acid within an organism's genome. In another embodiment, engineered can refer to alterations, additions, and/or deletion of genes. An "engineered cell" can refer to a cell with an added, deleted and/or altered gene. The term "cell" or "engineered cell" and their grammatical equivalents as used herein can refer to a cell of human or non-human animal origin.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of ordinary skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. ligand-mediated receptor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg;

(5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are well established and include, for example, those disclosed by Walder et al. (Gene 42:133, 1986); Bauer et al. (Gene 37:73, 1985); Craik (BioTechniques, Jan. 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of a polypeptide also can be substituted, generally with serine, to improve the oxidative stability of the molecule and prevent aberrant crosslinking. Conversely, cysteine bond(s) can be added to a polypeptide to improve its stability or facilitate oligomerization.

As used herein, the term "DNA" is defined as deoxyribonucleic acid. The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g. a CAR polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra-chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. acute lymphoblastic leukemia or other cancer, disease, or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier in which the active ingredient would not be found to occur in nature.

As used herein, the term "administering," refers to the placement of a therapeutic or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined within the description of the various aspects and embodiments of the technology of the following.

BRIEF DESCRIPTION OF THE DRAWINGS

FIG. 2A demonstrates BCMA expression in bone marrow cells from a multiple myeloma patient (bottom histogram) and in a multiple myeloma cell line (RPMI 8226, middle histogram). FIG. 2B depicts results of experiments in which CAR T and multiple myeloma (RPMI 8226) cells (GFP+) were co-cultured in the presence of propidium iodide at a 1:1 effector:target (E:T) ratio. Images were taken at 0 and 24 hours using an EVOS® FL fluorescence imager. FIG. 2C depicts specific cell lysis of multiple myeloma measured by end-point luminescence at different effector:target cell ratios after 16-hour co-culture. UTD=Untransduced cells.

FIGS. 54A-54C show in vitro cytotoxic activity of CAR-37 T cells.

FIG. 58A depicts an experimental schematic. On Day −39, mice were administered $1 \times 10^6$ PDX_98848 MCL PDX cells intravenously. Flow cytometry was performed on days −28 and −14. BLI was performed on Day −1. On day 0, $3 \times 10^6$ UTD (control) or CART positive cells (CAR-37 H-L or CAR-19) were administered intravenously into the mice. Mice were imaged on days 3, 7, 10, 14, 17, 21, and 35, and tumor growth was analyzed measuring bioluminescence (FIGS. 58B and 58C). CAR-37 T cells had strong anti-tumor efficacy against MCL PDX tumors in vivo.

DETAILED DESCRIPTION

Figure 1:
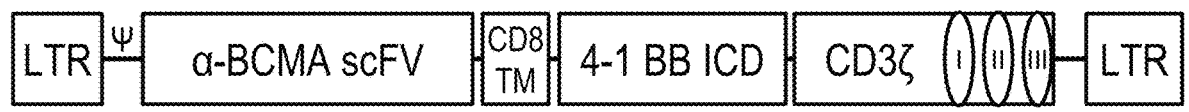
FIG. 1 depicts a schematic diagram of the generic configuration of a BCMA-targeted CAR. The lentiviral vector construct contains a single-chain variable region derived from a BCMA-specific monoclonal antibody linked to a CD8 transmembrane domain (CD8 TM), followed by the intracellular domain of 4-1BB (4-1BB ICD, CD137) and the CD3ζ module showing the three putative ITAMs (I, II, III).

To date, CARs have generally included a full length CD3ζ signaling domain. CD3ζ is thought to mediate "signal 1" in T cell activation. However, these signaling domains are phosphorylated upon T cell activation and have been associated with proliferation, cytokine secretion, cytotoxicity, and activation-induced cell death. As described herein, the present technology utilizes alternative signaling domains that decouple the cytotoxic signal from the activation-induced cell death signal mediated by engagement of the CAR and activation of CD3 zeta. This change, and others described herein, provide more potent CAR-alternative T cells compared to CAR-original T cells.

Embodiments of the technology described herein relate to the discovery that including an alternative signal 1 domain in a CAR construct results in a more efficient CAR T cell. CAR T cells with alternative signal 1 domains exhibit a higher capacity for treating disease, for example, cancer, compared to CAR T cells that utilize the original signal 1 domain.

Accordingly, one aspect of the technology described herein relates to a CAR polypeptide comprising: an extracellular domain comprising a target-binding sequence; a transmembrane domain (including, for example, a transmembrane domain of a co-stimulatory ligand); and a T cell intracellular signaling domain that lacks a functional ITAM3 sequence.

Another aspect of the technology described herein relates to a CAR polypeptide comprising: an extracellular domain comprising a BCMA-binding sequence; a transmembrane domain comprising the transmembrane domain of CD8 or 4-1BB; and an intracellular domain comprising a T-cell signaling domain.

Another aspect of the technology described herein relates to a CAR polypeptide comprising: an extracellular domain comprising a CD37-binding sequence; a transmembrane domain comprising the transmembrane domain of CD8 or 4-1BB; and an intracellular domain comprising a T-cell signaling domain.

Considerations necessary to make and use these and other aspects of the technology are described in the following.

Chimeric Antigen Receptors

The technology described herein provides improved CARs for use in immunotherapy. The following discusses CARs and the various improvements.

It should be understood that while BCMA and CD37 are discussed herein as examples of CAR targets, they are just that: examples. The principles described herein with respect to improvements in CAR and therefore CAR T design can be applied to CARs that target any target or antigen, including any cell-surface target or antigen.

The terms "chimeric antigen receptor" or "CAR" or "CARs" as used herein refer to engineered T cell receptors, which graft a ligand or antigen specificity onto T cells (for example naïve T cells, central memory T cells, effector memory T cells or combinations thereof). CARs are also known as artificial T-cell receptors, chimeric T-cell receptors or chimeric immunoreceptors.

A CAR places a chimeric extracellular target-binding domain that specifically binds a target, e.g., a polypeptide, expressed on the surface of a cell to be targeted for a T cell response onto a construct including a transmembrane domain and intracellular domain(s) of a T cell receptor molecule. In one embodiment, the chimeric extracellular target-binding domain comprises the antigen-binding domain(s) of an antibody that specifically binds an antigen expressed on a cell to be targeted for a T cell response. The properties of the intracellular signaling domain(s) of the CAR can vary as known in the art and as disclosed herein, but the chimeric target/antigen-binding domains(s) render the receptor sensitive to signaling activation when the chimeric target/antigen binding domain binds the target/antigen on the surface of a targeted cell.

With respect to intracellular signaling domains, so-called "first-generation" CARs include those that solely provide CD3zeta (CD3ζ) signals upon antigen binding. So-called "second-generation" CARs include those that provide both co-stimulation (e.g., CD28 or CD 137) and activation (CD3ζ) domains, and so-called "third-generation" CARs include those that provide multiple costimulatory (e.g., CD28 and CD 137) domains and activation domains (e.g., CD3ζ). In various embodiments, the CAR is selected to have high affinity or avidity for the target/antigen—for example, antibody-derived target or antigen binding domains will generally have higher affinity and/or avidity for the target antigen than would a naturally-occurring T cell receptor. This property, combined with the high specificity one can select for an antibody provides highly specific T cell targeting by CAR T cells.

As used herein, a "CAR T cell" or "CAR-T" refers to a T cell which expresses a CAR. When expressed in a T cell, CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape.

As used herein, the term "extracellular target binding domain" refers to a polypeptide found on the outside of the cell which is sufficient to facilitate binding to a target. The extracellular target binding domain will specifically bind to its binding partner, i.e. the target. As non-limiting examples, the extracellular target-binding domain can include an antigen-binding domain of an antibody, or a ligand, which recognizes and binds with a cognate binding partner (for example, BCMA or CD37) protein. In this context, a ligand is a molecule which binds specifically to a portion of a protein and/or receptor. The cognate binding partner of a ligand useful in the methods and compositions described herein can generally be found on the surface of a cell. Ligand:cognate partner binding can result in the alteration of the ligand-bearing receptor, or activate a physiological response, for example, the activation of a signaling pathway. In one embodiment, the ligand can be non-native to the genome. Optionally, the ligand has a conserved function across at least two species. In one embodiment, the extracellular target binding domain comprises a non-antibody ligand (e.g., A PRoliferation-Inducing Ligand (APRIL)).

Antibody Reagents

In various embodiments, the CARs described herein comprise an antibody reagent or an antigen-binding domain thereof as an extracellular target-binding domain.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like. Fully human antibody binding domains can be selected, for example, from phage display libraries using methods known to those of ordinary skill in the art.

The $V_H$ and $V_L$ regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each $V_H$ and $V_L$ is typically composed of three CDRs and four FRs, arranged from amino-terminus to carboxy-terminus in the following order: FR1, CDR1, FR2, CDR2, FR3, CDR3, FR4.

In one embodiment, the antibody or antibody reagent is not a human antibody or antibody reagent, (i.e., the antibody or antibody reagent is mouse), but has been humanized. A "humanized antibody or antibody reagent" refers to a non-human antibody or antibody reagent that has been modified at the protein sequence level to increase its similarity to antibody or antibody reagent variants produced naturally in humans. One approach to humanizing antibodies employs the grafting of murine or other non-human CDRs onto human antibody frameworks.

In one embodiment, a CAR's extracellular target binding domain comprises or consists essentially of a single-chain Fv (scFv) fragment created by fusing the $V_H$ and $V_L$ domains of an antibody, generally a monoclonal antibody, via a flexible linker peptide. In various embodiments, the scFv is fused to a transmembrane domain and to a T cell receptor intracellular signaling domain, e.g., an engineered intracellular signaling domain as described herein.

Antibody binding domains and ways to select and clone them are well known to those of ordinary skill in the art. In another embodiment, the antibody reagent is an anti-CD37 antibody reagent and has the sequence selected from SEQ ID NO: 5 or 9. In one embodiment, the anti-OTK3 antibody reagent corresponds to the sequence of SEQ ID NO: 5 or 9; or comprises the sequence of SEQ ID NO: 5 or 9; or comprises a sequence with at least 80%, at least 85%, at least 90%, at least 95%, at least 96%, at least 97%, at least 98%, at least 99% or greater sequence identity to the sequence of SEQ ID NO: 5 or 9.

In another embodiment, the antibody reagent is an anti-BCMA antibody reagent and has the sequence of SEQ ID NO: 1. In one embodiment, the anti-CD28 antibody corresponds to the sequence of SEQ ID NO: 1; or comprises the sequence of SEQ ID NO: 1; or comprises a sequence with at least 80%, at least 85%, at least 90%, at least 95%, at least 96%, at least 97%, at least 98%, at least 99% or greater sequence identity to the sequence of SEQ ID NO: 1.

In one embodiment, the CARs useful in the technology described herein comprise at least two antigen-specific targeting regions, an extracellular domain, a transmembrane domain, and an intracellular signaling domain. In such embodiments, the two or more antigen-specific targeting regions target at least two different antigens and may be arranged in tandem and separated by linker sequences. In another embodiment, the CAR is a bispecific CAR. A bispecific CAR is specific to two different antigens.

Target/Antigen

Any cell-surface moiety can be targeted by a CAR. Most often, the target will be a cell-surface polypeptide differentially or preferentially expressed on a cell one wishes to target for a T cell response. In this regard, tumor antigens or tumor-associated antigens provide attractive targets, providing a means to target tumor cells while avoiding or at least limiting collateral damage to non-tumor cells or tissues. Non-limiting examples of tumor antigens or tumor-associated antigens include CEA, Immature laminin receptor, TAG-72, HPV E6 and E7, BING-4, Calcium-activated chloride channel 2, Cyclin B1, 9D7, Ep-CAM, EphA3, Her2/neu, Telomerase, Mesotheliun, SAP-1, Survivin, BAGE family, CAGE family, GAGE family, MAGE family, SAGE family, XAGE family, NY-ESO-1/LAGE-1, PRAME, SSX-2, Melan-A/MART-1, Gp100/pme117, Tyrosinase, TRP-1/-2, MC1R, BRCA1/2, CDK4, MART-2, p53, Ras, MUC1, and TGF-βRII.

In one embodiment, the target is B cell maturation antigen (BCMA), also known as tumor necrosis factor receptor superfamily member 17 (TNFRSF17). BCMA is a cell surface receptor expressed preferentially on mature B lymphocytes that specifically recognizes B cell activating factor (BAFF). BCMA sequences are known for a number of species, e.g., human BCMA (NCBI Gene ID: 608) polypeptide (e.g., NCBI Ref Seq NP_001183.2) and mRNA (e.g., NCBI Ref Seq NM_001192.2). BCMA can refer to human BCMA, including naturally occurring variants, molecules, and alleles thereof. In some embodiments of any of the aspects, e.g., in veterinary applications, BCMA can refer to the BCMA of, e.g., dog, cat, cow, horse, pig, and the like. Homologs and/or orthologs of human BCMA are readily identified for such species by one of skill in the art, e.g., using the NCBI ortholog search function or searching available sequence data for a given species for sequence similar to a reference BCMA sequence.

In one embodiment, the BCMA-binding sequence comprises a ligand of BCMA or an antibody reagent that specifically binds BCMA. In one embodiment, the antibody reagent that specifically binds BCMA is a scFv from a humanized anti-BCMA m murine antibody. The orientation of a humanized murine antibody-derived single-chain variable fragment can be $V_L$-$V_H$ or $V_H$-$V_L$.

In one embodiment, the target is CD37. CD37 is cell surface protein that contains four hydrophobic transmembrane domains. CD37 is expressed exclusively on immune cells; CD37 is highly expressed on mature B cells, and moderately expressed on T cells and myeloid cells. CD37 sequences are known for a number of species, e.g., human CD37 (NCBI Gene ID: 951) polypeptide (e.g., NCBI Ref Seq NP_001035120.1) and mRNA (e.g., NCBI Ref Seq NM_001040031.1). CD37 can refer to human CD37, including naturally occurring variants, molecules, and alleles thereof. In some embodiments of any of the aspects, e.g., in veterinary applications, CD37 can refer to the CD37 of, e.g., dog, cat, cow, horse, pig, and the like. Homologs and/or orthologs of human CD37 are readily identified for such species by one of skill in the art, e.g., using the NCBI ortholog search function or searching available sequence data for a given species for sequence similar to a reference CD37 sequence.

In one embodiment, the CD37-binding sequence comprises a ligand of CD37 or an antibody reagent that specifically binds CD37.

Transmembrane Domain

Each CAR as described herein necessarily includes a transmembrane domain that joins the extracellular target-binding domain to the intracellular signaling domain.

As used herein, "transmembrane domain" (TM domain) refers to the generally hydrophobic region of the CAR which crosses the plasma membrane of a cell. The TM domain can be the transmembrane region or fragment thereof of a transmembrane protein (for example a Type I transmembrane protein or other transmembrane protein), an artificial hydrophobic sequence, or a combination thereof. While specific examples are provided herein and used in the Examples, other transmembrane domains will be apparent to those of skill in the art and can be used in connection with alternate embodiments of the technology. A selected transmembrane region or fragment thereof would preferably not interfere with the intended function of the CAR. As used in relation to a transmembrane domain of a protein or polypeptide, "fragment thereof" refers to a portion of a transmembrane domain that is sufficient to anchor or attach a protein to a cell surface.

In one embodiment, a CAR's transmembrane domain or fragment thereof is derived from or comprises the transmembrane domain of CD8. In an alternate embodiment, the transmembrane domain or fragment thereof of the CAR described herein comprises a transmembrane domain selected from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

CD8 is an antigen preferentially found on the cell surface of cytotoxic T lymphocytes. CD8 mediates cell-cell interactions within the immune system, and acts as a T cell coreceptor. CD8 consists of an alpha (CD8a) and beta (CD8(3) chain. CD8a sequences are known for a number of species, e.g., human CD8a, (NCBI Gene ID: 925) polypeptide (e.g., NCBI Ref Seq NP_001139345.1) and mRNA (e.g., NCBI Ref Seq NM_000002.12). CD8 can refer to human CD8, including naturally occurring variants, molecules, and alleles thereof. In some embodiments of any of the aspects, e.g., in veterinary applications, CD8 can refer to the CD8 of, e.g., dog, cat, cow, horse, pig, and the like. Homologs and/or orthologs of human CD8 are readily identified for such species by one of skill in the art, e.g., using the NCBI ortholog search function or searching available sequence data for a given species for sequence similar to a reference CD8 sequence.

Co-Stimulatory Domain

Each CAR described herein comprises an intracellular domain of a co-stimulatory molecule, or co-stimulatory domain. As used herein, the term "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, the intracellular domain is the intracellular domain of 4-1BB.

4-1BBL is a type 2 transmembrane glycoprotein belonging to the TNF superfamily. 4-1BBL is expressed on activated T lymphocytes. 4-1BBL sequences are known for a number of species, e.g., human 4-1BBL, also known as TNFSF9 (NCBI Gene ID: 8744) polypeptide (e.g., NCBI Ref Seq NP_003802.1) and mRNA (e.g., NCBI Ref Seq NM_003811.3). 4-1BBL can refer to human 4-1BBL, including naturally occurring variants, molecules, and alleles thereof. In some embodiments of any of the aspects, e.g., in veterinary applications, 4-1BBL can refer to the 4-1BBL of, e.g., dog, cat, cow, horse, pig, and the like. Homologs and/or orthologs of human 4-1BBL are readily identified for such species by one of skill in the art, e.g., using the NCBI ortholog search function or searching available sequence data for a given species for sequence similar to a reference 4-1BBL sequence.

Intracellular Signaling Domain

CARs as described herein comprise an intracellular signaling domain. An "intracellular signaling domain," refers to the part of a CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

CD3 is a T cell co-receptor that facilitates T lymphocytes activation when simultaneously engaged with the appropriate co-stimulation (e.g., binding of a co-stimulatory molecule). A CD3 complex consists of 4 distinct chains; mammal CD3 consists of a CD3γ chain, a CD3δ chain, and two CD3ε chains. These chains associate with a molecule known as the T cell receptor (TCR) and the CD3ζ to generate an activation signal in T lymphocytes. A complete TCR complex comprises a TCR, CD3ζ, and the complete CD3 complex.

In some embodiments of any aspect, a CAR polypeptide described herein comprises an intracellular signaling domain that comprises an Immunoreceptor Tyrosine-based Activation Motif or ITAM from CD3 zeta (CD3ζ). In some embodiments of any aspect, the ITAM comprises three motifs of ITAM of CD3ζ (ITAM3). In some embodiments of any aspect, the three motifs of ITAM of CD3 are mutated.

ITAMs are known as a primary signaling domains which regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Non-limiting examples of ITAM-containing intracellular signaling domains that are of particular use in the technology include those derived from TCRζ, FcRγ, FcRβ, CD3γ, CD3θ, CD3ε, CD3ε, CD3ζ, CD22, CD79a, CD79b, and CD66d.

One skilled in the art will be capable of introducing mutations into the nucleic acid sequence of a gene or gene product, for example an ITAM, using standard techniques. For example, point mutations can be introduced via site-directed point mutagenesis, a PCR technique. Site-directed mutagenesis kits are commercially available, for instance, through New England Biolabs; Ipswich, Mass. Non-limiting examples of alternative methods to introduce point mutations to the nucleic acid sequence of a gene or gene product include cassette mutagenesis or whole plasmid mutagenesis.

In one embodiment, the ITAM utilized in the CAR is based on alternatives to CD3ζ, including mutated ITAMs from CD3ζ (which contains 3 ITAM motifs), truncations of CD3, and alternative splice variants known as CD3ε, CD3θ, and artificial constructs engineered to express fusions between CD3ε or CD3θ and CD3ζ.

In one embodiment, the CD3ζ ITAM3 sequence corresponds to the sequence of SEQ ID NO: 13.; or comprises the sequence of SEQ ID NO: 13; or comprises a sequence with at least 80%, at least 85%, at least 90%, at least 95%, at least 96%, at least 97%, at least 98%, at least 99% or greater sequence identity to the sequence of SEQ ID NO: 13.

In one embodiment, the intracellular signaling domain comprises a CD3ζ ITAM3 sequence selected from SEQ ID NOs: 13, 14, 33, or 34. In one embodiment, the tyrosine residues are mutated to phenylalanine residues, thereby inhibiting the phosphorylation of the native tyrosine residues. Exemplary tyrosine residues that can be mutated include any tyrosine residue described in Examples 9 or 10. It is contemplated that the tyrosine residues can be mutated to any residue that results in the inhibition of tyrosine phosphorylation. In another embodiment of any aspect, tyrosines are mutated in at least one, at least two, or all three ITAMs (e.g., ITAM I, II, and III).

In one embodiment, the T-cell intracellular signaling domain comprises the ITAMs of CD3 eta (CDR), CD3 theta (CD3θ) or CD3. In one embodiment, the T-cell intracellular signaling domain is the ITAM of CD3 eta (CDR), CD3 theta (CD3θ) or CD3.

In one embodiment, the intracellular signaling domain comprises an CD3ζ ITAM3 sequence comprising a deletion relative to the CD3ζ ITAM3 sequence of SEQ ID NO: 13.

A deletion relative to the CD3ζ ITAM3 sequence can be performed using techniques well known in the art, for example, CRISPR, TALEN or ZFN technology. Methods of engineering nucleases to achieve a desired sequence specificity are known in the art and are described, e.g., in Kim (2014); Kim (2012); Belhaj et al. (2013); Urnov et al. (2010); Bogdanove et al. (2011); Jinek et al. (2012) Silva et al. (2011); Ran et al. (2013); Carlson et al. (2012); Guerts et al. (2009); Taksu et al. (2010); and Watanabe et al. (2012); each of which is incorporated by reference herein in its entirety. In alternate embodiments of any aspect, a deletion relative to the ITAM3 sequence can be done via inhibitory nucleic acid. As used herein, "inhibitory nucleic acid" refers to a nucleic acid molecule which can inhibit the expression of a target, e.g., double-stranded RNAs (dsRNAs), inhibitory RNAs (iRNAs), and the like. Inhibitory nucleic acid technology is more fully described in Wilson, R C, and Doudna, J A. (2103) Annual Review of Biophysics 42(217-239) and reference cited therein.

Experimental data provided herein show that variants of the intracellular signaling domain described herein results in a more efficient CAR T cell. It is expected that replacing the intracellular signaling domain of any CAR T cell with any intracellular signaling domain variant described herein would improve the efficacy of the CAR T cell.

A more detailed description of CARs and CAR T cells can be found in Maus et al. Blood 2014 123:2624-35; Reardon et al. Neuro-Oncology 2014 16:1441-1458; Hoyos et al.

Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In one embodiment, the CAR further comprises a linker domain. As used herein "linker domain" refers to an oligo- or polypeptide region from about 2 to 100 amino acids in length, which links together any of the domains/regions of the CAR as described herein. In some embodiment, linkers can include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In one embodiment, the linker region is T2A derived from Thosea asigna virus. Non-limiting examples of linkers that can be used in this technology include P2A and F2A.

In one embodiment, a CAR as described herein further comprises a reporter molecule, e.g., to permit for non-invasive imaging (e.g., positron-emission tomography PET scan). In a bispecific CAR that includes a reporter molecule, the first extracellular binding domain and the second extracellular binding domain can include different or the same reporter molecule. In a bispecific CAR T cell, the first CAR and the second CAR can express different or the same reporter molecule. In another embodiment, a CAR as described herein further comprises a reporter molecule (for example hygromycin phosphotransferase (hph)) that can be imaged alone or in combination with a substrate or chemical (for example 9-[4-[$^{18}$F]fluoro-3-(hydroxymethyl)butyl]guanine ([$^{18}$F]FHBG)). In another embodiment, a CAR as described herein further comprises nanoparticles at can be readily imaged using non-invasive techniques (e.g., gold nanoparticles (GNP) functionalized with $^{64}Cu^{2+}$). Labeling of CAR T cells for non-invasive imaging is reviewed, for example in Bhatnagar P, et al. Integr Biol. (Camb). 2013 January; 5(1): 231-238, and Keu K V, et al. Sdci Transl Med. 2017 Jan. 18; 9(373), which are incorporated herein by reference in their entireties.

GFP and mCherry are demonstrated herein as fluorescent tags useful for imaging a CAR expressed on a T cell (e.g., a CAR T cell). It is expected that essentially any fluorescent protein known in the art can be used as a fluorescent tag for this purpose. For clinical applications, the CAR need not include a fluorescent tag or fluorescent protein.

In one embodiment, the CAR polypeptide comprises a BCMA binding domain, CD8 transmembrane domain, 4-1 BB costimulatory domain, a CD3ζ signaling domain, a T2A linker, and an mCherry protein. In another embodiment, the CD3ζ domain can be replaced with CD3ε, CD3θ, and/or other ITAM-containing variants of CD3-related signaling domains.

In one embodiment, the CAR polypeptide sequence corresponds to, or comprises, or comprises a sequence with at least 80%, at least 85%, at least 90%, at least 91%, at least 92%, at least 93%, at least 94%, at least 95%, at least 96%, at least 97%, at least 98%, at least 99% or greater sequence identity of a sequence selected from SEQ ID NO: 15 or 35-40.

In one embodiment, the CAR polypeptide comprises a CD37 binding domain, CD8 transmembrane domain, 4-1 BB co-stimulatory domain, a CD3ζ signaling domain, a T2A linker, and an mCherry protein. In another embodiment, the CD3ζ domain can be replaced with CD3ε, CD3θ, and/or other ITAM-containing variants of CD3-related signaling domains.

In one embodiment, the CAR polypeptide sequence corresponds to, or comprises, or comprises a sequence with at least 80%, at least 85%, at least 90%, at least 91%, at least 92%, at least 93%, at least 94%, at least 95%, at least 96%, at least 97%, at least 98%, at least 99% or greater sequence identity of a sequence selected from SEQ ID NO: 21 or 27.

One aspect of the technology described herein relates to a mammalian cell comprising any of the CAR polypeptides described herein; or a nucleic acid encoding any of the CAR polypeptides described herein. In one embodiment, the mammalian cell comprises an antibody, antibody reagent, antigen-binding portion thereof, or any of the CARs described herein, or a nucleic acid encoding such an antibody, antibody reagent, antigen-binding portion thereof, or any of the CARs described herein. The mammalian cell or tissue can be of human, primate, hamster, rabbit, rodent, cow, pig, sheep, horse, goat, dog or cat origin, but any other mammalian cell may be used. In a preferred embodiment of any aspect, the mammalian cell is human.

In one embodiment, the cell is a T cell. In alternate embodiments of any aspect, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; a NK cell; a NKT cell; lymphocytes, such as B cells and T cells; and myeloid cells, such as monocytes, macrophages, eosinophils, mast cells, basophils, and granulocytes.

In one embodiment, the cell is obtained from an individual having or diagnosed as having cancer, a plasma cell disorder, or autoimmune disease.

"Cancer" as used herein can refer to a hyperproliferation of cells whose unique trait— loss of normal cellular control—results in unregulated growth, lack of differentiation, local tissue invasion, and metastasis, and can be leukemia, lymphoma, multiple myeloma, or a solid tumor. Non-limiting examples of leukemia include acute myeloid leukemia (AML), Chronic myeloid leukemia (CML), Acute lymphocytic leukemia (ALL), and Chronic lymphocytic leukemia (CLL). In one embodiment, the cancer is ALL or CLL. Non-limiting examples of lymphoma include Diffuse large B-cell lymphoma (DLBCL), Follicular lymphoma, Chronic lymphocytic leukemia (CLL), Small lymphocytic lymphoma (SLL), Mantle cell lymphoma (MCL), Marginal zone lymphomas, Burkitt lymphoma, hairy cell leukemia (HCL), and T cell lymphoma (e.g., peripheral T cell lymphoma (PTCL), including cutaneous T cell lymphoma (CTCL) and anaplastic large cell lymphoma (ALCL)). In one embodiment, the cancer is DLBCL or Follicular lymphoma. Non-limiting examples of solid tumors include Adrenocortical Tumor, Alveolar Soft Part Sarcoma, Carcinoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors (Solid Tumor), Giant Cell Tumor of Bone and Soft Tissue, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, or organs, and can be sarcomas or carcinomas. It is contemplated that any aspect of the technology described herein can be used to treat all types of cancers, including cancers not listed in the instant application. As used herein, the term "tumor" refers to an abnormal growth of cells or tissues, e.g., of malignant type or benign type.

As used herein, an "autoimmune disease or disorder" is characterized by the inability of one's immune system to distinguish between a foreign cell and a healthy cell. This results in one's immune system targeting one's healthy cells for programmed cell death. Non-limiting examples of an autoimmune disease or disorder include inflammatory arthritis, type 1 diabetes mellitus, multiples sclerosis, psoriasis, inflammatory bowel diseases, SLE, and vasculitis, allergic inflammation, such as allergic asthma, atopic dermatitis, and contact hypersensitivity. Other examples of auto-immune-related disease or disorder, but should not be construed to be limited to, include rheumatoid arthritis, multiple sclerosis (MS), systemic lupus erythematosus, Graves' disease (overactive thyroid), Hashimoto's thyroiditis (underactive thyroid), celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/ giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis and fibromyalgia (FM).

In one embodiment, the mammalian cell is obtained for a patient having an immune system disorder that results in abnormally low activity of the immune system, or immune deficiency disorders, which hinders one's ability to fight a foreign cell, (i.e., a virus or bacterial cell).

A plasma cell is a white blood cell produces from B lymphocytes which function to generate and release antibodies needed to fight infections. As used herein, a "plasma cell disorder or disease" is characterized by abnormal multiplication of a plasma cell. Abnormal plasma cells are capable of "crowding out" healthy plasma cells, which results in a decreased capacity to fight a foreign object, such as a virus or bacterial cell. Non-limiting examples of plasma cell disorders include amyloidosis, Waldenstrom's macroglobulinemia, osteosclerotic myeloma (POEMS syndrome), Monoclonal gammopathy of unknown significance (MGUS), and plasma cell myeloma.

T cells can be obtained from a subject using standard techniques known in the field. For example, T cells can be isolated from peripheral blood taken from a donor or patient. T cells can be isolated from a mammal. Preferably, T cells are isolated from a human.

A cell, for example a T cell, can be engineered to comprise any of the CAR polypeptides described herein; or a nucleic acid encoding any of the CAR polypeptides described herein. In one embodiment, the any of the CAR polypeptides described herein are comprised in a lentiviral vector. The lentiviral vector is used to express the CAR polypeptide in a cell using infection standard techniques.

Retroviruses, such as lentiviruses, provide a convenient platform for delivery of nucleic acid sequences encoding a gene, or chimeric gene of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety. Lentiviral system for efficient DNA delivery can be purchased from OriGene; Rockville, Md. In alternative embodiments, the CAR polypeptide of any of the CARS described herein are expressed in the mammalian cell via transfection or electroporation of an expression vector comprising nucleic acid encoding the CAR. Transfection or electroporation methods are known in the art.

Efficient expression of the CAR polypeptide of any of the CAR polypeptides described herein can be assessed using standard assays that detect the mRNA, DNA, or gene product of the nucleic acid encoding the CAR. For example, RT-PCR, FACS, northern blotting, western blotting, ELISA, or immunohistochemistry.

In one embodiment, the CAR polypeptide described herein is constitutively expressed. In one embodiment, the CAR polypeptide described herein is encoded by recombinant nucleic acid sequence.

One aspect of the technology described herein relates to a method of treating cancer, a plasma cell disorder, or an autoimmune disease in a subject in need thereof, the method comprising: engineering a T cell to comprise any of the CAR polypeptides described herein on the T cell surface; and administering the engineered T cell to the subject.

One aspect of the technology described herein relates to a method of treating cancer, a plasma cell disorder, or an autoimmune disease in a subject in need thereof, the method comprising: administering the cell of any of the mammalian cells comprising the any of the CAR polypeptides described herein.

Cluster differentiation (CD) molecules are cell surface markers present on leukocytes. As a leukocyte differentiates and matures its CD profile changes. In the case that a leukocytes turns into a cancer cell, (i.e., a lymphoma), its CD profile is important in diagnosing the disease. The treatment and prognosis of certain types of cancers is reliant on determining the CD profile of the cancer cell. "CDX+", wherein "X" is a CD marker, indicates the CD marker is present in the cancer cell, while "CDX−" indicates the marker is not present. One skilled in the art will be capable of assessing the CD molecules present on a cancer cell using standard techniques, for example using immunofluorescence to detect commercially available antibodies bound to the CD molecules.

In one embodiment, the cancer expresses a CD and tumor antigen. In one embodiment, the cancer is a CD37+ or BCMA+ cancer. In one embodiment, the CD37+ cancer is lymphoma or leukemia. In one embodiment, lymphoma is B-cell Non-Hodgkin Lymphoma (NHL), mantle cell lymphoma, Burkitt's lymphoma, B cell lymphoblastic lymphoma or T cell lymphoma (e.g., peripheral T cell lymphoma (PTCL), including cutaneous T-cell lymphoma (CTCL) and anaplastic large cell lymphoma (ALCL)).

One aspect of the technology described herein relates to a method of treating cancer, a plasma cell disorder, or an autoimmune disease in a subject in need thereof, the method comprising: engineering a T cell to comprise any of the CAR polypeptides described herein on the T cell surface; administering the engineered T cell to the subject; wherein the subject is non-responsive to anti-CD19 and/or anti-CD20 therapy.

Cancer cells can evolve in response to treatment to alter its CD profile in order to evade said treatment. For example, a patient with CD19+ leukemia can be treated with an anti-CD19 therapy. Following treatment, the cancer cell can relapse, or come back after treatment, and no longer express the CD19 marker, resulting in CD19− leukemia. This cancer cell will no longer be targetable by an anti-CD19 therapy. In one embodiment, the subject is non-responsive, or refractory to anti-CD19 and/or anti-CD20 therapy. In one embodiment, the subject has a cancer that is CD19− and/or CD20−. In one embodiment, the subject has a cancer that is relapsed and no longer expresses CD19 or CD20.

Another aspect of the technology described herein relates to a method of treating cancer, a plasma cell disorder, or an autoimmune disease in a subject in need thereof, the method comprising administering any of the mammalian cells comprising the any of the CAR polypeptides described herein to the subject, wherein the cell comprises CAR comprising an extracellular domain comprising a CD37-binding sequence; wherein the subject is non-responsive to anti-CD19 and/or anti-CD20 therapy.

Another aspect of the technology described herein relates to a method of treating cancer, a plasma cell disorder, or an autoimmune disease in a subject in need thereof, the method comprising: selecting a subject who is non-responsive to anti-CD19 and/or anti-CD20 therapy; engineering a T cell to comprise any of the CAR polypeptides described herein on the T cell surface; administering the engineered CAR T cell to the subject; wherein the subject is non-responsive to anti-CD19 and/or anti-CD20 therapy.

Another aspect of the technology described herein relates to a method of treating cancer, a plasma cell disorder, or an autoimmune disease in a subject in need thereof, the method comprising: selecting a subject who is non-responsive to anti-CD19 and/or anti-CD20 therapy; administering any of the mammalian cells comprising the any of the CAR polypeptides described herein to the subject, wherein the cell comprises CAR comprising an extracellular domain comprising a CD37-binding sequence; wherein the subject is non-responsive to anti-CD19 and/or anti-CD20 therapy.

Another aspect of the technology described herein relates to a method of treating cancer, a plasma cell disorder, or an autoimmune disease in a subject in need thereof, the method comprising: engineering a T cell to comprise any of the CAR polypeptides described herein on the T cell surface; administering the engineered CAR T cell to the subject; wherein the subject is concurrently administered an anti-CD19 and/or anti-CD20 therapy.

Another aspect of the technology described herein relates to a method of treating cancer, a plasma cell disorder, or an autoimmune disease in a subject in need thereof, the method comprising administering any of the mammalian cells comprising the any of the CAR polypeptides described herein to the subject, wherein the cell comprises CAR comprising an extracellular domain comprising a CD37-binding sequence; wherein the subject is concurrently administered an anti-CD19 and/or anti-CD20 therapy.

In some embodiments of any of the aspect, the engineered CAR-T cell is stimulated and/or activated prior to administration to the subject.

Administration

In some embodiments, the methods described herein relate to treating a subject having or diagnosed as having cancer, a plasma cell disease or disorder, or an autoimmune disease or disorder with a mammalian cell comprising any of the CAR polypeptides described herein, or a nucleic acid encoding any of the CAR polypeptides described herein. As used herein, a "CAR T cells as described herein" refers to a mammalian cell comprising any of the CAR polypeptides described herein, or a nucleic acid encoding any of the CAR polypeptides described herein. As used herein, a "condition" refers to a cancer, a plasma cell disease or disorder, or an autoimmune disease or disorder. Subjects having a condition can be identified by a physician using current methods of diagnosing the condition. Symptoms and/or complications of the condition, which characterize these conditions and aid in diagnosis are well known in the art and include but are not limited to, fatigue, persistent infections, and persistent bleeding. Tests that may aid in a diagnosis of, e.g. the condition, but are not limited to, blood screening and bone marrow testing, and are known in the art for a given condition. A family history for a condition, or exposure to risk factors for a condition can also aid in determining if a subject is likely to have the condition or in making a diagnosis of the condition.

The compositions described herein can be administered to a subject having or diagnosed as having a condition. In some embodiments, the methods described herein comprise administering an effective amount of activated CAR T cells described herein to a subject in order to alleviate a symptom of the condition. As used herein, "alleviating a symptom of the condition" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. In one embodiment, the compositions described herein are administered systemically or locally. In a preferred embodiment, the compositions described herein are administered intravenously. In another embodiment, the compositions described herein are administered at the site of a tumor.

The term "effective amount" as used herein refers to the amount of activated CAR T cells needed to alleviate at least one or more symptom of the disease or disorder, and relates to a sufficient amount of the cell preparation or composition to provide the desired effect. The term "therapeutically effective amount" therefore refers to an amount of activated CAR T cells that is sufficient to provide a particular anti-condition effect when administered to a typical subject. An effective amount as used herein, in various contexts, would also include an amount sufficient to delay the development of a symptom of the disease, alter the course of a symptom disease (for example but not limited to, slowing the progression of a condition), or reverse a symptom of the condition. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of activated CAR T cells, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for bone marrow testing, among others. The dosage can be determined by a physician and adjusted, as necessary, to suit observed effects of the treatment.

In one aspect of the technology, the technology described herein relates to a pharmaceutical composition comprising activated CAR T cells as described herein, and optionally a pharmaceutically acceptable carrier. The active ingredients of the pharmaceutical composition at a minimum comprise activated CAR T cells as described herein. In some embodiments, the active ingredients of the pharmaceutical composition consist essentially of activated CAR T cells as described herein. In some embodiments, the active ingredients of the pharmaceutical composition consist of activated CAR T cells as described herein. Pharmaceutically acceptable carriers for cell-based therapeutic formulation include saline and aqueous buffer solutions, Ringer's solution, and serum component, such as serum albumin, HDL and LDL. The terms such as "excipient", "carrier", "pharmaceutically acceptable carrier" or the like are used interchangeably herein.

In some embodiments, the pharmaceutical composition comprising activated CAR T cells as described herein can be a parenteral dose form. Since administration of parenteral dosage forms typically bypasses the patient's natural defenses against contaminants, the components apart from the CAR T cells themselves are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Any of these can be added to the activated CAR T cells preparation prior to administration.

Suitable vehicles that can be used to provide parenteral dosage forms of activated CAR T cells as disclosed within are well known to those skilled in the art. Examples include, without limitation: saline solution; glucose solution; aqueous vehicles including but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

In some embodiments, the activated CAR T cells described herein are administered as a monotherapy, i.e., another treatment for the condition is not concurrently administered to the subject.

A pharmaceutical composition comprising the T cells described herein can generally be administered at a dosage of $10^4$ to $10^9$ cells/kg body weight, in some instances $10^5$ to $10^6$ cells/kg body weight, including all integer values within those ranges. If necessary, T cell compositions can also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated CAR T cells to a subject and then subsequently redraw blood (or have an apheresis performed), activate T cells therefrom as described herein, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

Modes of administration can include, for example intravenous (i.v.) injection or infusion. The compositions described herein can be administered to a patient transarterially, intratumorally, intranodally, or intramedullary. In some embodiments, the compositions of T cells may be injected directly into a tumor, lymph node, or site of infection. In one embodiment, the compositions described herein are administered into a body cavity or body fluid (e.g., ascites, pleural fluid, peritoneal fluid, or cerebrospinal fluid).

In a particular exemplary aspect, subjects may undergo leukapheresis, wherein leukocytes are collected, enriched, or depleted ex vivo to select and/or isolate the cells of interest, e.g., T cells. These T cell isolates can be expanded by contact with an aAPC as described herein, e.g., an aAPC expressing anti-CD28 and anti-CD3 CDRs as described herein and treated such that one or more CAR constructs of the technology may be introduced, thereby creating a CAR T cell. Subjects in need thereof can subsequently undergo standard treatment with high dose chemotherapy followed by peripheral blood stem cell transplantation. Following or concurrent with the transplant, subjects can receive an infusion of the expanded CAR T cells. In one embodiment, expanded cells are administered before or following surgery.

In some embodiments, lymphodepletion is performed on a subject prior to administering one or more CAR T cell as described herein. In such embodiments, the lymphodepletion can comprise administering one or more of melphalan, Cytoxan®, cyclophosphamide, and fludarabine.

The dosage of the above treatments to be administered to a patient will vary with the precise nature of the condition being treated and the recipient of the treatment. The scaling of dosages for human administration can be performed according to art-accepted practices.

In some embodiments, a single treatment regimen is required. In others, administration of one or more subsequent doses or treatment regimens can be performed. For example, after treatment biweekly for three months, treatment can be repeated once per month, for six months or a year or longer. In some embodiments, no additional treatments are administered following the initial treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Combinational Therapy

The activated CAR T cells described herein can be used in combination with other known agents and therapies. In one embodiment, the subject is further administered an anti-BCMA therapy. In one embodiment, the subject is resistant to anti-BCMA therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The activated CAR T cells described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed. The CAR T therapy and/or other therapeutic agents, procedures or modalities can be administered during periods of active disorder, or during a period of remission or less active disease. The CAR T therapy can be administered before another treatment, concurrently with the treatment, post-treatment, or during remission of the disorder.

When administered in combination, the activated CAR T cells and the additional agent (e.g., second or third agent), or all, can be administered in an amount or dose that is higher, lower or the same as the amount or dosage of each agent used individually, e.g., as a monotherapy. In certain embodiments, the administered amount or dosage of the activated CAR T cells, the additional agent (e.g., second or third agent), or all, is lower (e.g., at least 20%, at least 30%, at least 40%, or at least 50%) than the amount or dosage of each agent used individually. In other embodiments, the amount or dosage of the activated CAR T cells, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect. In further embodiments, the activated CAR T cells described herein can be used in a treatment regimen in combination with surgery, chemotherapy, radiation, an mTOR pathway inhibitor, immunosuppressive agents, such as cyclosporin, azathioprine, methotrexate, mycophenolate, and FK506, antibodies, or other immunoablative agents such as CAMPATH®, anti-CD3 antibodies or other antibody therapies, Cytoxan®, fludarabine, rapamycin, mycophenolic acid, steroids, FR901228, cytokines, or a peptide vaccine, such as that described in Izumoto et al. 2008 J Neurosurg 108:963-971.

In one embodiment, the activated CAR T cells described herein can be used in combination with a checkpoint inhibitor. Exemplary checkpoint inhibitors include anti-PD-1 inhibitors (Nivolumab, MK-3475, Pembrolizumab, Pidilizumab, AMP-224, AMP-514), anti-CTLA4 inhibitors (Ipilimumab and Tremelimumab), anti-PDL1 inhibitors (Atezolizumab, Avelomab, MSB0010718C, MEDI4736, and MPDL3280A), and anti-TIM3 inhibitors.

In one embodiment, the activated CAR T cells described herein can be used in combination with a chemotherapeutic agent. Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan®), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5- fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™) ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deferolimus, (1R,2R,45)-4-[(2R)-2[(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.04'9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (Afinitor® or RAD001); rapamycin (AY22989, Sirolimus®); simapimod (CAS 164301-51-3); emsirolimus, (5-{2,4-Bis[(3S,)-3-methylmorpholin-4-yl]pyrido[2,3-i]pyrimidin-7-yl}-2-methoxyphenyl)methanol (AZD8055); 2-Amino-8-[iraw5,-4-(2-hydroxyethoxy)cyclohexyl]-6-(6-methoxy-3-pyridinyl)-4-methyl-pyrido[2,3-JJpyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartylL-serine- (SEQ ID NO: 41), inner salt (SF1126, CAS 936487-67-1), and XL765. Exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and Rubex®); bleomycin (lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary *vinca* alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-((5)-1-(((5)-4-methyl-1-((R)-2-methyloxiran-2-yl)-1-oxopentan-2-yl)amino)-1-oxo-3-phenylpropan-2-yl)-2-((5)-2-(2-morpholinoacetamido)-4- phenylbutanamido)-pentanamide); marizomib (NPT0052); ixazomib citrate (MLN-9708); delanzomib (CEP-18770); and O-Methyl-N-[(2-methyl-5-thiazolyl)carbonyl]-L-seryl-O-methyl-N-[(11S')-2-[(2R)-2-methyl-2-oxiranyl]-2-oxo-1-(phenylmethyl)ethyl]-L-serinamide (ONX-0912).

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In an embodiment, activated CAR T cells described herein are administered to a subject in combination with a molecule that decreases the level and/or activity of a molecule targeting GITR and/or modulating GITR functions, a molecule that decreases the Treg cell population, an mTOR inhibitor, a GITR agonist, a kinase inhibitor, a non-receptor tyrosine kinase inhibitor, a CDK4 inhibitor, and/or a BTK inhibitor.

Efficacy

The efficacy of activated CAR T cells in, e.g. the treatment of a condition described herein, or to induce a response as described herein (e.g. a reduction in cancer cells) can be determined by the skilled clinician. However, a treatment is considered "effective treatment," as the term is used herein, if one or more of the signs or symptoms of a condition described herein is altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

Efficacy can also be measured by a failure of an individual to worsen as assessed by hospitalization, or need for medical interventions (i.e., progression of the disease is halted). Methods of measuring these indicators are known to those of skill in the art and/or are described herein.

Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy of a given approach can be assessed in animal models of a condition described herein, for example treatment of ALL. When using an experimental animal model, efficacy of treatment is evidenced when a statistically significant change in a marker is observed.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior technology or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A chimeric antigen receptor (CAR) polypeptide comprising:
    a. an extracellular domain comprising a target-binding sequence;
    b. a transmembrane domain;
    c. a co-stimulatory domain; and
    d. a T cell intracellular signaling domain that lacks a functional ITAM3 sequence.
2. The CAR polypeptide of paragraph 1, wherein the transmembrane domain is the transmembrane domain from is CD8 or 4-1BB.
3. The CAR polypeptide of paragraph 1, wherein the co-stimulatory domain is the co-stimulatory domain of 4-1BB.
4. The CAR polypeptide of any of paragraphs 1-3, wherein the intracellular signaling domain comprises a CD3ζ ITAM3 sequence selected from SEQ ID NOs: 13, 14, 33, or 34.
5. The CAR polypeptide of any of paragraphs 1-4, wherein the intracellular signaling domain comprises a CD3ζ ITAM3 sequence comprising a deletion relative to the CD3ζ ITAM3 sequence of SEQ ID NO: 13.
6. The CAR polypeptide of any of paragraphs 1-5, wherein the T-cell intracellular signaling domain is the intracellular signaling domain of CD3ε or CD3θ.
7. The CAR polypeptide of any of paragraphs 1-6, wherein the target-binding sequence comprises a ligand of the target or an antibody reagent that specifically binds the target.
8. The CAR polypeptide of any of paragraphs 1-7, wherein the target is B cell maturation antigen (BCMA).
9. The CAR polypeptide of any of paragraphs 1-8, wherein the target is CD37.
10. The CAR polypeptide of any of paragraphs 1-9, wherein the antibody reagent comprises an scFv.
11. The CAR polypeptide of any of paragraphs 1-10, wherein the antibody reagent has the sequence selected from SEQ ID NO: 1, 5, or 9.
12. A chimeric antigen receptor (CAR) polypeptide comprising:
    a. an extracellular domain comprising a BCMA-binding sequence;
    b. a transmembrane domain of CD8;
    c. a co-stimulatory domain of a 4-1BB; and
    d. a T cell intracellular signaling domain that lacks a functional ITAM3 sequence.
13. The CAR polypeptide of paragraph 12, wherein the BCMA-binding sequence comprises a ligand of BCMA or an antibody reagent that specifically binds BCMA.
14. The CAR polypeptide of any of paragraphs 12-13, wherein the antibody reagent comprises a scFv.
15. The CAR polypeptide of any of paragraphs 12-14, wherein the antibody reagent the sequence of SEQ ID NO: 1
16. The CAR polypeptide of any of paragraphs 12-15, wherein the intracellular signaling domain comprises a CD3ζ ITAM3 sequence selected from SEQ ID NOs: 13, 14, 33, or 34.
17. The CAR polypeptide of any of paragraphs 12-16, wherein the intracellular signaling domain comprises a CD3ζ ITAM3 sequence comprising a deletion relative to the CD3ζ ITAM3 sequence of SEQ ID NO: 13.
18. A chimeric antigen receptor (CAR) polypeptide comprising:
    a. an extracellular domain comprising a CD37-binding sequence;
    b. a transmembrane domain of CD8;
    c. a co-stimulatory domain of a 4-1BB; and
    d. a T cell intracellular signaling domain that lacks a functional ITAM3 sequence.

19. The CAR polypeptide of paragraph 18, wherein the CD37-binding sequence comprises a ligand of CD37 or an antibody reagent that specifically binds BCMA.

20. The CAR polypeptide of any of paragraphs 18-19, wherein the antibody reagent comprises a scFv.

21. The CAR polypeptide of any of paragraphs 18-20, wherein the scFv has a sequence selected from SEQ ID NO: 5 or 9.

22. The CAR polypeptide of any of paragraphs 18-21, wherein the intracellular signaling domain comprises a CD3ζ ITAM3 sequence selected from SEQ ID NOs: 13, 14, 33, or 34.

23. The CAR polypeptide of any of paragraphs 18-22, wherein the intracellular signaling domain comprises a CD3ζ ITAM3 sequence comprising a deletion relative to the CD3ζ ITAM3 sequence of SEQ ID NO: 13.

24. A mammalian cell comprising:
    a. the CAR polypeptide of any of paragraphs 1-23; or
    b. a nucleic acid encoding any of the CAR polypeptides of any of paragraphs 1-23.

25. The cell of paragraph 24, wherein the cell is a T cell.

26. The cell of any of paragraphs 24-25, wherein the cell is a human cell.

27. The cell of any of paragraphs 24-26, wherein the cell is obtained from an individual having or diagnosed as having cancer, a plasma cell disorder, or autoimmune disease.

28. A method of treating cancer, a plasma cell disorder, or an autoimmune disease in a subject in need thereof, the method comprising:
    a. engineering a T cell to comprise a CAR polypeptide of any of paragraphs 1-22 on the T cell surface;
    b. administering the engineered T cell to the subject.

29. A method of treating cancer, a plasma cell disorder, or an autoimmune disease in a subject in need thereof, the method comprising:
    a. administering the cell of any of paragraphs 24-28 to the subject.

30. The method of any of paragraphs 28-29, wherein the cancer is a CD37+ or BCMA+ cancer.

31. The method of any of paragraphs 28-30, wherein the CD37+ cancer is lymphoma or leukemia.

32. The method of paragraph 31, wherein the lymphoma is B-cell Non-Hodgkin Lymphoma (NHL), mantle cell lymphoma, Burkitt's lymphoma, B cell lymphoblastic lymphoma or T cell lymphoma (e.g., peripheral T cell lymphoma (PTCL), including cutaneous T-cell lymphoma (CTCL) and anaplastic large cell lymphoma (ALCL)).

33. A method of treating cancer, a plasma cell disorder, or an autoimmune disease in a subject in need thereof, the method comprising:
    a. engineering a T cell to comprise a CAR polypeptide of paragraph 18 on the T cell surface;
    b. administering the engineered T cell to the subject;
    wherein the subject is non-responsive to anti-CD19 and/or anti-CD20 therapy.

34. A method of treating cancer, a plasma cell disorder, or an autoimmune disease in a subject in need thereof, the method comprising administering a cell of any of paragraphs 24-27 to the subject, wherein the cell comprises CAR comprising an extracellular domain comprising a CD37-binding sequence;
    wherein the subject is non-responsive to anti-CD19 and/or anti-CD20 therapy.

35. A method of treating cancer, a plasma cell disorder, or an autoimmune disease in a subject in need thereof, the method comprising:
    a. selecting a subject who is non-responsive to anti-CD19 and/or anti-CD20 therapy;
    b. engineering a T cell to comprise a CAR polypeptide of paragraph 18 on the T cell surface;
    c. administering the engineered T cell to the subject;
    wherein the subject is non-responsive to anti-CD19 and/or anti-CD20 therapy.

36. A method of treating cancer, a plasma cell disorder, or an autoimmune disease in a subject in need thereof, the method comprising:
    a. selecting a subject who is non-responsive to anti-CD19 and/or anti-CD20 therapy;
    b. administering a cell of any of paragraphs 24-27 to the subject, wherein the cell comprises CAR comprising an extracellular domain comprising a CD37-binding sequence;
    wherein the subject is non-responsive to anti-CD19 and/or anti-CD20 therapy.

37. A method of treating cancer, a plasma cell disorder, or an autoimmune disease in a subject in need thereof, the method comprising:
    a. engineering a T cell to comprise a CAR polypeptide of paragraph 18 on the T cell surface;
    b. administering the engineered T cell to the subject;
    wherein the subject is concurrently administered an anti-CD19 and/or anti-CD20 therapy.

38. A method of treating cancer, a plasma cell disorder, or an autoimmune disease in a subject in need thereof, the method comprising administering a cell of any of paragraphs 24-27 to the subject, wherein the cell comprises CAR comprising an extracellular domain comprising a CD37-binding sequence;
    wherein the subject is concurrently administered an anti-CD19 and/or anti-CD20 therapy.

39. A composition comprising the CAR T cells of paragraphs 1-27 formulated for the treatment of cancer.

40. The composition of paragraph 39, further comprising a pharmaceutically acceptable carrier.

41. The method of paragraph 31, wherein the leukemia is acute myeloid leukemia (AML).

EXAMPLES

Example 1

Described herein are methods and compositions relating to "alternative signal 1" domains based on alternatives to CD3 zeta, including mutated ITAMs from CD3ζ (which contains 3 ITAM motifs), truncations of CD3 zeta, and alternative splice variants known as CD3 eta, CD3θ, and artificial constructs engineered to express fusions between CD3 eta or theta and zeta. Thus, described herein are alternative signal 1 transducers to form optimally signaling CARs. The resulting alternative CARs decouple the cytotoxic signal from the activation-induced cell death signal which is mediated by engagement of the CAR and activation of CD3 zeta, thus resulting in more potent CAR-alternative T cells compared to CAR-original T cells. These CAR T cells are contemplated for use in the treatment of cancer, infectious diseases, and transplantation indications.

Example 2

Development and optimization of a genetically-engineered T cell therapy for advanced multiple myeloma.

It is contemplated herein that T cells can be genetically engineered to target the B cell maturation antigen (BCMA), a transmembrane receptor constitutively expressed on multiple myeloma cells, for use as adoptive immunotherapy for advanced multiple myeloma.

The use of T cells engineered with a chimeric antigen receptor (CAR) in the clinic has achieved unprecedented results in the treatment of leukemias and lymphomas in the past five years. CAR T cells targeting CD19, a molecule expressed on leukemic B cells, induce complete remission in—95% of patients suffering from relapsed or refractory (r/r) acute lymphoblastic leukemia (ALL). The remarkable effects of this novel therapy have also been observed in patients with (r/r) follicular lymphoma, diffuse large B cell lymphoma, and chronic lymphocytic leukemia (3,5,6,9).

B-cell maturation antigen (BCMA) is a member of the tumor necrosis receptor family (TNRF) which is constitutively expressed as a transmembrane protein in terminally differentiated B cells. Binding of BCMA with its cognate ligands results in the generation of pro-survival and proliferative cues to mature B cells, plasma cells, and multiple myeloma cells (10). Described herein is the development of a CAR based on the single-chain variable region (scFv) of a monoclonal antibody (mAb) specific for human BCMA (11). In addition, multiple versions of this CAR are examined for decoupling of T-cell intrinsic functions such as cellular expansion and cytokine production. The approach examines modification of signaling capacity of CAR T cells to dampen cytokine release without affecting their proliferative potential, as the major CAR T-cell-associated toxicity has been associated with the production of cytokines (clinically defined as cytokine release syndrome, CRS). Finally, these modified CARs can be utilized in pre-clinical studies and in a dose-escalating phase I clinical trial to treat patients suffering from advanced multiple myeloma. The generic configuration of the proposed BCMA-targeted CAR is shown in FIG. 1.

Figure 2A:
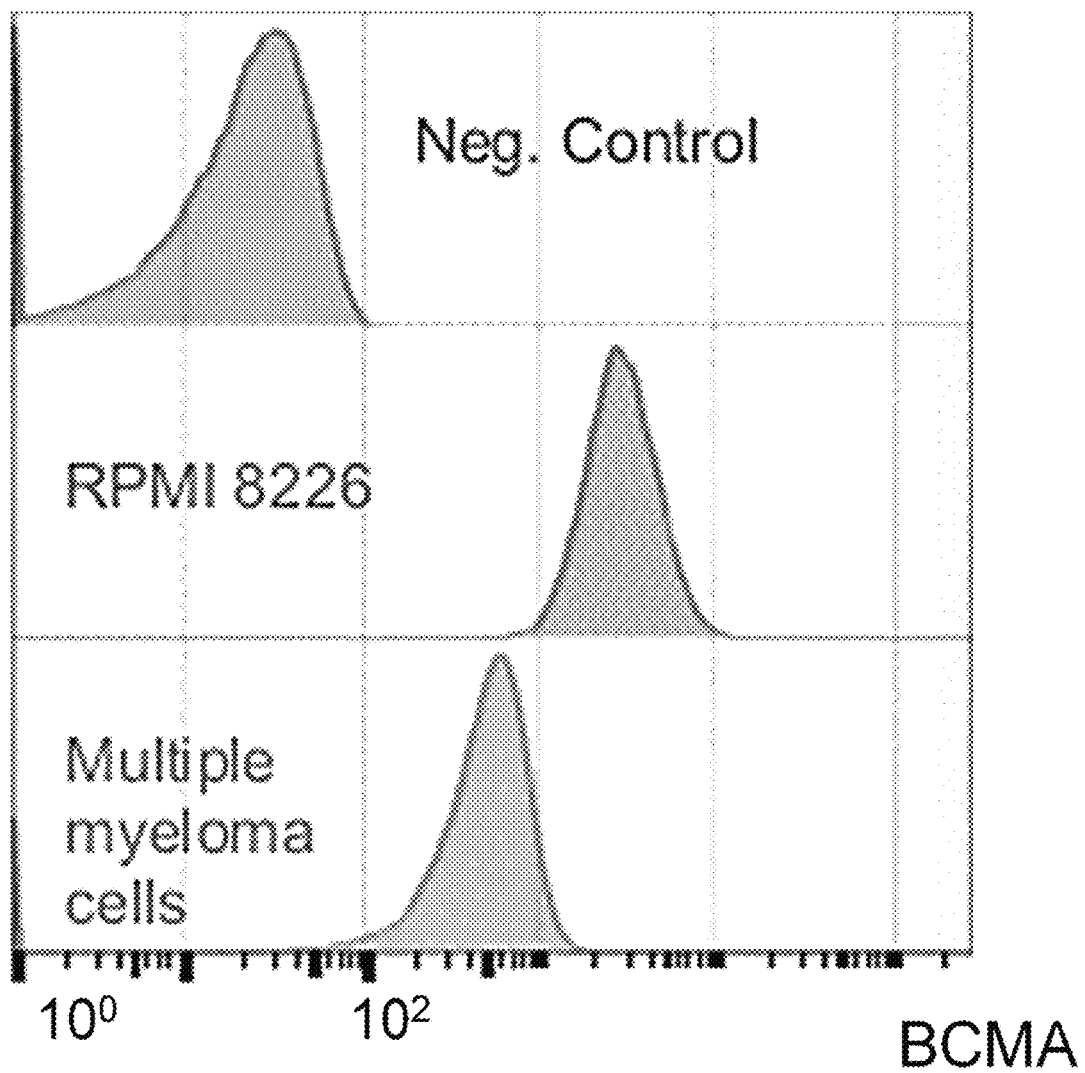
FIGS. 2A-2C demonstrate that primary human T cells transduced with an anti-BCMA CAR have anti-myeloma cytotoxic activity in vitro. BCMA-specific CAR T cells lyse target myeloma cells.
Figure 2B:
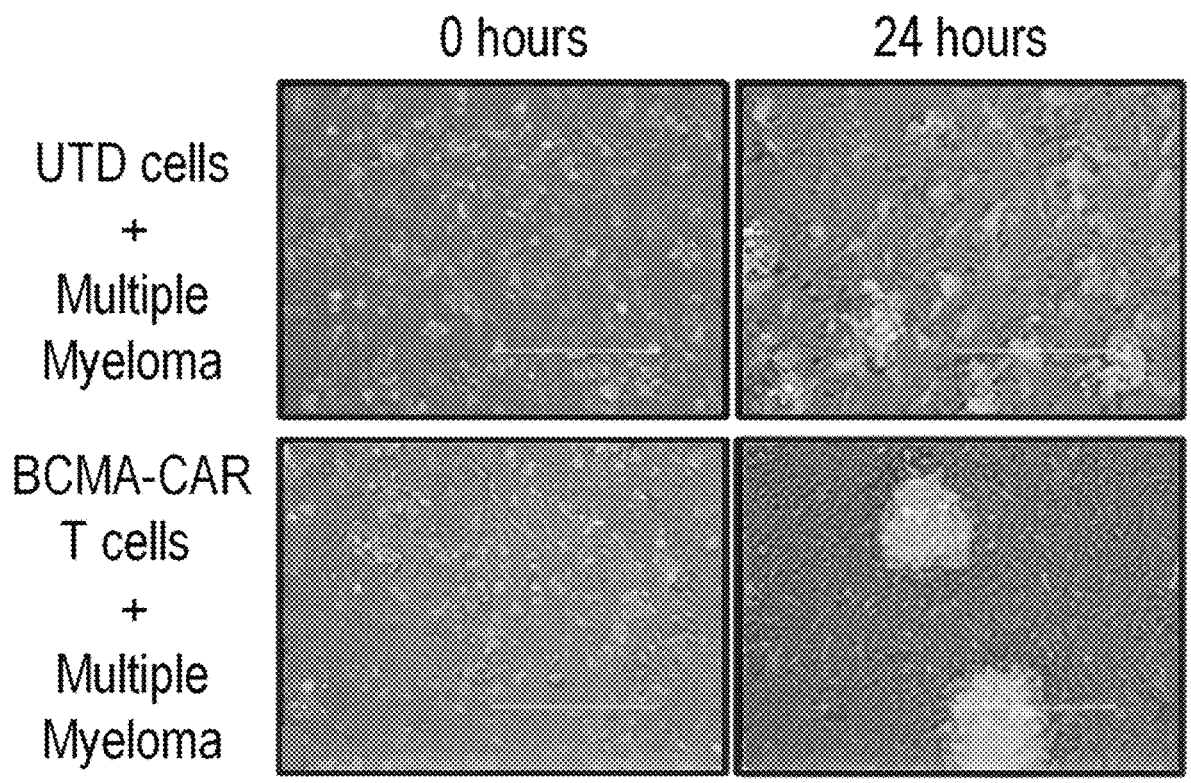
Figure 2C:
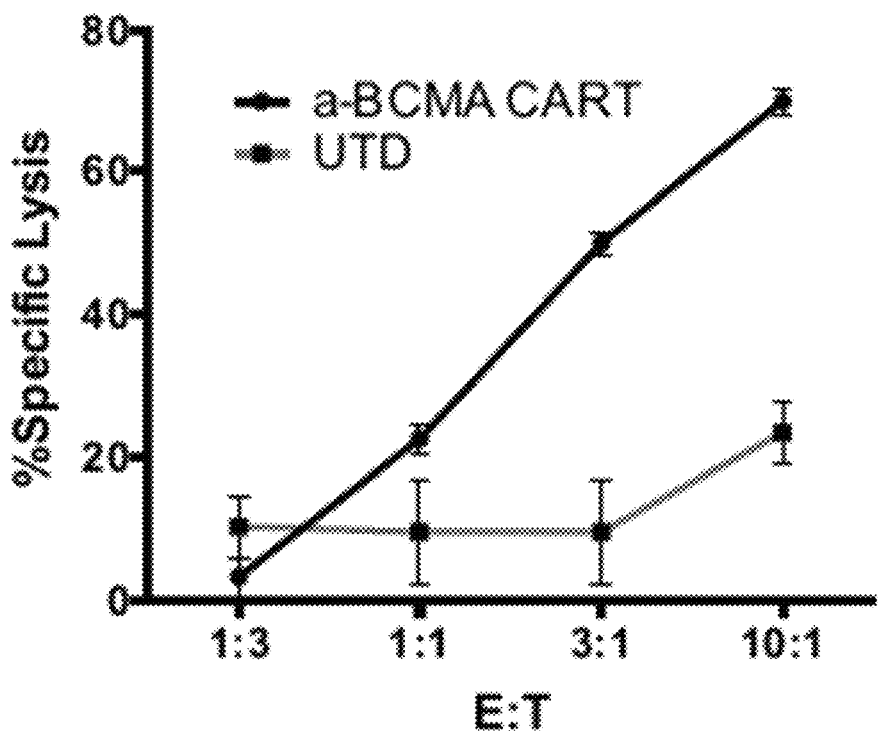

Described herein is the characterization and validation of a BCMA-targeted chimeric antigenic receptor (CAR) to treat advanced multiple myeloma, e.g., a BCMA-specific CAR is described herein. Preliminary data indicate that primary human T cells transduced with this CAR (FIG. 1) have anti-myeloma cytotoxic activity in vitro (FIGS. 2A-2C). The production of anti-BCMA CAR T cells can be optimized by modifying the components of the CAR (scFv and intracellular domains). Established reagents are available for the detection of this CAR by flow cytometry and qPCR. This CAR can be further characterized using in vitro functional analyses such as cytokine production, proliferation, tumor lysis, and transduction efficiency assays. In addition, multiple BCMA-targeted CARs with modifications in the CD3ζ signaling domain. Specifically, variants of this CAR can be produced by mutating tyrosine to phenylalanine as single-point mutations in all three activation modules, or ITAMs (I, II, and III), within the CD3ζ domain (shown in FIG. 1). These ITAMs are phosphorylated upon T cell activation and have been associated with proliferation, cytokine secretion, cytotoxicity, and activation-induced cell death (8). Described herein is the examination of the functional capacity and the persistence of these CAR mutants in comparison with the wild-type version. Alterations within the TCR signaling domain result in the dissociation of T-cell effector functions (i.e., cytokine production, cytotoxicity) and proliferation. This has been shown to occur in mouse T cells (Rosenberg), but has not previously been demonstrated in human T cells nor in the context of a CAR molecule. Described herein is the transduction of normal human T cells with various CAR configurations and testing of them against myeloma cell lines such as RPMI-8226 and U266, and against primary human myeloma tumor cells obtained from patients at MGH under an IRB-approved protocol. The responsiveness of the CAR T cells is also tested against cell lines that express varying degrees of BCMA (FIG. 2A).

Figure 3:
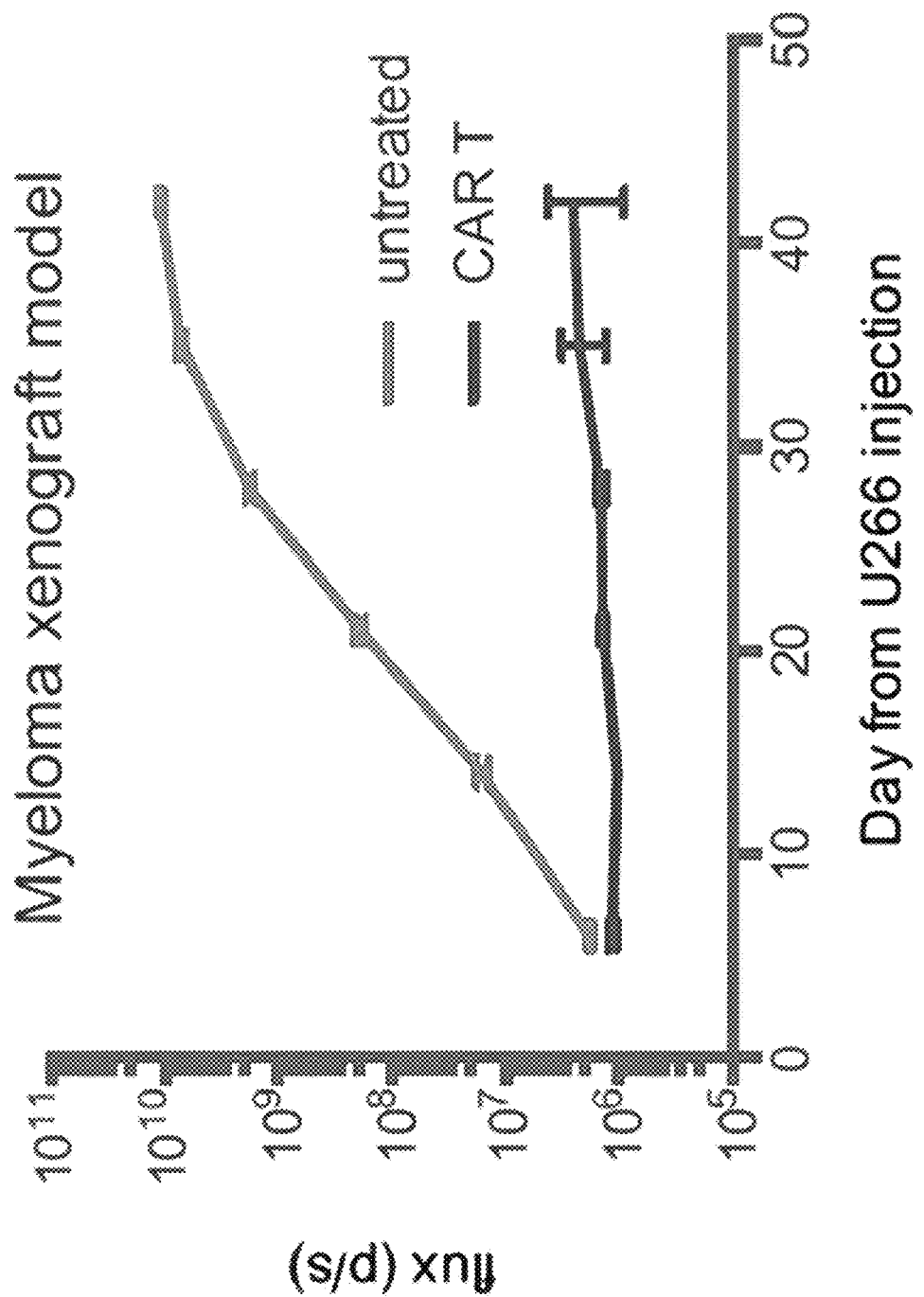
FIG. 3 depicts a graph of results obtained with a xenograft model of multiple myeloma described herein. Assessment of tumor growth by intra-vital bioluminescence (BLI) detection using a luciferase-expressing multiple myeloma cell line (U266). BLI was evaluated at increasing time points in immunodeficient mice that were co-injected with CAR T cells (dark gray line) or left untreated (light gray line) using an IVIS® Spectrum Imaging System.

To validate BCMA-directed CAR T cells using xenogeneic models of multiple myeloma. Immunodeficient NSG mice grafted with human tumors and human T cells have emerged as the standard pre-clinical animal model in which to test CAR T cell functions. A xenograft model of multiple myeloma (FIG. 3) was developed in the context of a different CAR (which is not suitable for clinical translation but can serve as a control). Briefly, luciferase-expressing myeloma cells are injected in NSG mice at day 0. BCMA-directed CAR T cells are injected intravenously at day 6 (allowing some time for tumor engraftment) at different concentrations (1, 5, and 10 million CAR T cells/mouse) along with appropriate cohorts of mice injected with untransduced T cell controls. Mice are imaged weekly to determine tumor burden by bioluminescence. This assay can be used to develop a CAR T cell with the most optimal tumor-killing, proliferative, and survival capabilities.

Statistical Analysis

Since most of these experiments are performed simultaneously in comparison to a single control dataset, the majority of the results are analyzed by unpaired Student's t-tests. p-values less than 0.05 as statistically significant. All experiments will be repeated with T cells from at least 3 healthy donors.

REFERENCES

1. Melenhorst J J, Lacey S., Bedoya F. Chimeric antigen receptor T cells: Self-replicating drugs for cancer. Curr Drug Targets (2015).
2. Maus, M. V., Grupp, S. A., Porter, D. L. & June, C. H. Antibody modified T cells: CARs take the front seat for hematologic malignancies. Blood (2014).
3. Maus, M. V., et al. Adoptive immunotherapy for cancer or viruses. Annual review of immunology 32, 189-225 (2014).
4. Sadelain, M., Riviere, I. & Brentjens, R. Targeting tumours with genetically enhanced T lymphocytes. Nature reviews. Cancer 3, 35-45 (2003).
5. Grupp, S. A., et al. Chimeric antigen receptor-modified T cells for acute lymphoid leukemia. New England Journal of Medicine 368, 1509-1518 (2013).
6. Maude, S. L., Teachey, D. T., Porter, D. L. & Grupp, S. A. CD19-targeted chimeric antigen receptor T-cell therapy for acute lymphoblastic leukemia. Blood 125, 4017-4023 (2015).
7. Ledford, H. Immunotherapy's cancer remit widens. Nature 497, 544 (2013). Combadiere, B., et al. Qualitative and quantitative contributions of the T cell receptor zeta chain to mature T cell apoptosis. The Journal of experimental medicine 183, 2109-2117 (1996).
8. Kochenderfer, J. N., Yu, Z., Frasheri, D., Restifo, N. P. & Rosenberg, S. A. Adoptive transfer of syngeneic T cells transduced with a chimeric antigen receptor that recognizes murine CD19 can eradicate lymphoma and normal B cells. Blood 116, 3875-3886 (2010).
9, Carpenter, R. O., et al. B-cell maturation antigen is a promising target for adoptive T-cell therapy of multiple myeloma. Clinical cancer research: an official journal of the American Association for Cancer Research 19, 2048-2060 (2013).

10. Tai, Y. T., et al. Novel anti-B-cell maturation antigen antibody-drug conjugate (GSK2857916) selectively induces killing of multiple myeloma. Blood 123, 3128-3138 (2014).

Figure 4:
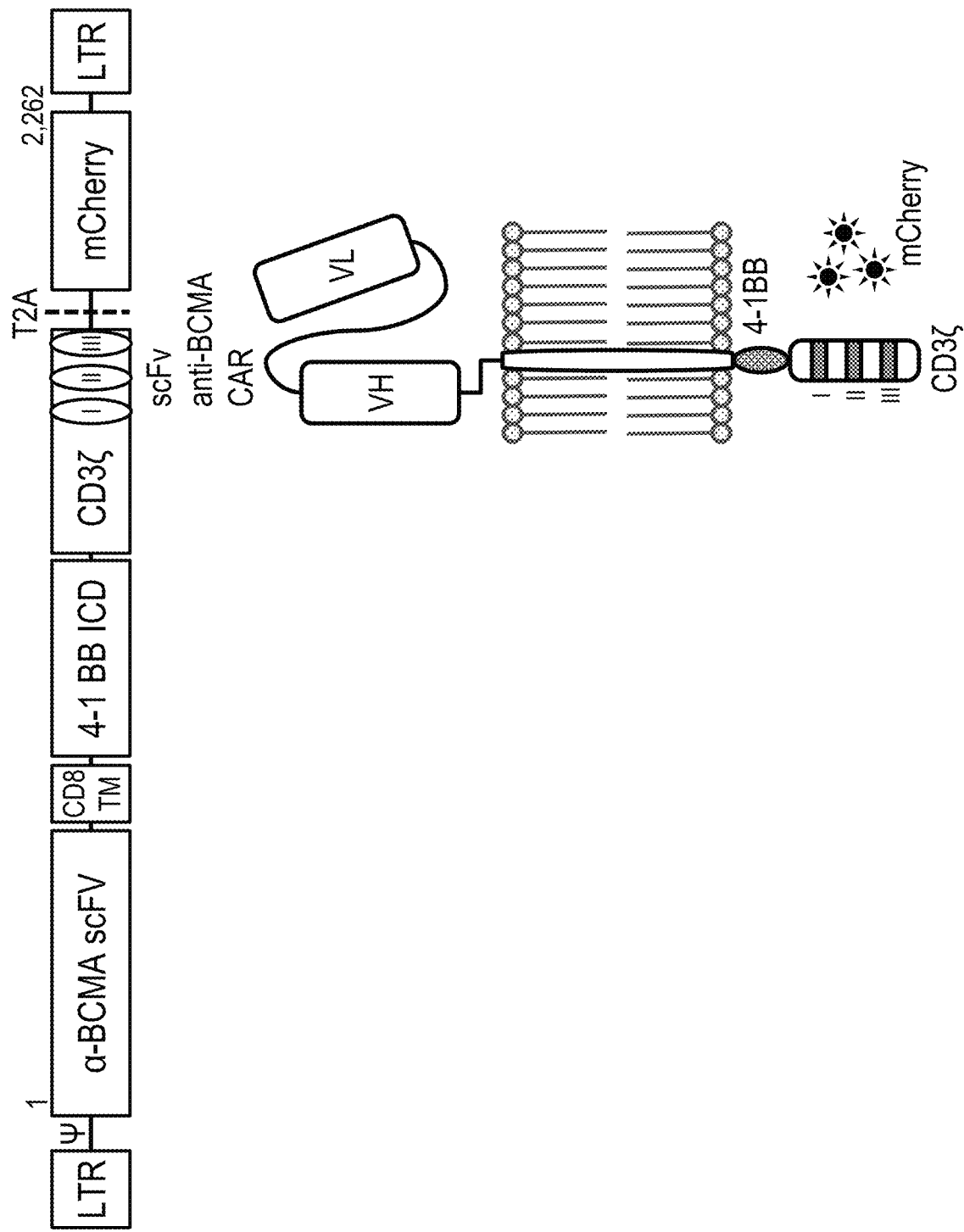
FIG. 4 depicts schematic diagrams of an anti-BCMA CAR construct.

Example 3 scFv from a humanized anti-BCMA mAb was used to construct anti-BCMA CAR construct cloned into a lentivirus vector (FIG. 4). Intracellular domains are 4-1BB (CD137) ICD linked to CD3ζ. ITAMS (I, II, and III) shown. T2A self-cleaving peptide followed by an mCherry reporter gene.

Figure 5:
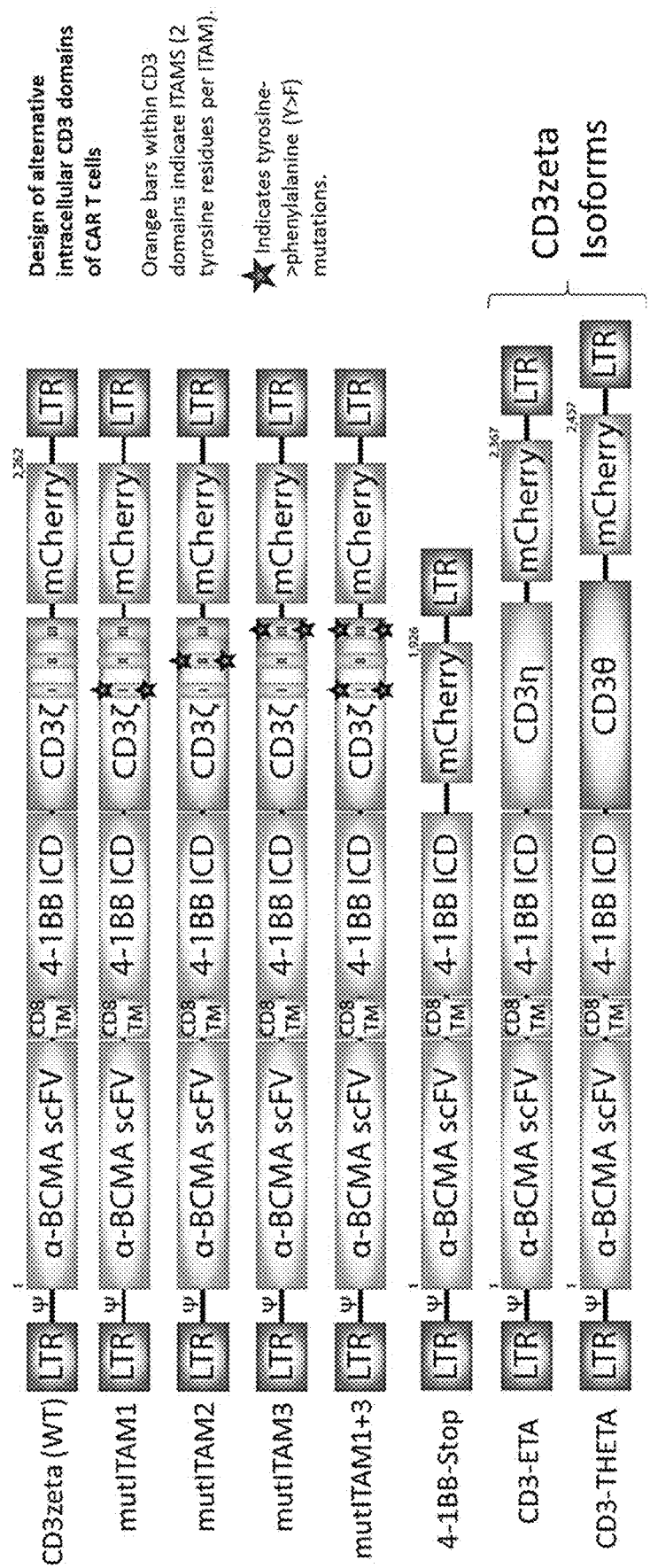
FIG. 5 depicts schematic CAR construct diagrams of alternative intracellular domains.
Figure 6:
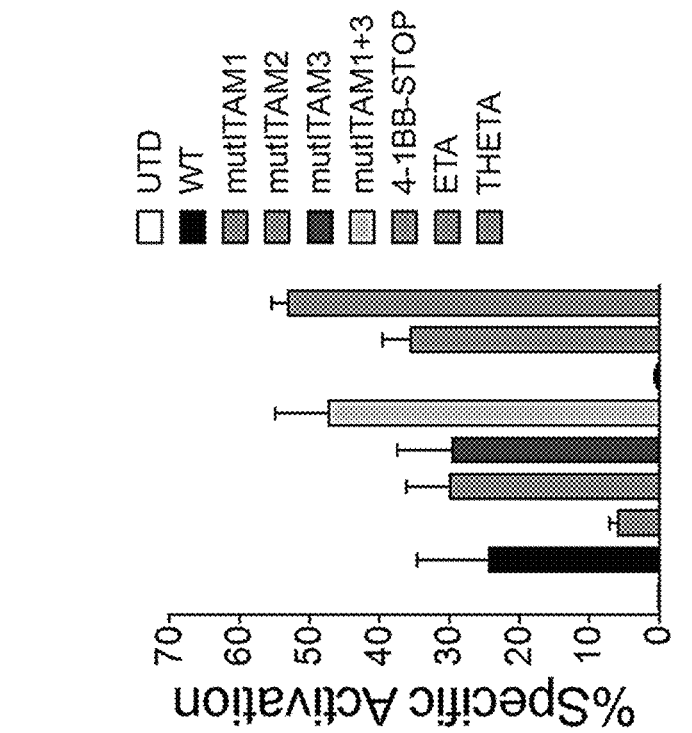
FIG. 6 depicts a diagram of the experimental approach and a graph of the specific activation of the indicated CARs.
Figure 6:
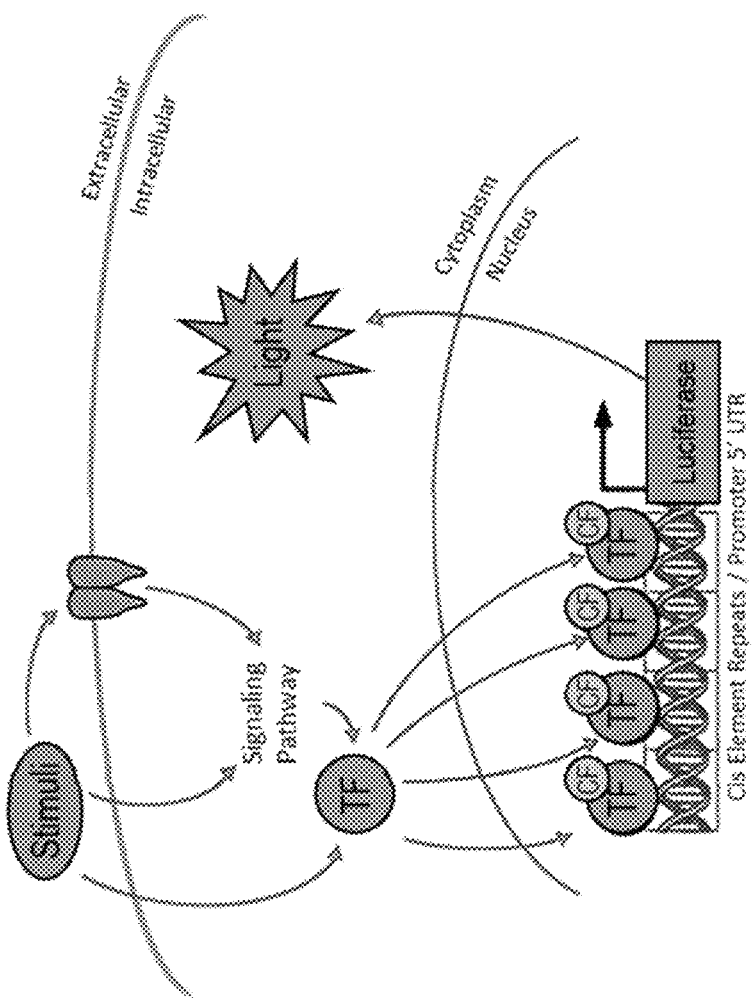
Figure 7:
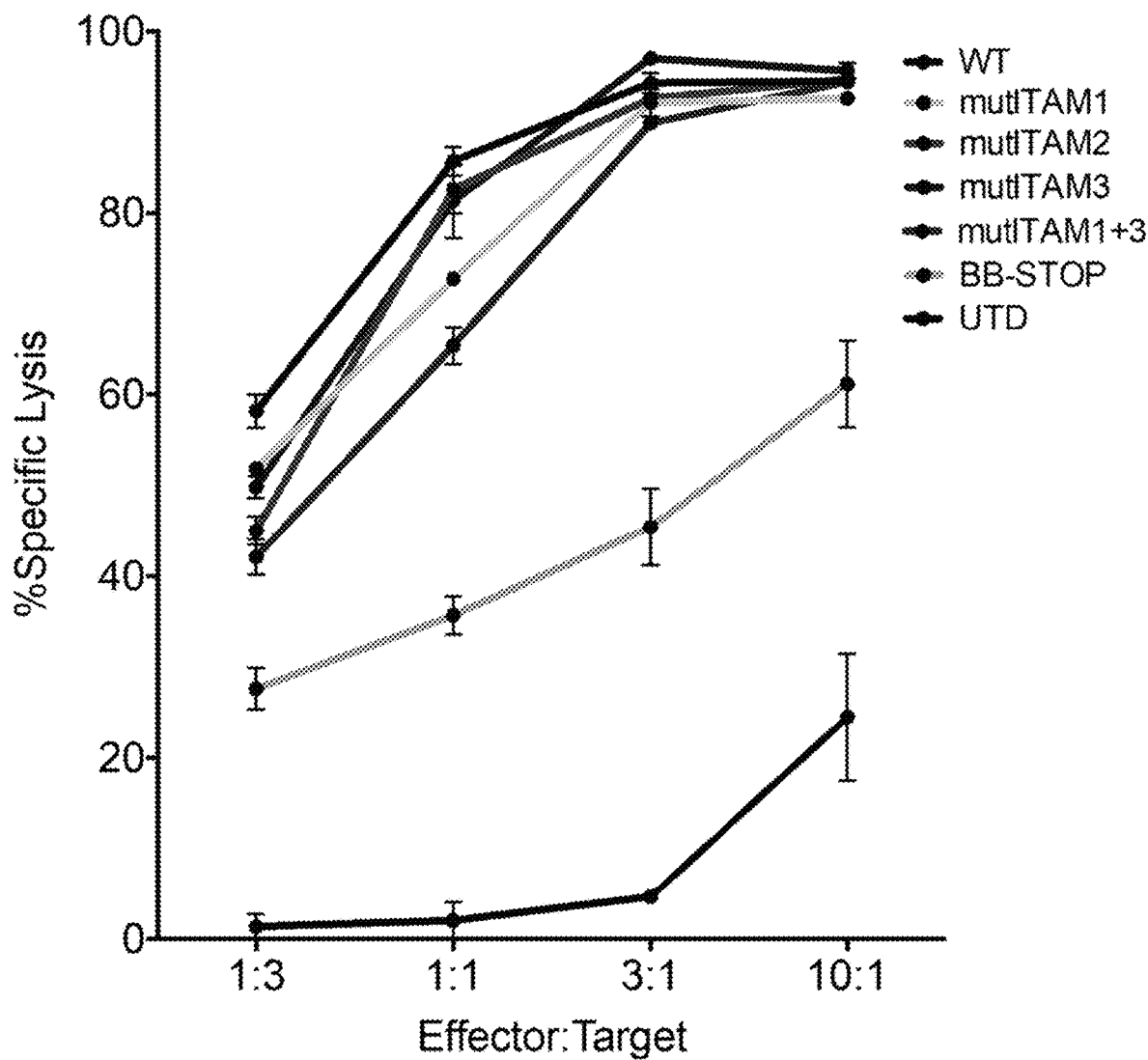
FIG. 7 depicts a graph of the cytotoxicity of the indicated CAR Ts.
Figure 8:
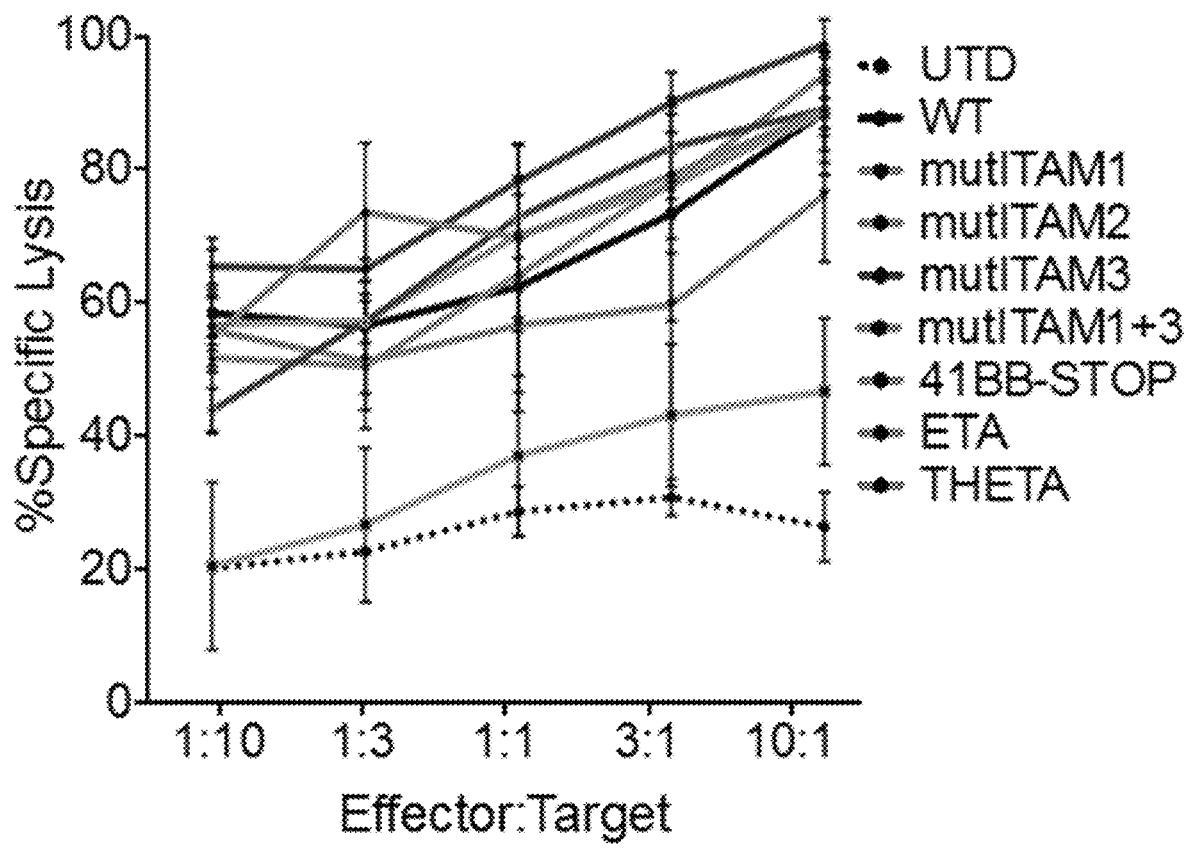
FIG. 8 depicts a graph of CAR-specific cytotoxicity for the indicated anti-BCMA-CAR configurations

CARs with alternative intracellular signaling domains were constructed (FIG. 5) and tested for activation (FIG. 6). All CARs displayed equivalent cytotoxicity, except for BB-STOP CAR (FIG. 7). CAR-specific cytotoxicity was also tested over a range of concentrations (FIG. 8).

Figure 9:
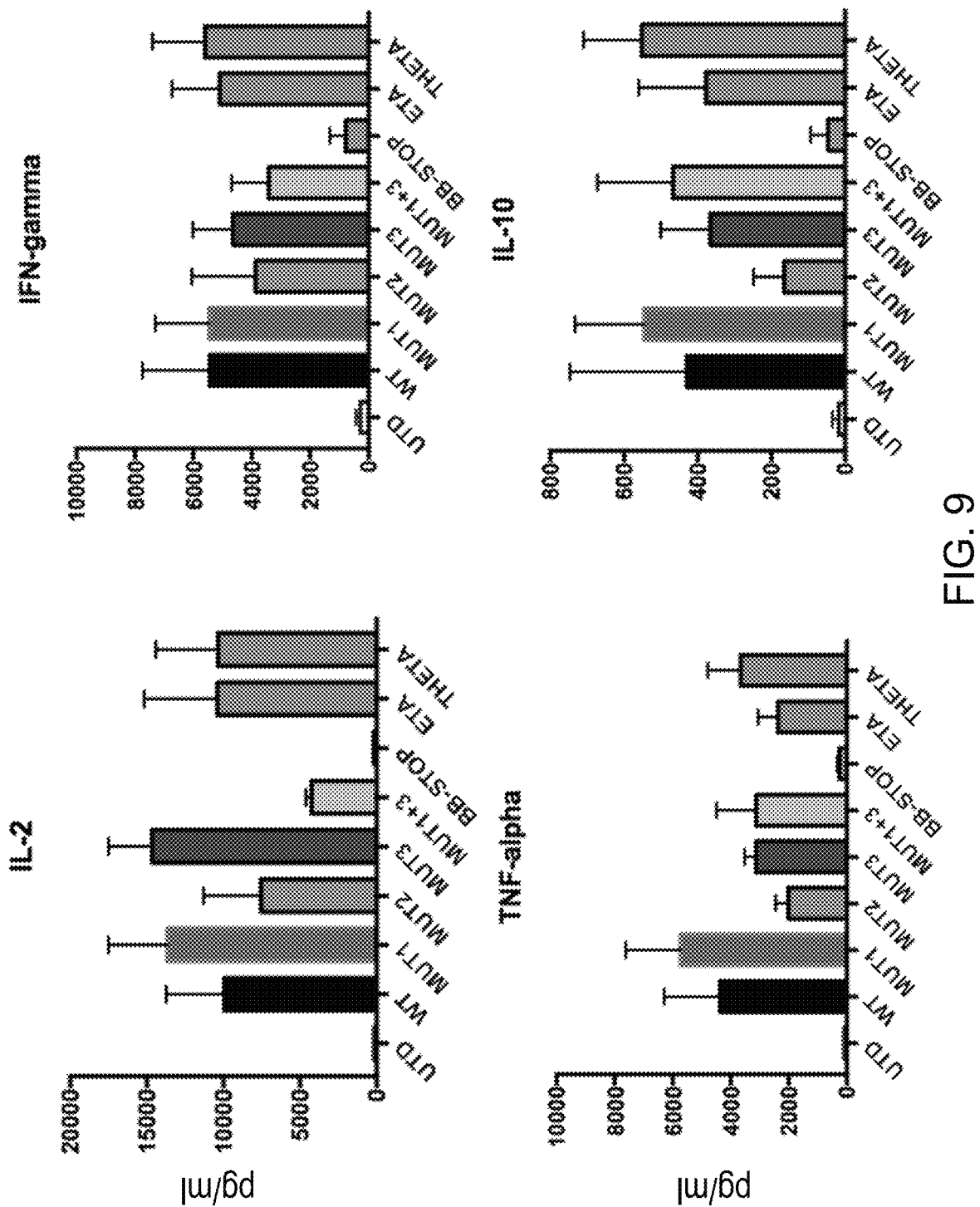
FIG. 9 depicts graphs of cytokine production by the indicated CAR Ts.
Figure 9:
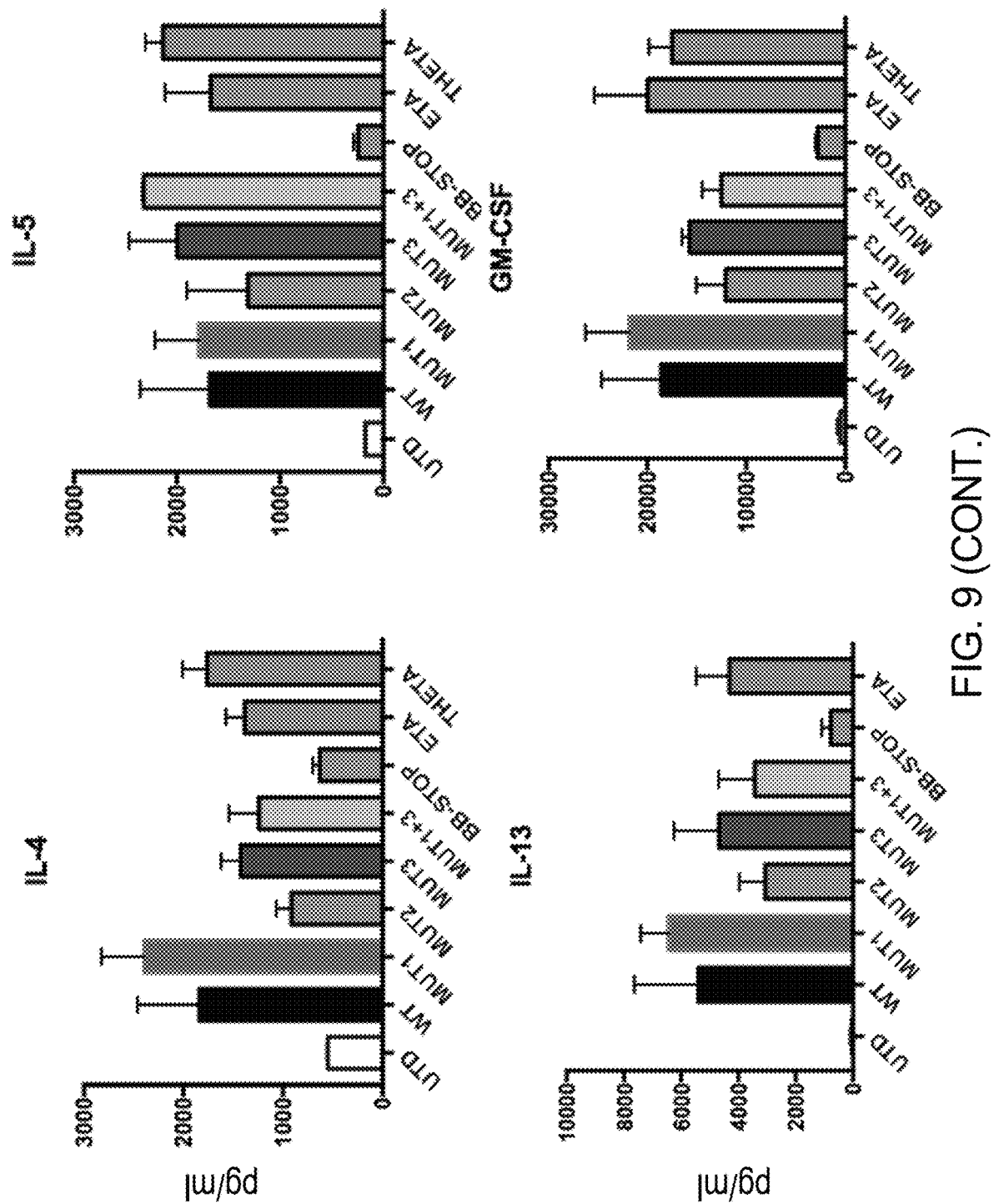
Figure 10:
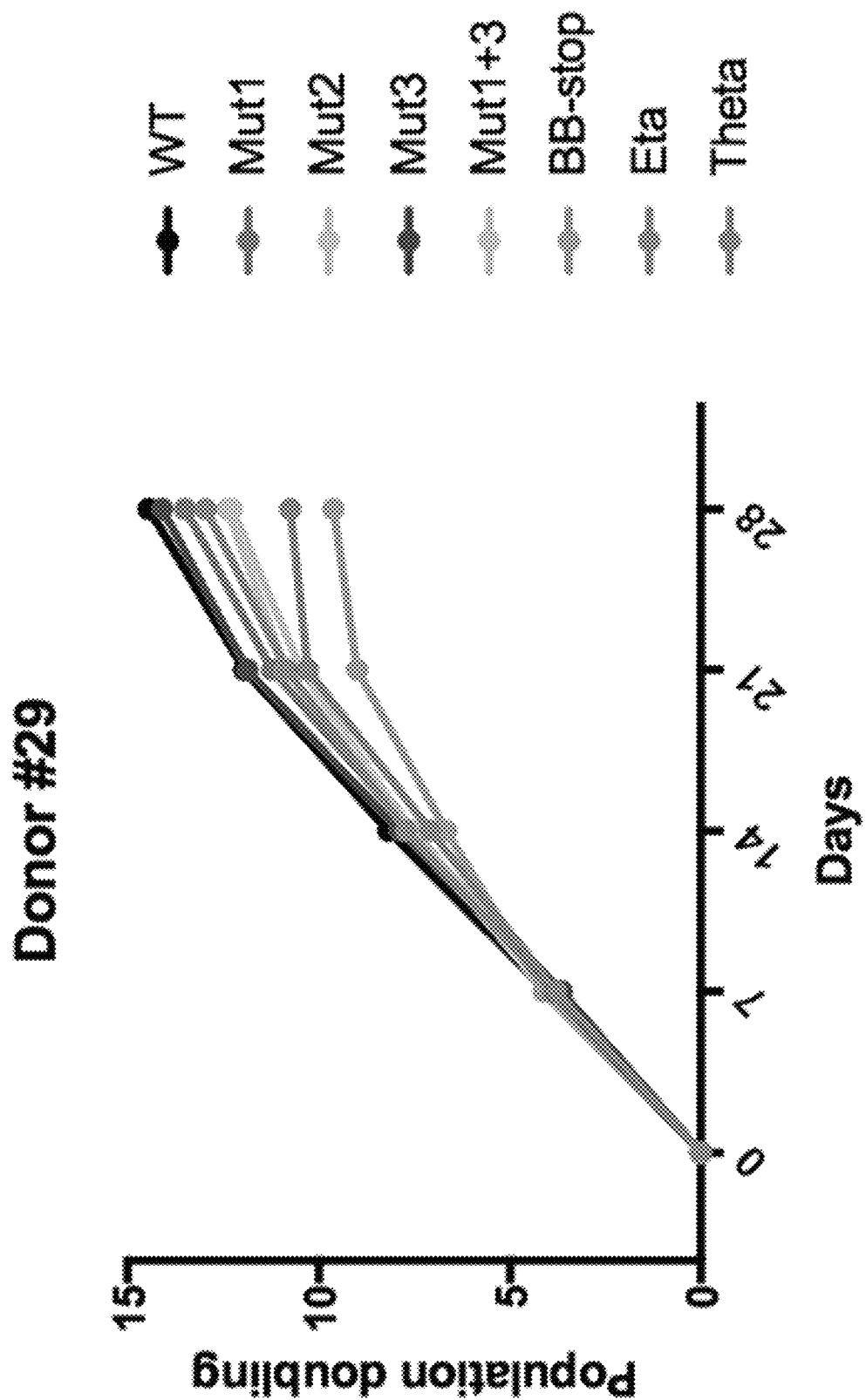
FIG. 10 depicts a graph of CAR-specific proliferation for the indicated CAR Ts. CAR T cells are stimulated every seven days with K562-BCMA+ cells. CAR Ts are counted every two days.

CAR-specific cytokine production was examined and no statistically significant difference was found using 3 normal donors and one-way ANOVA (FIG. 9). CAR-specific proliferation was examined using 1 normal donor and no statistically significant differences were found between the CAR-Ts (FIG. 10).

Figure 11:
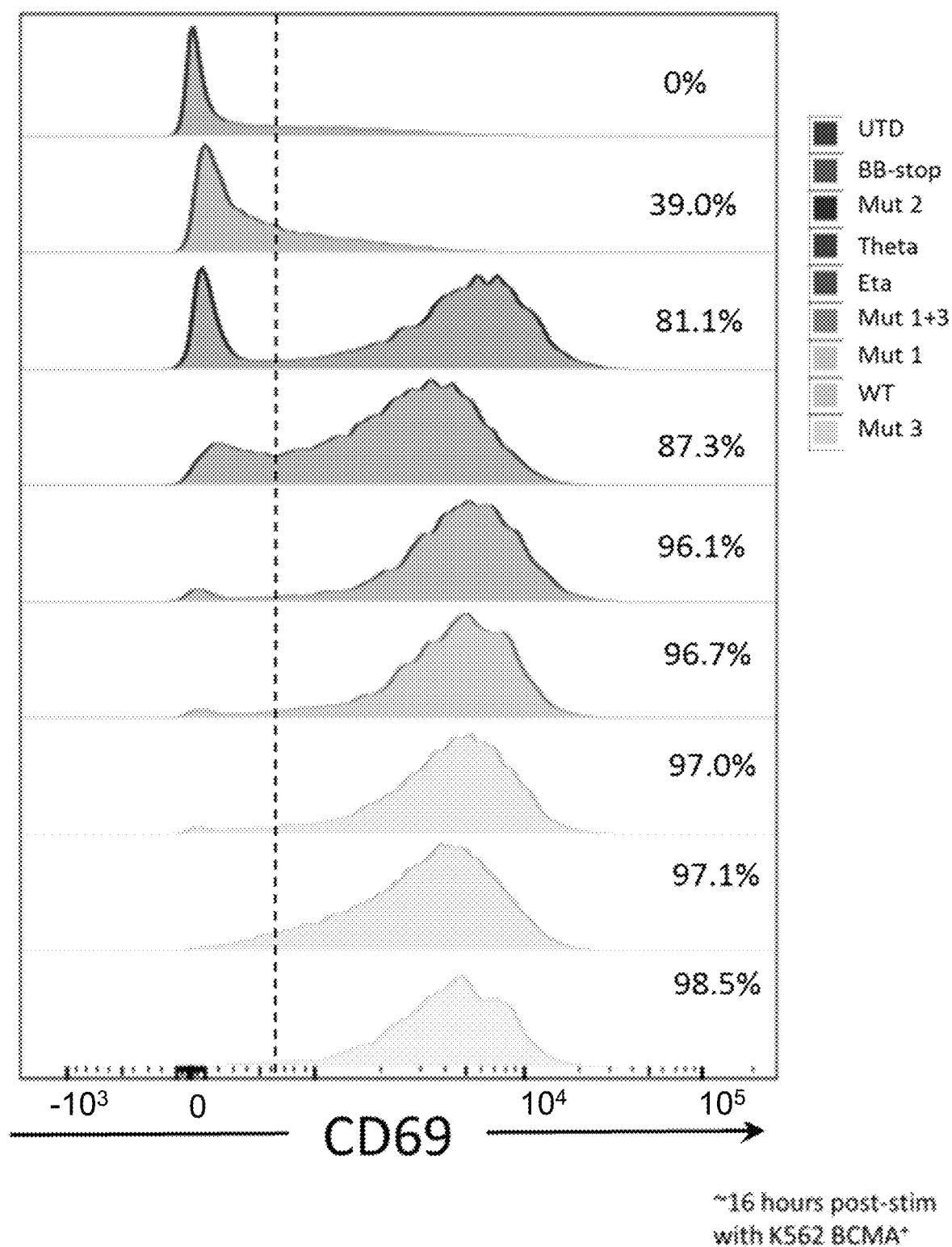
FIG. 11 depicts a graph of CD69 activation in CAR T cells bearing the indicated anti-BCMA CAR construct.

Expression of the early activation marker CD69 was examined after CAR stimulation (FIG. 11). No statistically significant difference was found between the CAR Ts.

Figure 12:
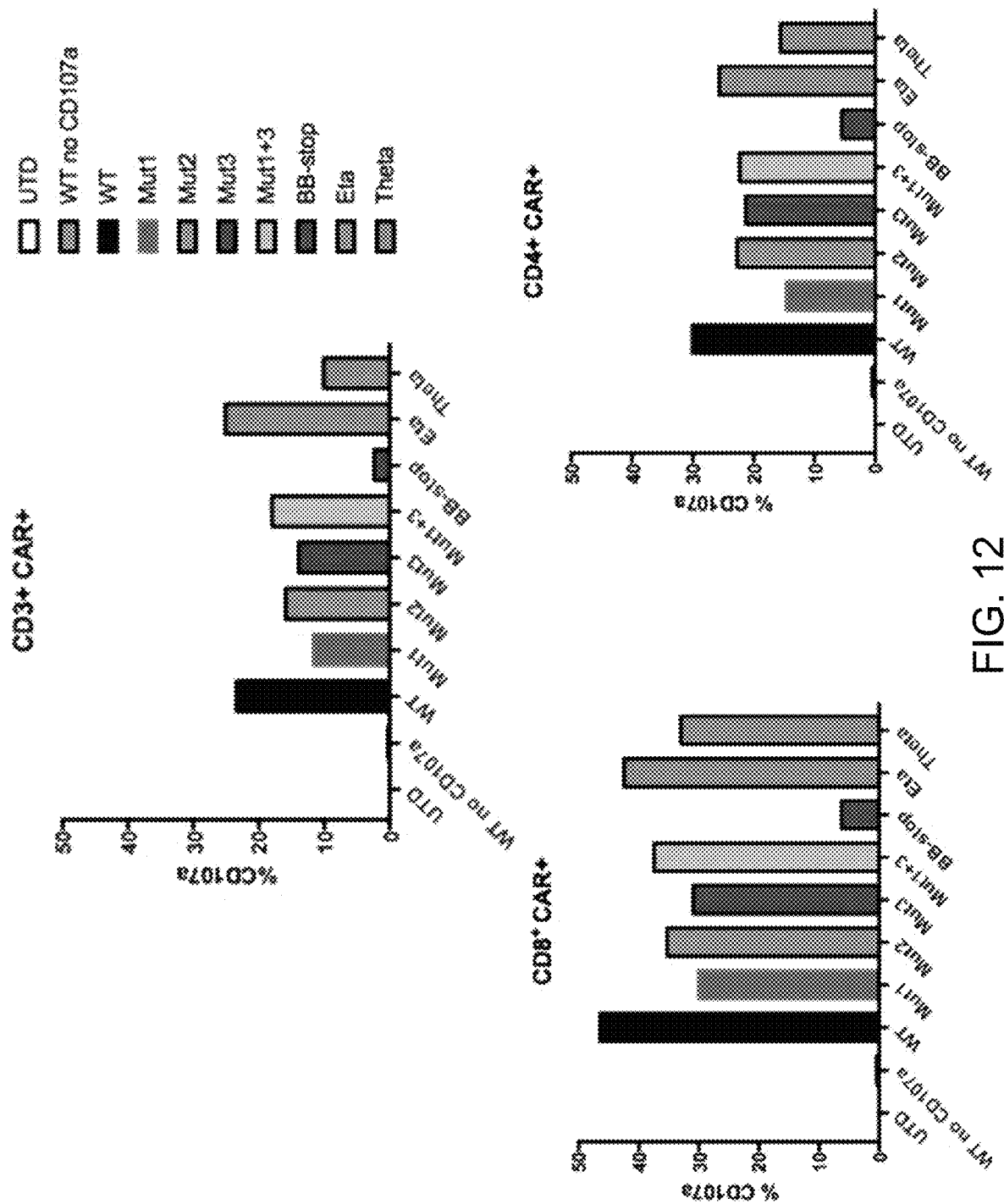
FIG. 12 depicts the results of a CD107a degranulation assay.

CD107a degranulation was tested. ND29 degranulation was measured 5 hr after CAR stimulation with K562-BCMA$^+$ cells (FIG. 12). No statistically significant difference was found between the CAR-Ts.

Figure 13:
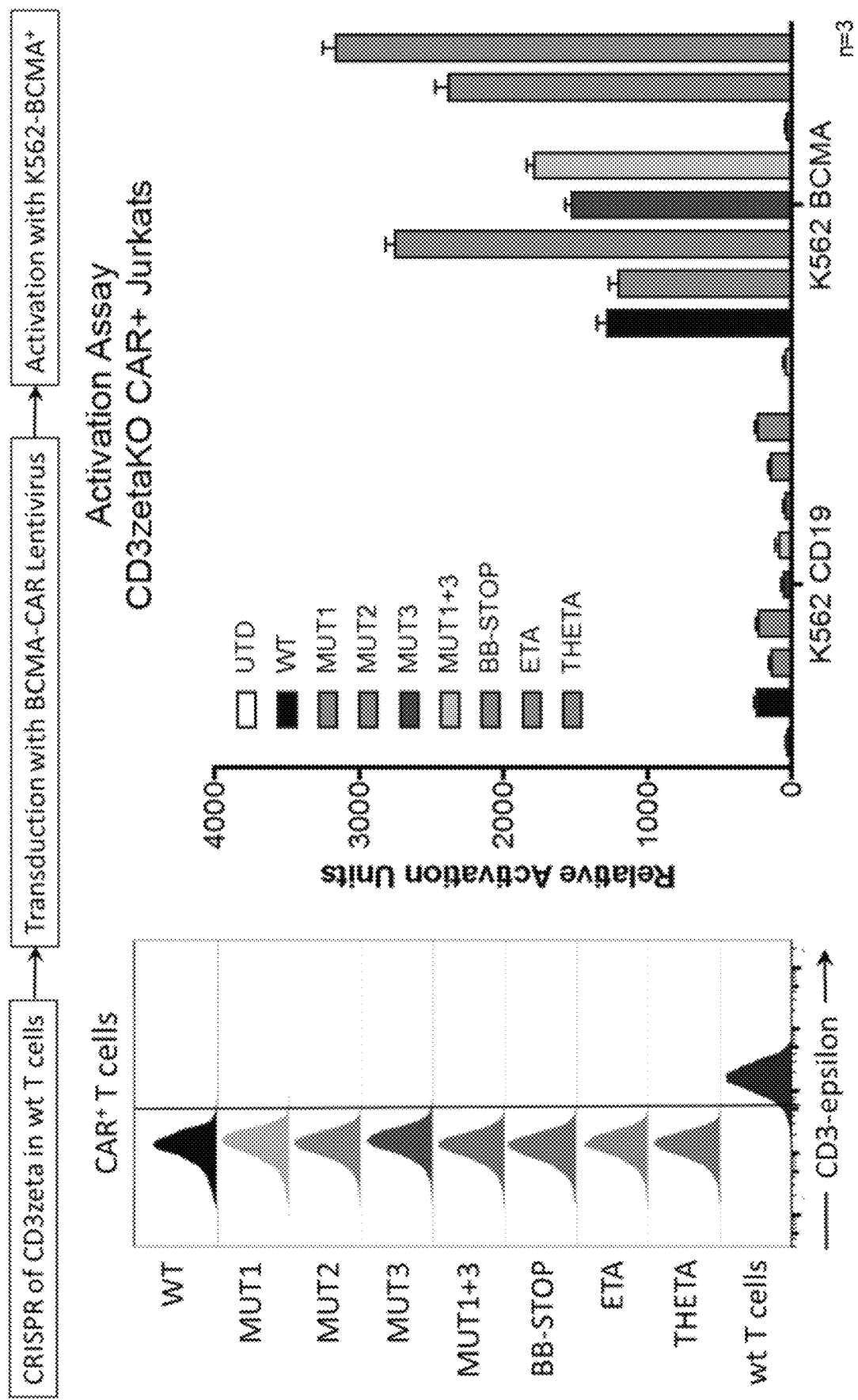
FIG. 13 demonstrates that CAR-specific activation is independent of endogenous ITAMs.

CD3ζ KO T cells were constructed and stained for CD3epsilon (also, CD3zeta, TCR alpha and beta). The cells were stimulated with K562-BCMA+ cells (FIG. 13). The results show that there are no significant differences in the activation levels produced by the different CARs tested. Accordingly, wild-type CD3ζ is not necessary for CAR function—other alternatives are available (mutants, isoforms).

Figure 14:
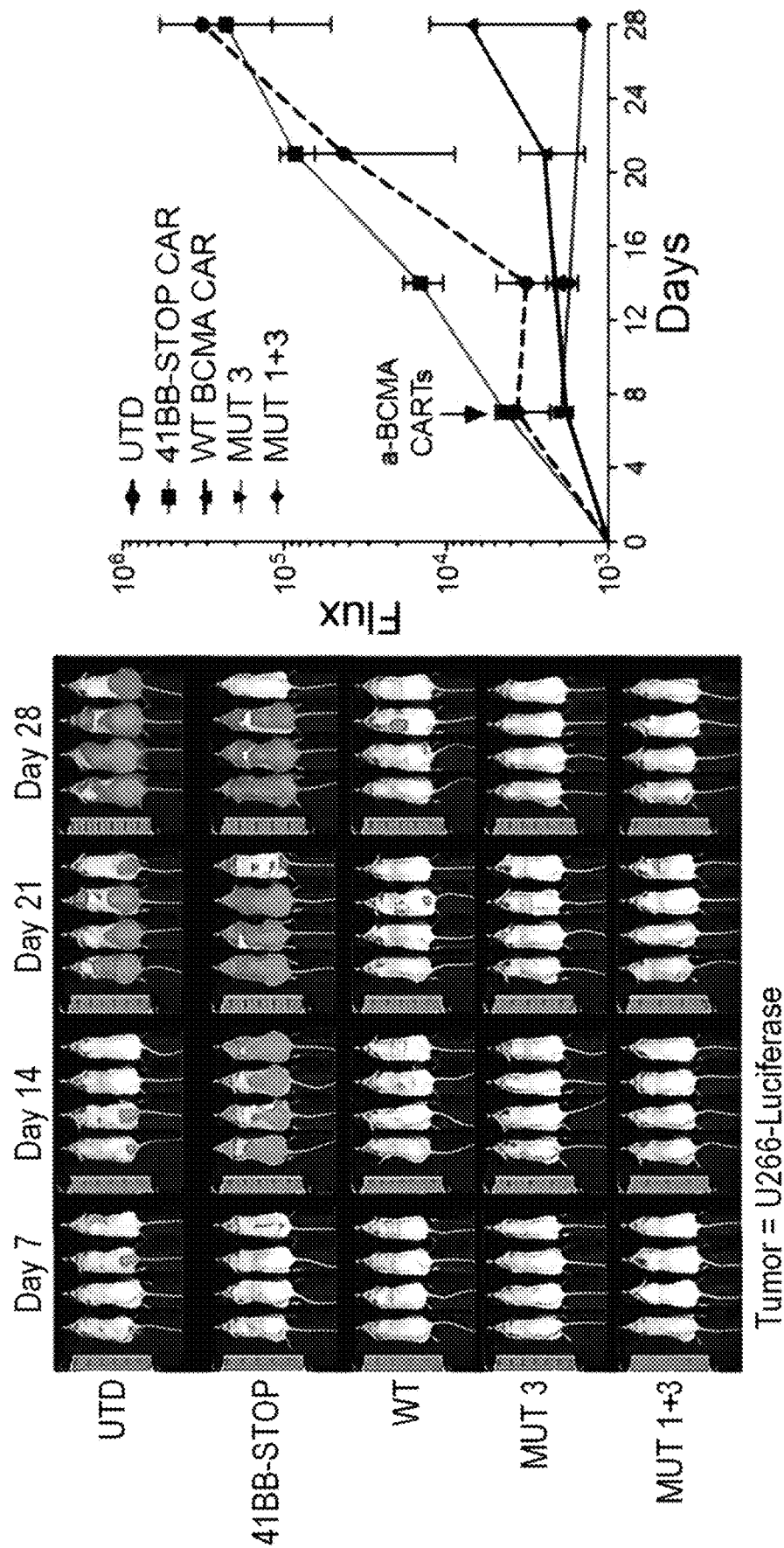
FIG. 14 depicts results of in vivo assays with the indicated CAR Ts.
Figure 15:
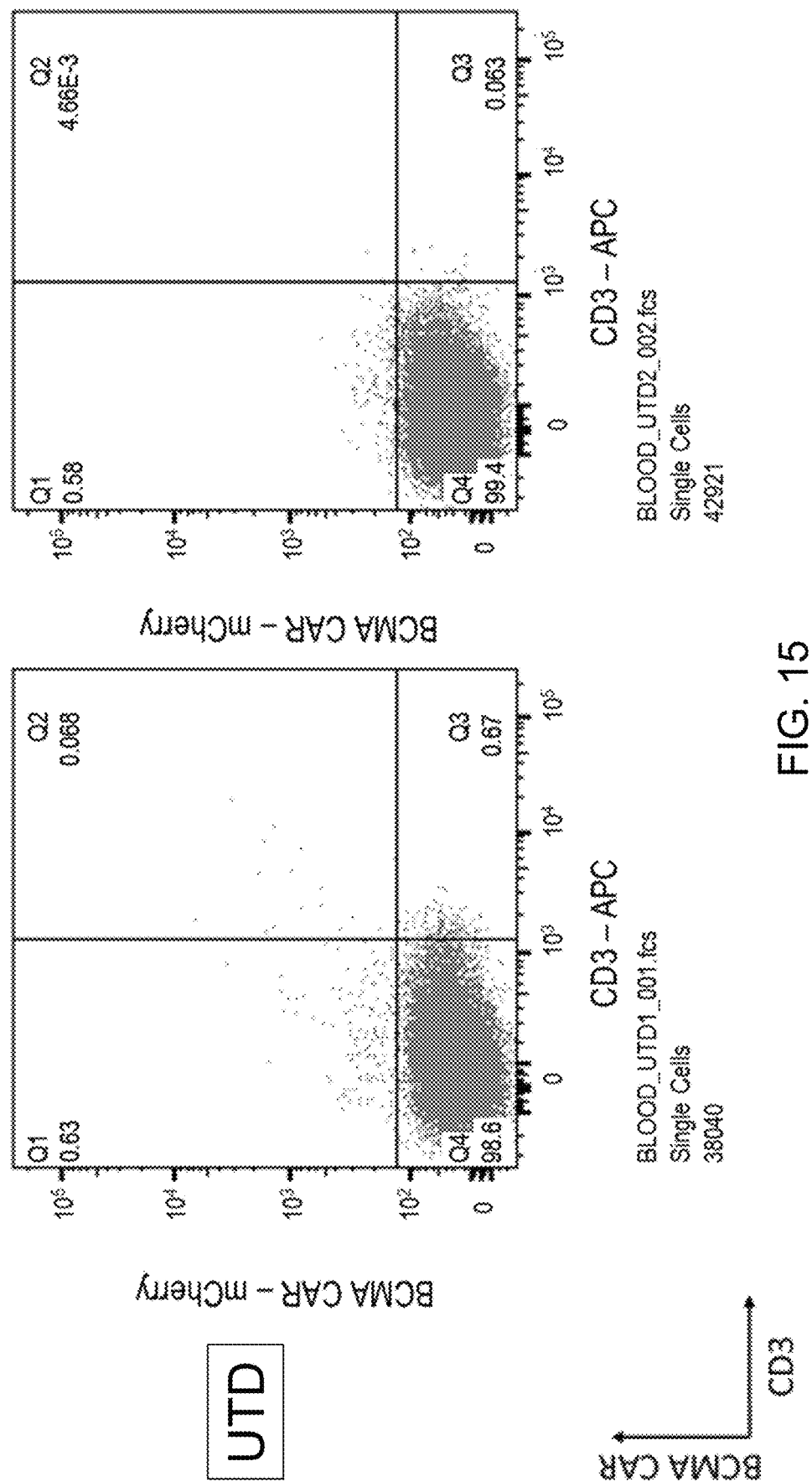
FIG. 15 depicts peripheral blood analysis of CAR T survival capacity.
Figure 15:
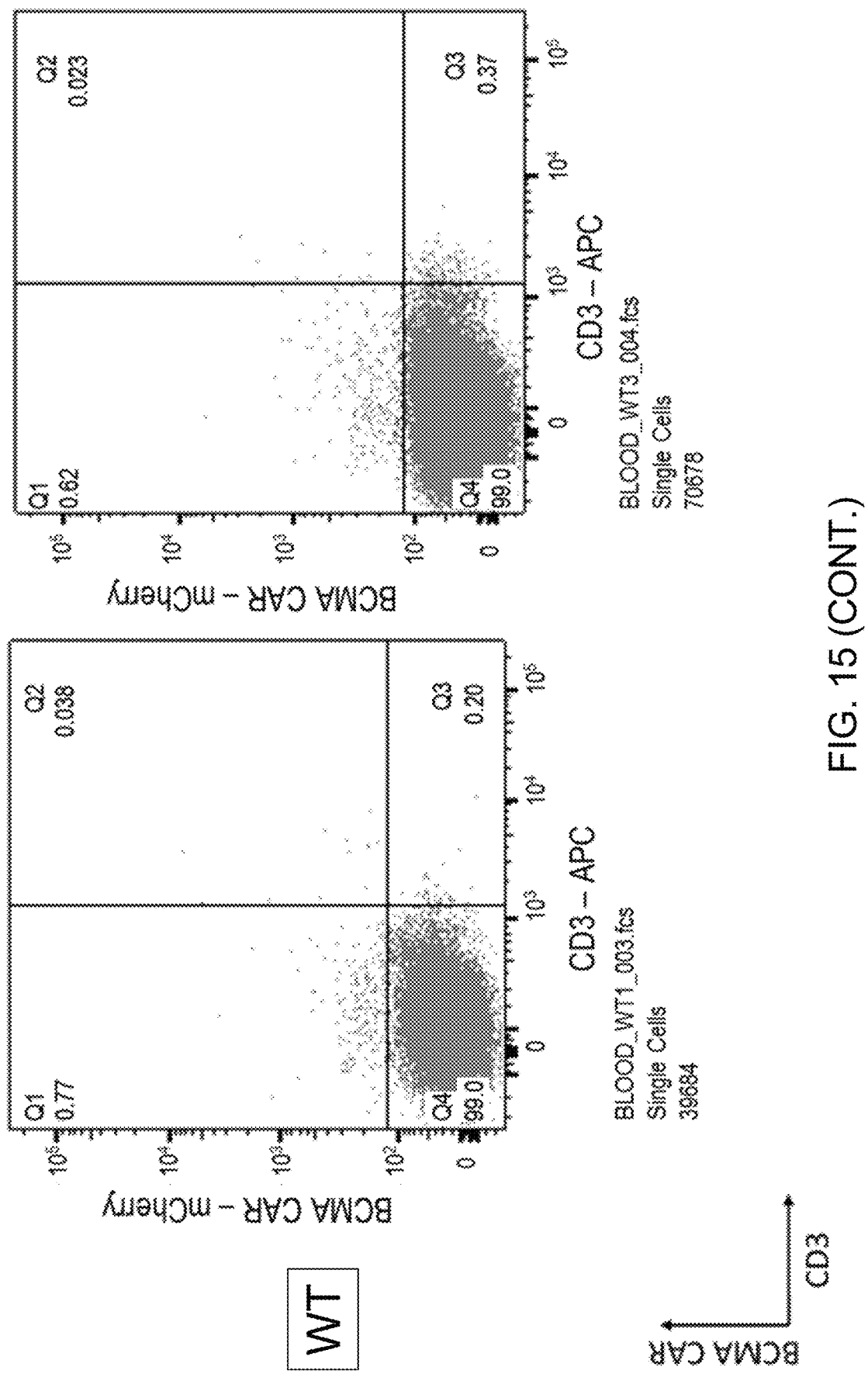
Figure 15:
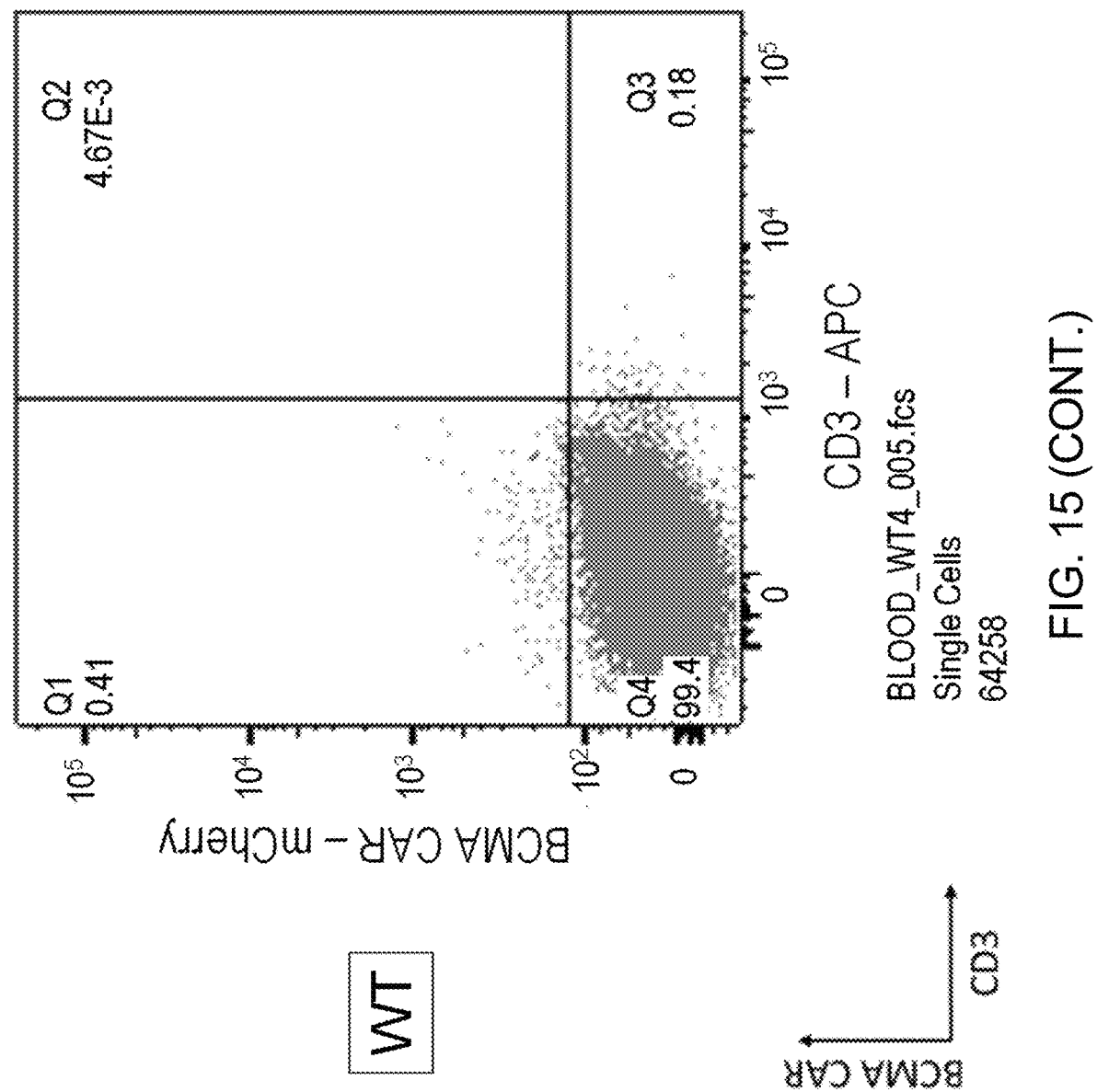
Figure 15:
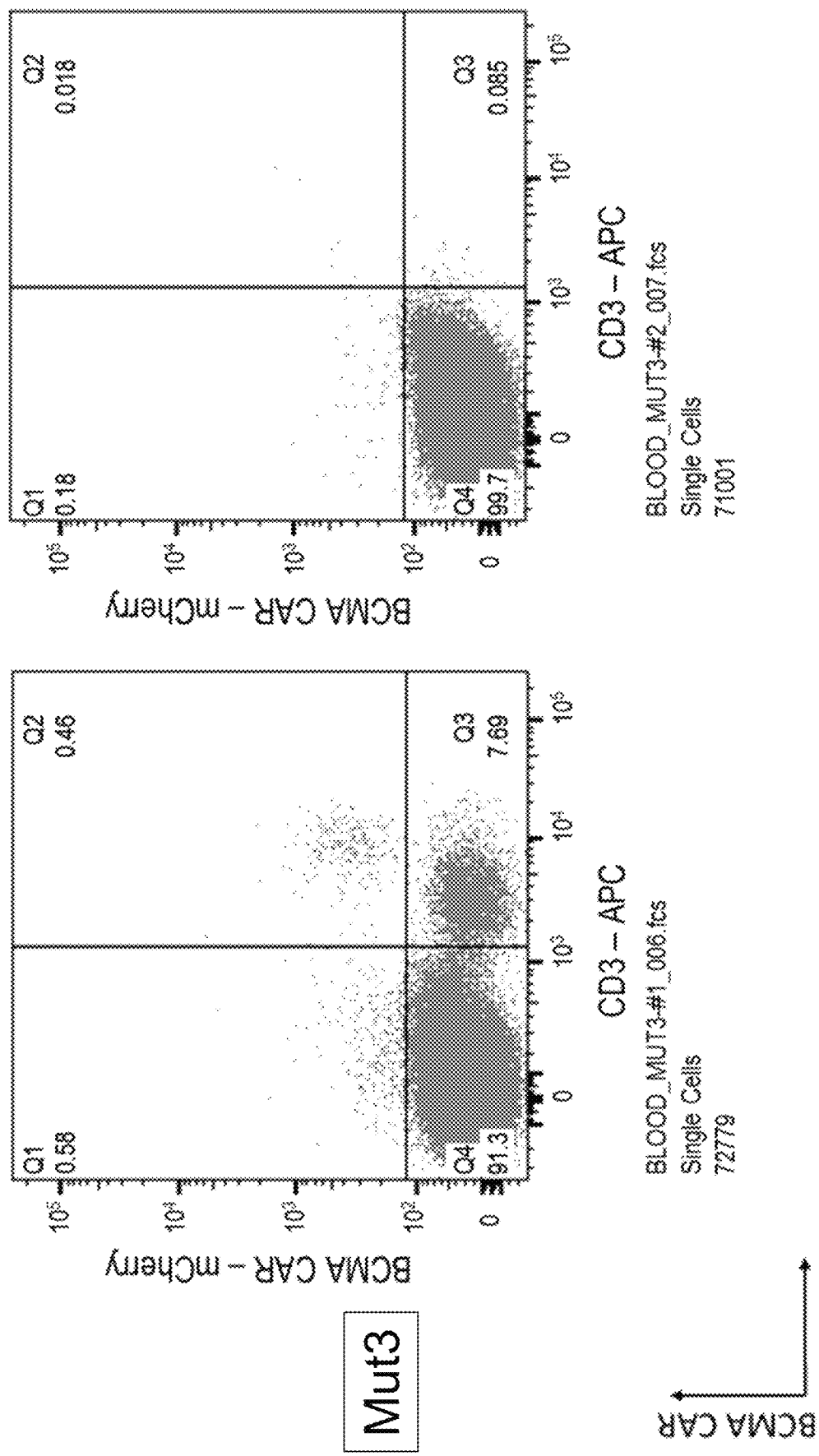
Figure 15:
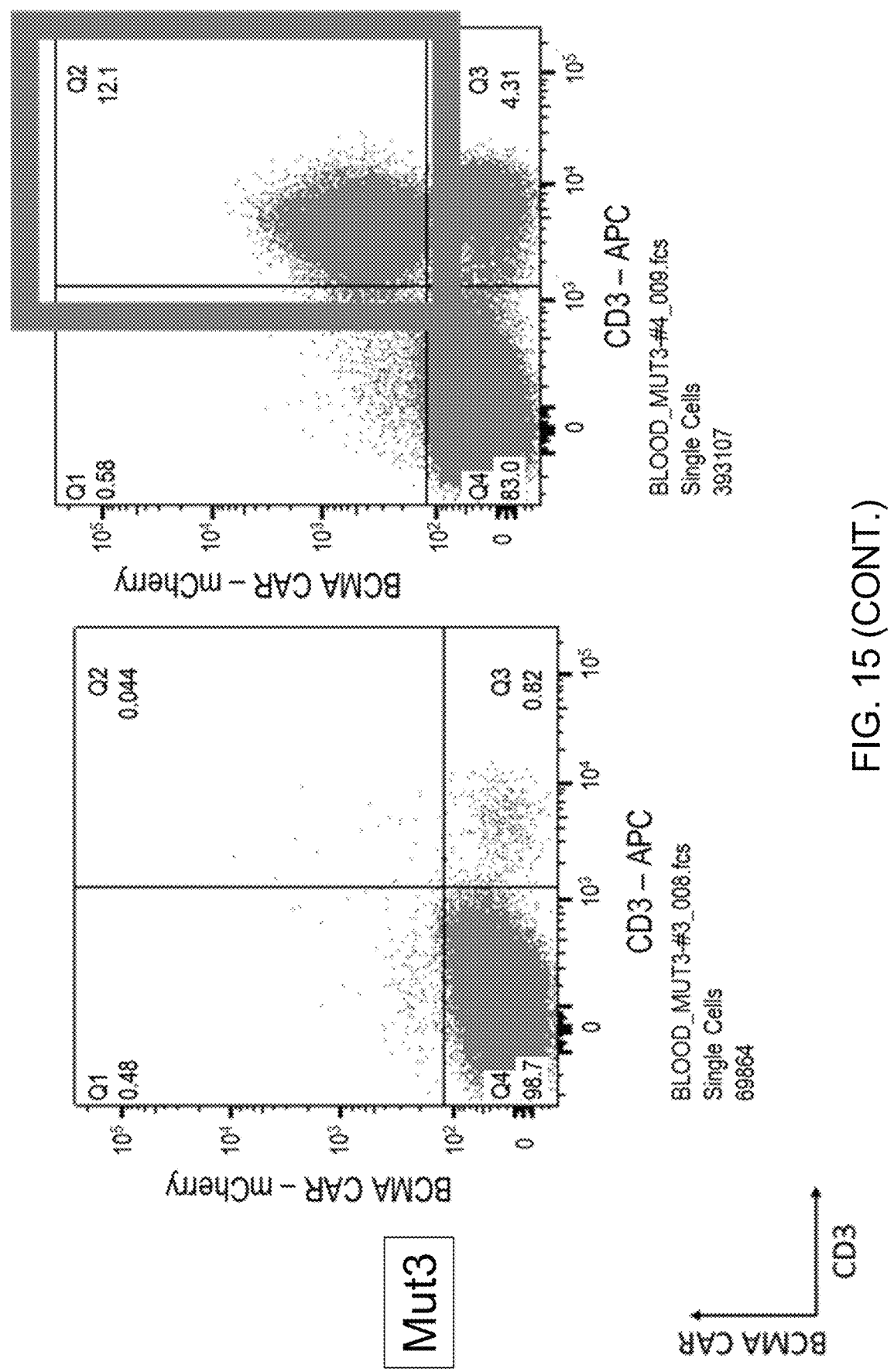

In in vivo assays, anti-BCMA CAR T Cells with mutITAM3 have better killing capacity and persistence (FIG. 14). Analysis of peripheral blood shows that CAR T cells that lack a functional ITAM3 have better survival capacity that cells having an intact CD3ζ (3 ITAMs) at 64 day post-infusion (FIG. 15).

Figure 16:
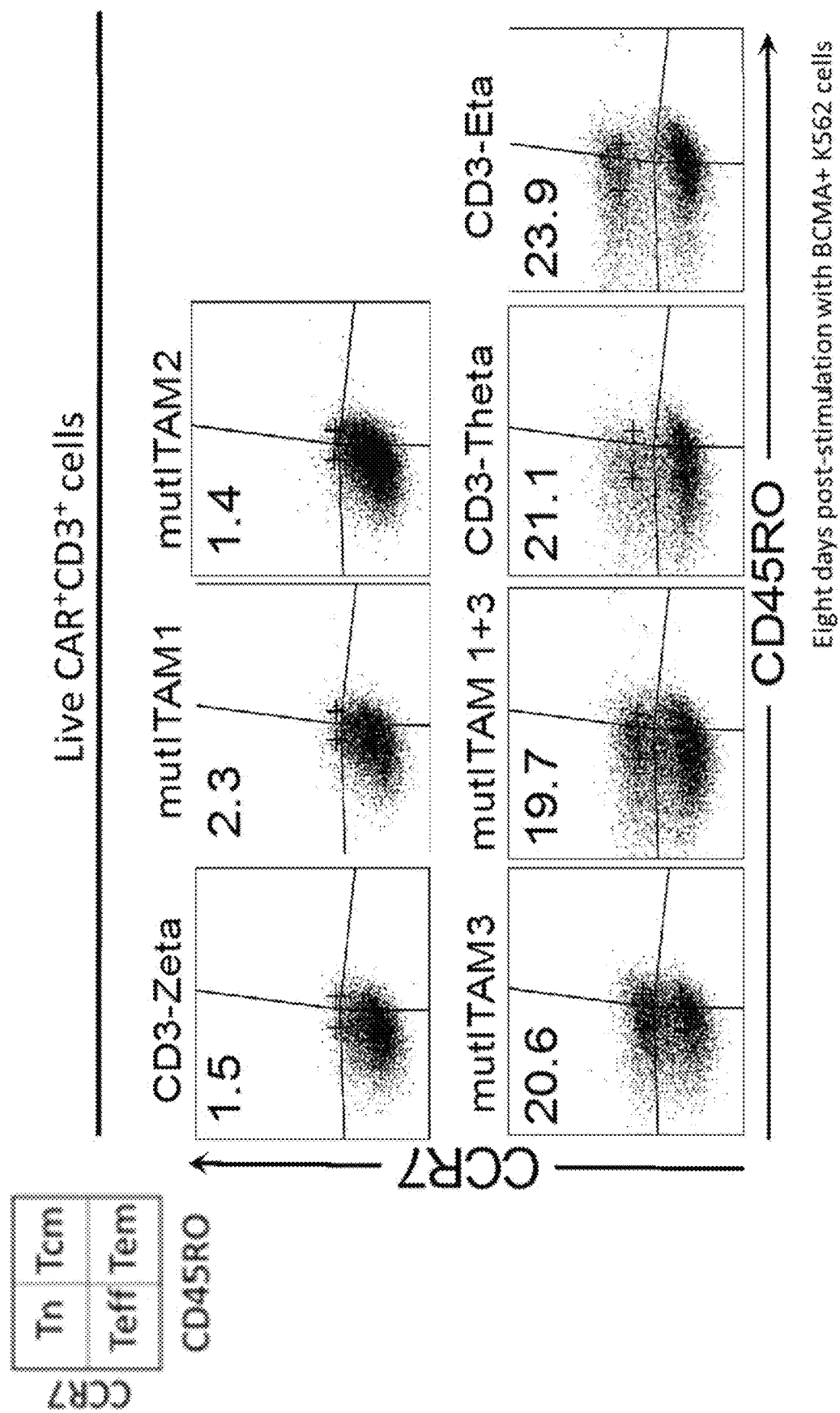
FIG. 16 depicts graphs demonstrating that inactivation or absence of ITAM3 Generates CAR T Cells with a phenotype associated with augmented survival capacity.
Figure 17:
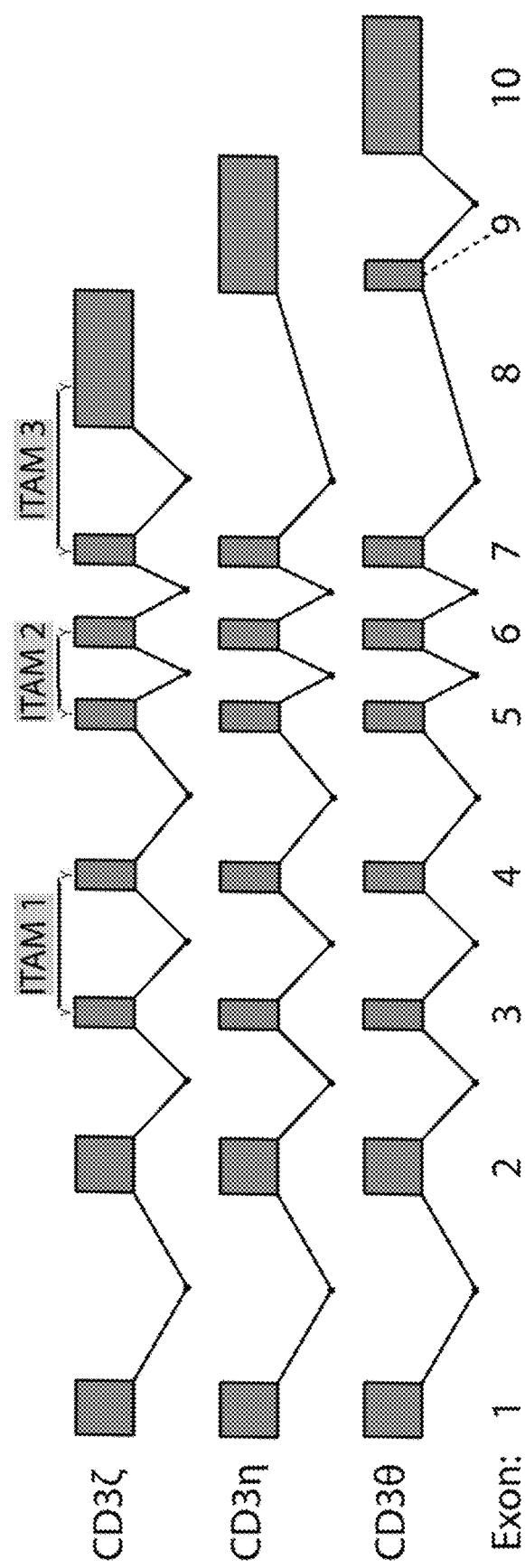
FIG. 17 depicts a schematic diagram of CD3 isoforms.
Figure 18:
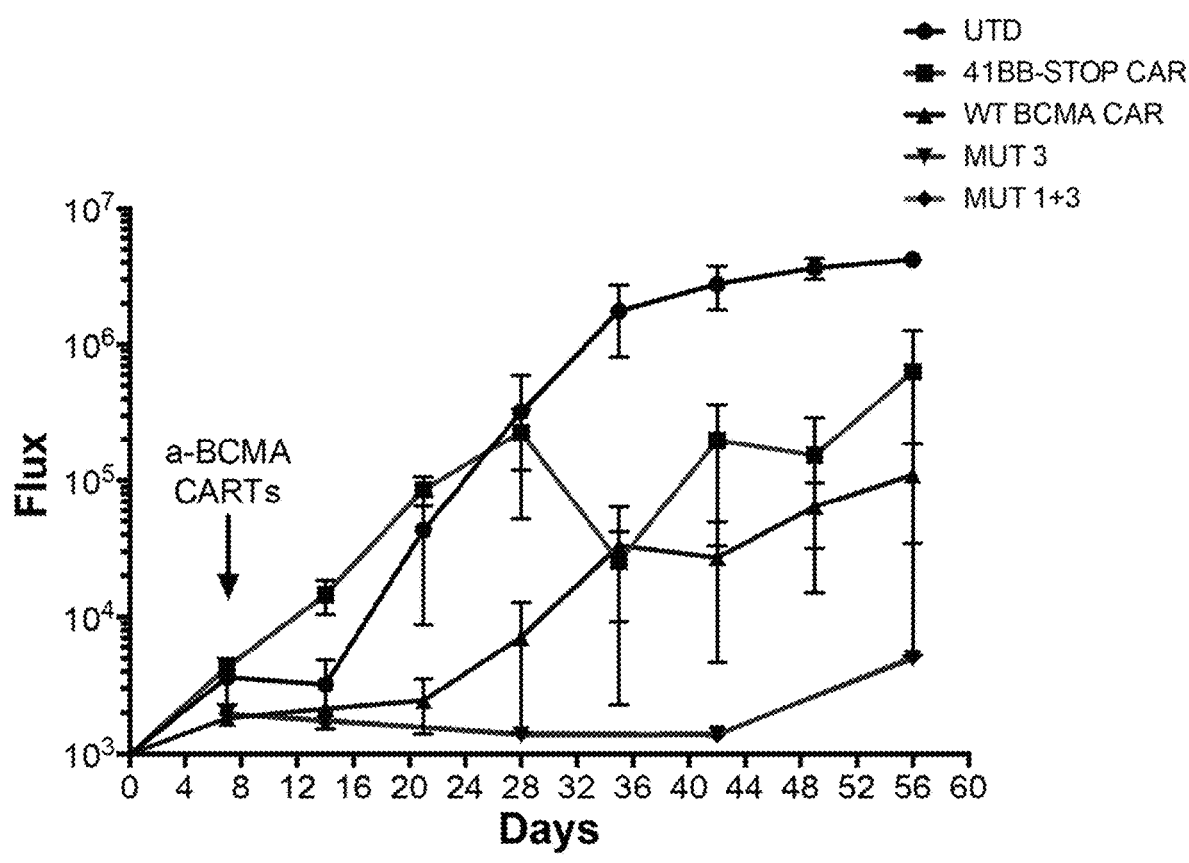
FIG. 18 depicts a graph of longitudinal analysis of tumor burden in NSG mice infused with anti-BCMA CAR T cells.
Figure 19:
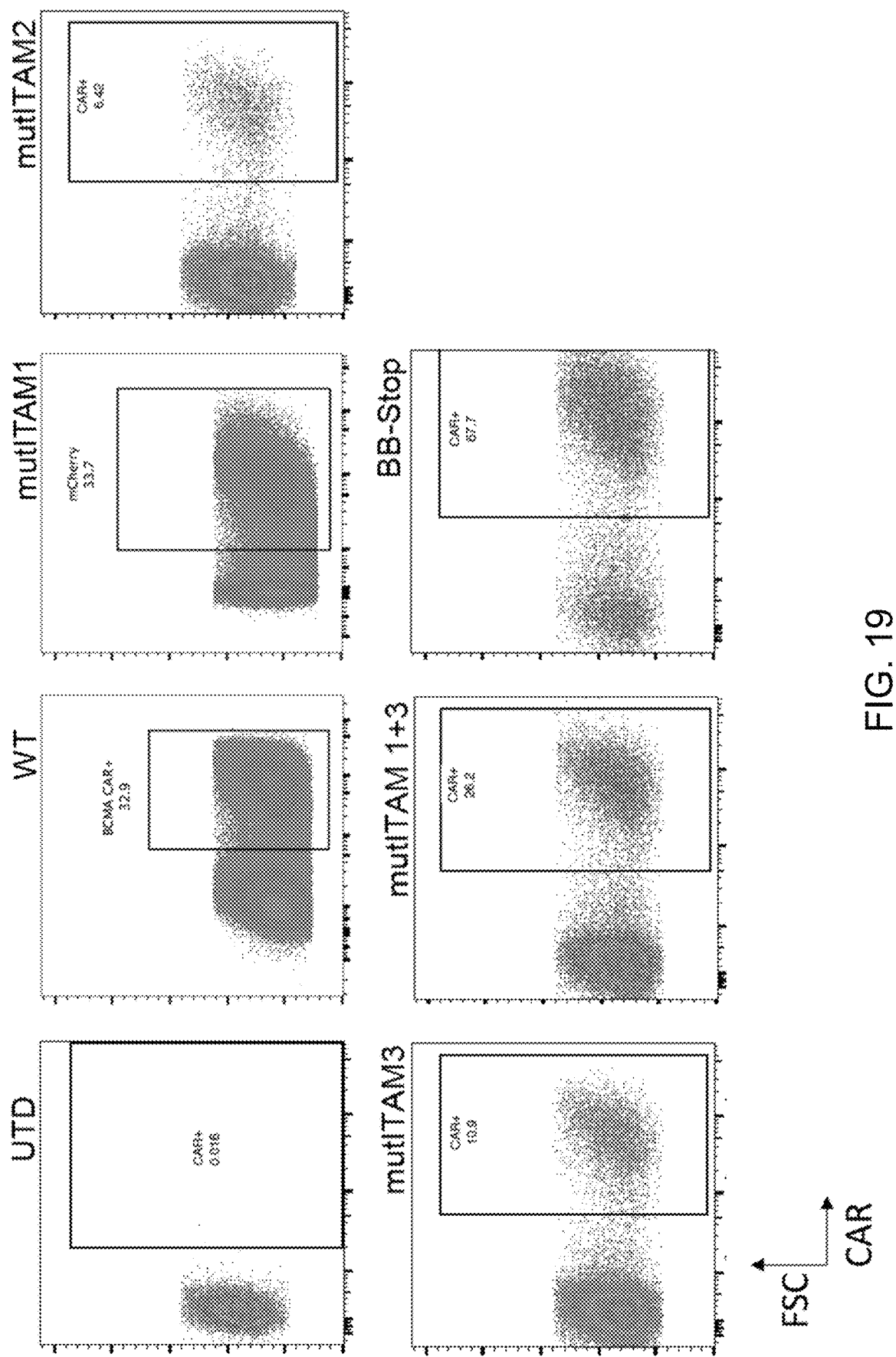
FIG. 19 demonstrates transduction efficiency in primary T cells (ND23).

CAR-T lacking ITAM3 were analyzed and found to differentiate into cells associated with better survival capacity such as naïve-like (stem cell memory) and central memory T cells (FIG. 16).

Described herein are CAR T cells targeting BCMA that can efficiently lyse multiple myeloma cells. All the BCMA-CARs tested (CD3ζ mutants and isoforms) have similar tumoricidal capacity as CAR T cells bearing a wild-type C CD3ζ domain. CARs with an inactive ITAM3 have better persistence in vivo, possibly due to higher percentage of stem cell memory T cells (Tscm).

Example 4

Figure 20:
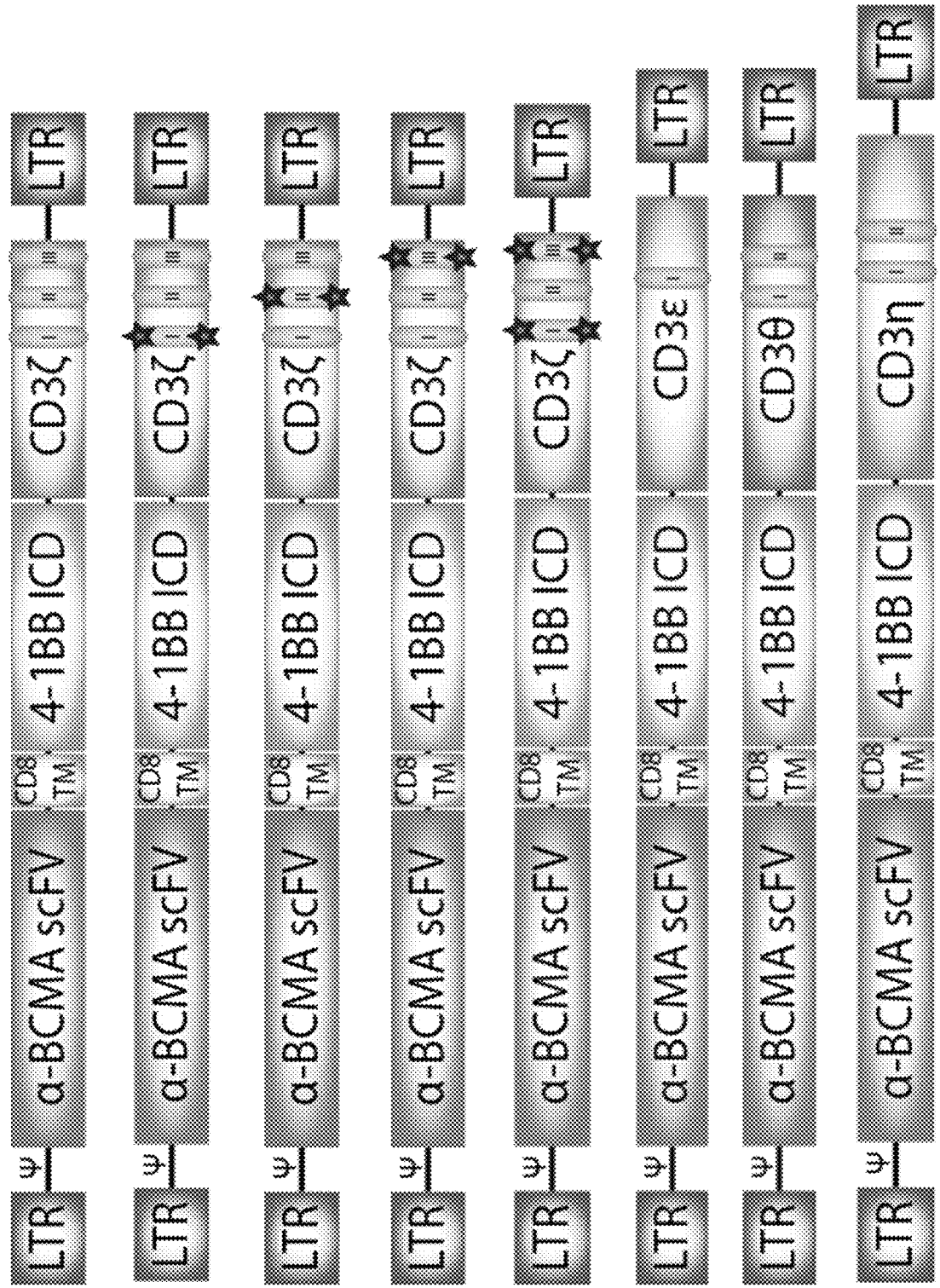
FIG. 20 depicts schematic diagrams of alternative CARs. Darker bars within CD3 domains indicate ITAMS (2 tyrosine residues per ITAM). * Indicate tyrosine to phenylalanine (Y>F) point mutations. T2A and mCherry not shown.
Figure 21A:
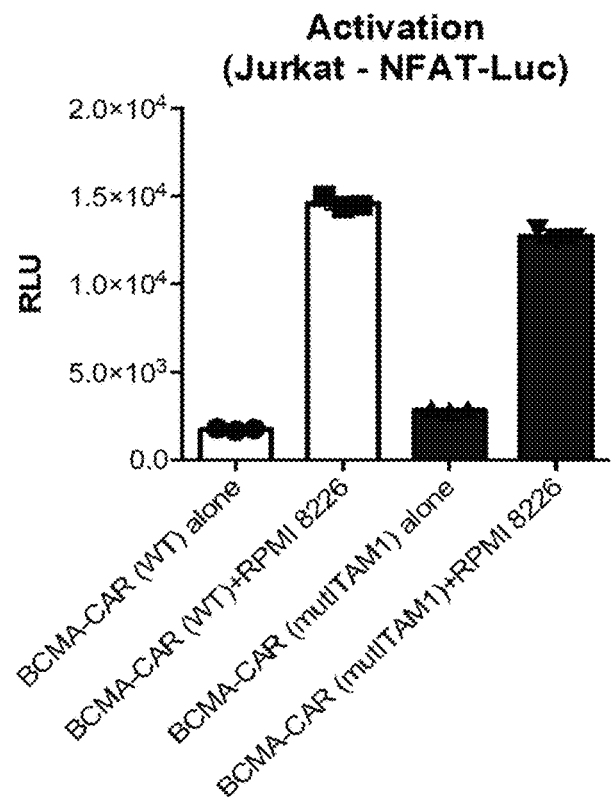
FIGS. 21A and 21B depict graphs of activation and in vitro cytotoxicity of the indicated CAR Ts.
Figure 21B:
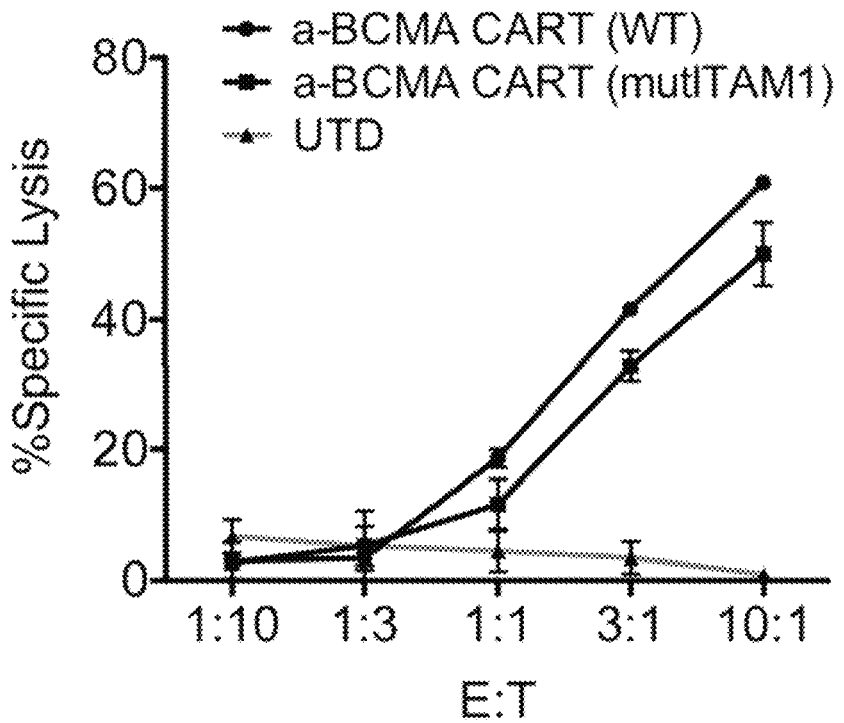

A number of alternative CARs were designed (FIG. 20). Activation and cytotoxicity of the resulting CAR Ts were tested (FIGS. 21A & 21B) but no significant difference in activation and in-vitro cytotoxicity of CAR T cells with signaling-deficient ITAM1 were detected.

Figure 22:
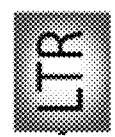
FIG. 22 depicts a schematic diagram of 4-1BBSTOP CAR. CD3ζ was removed from the CAR, instead of merely mutating ITAMs because of other basic rich sequences present within zeta.
Figure 22:
Figure 23:
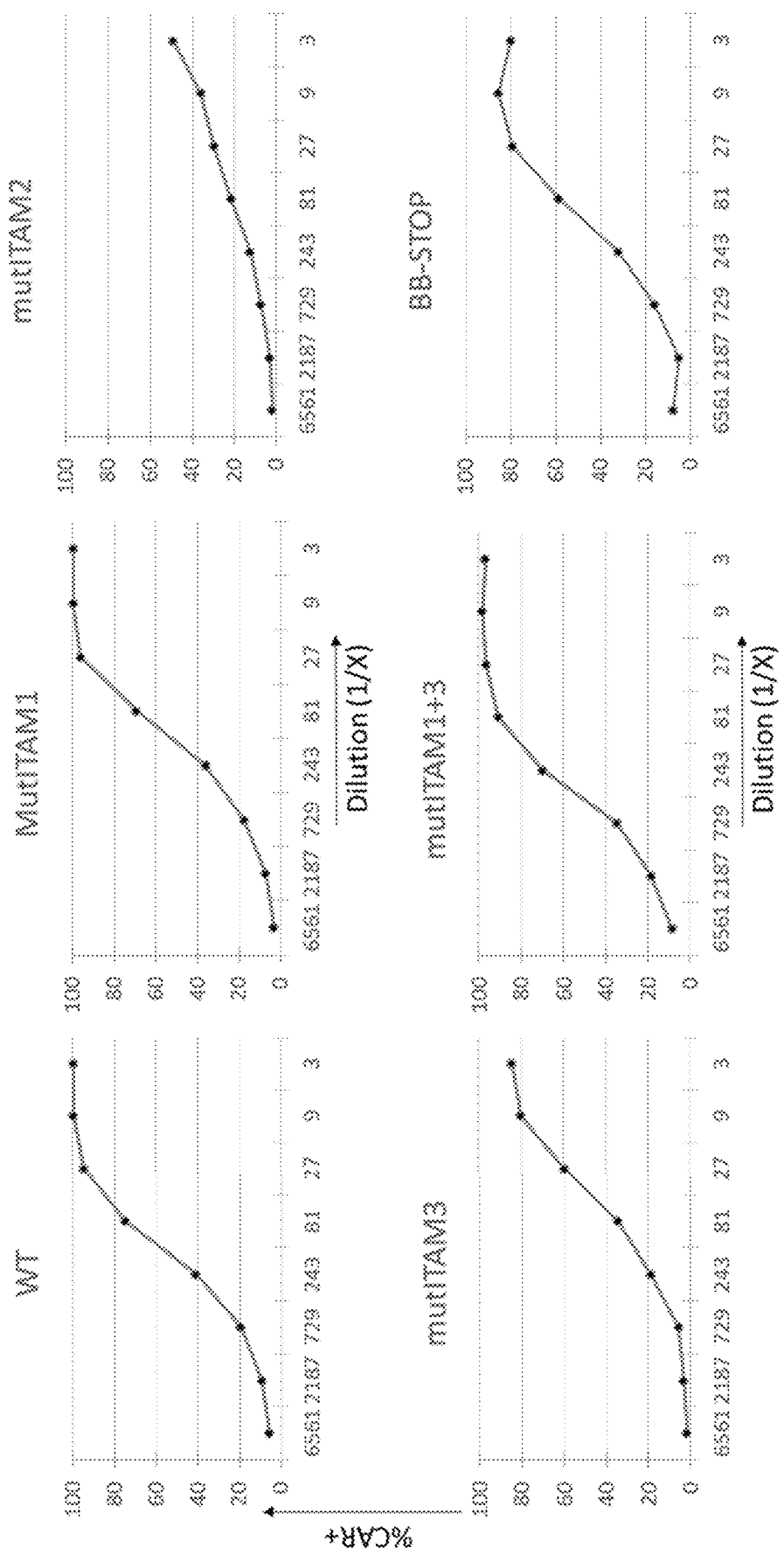
FIG. 23 depicts lentivirus titration with SupT1 cells.
Figure 24:
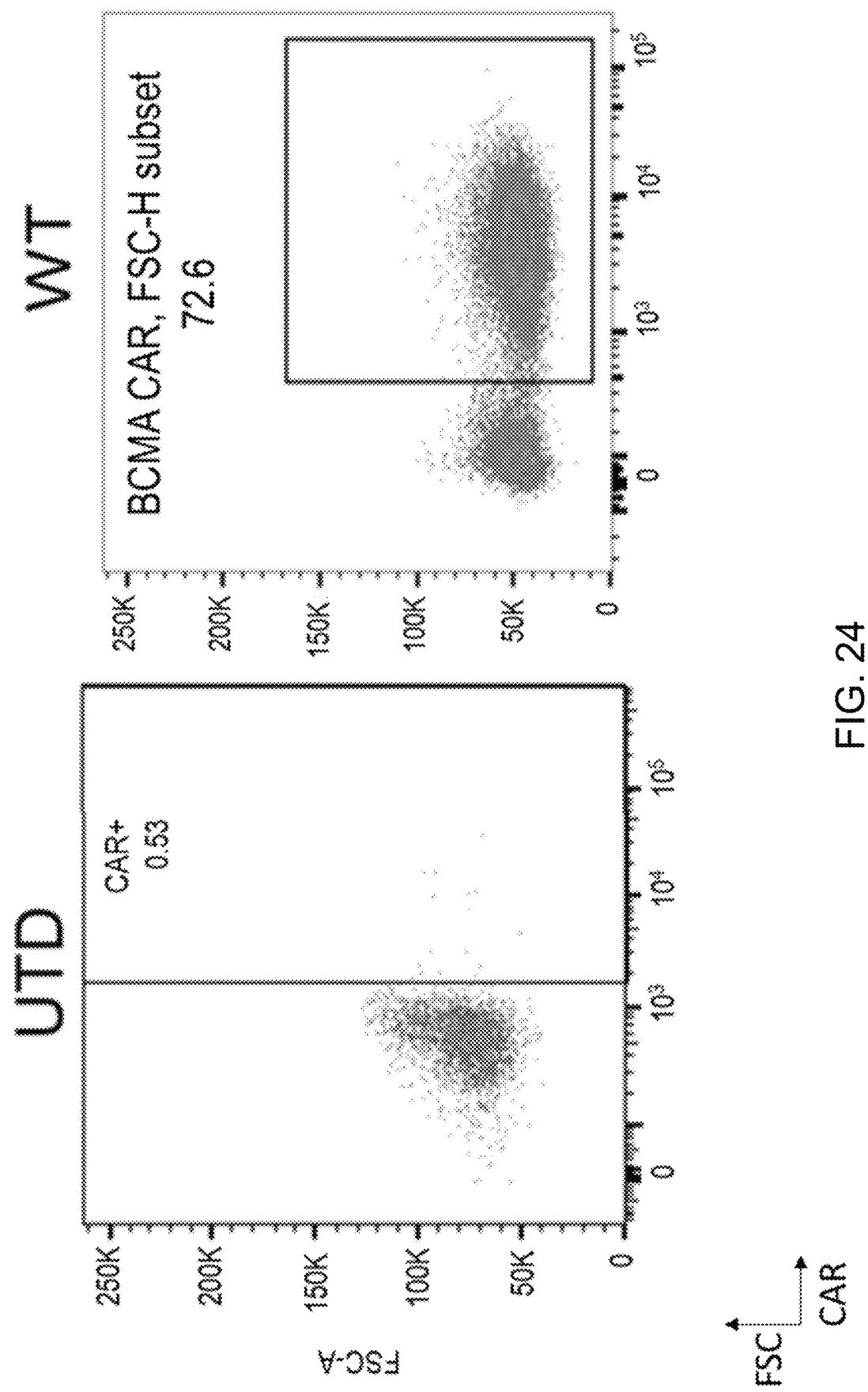
FIG. 24 depicts graphs of transduction efficiency in Jurkat T cells.
Figure 24:
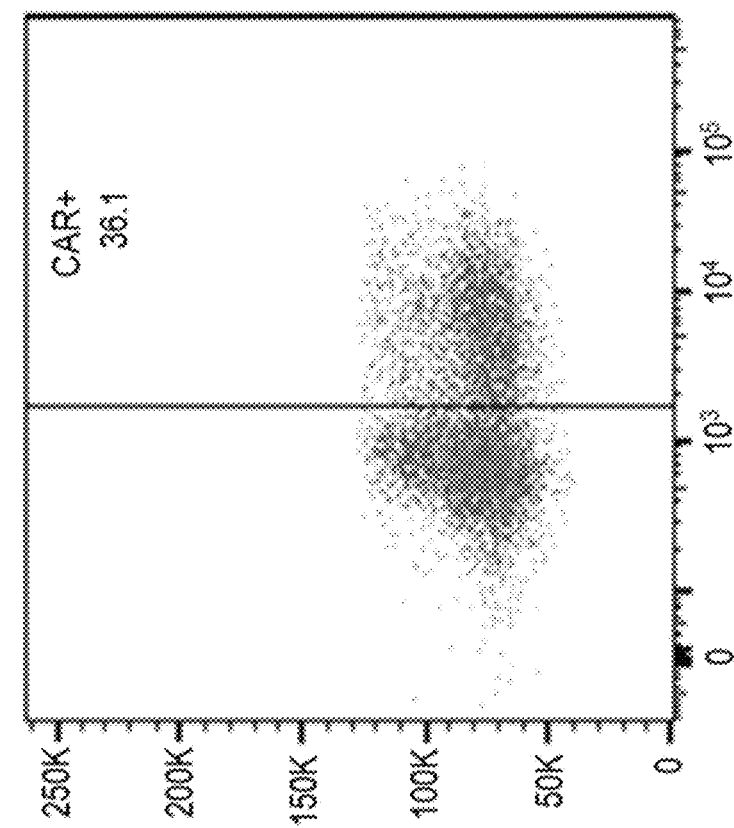
Figure 24:
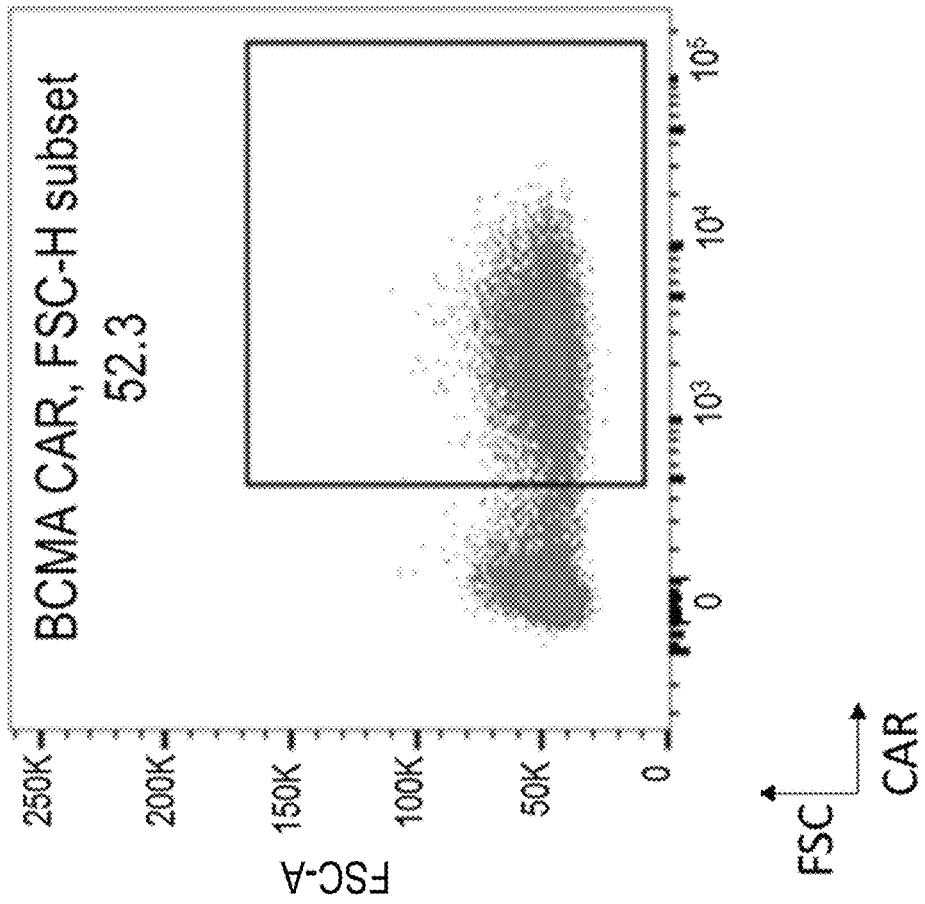
Figure 24:
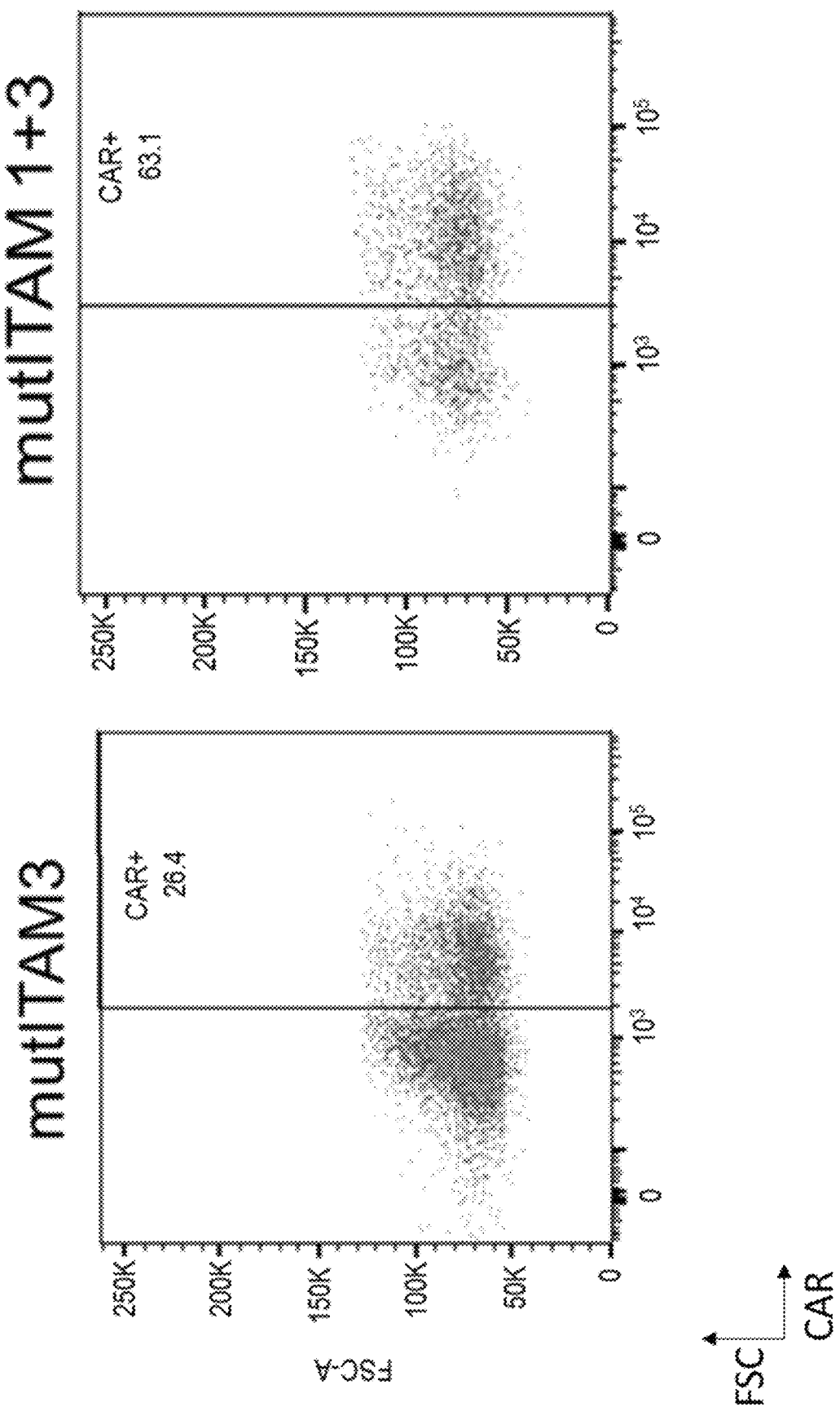
Figure 24:
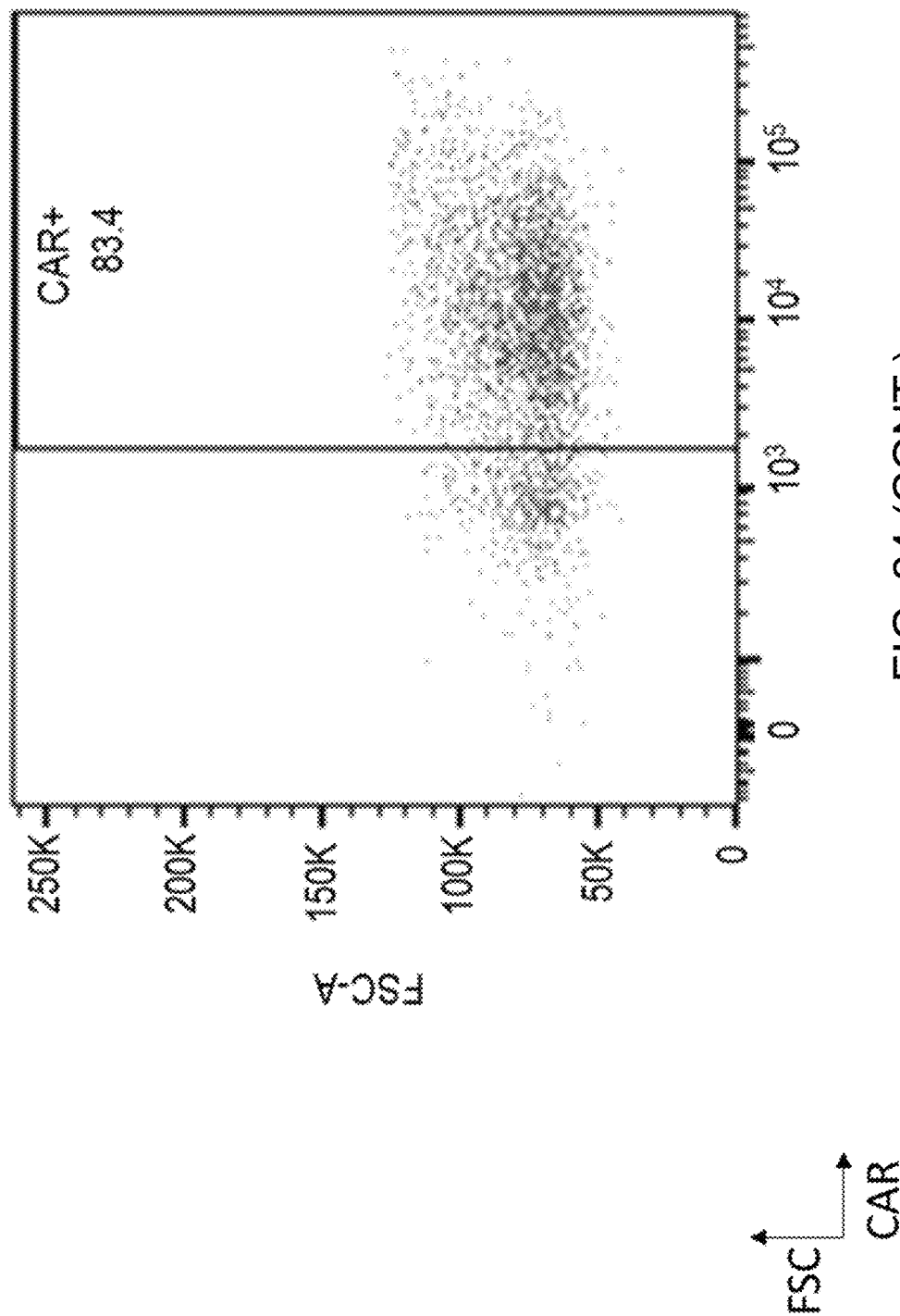
Figure 25:
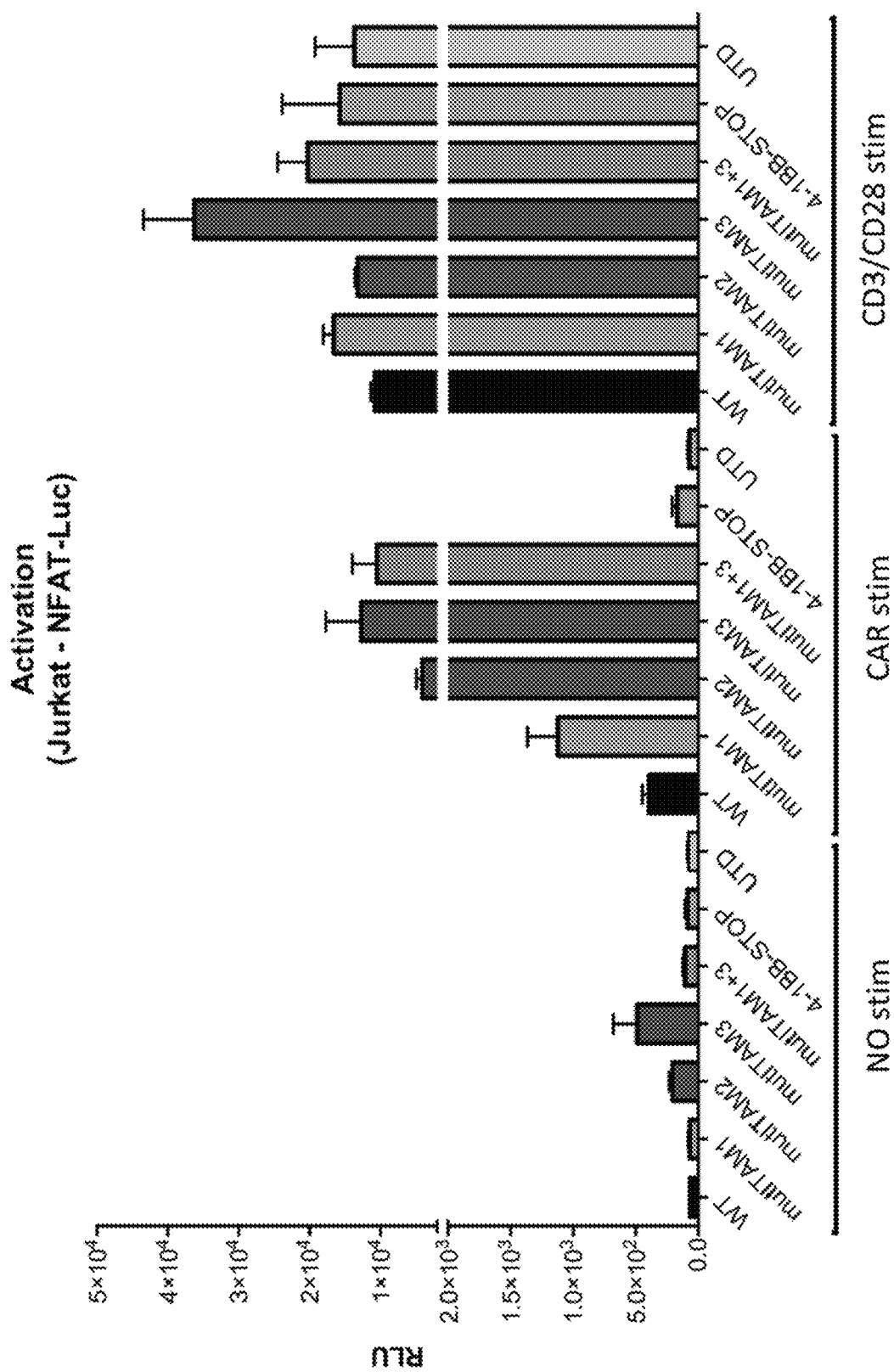
FIG. 25 depicts a graph of activation assays conducted with anti-BCMA expressing Jurkat T cells. Results shown are from two independent experiments.
Figure 26:
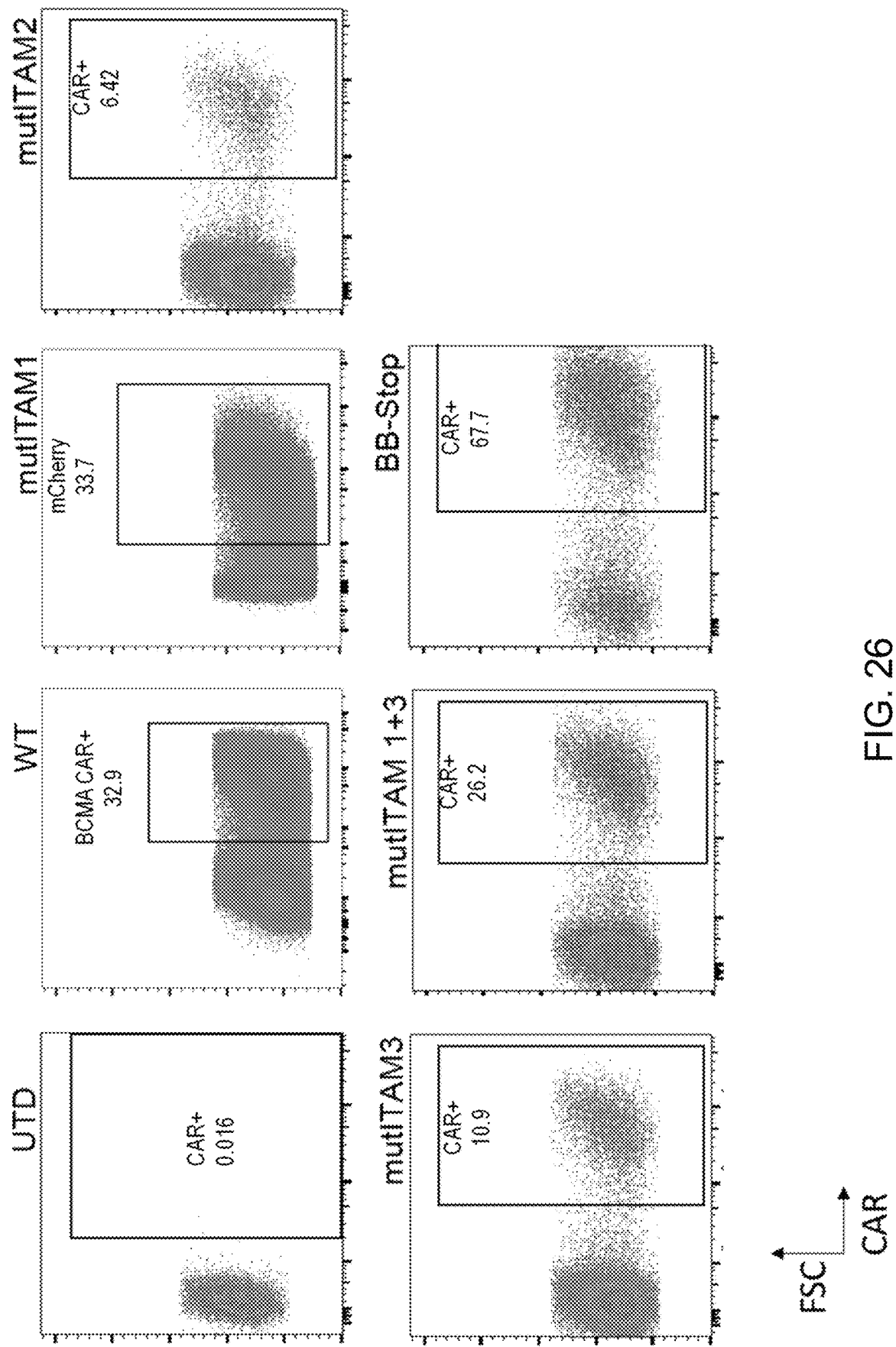
FIG. 26 depicts graphs of transduction efficiency in ND23 primary T cells.

To determine if the CD3ζ domain was necessary for CAR function, 4-1BBSTOP CAR was constructed (FIG. 22). The transduction efficiency of the CAR constructs was tested with Jurkat T cells (FIG. 24) and primary T cells (FIG. 26). Activation assays with anti-BCMA Jurkat T cells are shown in FIG. 25.

Figure 27:
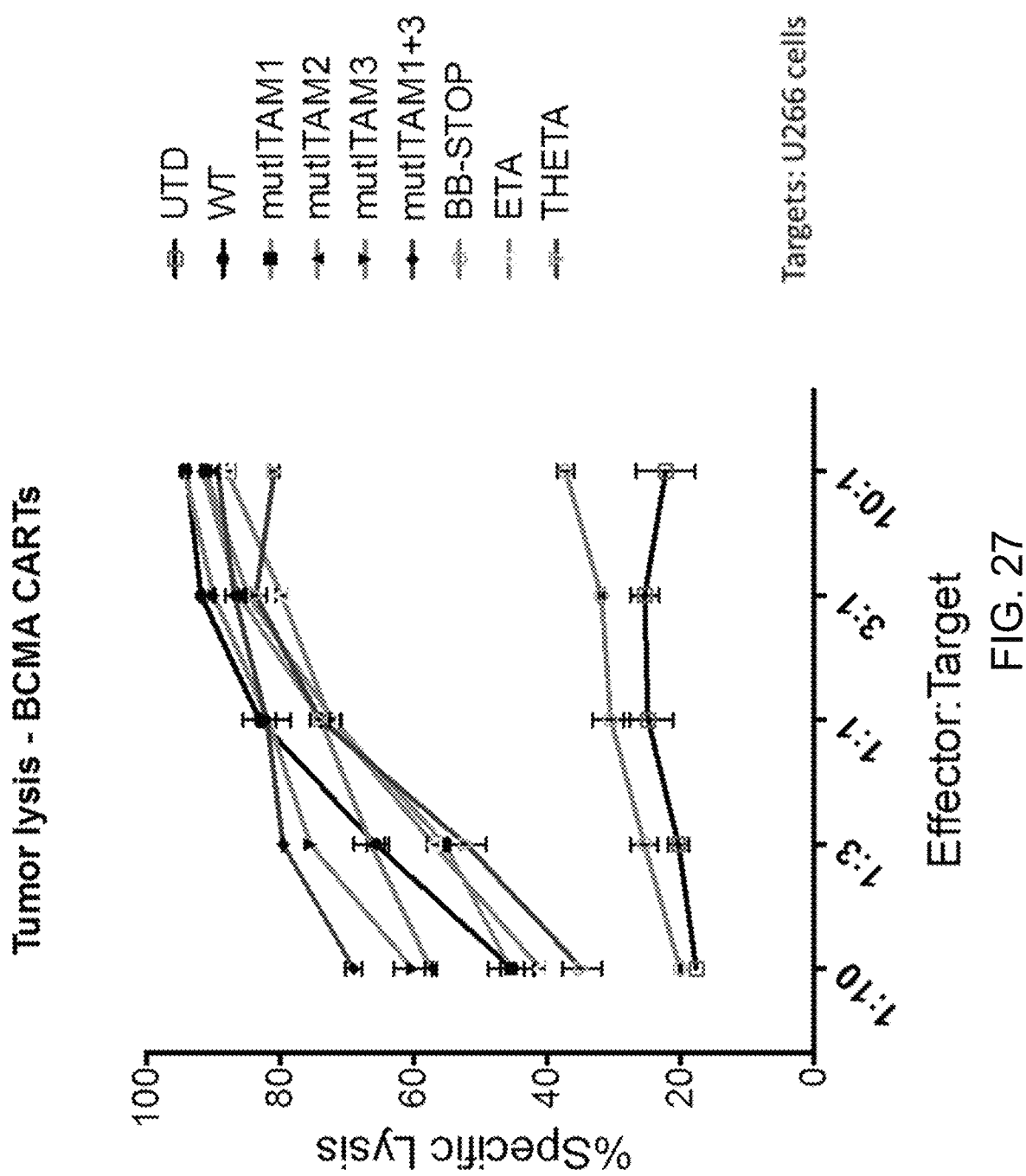
FIG. 27 depicts a graph of tumor killing activity of the indicated CAR T cells. T cells are ND19 T cells.
Figure 28:
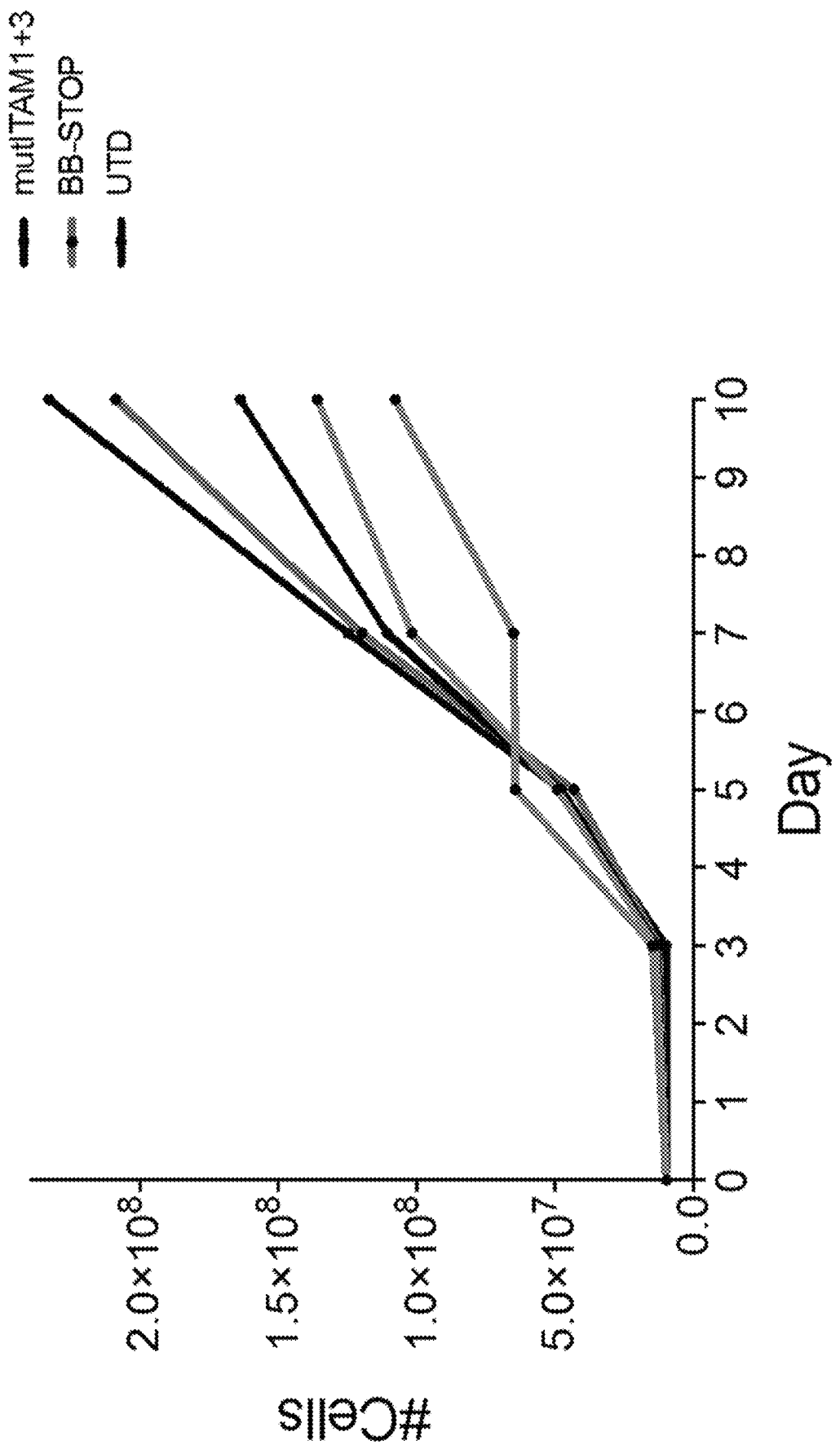
FIG. 28 depicts a graph of cell proliferation for the indicated ND23 anti-BCMA CAR T cells.
Figure 29:
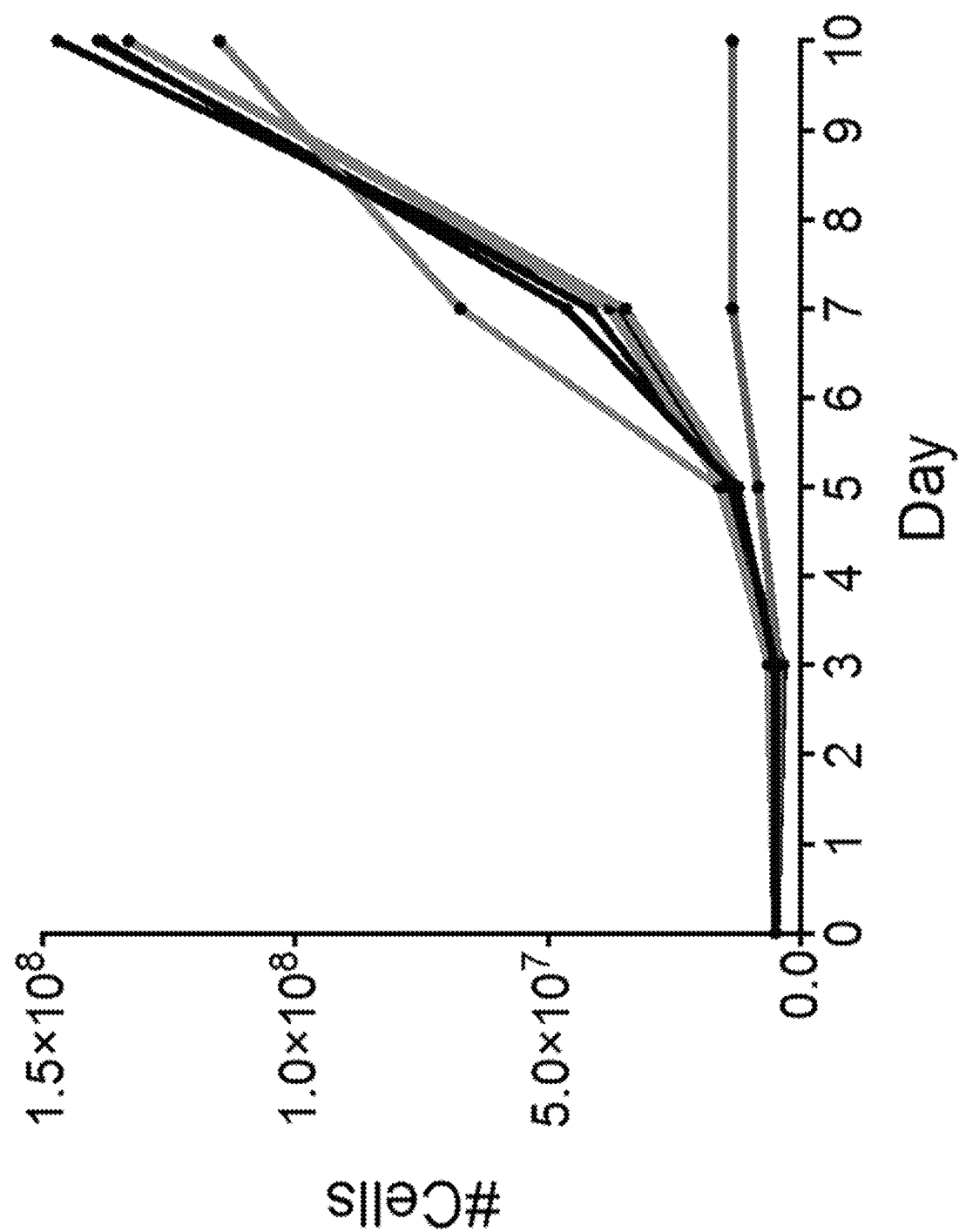
FIG. 29 depicts a graph of cell proliferation for the indicated ND19 anti-BCMA CAR T cells.

The tested constructs demonstrated tumor killing activity (FIG. 27) and proliferation in different T cell lines (FIGS. 28 and 29).

Figure 30:
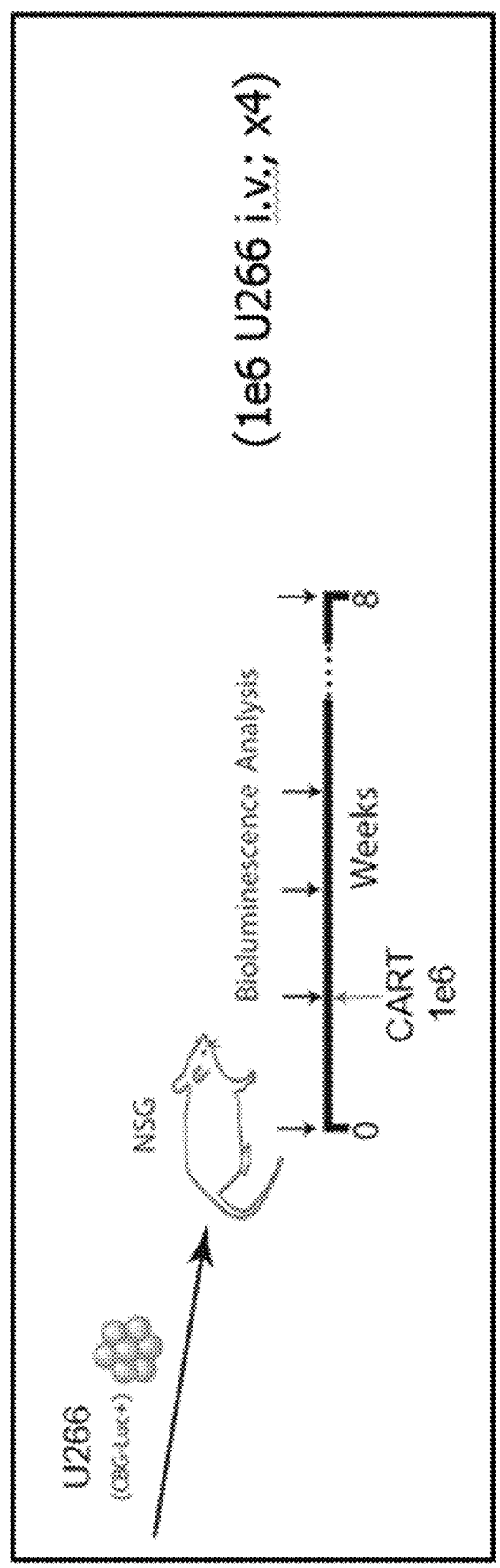
FIG. 30 depicts a schematic of the experimental approach used for in vivo tumor assays.
Figure 31:
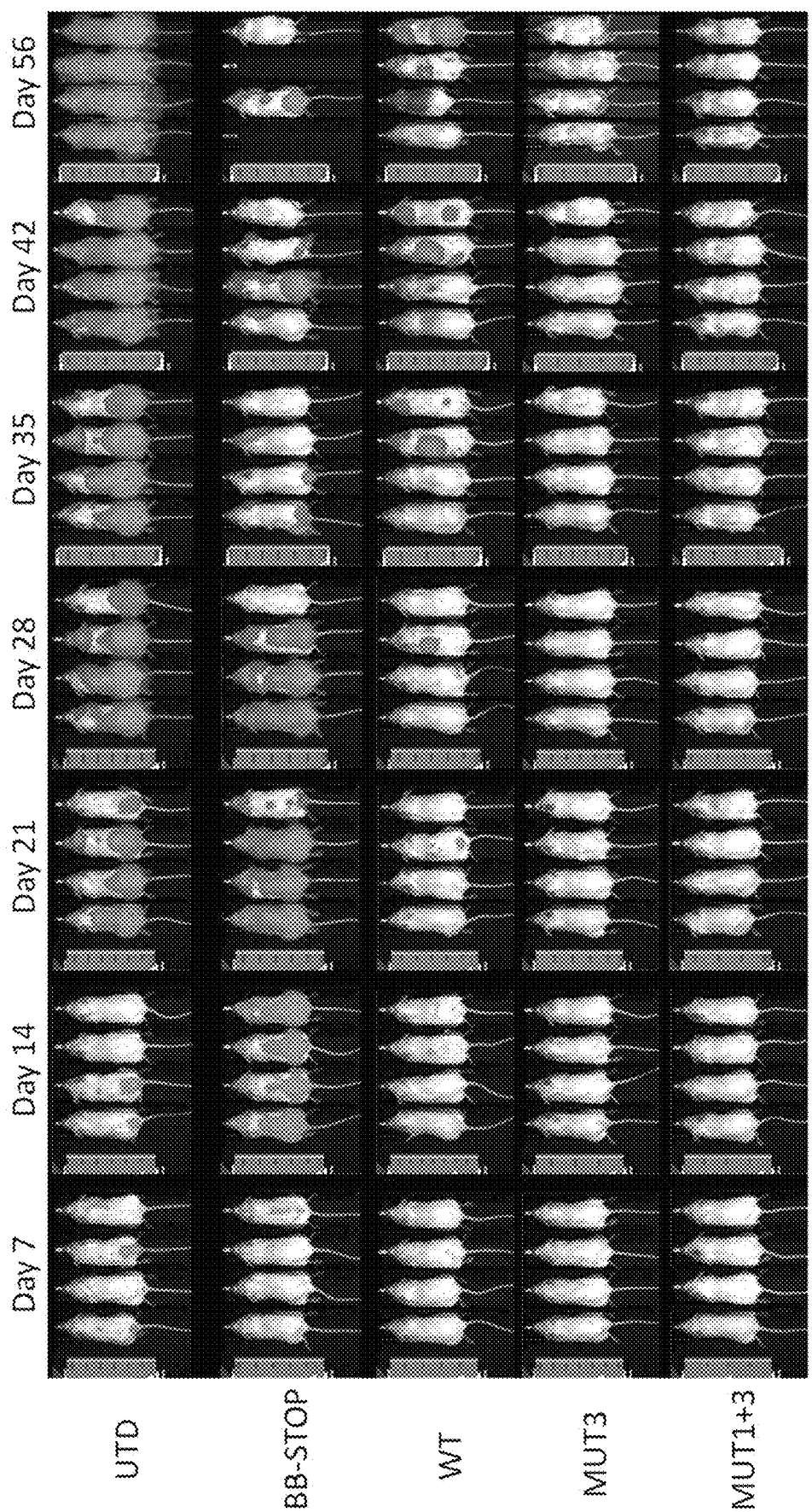
FIG. 31 depicts images of tumor burden in mice at the indicated time points.
Figure 32:
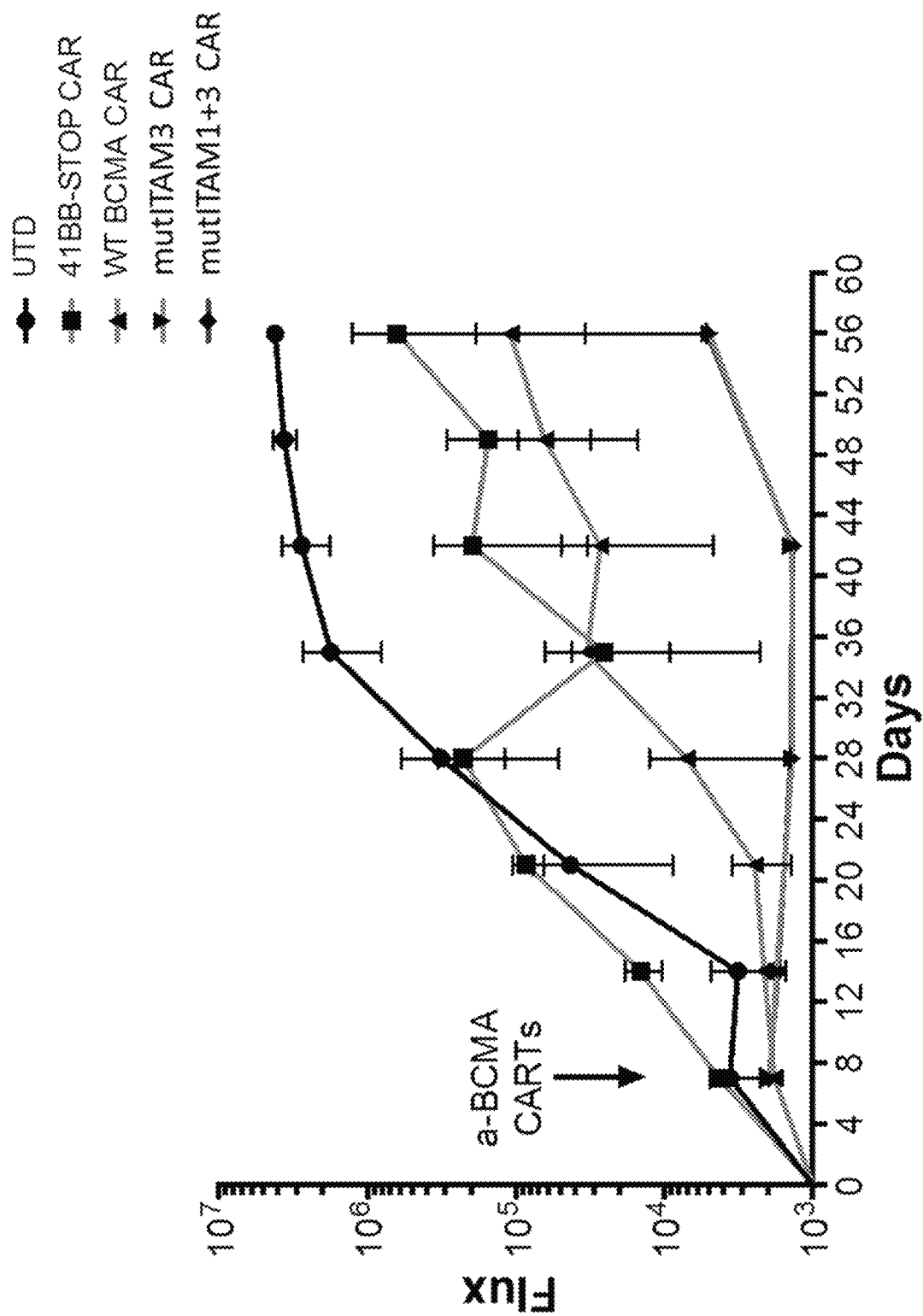
FIG. 32 depicts a graph of the tumor burden in mice at the indicated time points.
Figure 33:
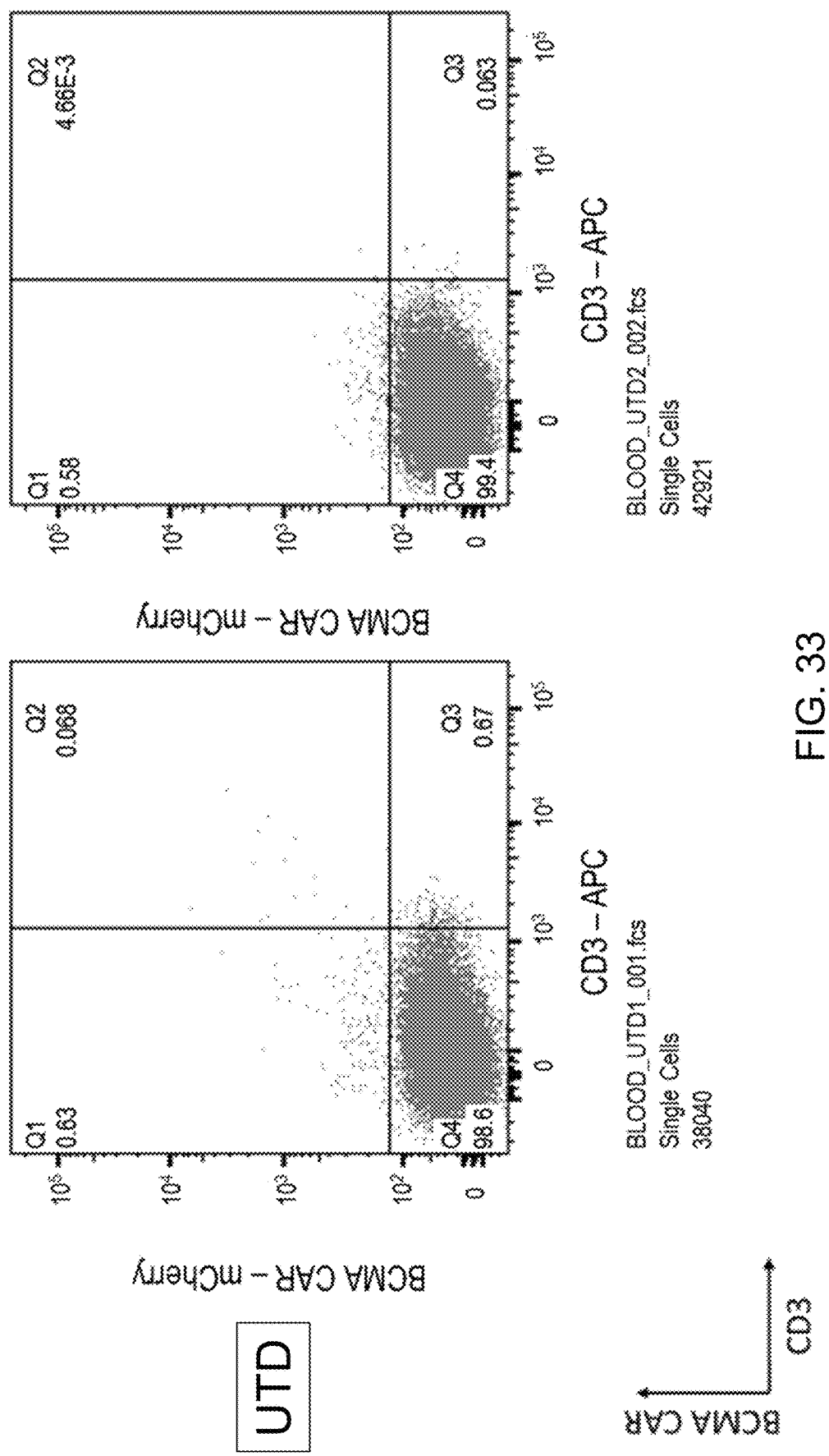
FIG. 33 depicts graphs of analysis of blood samples taken from mice 64 days after CAR T infusion.
Figure 33:
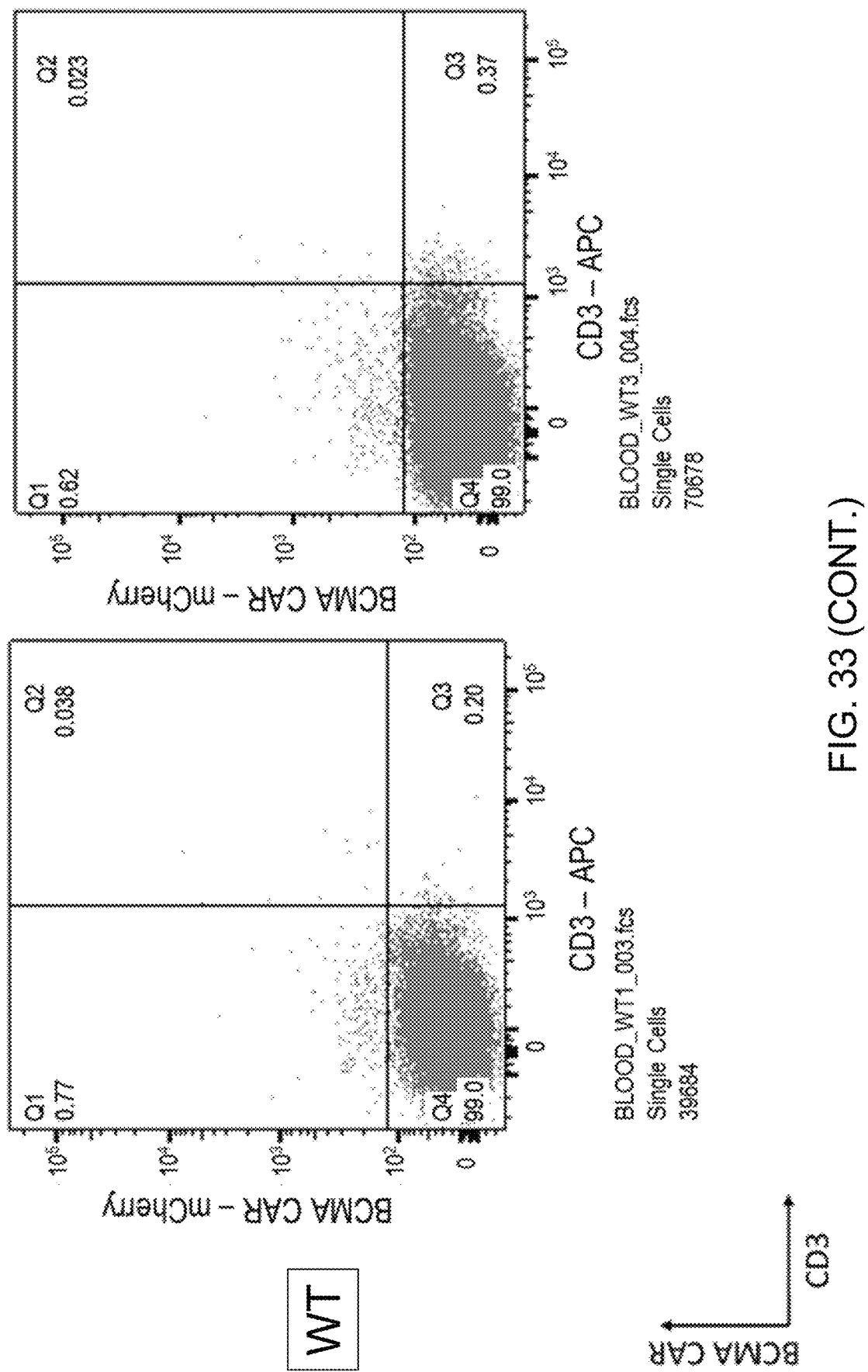
Figure 33:
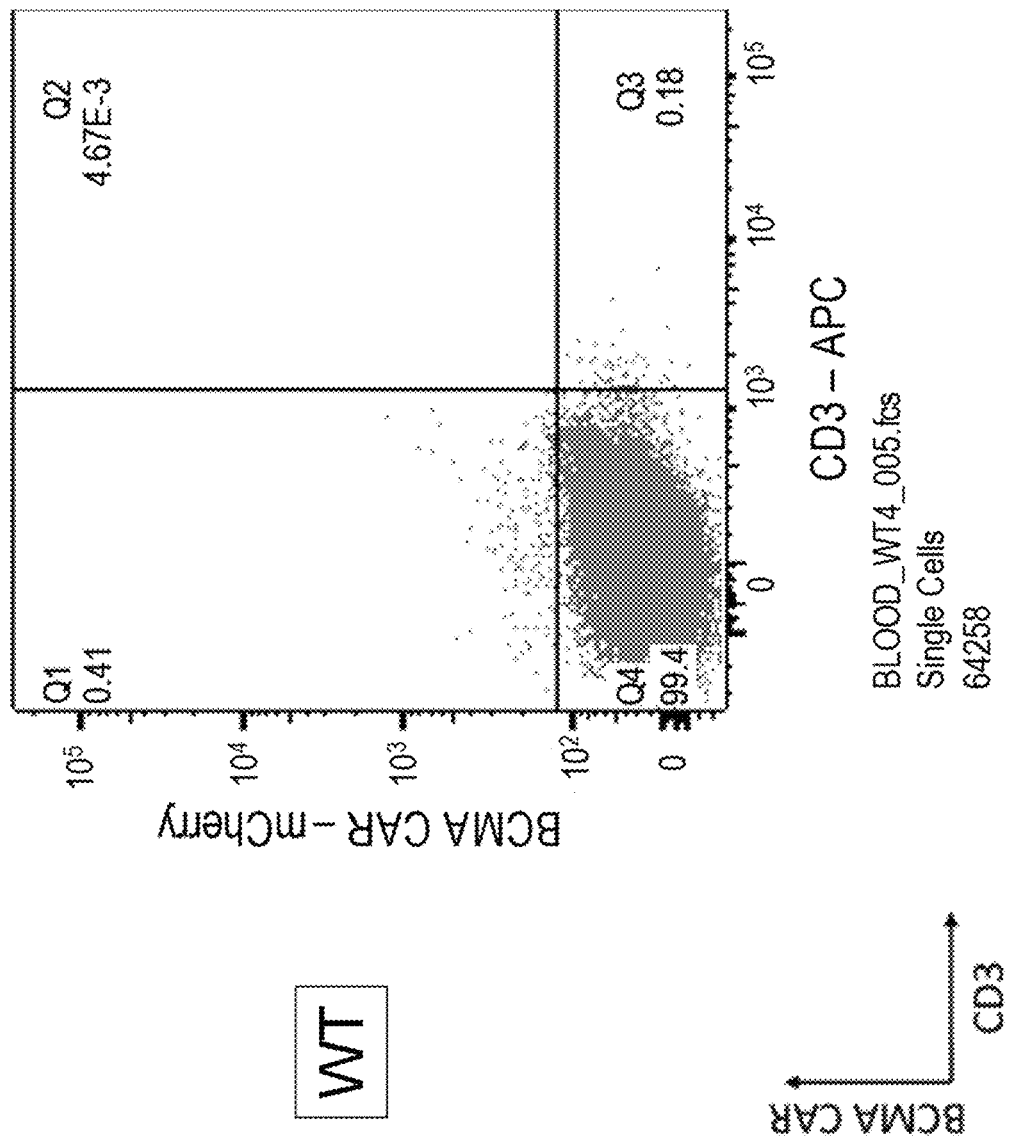
Figure 33:
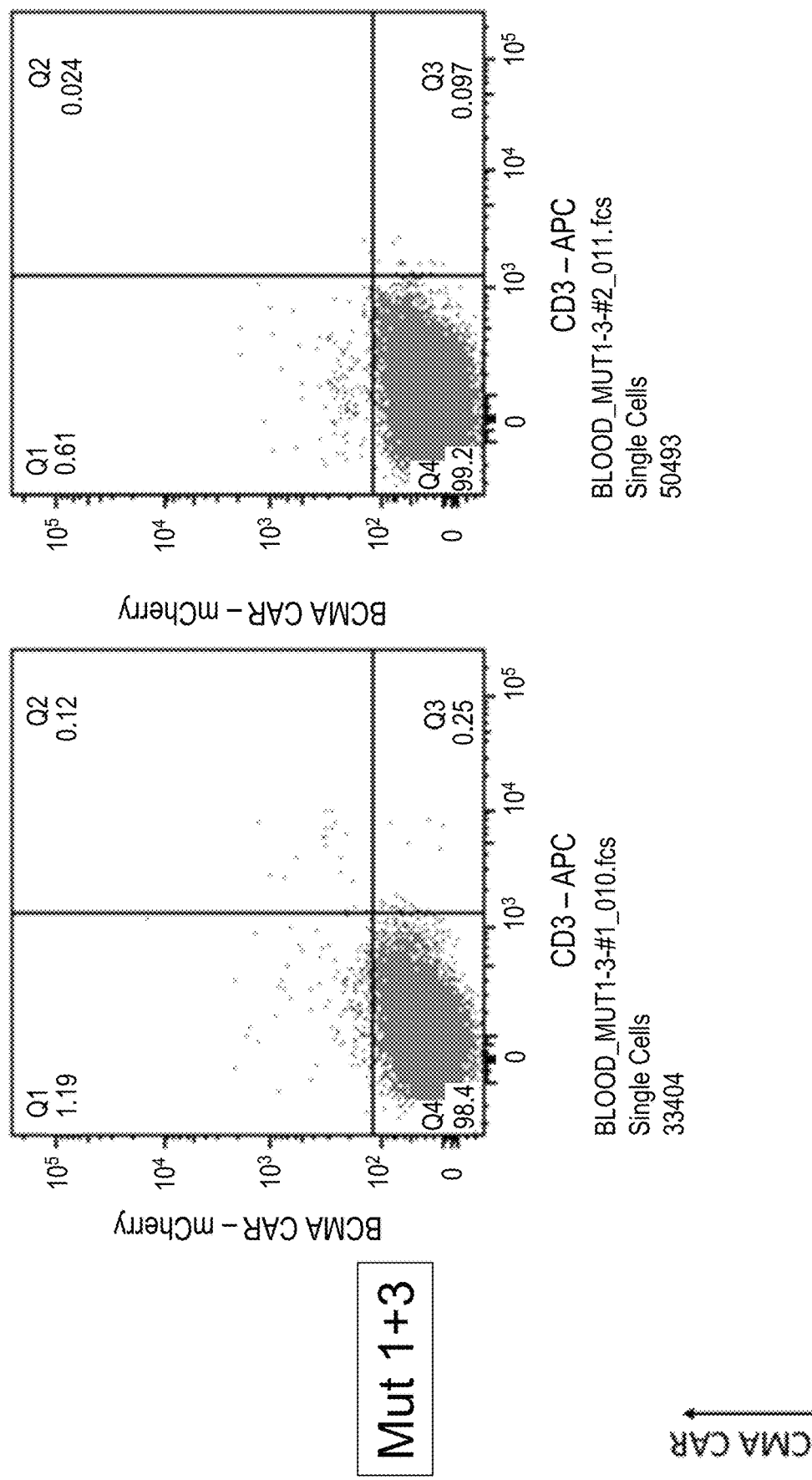
Figure 33:
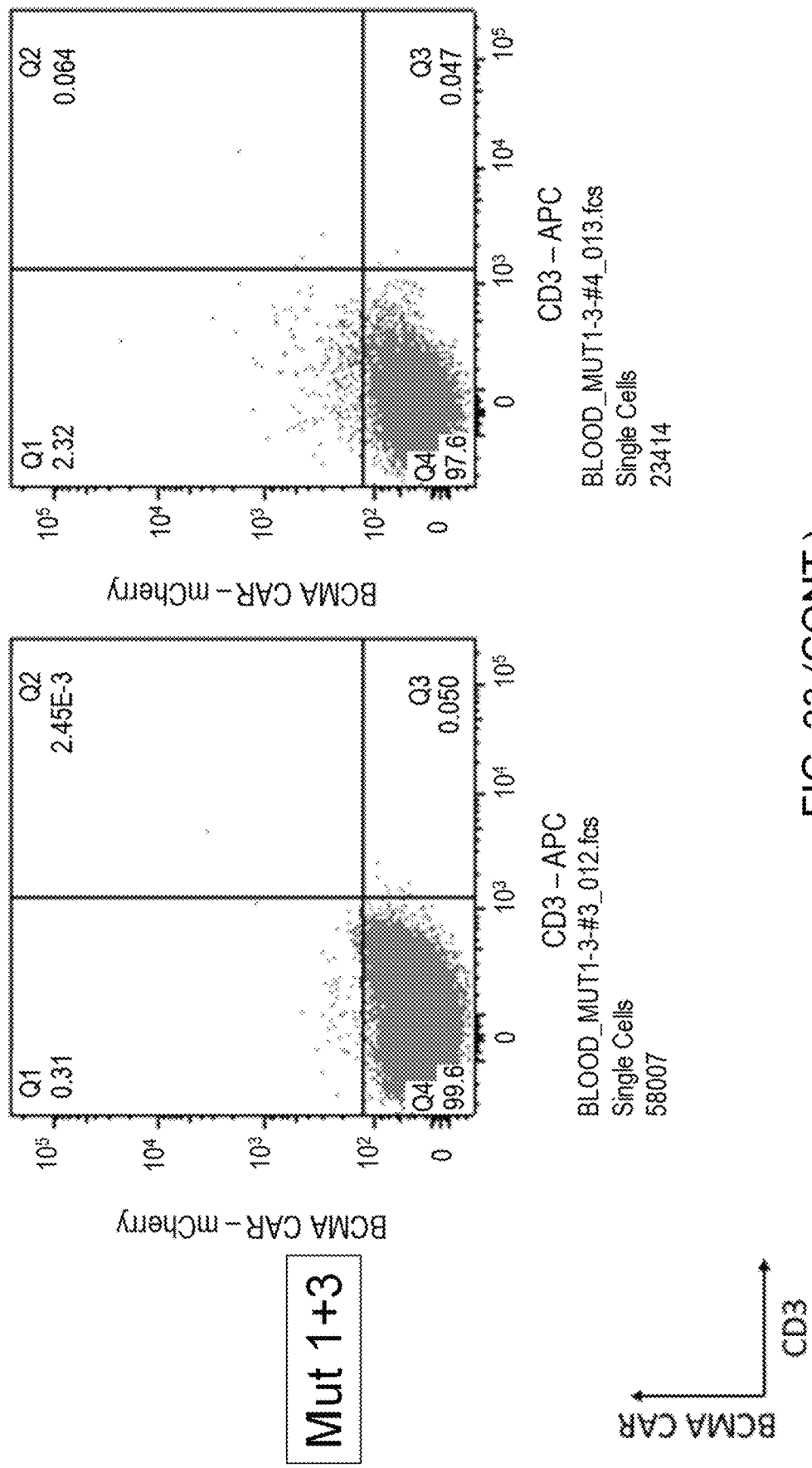
Figure 33:
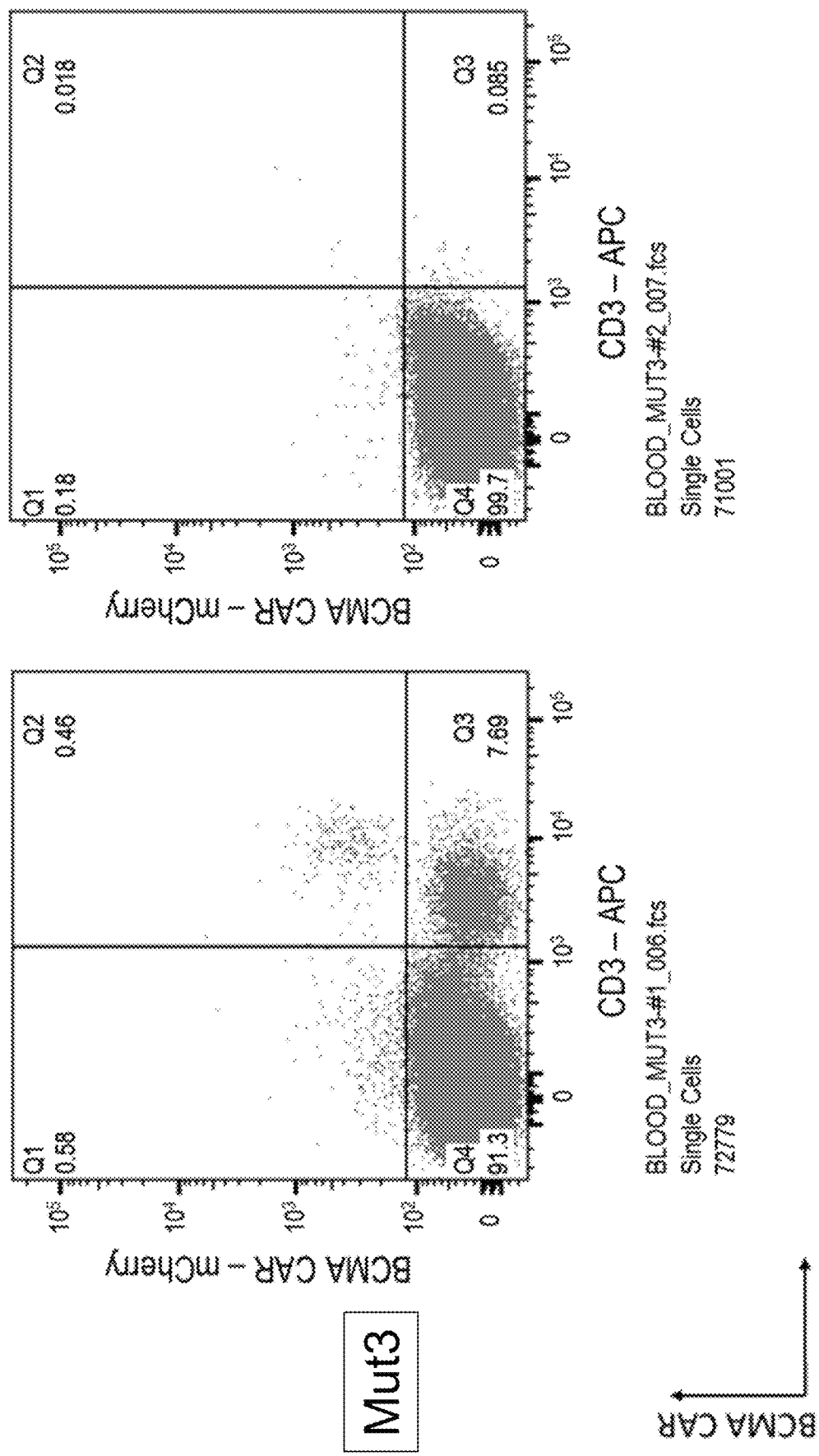
Figure 33:
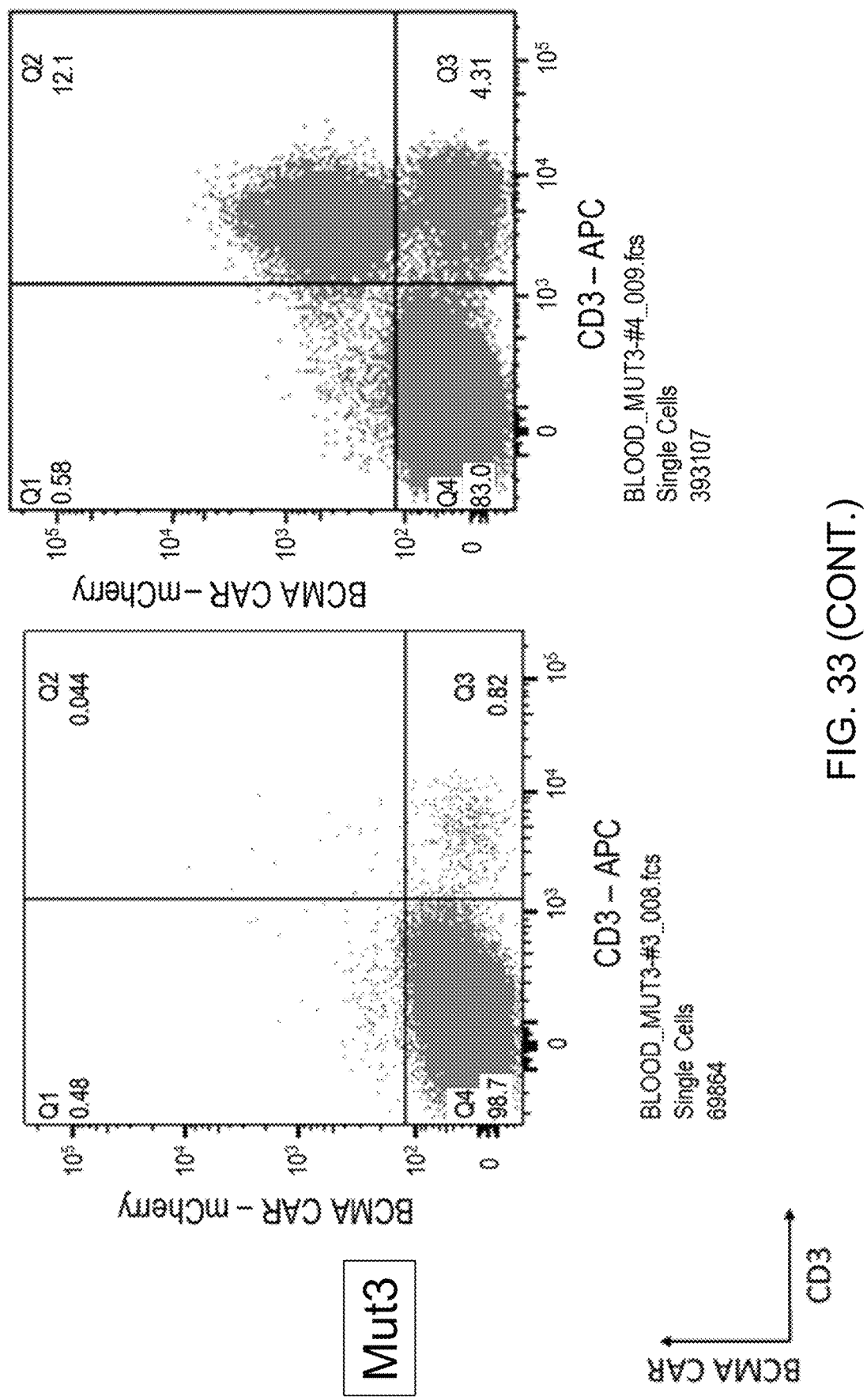

In vivo cytotoxicity was tested using 20 NSG mice (4 mice/condition) (FIG. 30). All mice were injected with 1e6 U266 cells i.v. on day 0. Anti-BCMA ND23 CAR T cells (1e6/mouse) and UTDs were injected at day 7. The CAR T were: UTD; WT; MutITAM3; MutITAM1+3; and BB-Stop. Mice were imaged every week to analyze tumor burden (FIG. 31; FIG. 32). At day 64, the mice were bled and analyzed for levels of anti-BCMA positive/CD3 positive cells (FIG. 33).

Example 5

Described herein is the use of genetically modified T cells expressing anti-CD37 chimeric antigen receptor (CAR) to treat CD37 positive malignancies including B cell-NHL. The CAR comprises CD37 binding domain, CD8 transmembrane domain, 4-1 BB costimulatory signaling region, and a CD3ζ signaling domain. In another embodiment, the CD3ζ domain can be replaced with CD3 eta, CD3 theta, and/or other ITAM-containing variants of CD3-related signaling domains. CAR T cells are generated by introducing a lentiviral vector comprising CD37-CAR in primary human T cells. In vitro data demonstrated specific activation, proliferation, and killing of CD37 positive cancer cells by anti-CD37 CAR T cells.

Figure 34:
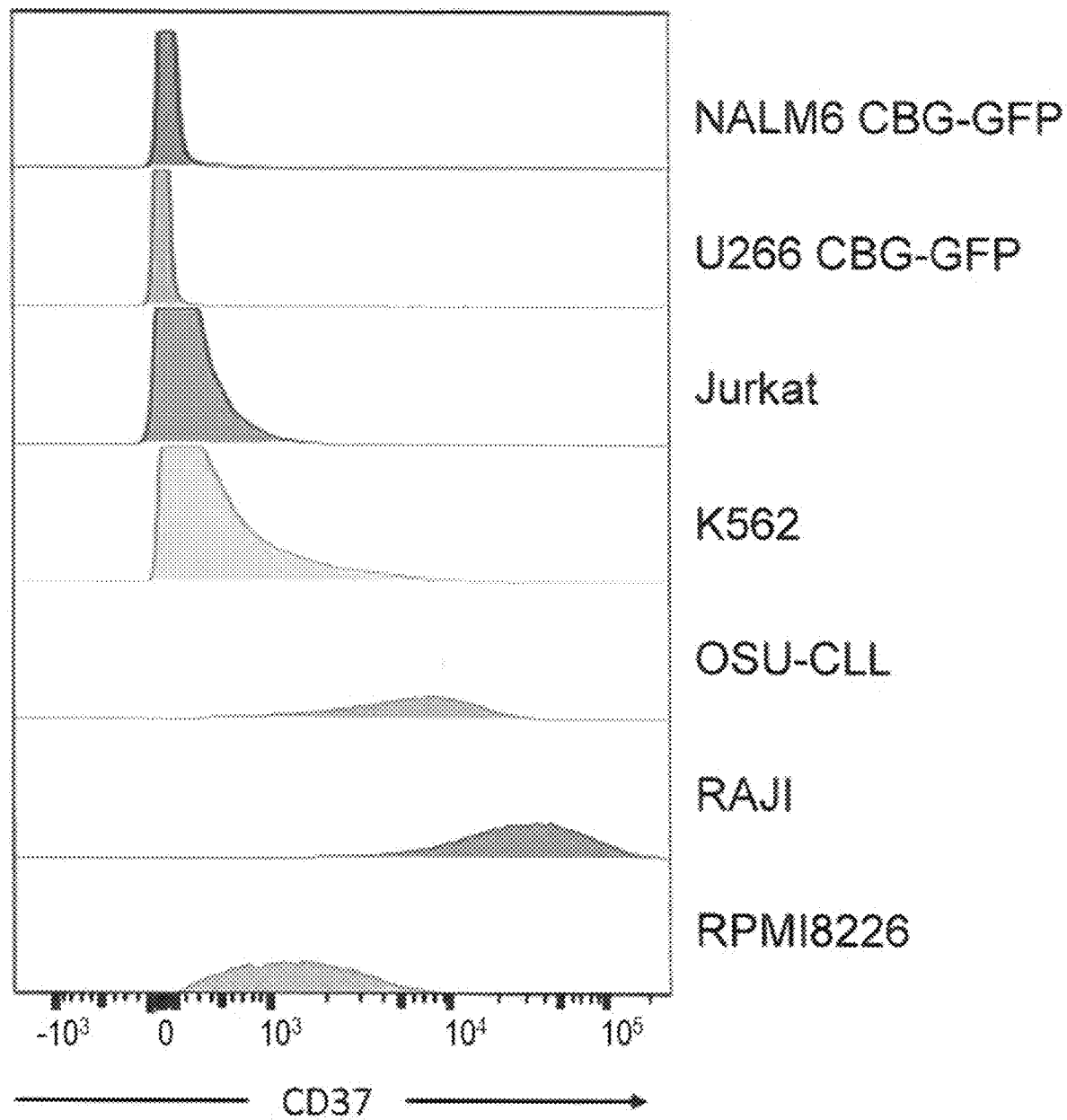
FIG. 34 depicts a graph of CD37 expression in the indicated cells.
Figure 35:
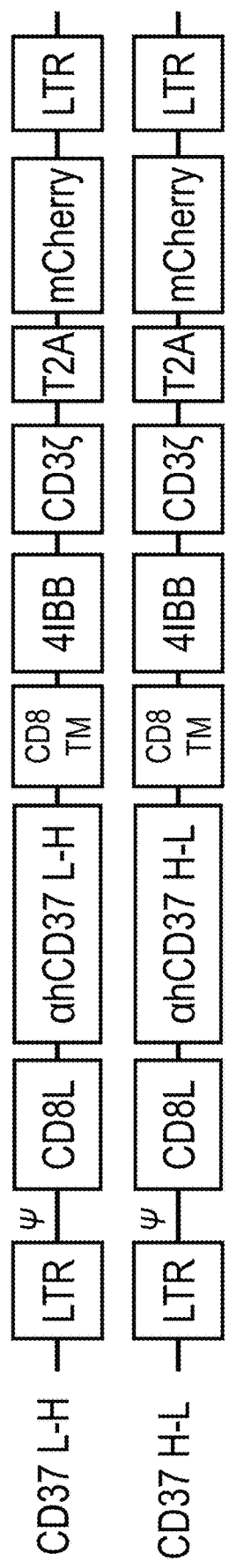
FIG. 35 depicts schematic diagrams of anti-CD37 CARs.
Figure 36:
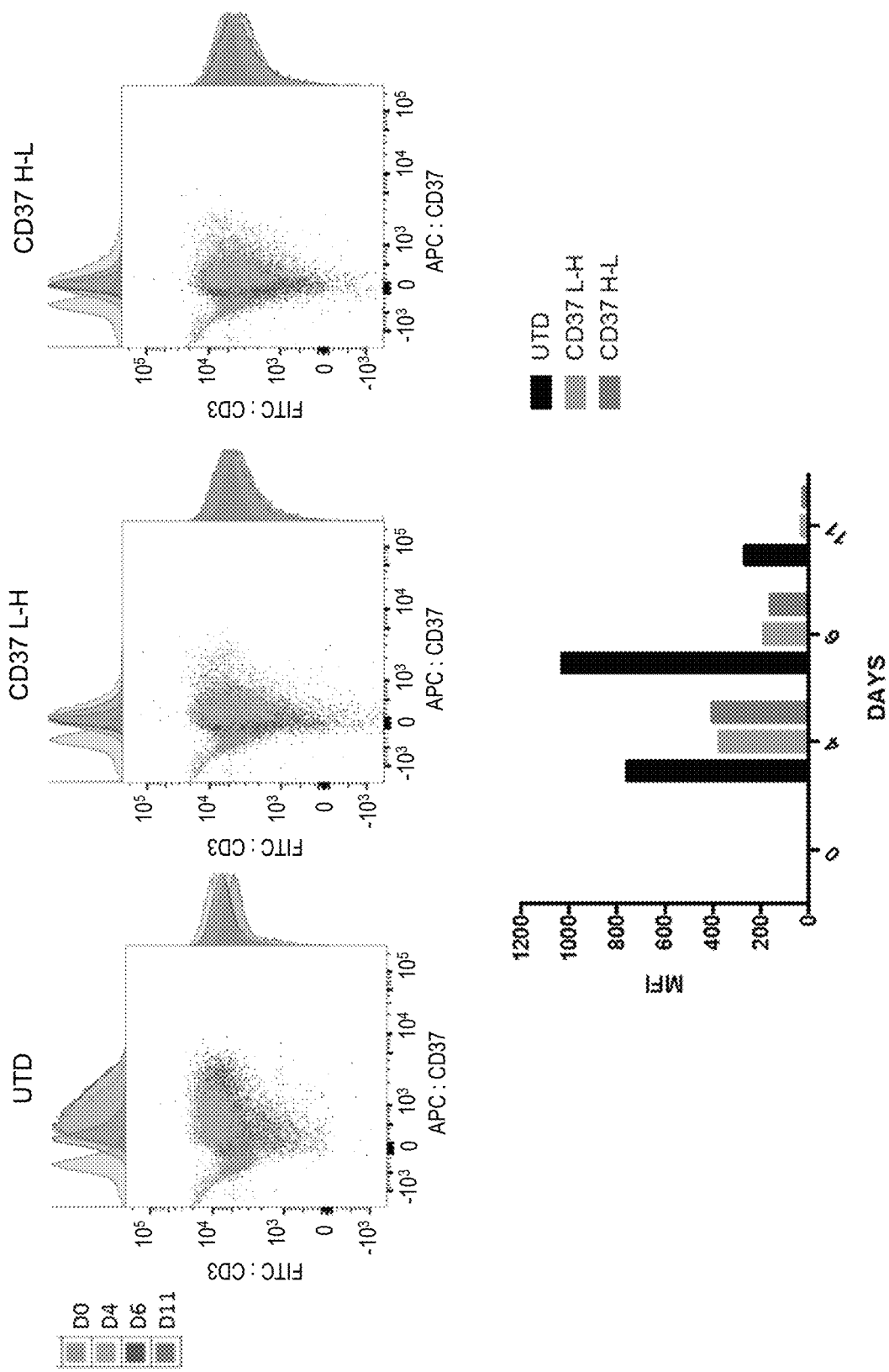
FIG. 36 depicts graphs of anti-CD37 CAR expression
Figure 37:
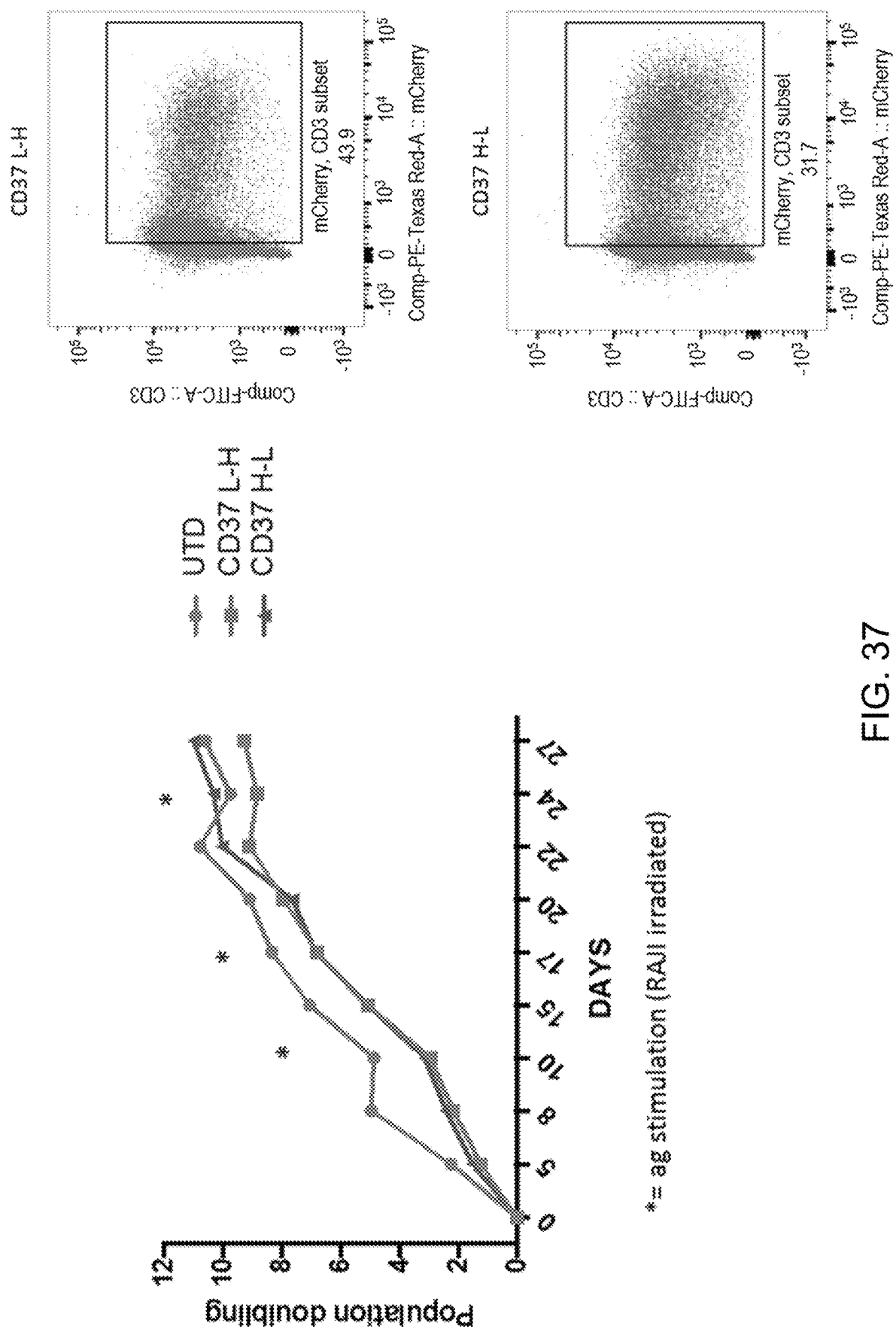
FIG. 37 depicts graphs of expansion of anti-CD37 CAR T cells.
Figure 38:
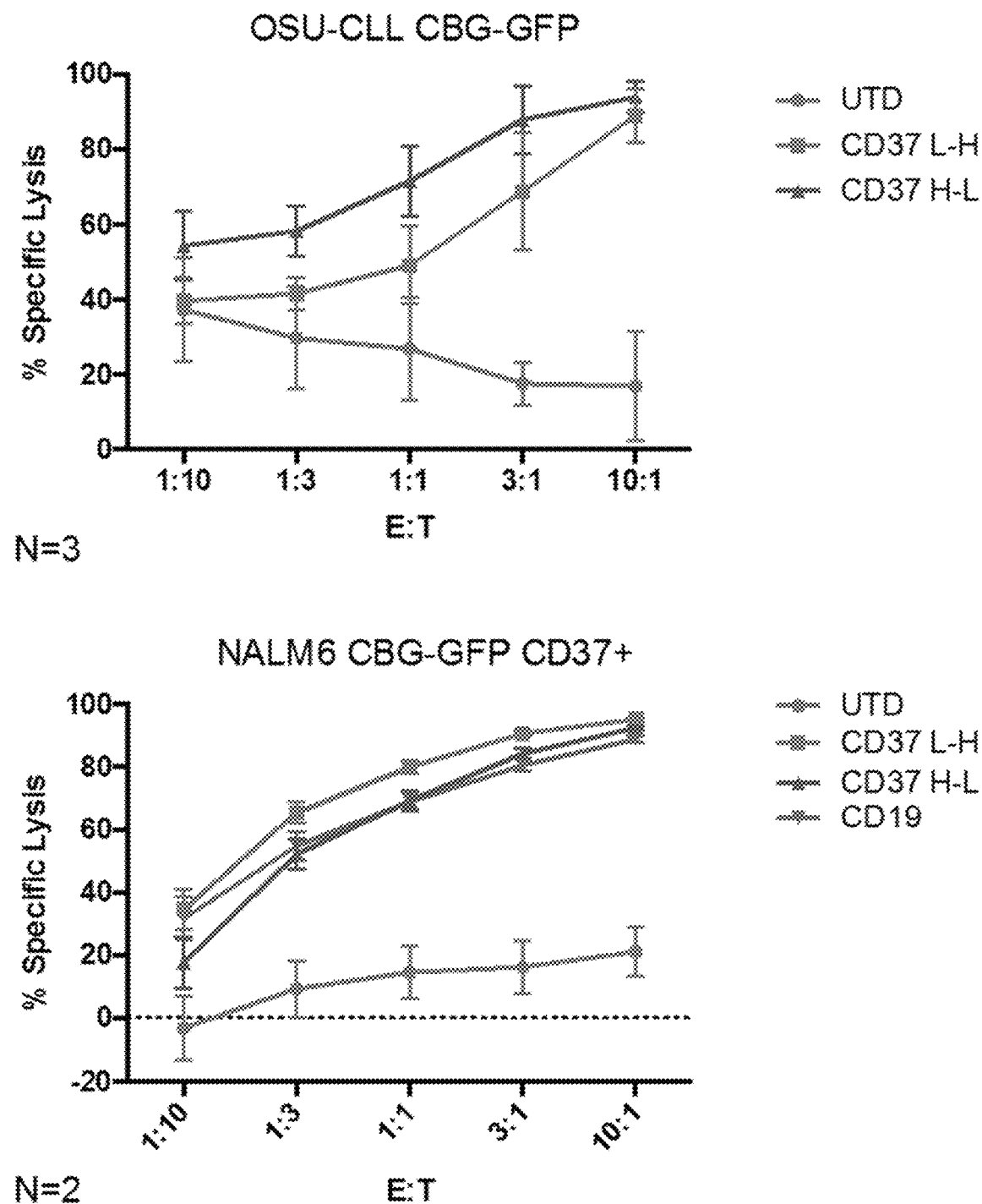
FIG. 38 depicts graphs of a cytotoxicity assay demonstrating that anti-CD37 CAR T cells lyse CD37 positive T cells.
Figure 38:
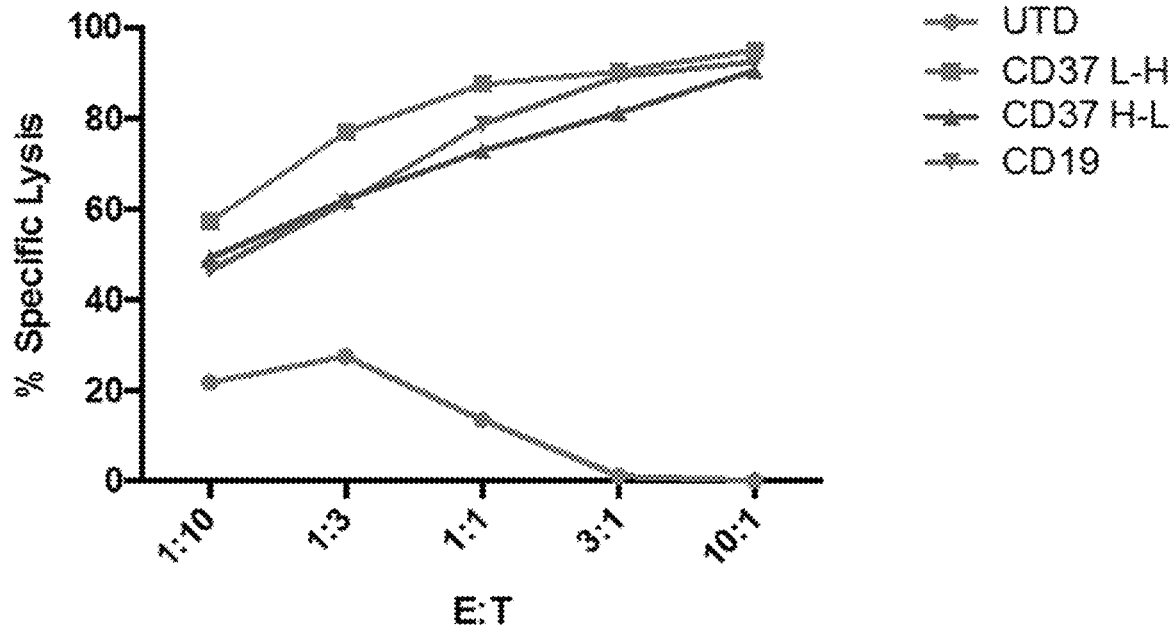
Figure 38:
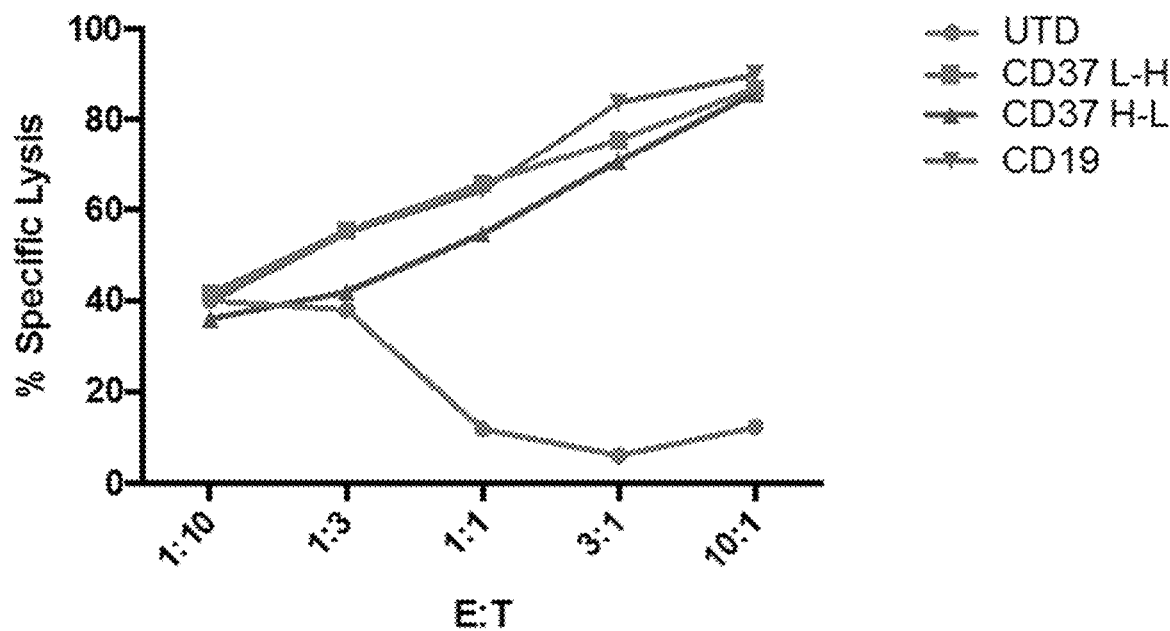
Figure 39:
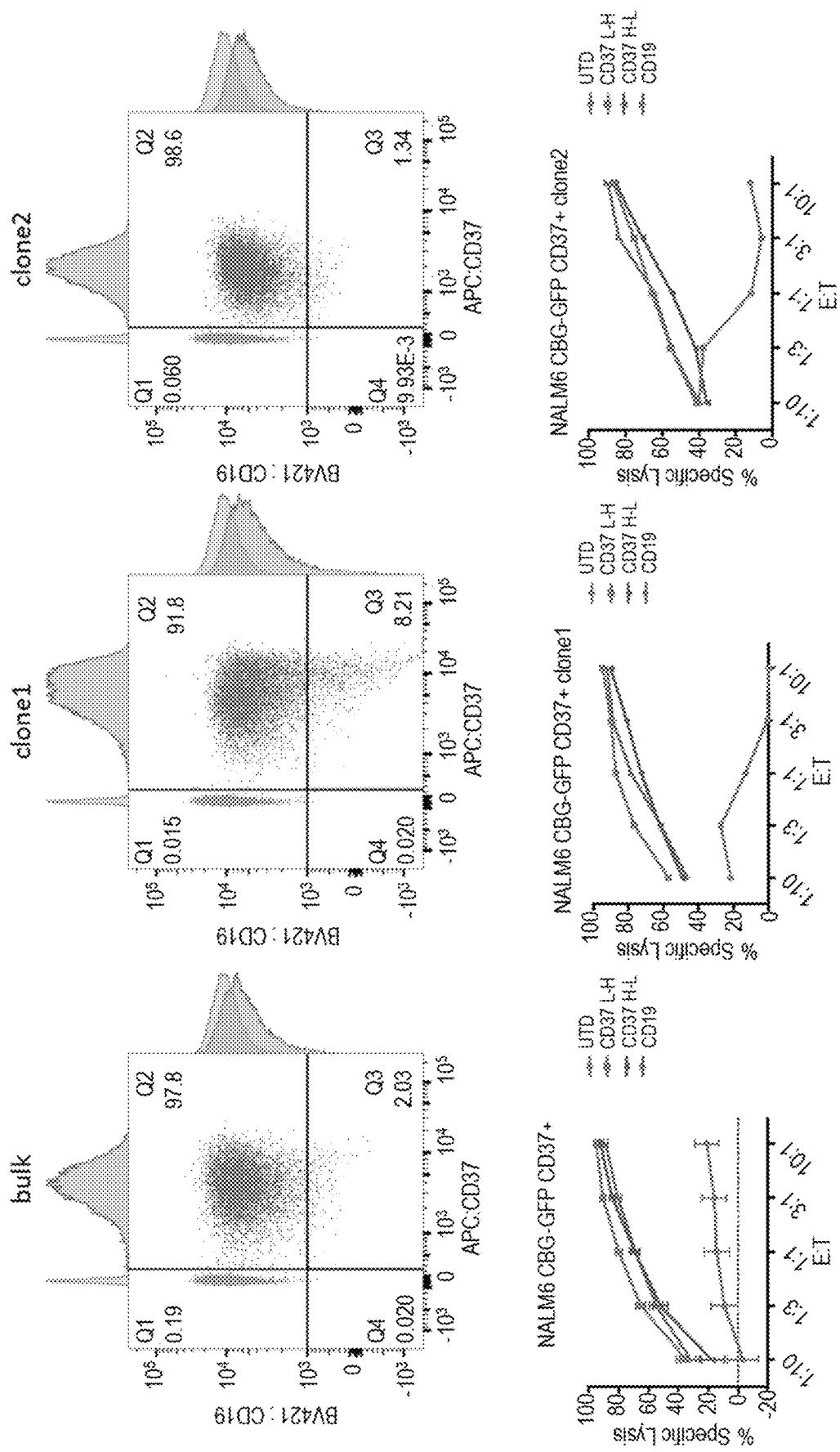
FIG. 39 depicts graphs of cytotoxicity assays and expression analysis of target clones.
Figure 40:
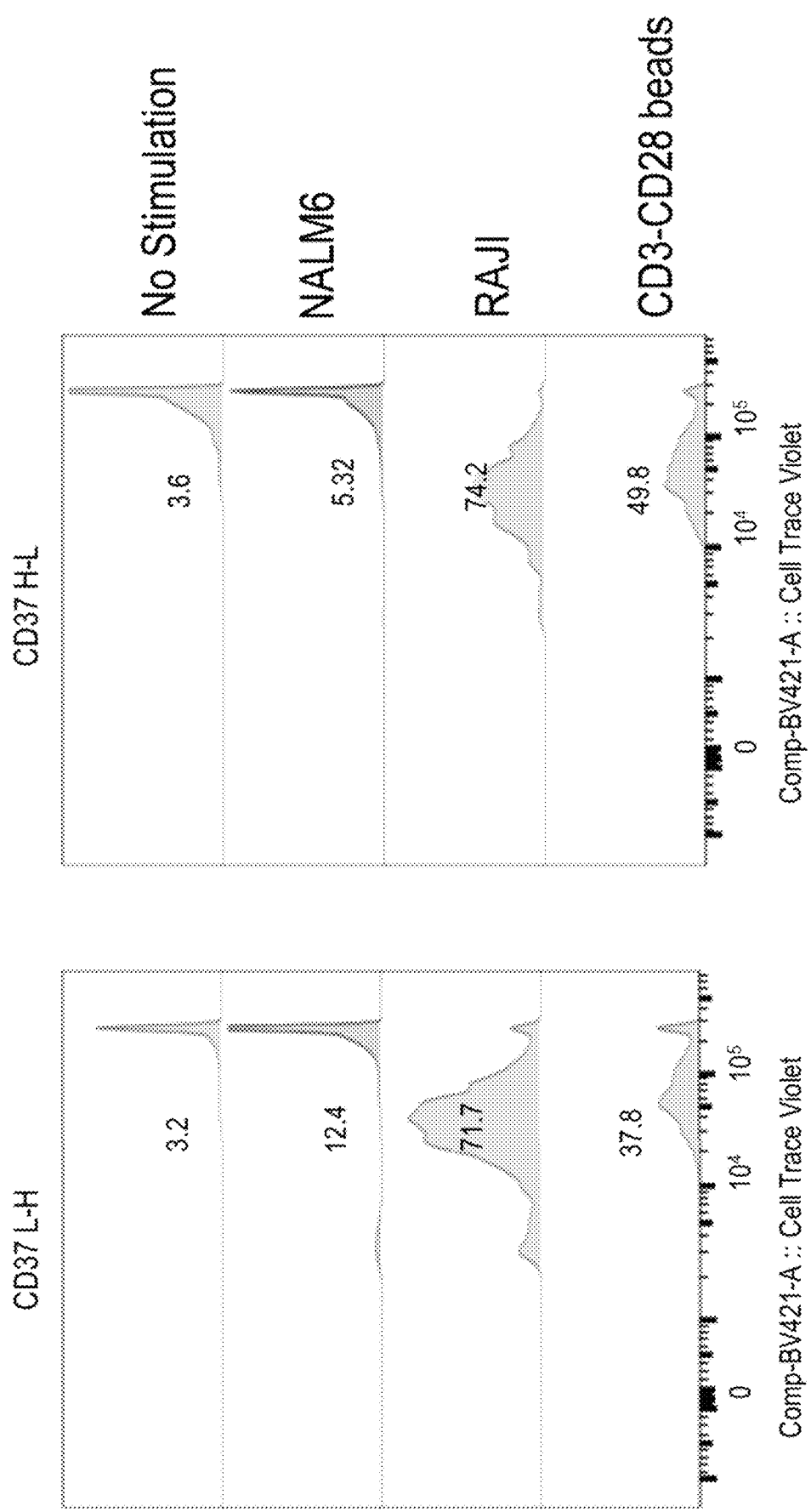
FIG. 40 depicts graphs of cell proliferation following stimulation of anti-CD37 CAR T cells with CD37. Assay was begun on day 17 and FACS was gated for CAR+.
Figure 40:
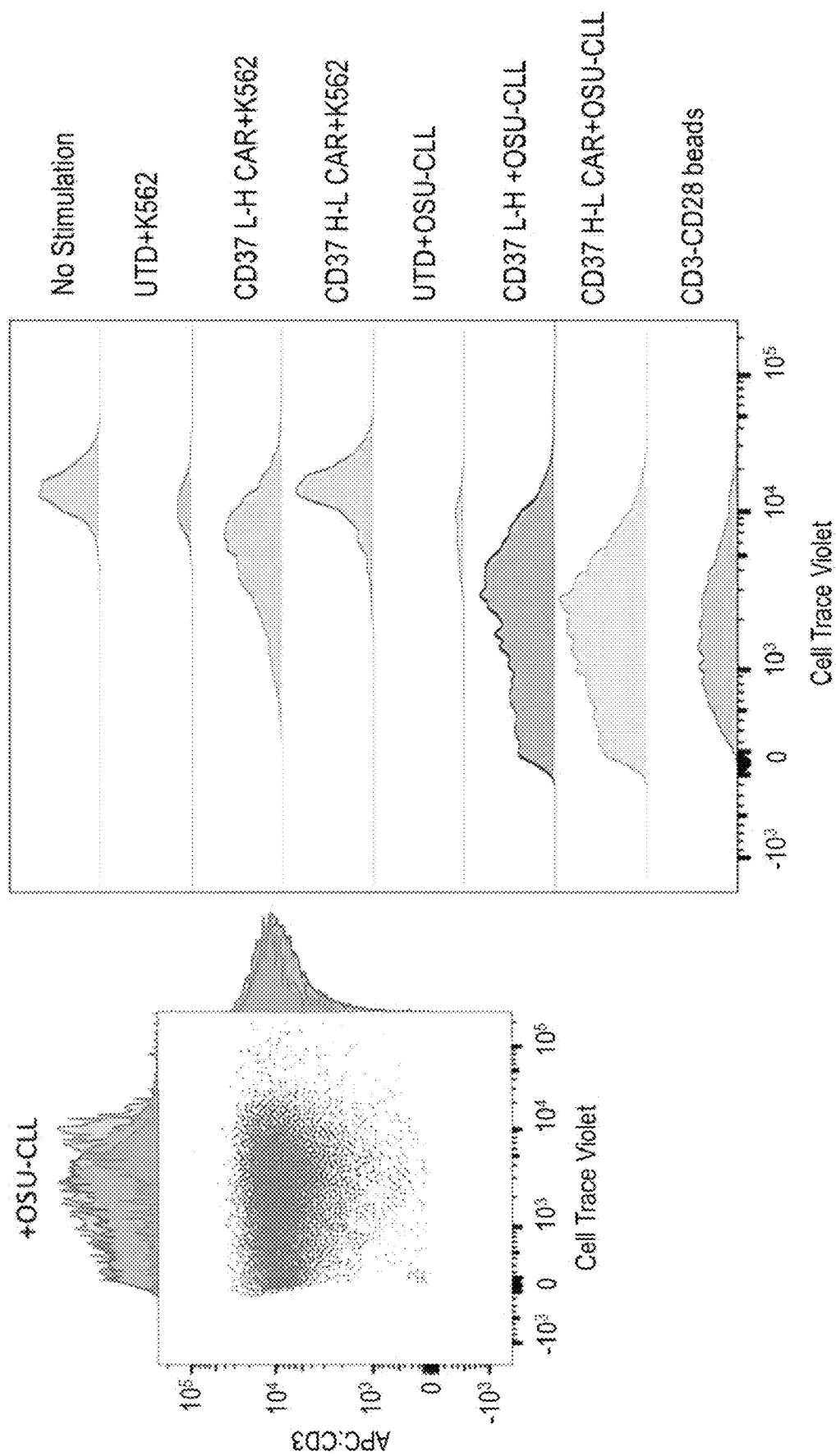

CD37 is detectable in certain cancer-related cell lines (FIG. 34). Anti-CD37 CARs were constructed (FIG. 35) and expressed in T cells (FIG. 36). Expansion of the T cells was measured (FIG. 37), and their ability to lyse target cancer cells demonstrated (FIG. 38). Anti-CD37 demonstrated proliferation in response to CD37 stimulation (FIG. 40).

Figure 41:
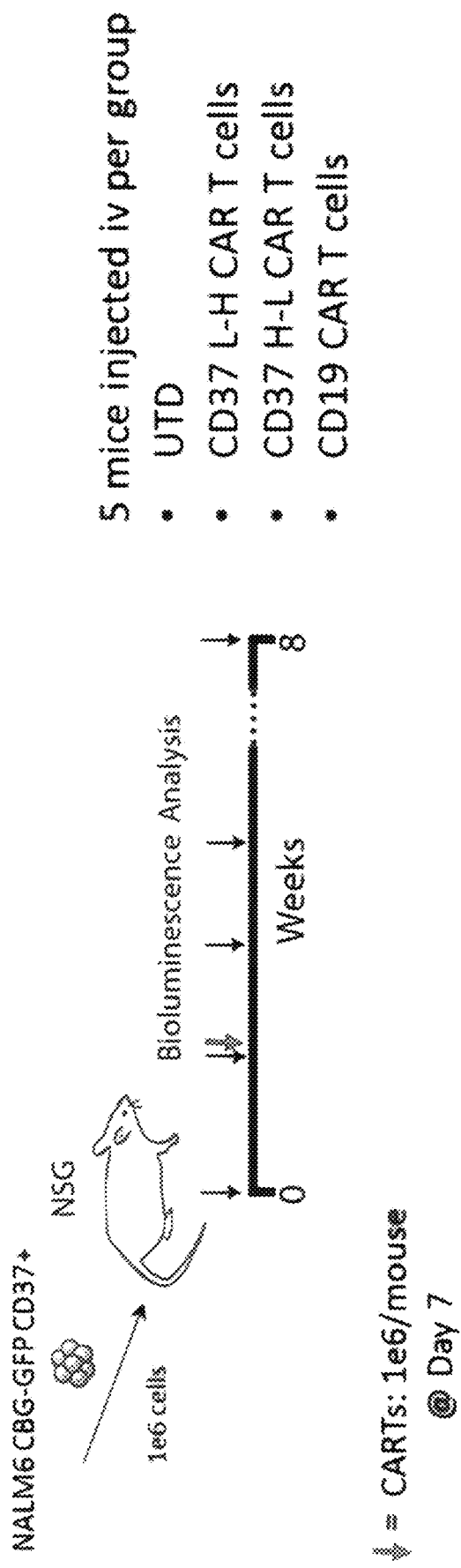
FIG. 41 depicts a schematic of experimental design for anti-CD37 CAR T cells engraftment and tumor clearance in NSG mice.
Figure 42:
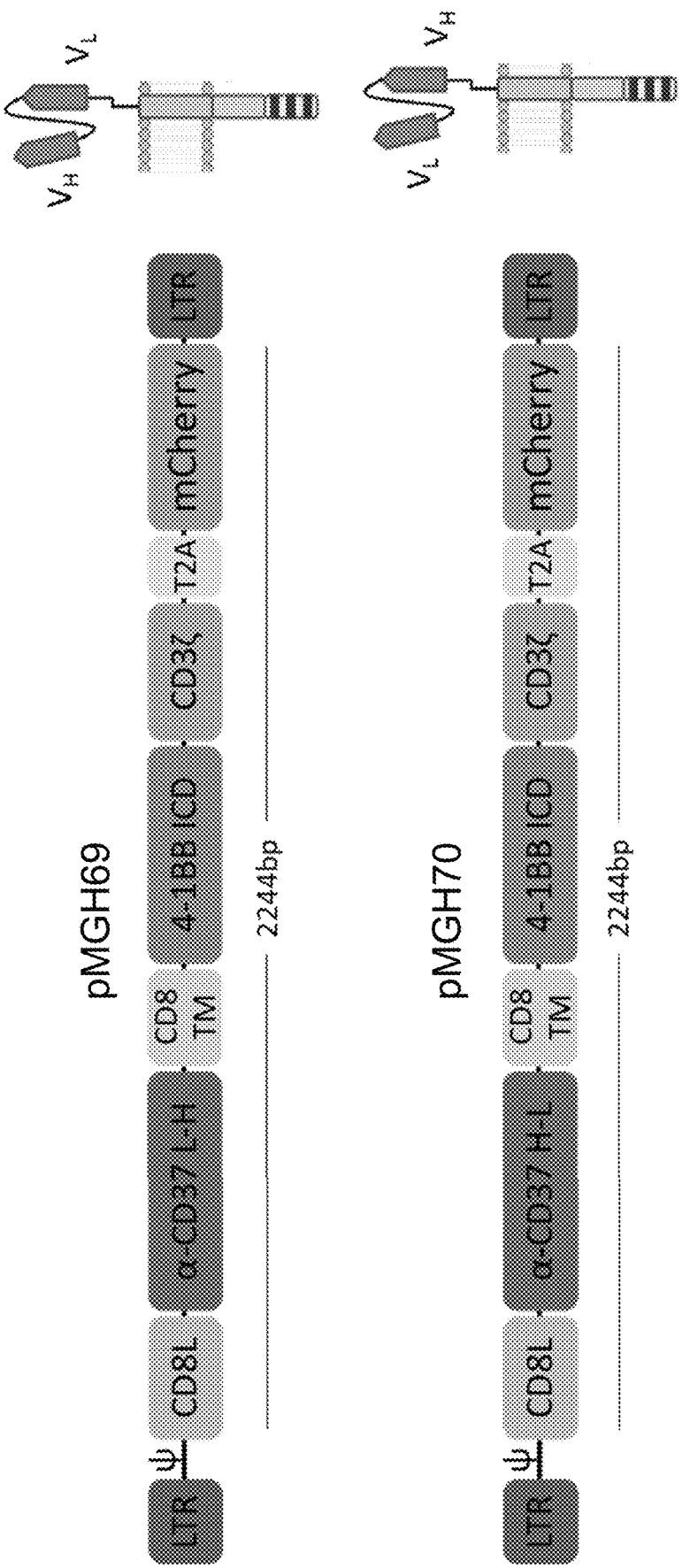
FIG. 42 depicts schematics of CAR design. pMGH69 (top construct): anti CD37scFv with light-heavy chains configuration. pMGH70 (bottom construct): anti CD37scFv with heavy—light chains configuration.

Anti-CD37 CAR Ts can be administered to mice to demonstrate tumor clearance in vivo (FIG. 41).

Example 6

Anti-CD37 chimeric antigen receptor T cells: a new potential therapeutic option for B-cell malignancies.

CD37 is a tetraspanin expressed on mature B cells but absent on early progenitors or terminally differentiated plasma cells. CD37 is highly expressed on malignant B cells in non-Hodgkin lymphomas (NHL), including mantle cell lymphoma (MCL), diffuse large B-cell lymphoma (DLBCL), follicular lymphoma (FL), Burkitt lymphoma and B-cell chronic lymphocytic leukemia (CLL); thus, CD37 represents a promising target for B-cell malignancies, particularly for variants that escape existing therapies targeting the common B cell antigens CD19 and CD20.

Described herein is an anti-CD37 CAR (CAR-37) for the treatment of B-cell malignancies. Specifically, described herein is a second-generation CAR, encoded by a lentiviral vector and bearing a 4-1BB costimulatory domain. Two different orientations of a humanized murine antibody-derived single-chain variable fragment ($V_L$-$V_H$ or $V_H$—$V_L$) were tested and a and pre-clinical data panel is provided herein.

Results

In vitro cytotoxic activity of CAR T-37 cells was evaluated by co-culturing CAR T-37 cells with CD37-expressing human tumor cell lines (RAJI, OSU-CLL and JEKO-1) at different effector to target ratios. CD37-directed CAR T cells demonstrated antigen-specific activation, proliferation, cytokine production, and cytotoxic activity in vitro in multiple models of B cell malignancy. Next, the anti-lymphoma efficacy was assessed in vivo in a mantle cell lymphoma model. CAR-37 treatment eliminated the tumor cells within 2 weeks, and mice maintained durable remissions. CAR T cells were detectable in the blood of mice after 7 days of injection. Ongoing studies are evaluating the long term persistence of CAR T cells in mice.

Discussion

Taken together these results demonstrate that T cells expressing anti-CD37 CAR have substantial activity in vitro and in vivo against B cell malignancies. These findings indicated that CD37-CAR T cells are a novel potential therapeutic agent for the treatment of patients with CD37 expressing tumors.

Example 7

Figure 43:
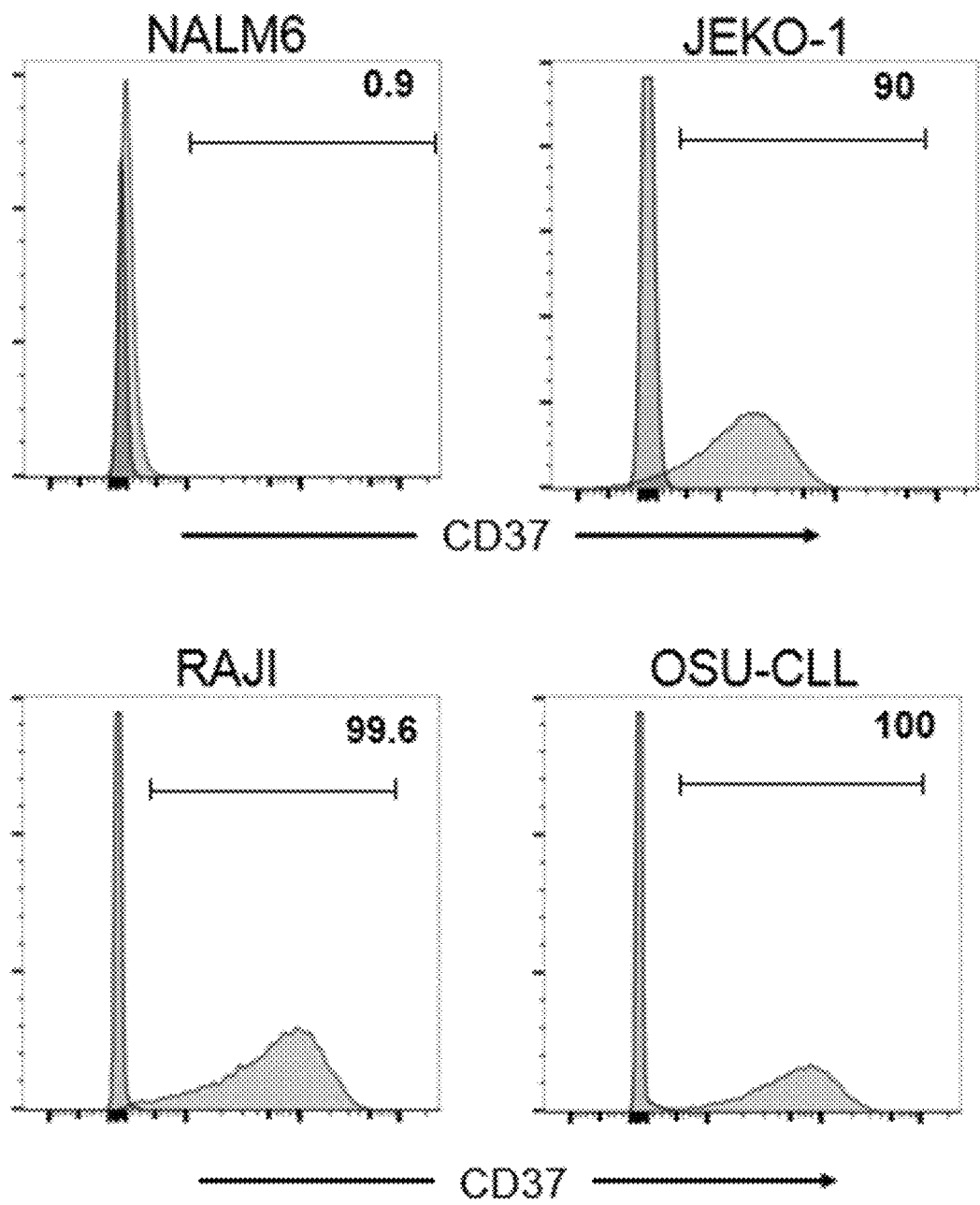
FIG. 43 depicts graphs of expression of CD37 on cancer cell lines by flow. Jeko-1 (MCL), RAJI (Burkitt lymphoma), and OSU-CLL (CLL) clearly express high level of CD37. NALM6 cells (ALL) do not express CD37.

CD37 is highly expressed in B cell malignancies (FIG. 43). Anti-CD37 CARs were constructed using the humanized anti-CD37 mAb BI836826 (Boehringer Ingelheim) and cloned into a lentivirus vector. Intracellular domains are 41BB (CD137) ICD linked to CD3zeta.

Figure 44:
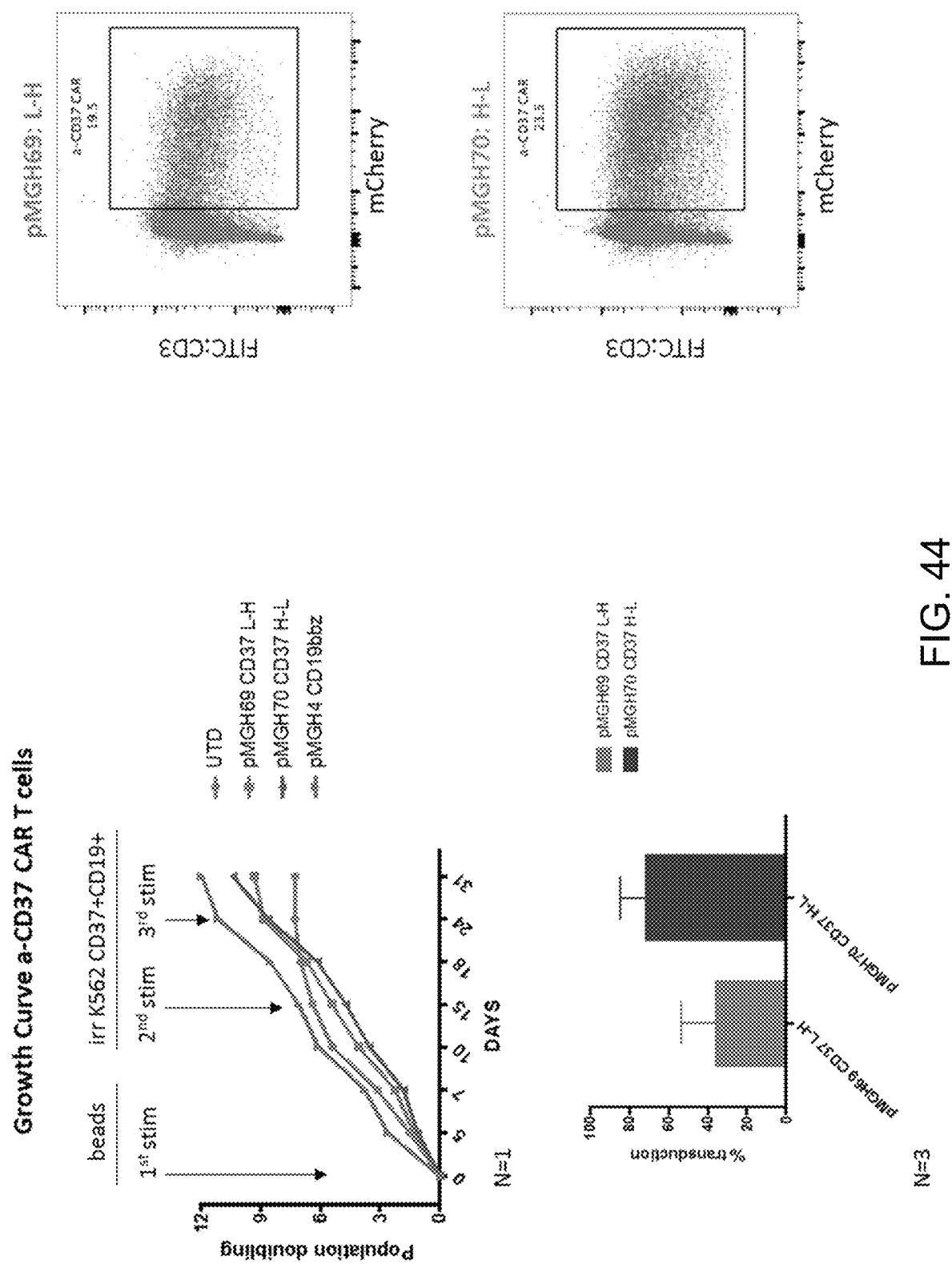
FIG. 44 demonstrates the generation and expansion of anti-CD37 CAR T cells. The graph on the left shows the growth curve for anti-CD37-CAR T cells. Starting at day 0 the T cells are expanded in vitro using Dyna-beads until day 10, then T cell are stimulated with antigen, in this case with irradiated K562 expressing CD37 and CD19. Graph on the right shows the transduction efficiency of this particular batch of CAR T cells at day 10 of culture (19.5% and 23.5 of the total cells are CAR Ts). Bottom left: transduction efficiency of 3 different normal donors.
Figure 45:
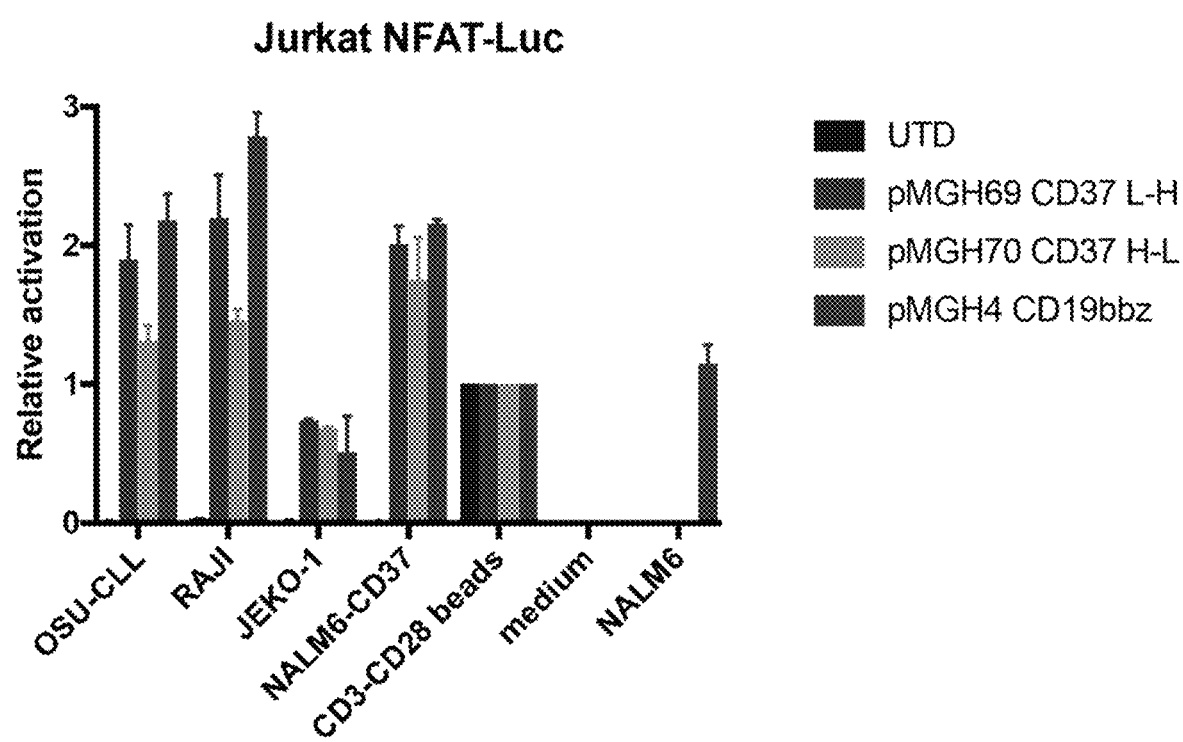
FIG. 45 demonstrates antigen specific activation. Jurkat-NFAT reporter cell line transduced with CD37-CAR constructs is activated in the presence of target cells (RAJI, OSU-CLL, Jeko-1, NALM-CD37) but not by NALM6 or media alone.
Figure 46:
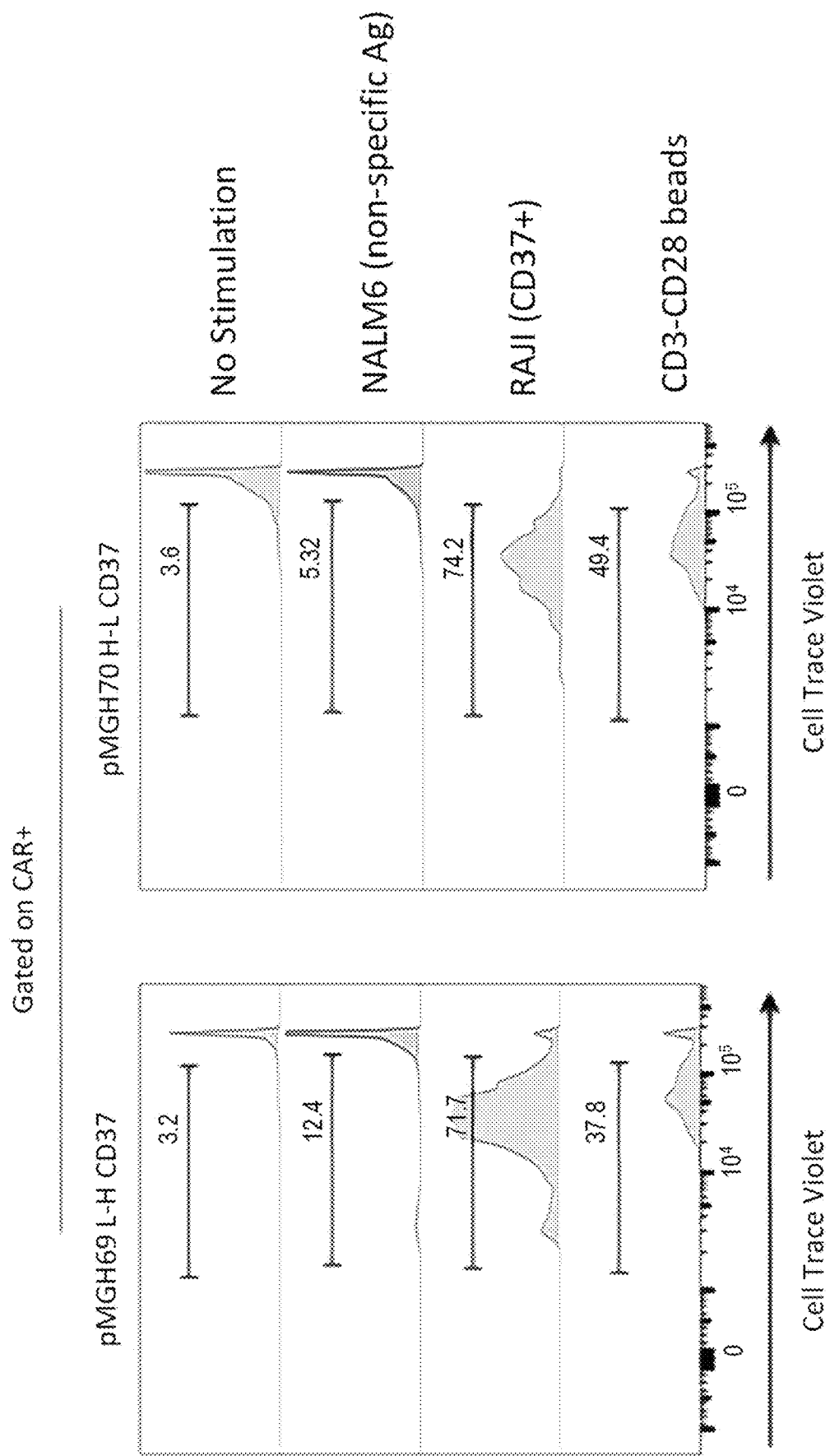
FIG. 46 depicts proliferation capacity of CAR T cells. Proliferation assay: CAR T cells are labeled with Cell-Trace™ Violet and co-cultured in presence or absence of antigen. The figure depicts CAR T cells expansion in the presence of CD37+ cells but not with cells negative for CD37.

The anti-CD37 CAR T cells were demonstrated to expand upon stimulation (FIG. 44) and activate (FIG. 45). Anti-CD37 CAR Ts expanded upon stimulation with the target antigen (FIG. 46).

Figure 47:
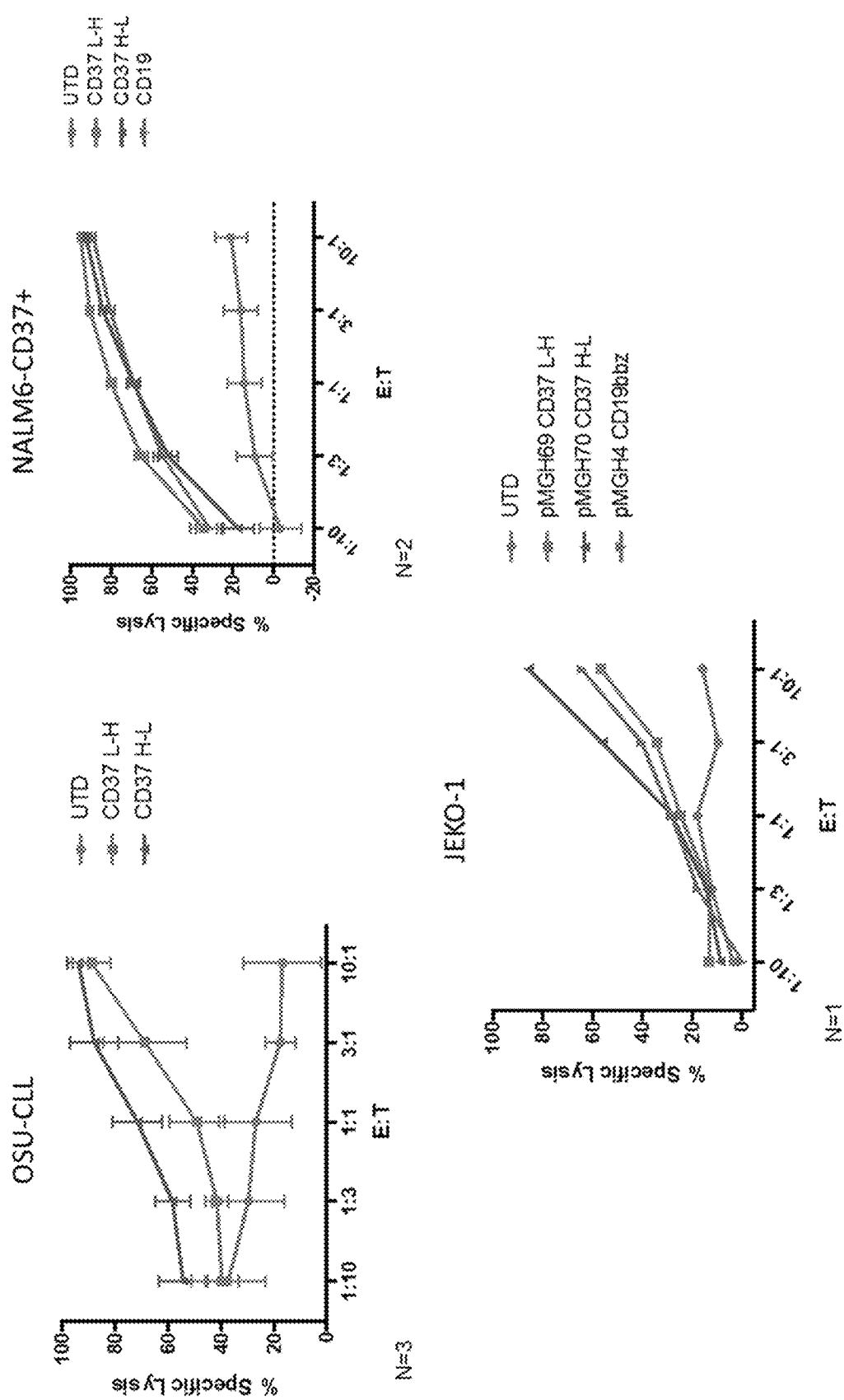
FIG. 47 demonstrates in vitro tumor cell killing. Cytotoxicity at 16 hours of CD37-CAR T, CD19-CAR or control T cells (UTD) when co-cultured at different E:T ratios with tumor cells. Increasing concentration of either CD37-CAR T or CAR T-19 led to similar levels of killing of target cells, while no killing was observed in the control group (UTD).
Figure 48:
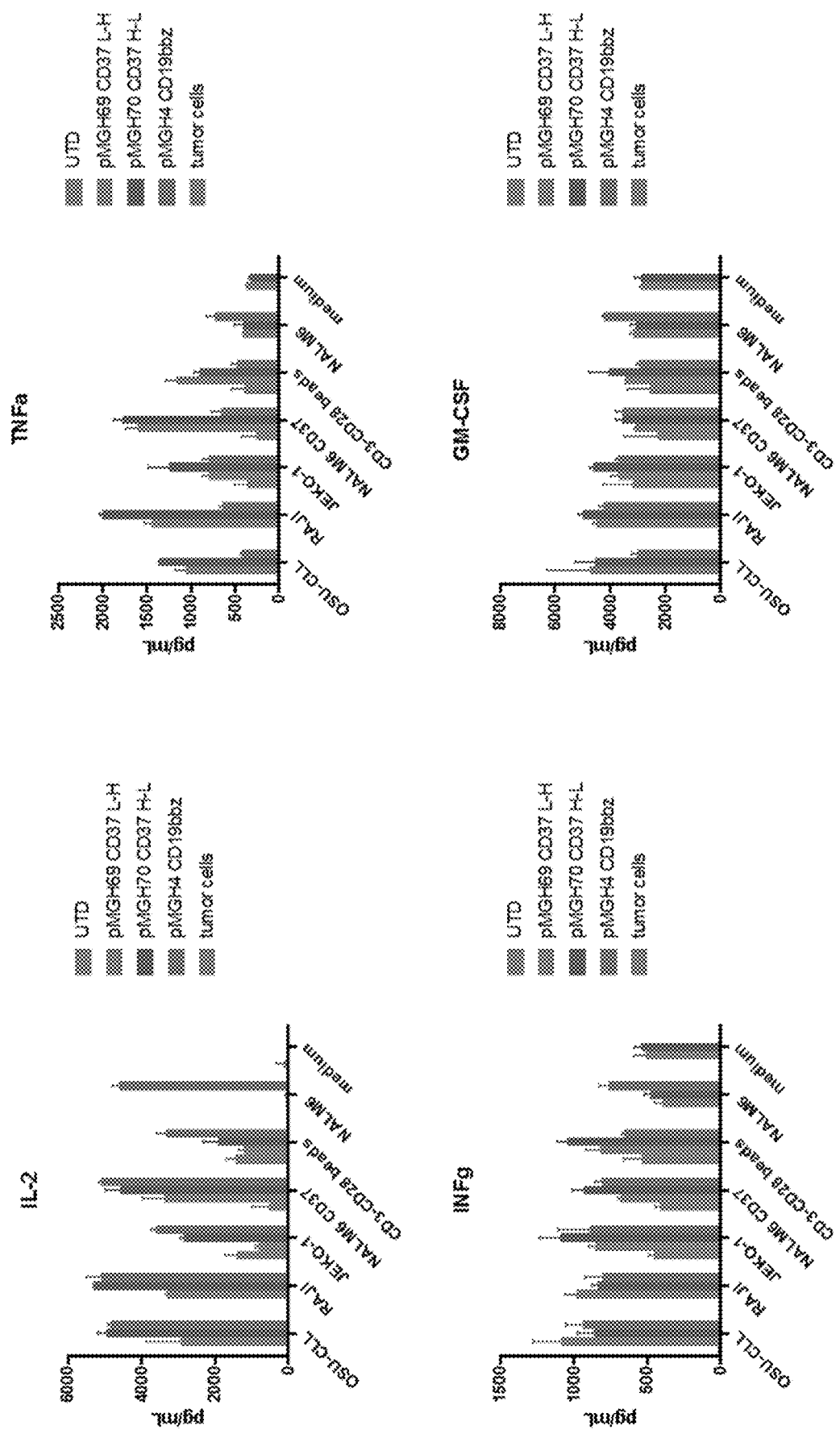
FIG. 48 demonstrates that cytokine production by CD37-CAR, CD19-CAR or UTD incubated with tumor cells for 16 hrs at 1:1 E:T ratio was analyzed in the culture supernatants by LUMINEX FLEXMAP 3D® assay. Technical duplicates (N=1 biological).
Figure 48:
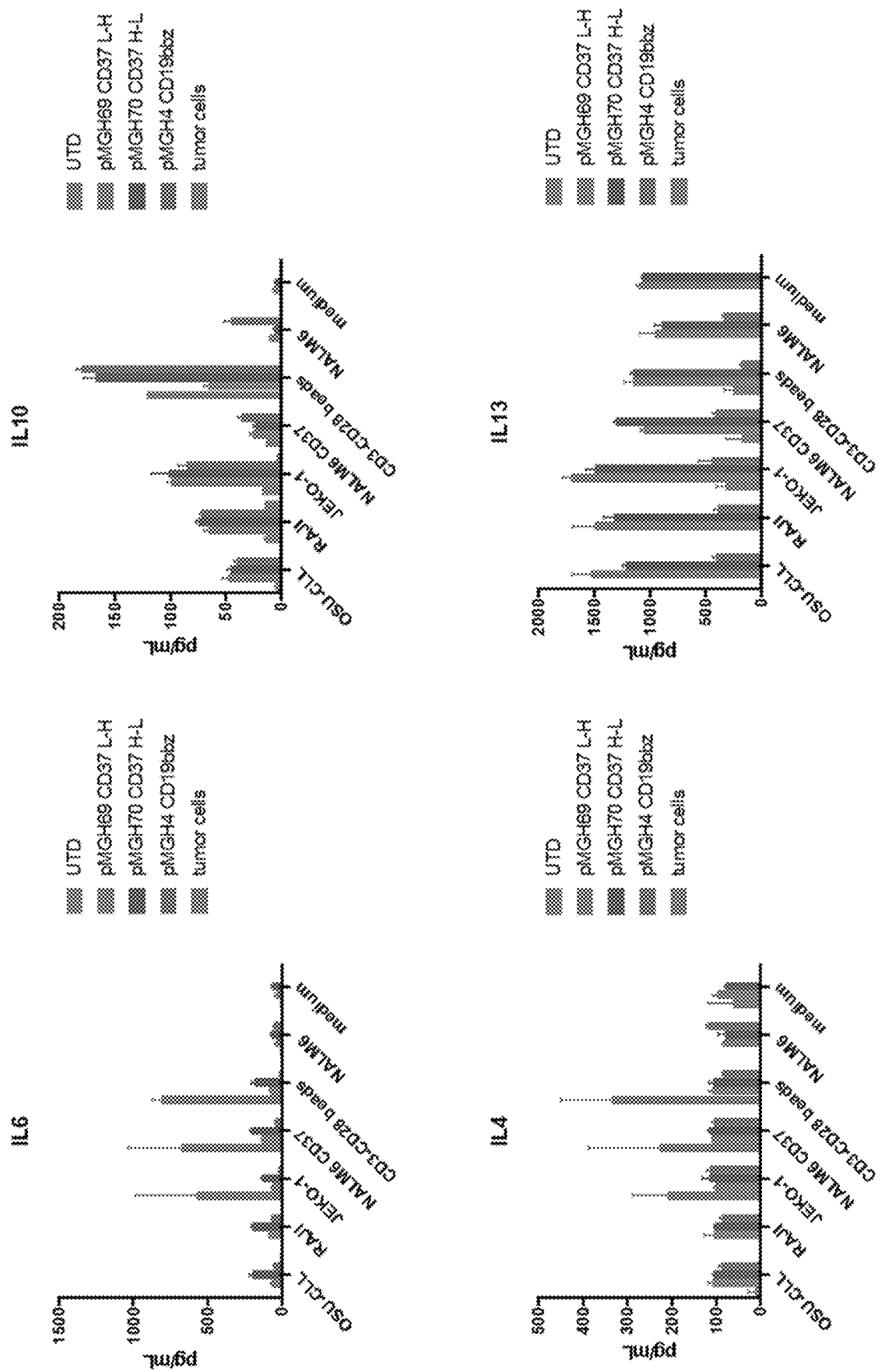
Figure 49:
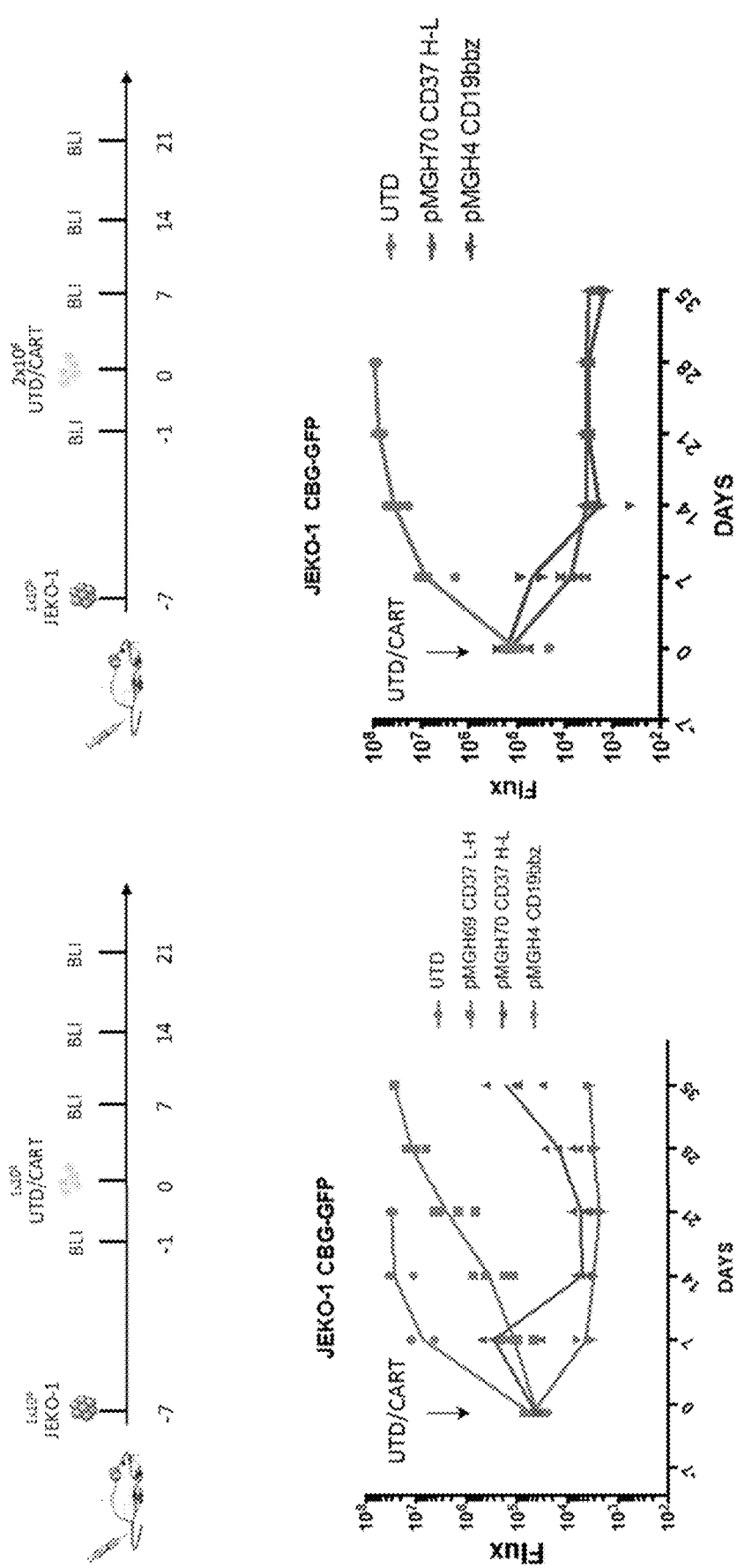
FIG. 49 depicts an experimental schematic: NSG mice were injected with 1e6 tumor cells (Jeko-1 CBG-GFP, i.v.). After 1 week mice were randomized according to tumor burden and injected with 1e6 (left) or 2e6 (right) positive CAR T cells or UTD cells. Mice were imaged every 7 days and tumor growth was analyzed measuring bioluminescence (represented in graphs). In both experiment, mice treated with UTD showed disease progression (blue line). CAR T-19 cells are capable of inducing responses in both conditions.
Figure 50:
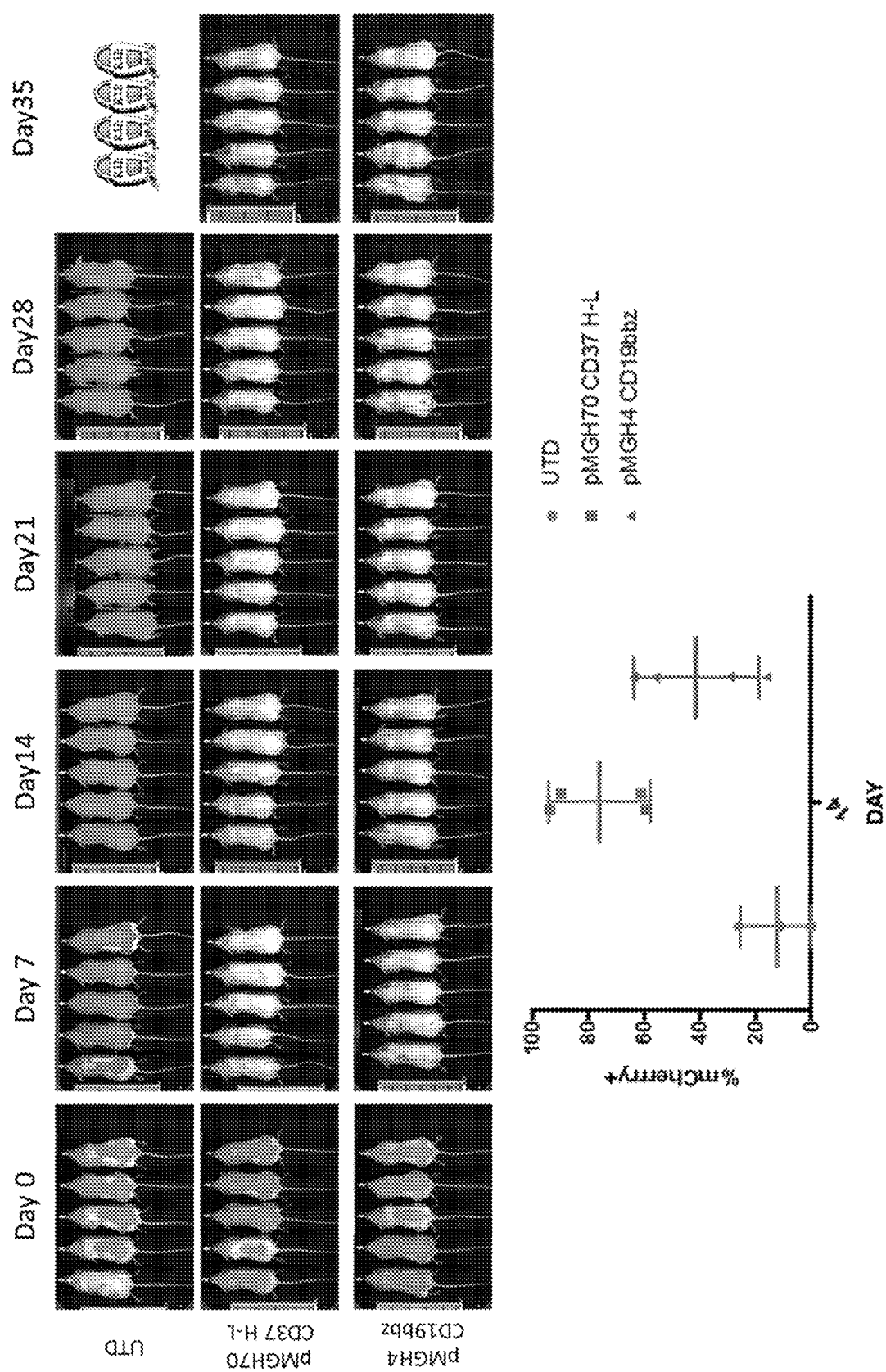
FIG. 50 demonstrates in vivo CAR efficacy. Representative mice of the second experiment are shown in the figure. Presence of CAR T cells in peripheral blood 14 days after T-cell injection. Cells from blood were stained and gated on the expression of human CD3. Percentage of mCherry positive cells (CAR+) is displayed in the graph.

The anti-CD37 CAR Ts were demonstrated to lyse tumor cells in vitro (FIG. 47) and the production of various cytokines was measured (FIG. 48). In vivo efficacy of the anti-CD37 CAR Ts was demonstrated (FIGS. 49, 50).

Example 8 scFv Sequences

BCMA scFv (SEQ ID NO: 1) comprises a VH chain (amino acids 1-121 (SEQ ID NO: 2)), a linker region (amino acids 122-141 (SEQ ID NO: 3)), and a VL chain (amino acids 142-249 (SEQ ID NO: 4)).

```
                                              (SEQ ID NO: 1)
QVQLVQSGAEVKKPGSSVKVSCKASGGTFSNYWMHWVRQAPGQGLEW

MGATYRGHSDTYYNQKFKGRVTITADKSTSTAYMELSSLRSEDTAVY

YCARGAIYNGYDVLDNWGQGTLVTVSSGGGGSGGGGSGGGGSGGGGS

DIQMTQSPSSLSASVGDRVTITCSASQDISNYLNWYQQKPGKAPKLL

IYYTSNLHSGVPSRFSGSGSGTDFTLTISSLQPEDFATYYCQQYRKL

PWTFGQGTKLEIKR
```

VH chain (SEQ ID NO: 2 (amino acids 1-121 of SEQ ID NO: 1))

```
                                              (SEQ ID NO: 2)
QVQLVQSGAEVKKPGSSVKVSCKASGGTFSNYWMHWVRQAPGQGLEW

MGATYRGHSDTYYNQKFKGRVTITADKSTSTAYMELSSLRSEDTAVY

YCARGAIYNGYDVLDNWGQGTLVTVSS
```

Linker region (SEQ ID NO: 3 (amino acids 122-141 of SEQ ID NO: 1))

```
                                              (SEQ ID NO: 3)
             GGGGSGGGGSGGGGSGGGGS
```

VL chain (SEQ ID NO: 4 (amino acids 142-249 SEQ ID NO: 1))

```
                                              (SEQ ID NO: 4)
DIQMTQSPSSLSASVGDRVTITCSASQDISNYLNWYQQKPGKAPKLL

IYYTSNLHSGVPSRFSGSGSGTDFTLTISSLQPEDFATYYCQQYRKL

PWTFGQGTKLEIKR
```

CD37 scFv VH-VL (SEQ ID NO: 5) comprises a VH chain (amino acids 1-116 (SEQ ID NO: 6)), a linker region (amino acids 117-136 (SEQ ID NO: 7)), and a VL chain (amino acids 137-244 (SEQ ID NO: 8)).

```
                                              (SEQ ID NO: 5)
AVQLVQSGAEVKKPGSSVKVSCKASGYSFTGYNMNWVRQAPGQGLEW

MGNIDPYYGGTTYNRKFKGRVTLTVDKSSSTAYMELSSLRSEDTAVY

YCARSVGPMDYWGQGTLVTVSSGGGGSGGGGSGGGGSGGGGSDIQMT

QSPSSLSASVGDRVTITCRTSENVYSYLAWYQQKPGKAPKLLVSSAK

TLAEFVPSRFSGSGSGTDFTLTISSLQPEDFATYFCQHHSDNPWTFG

QGTKVEIKR
```

VH chain (SEQ ID NO: 6 (amino acids 1-116 of SEQ ID NO: 5)

```
                                              (SEQ ID NO: 6)
AVQLVQSGAEVKKPGSSVKVSCKASGYSFTGYNMNWVRQAPGQGLEW

MGNIDPYYGGTTYNRKFKGRVTLTVDKSSSTAYMELSSLRSEDTAVY

YCARSVGPMDYWGQGTLVTVSS
```

Linker region (SEQ ID NO: 7 (amino acids 117-136 of SEQ ID NO: 5)

```
                                              (SEQ ID NO: 7)
             GGGGSGGGGSGGGGSGGGGS
```

VL chain (SEQ ID NO: 8 (amino acids 137-244 SEQ ID NO: 5)

```
                                              (SEQ ID NO: 8)
DIQMTQSPSSLSASVGDRVTITCRTSENVYSYLAWYQQKPGKAPKLL

VSSAKTLAEGVPSRFSGSGSGTDFTLTISSLQPEDFATYFCQHHSDN

PWTFGQGTKVEIKR
```

CD37 scFv VL-VH (SEQ ID NO: 9) comprises a VL chain (amino acids 1-108 (SEQ ID NO: 10)), a linker region (amino acids 109-128 (SEQ ID NO: 11)), and a VH chain (amino acids 129-244 (SEQ ID NO: 12)).

```
                                              (SEQ ID NO: 9)
DIQMTQSPSSLSASVGDRVTITCRTSENVYSYLAWYQQKPGKAPKLL

VSSAKTLAEGVPSRFSGSGSGTDFTLTISSLQPEDFATYFCQHHSDN

PWTFGQGTKVEIKRGGGGSGGGGSGGGGSGGGGSAVQLVQSGAEVKK

PGSSVKVSCKASGYSFTGYNMNWVRQAPGQGLEWMGNIDPYYGGTTY

NRKFKGRVTLTVDKSSSTAYMELSSLRSEDTAVYYCARSVGPMDYWG

QGTLVTVSS
```

VL chain (SEQ ID NO: 10 (amino acids 1-108 of SEQ ID NO: 9))

(SEQ ID NO: 10)
DIQMTQSPSSLSASVGDRVTITCRTSENVYSYLAWYQQKPGKAPKLL

VSSAKTLAEGVPSRFSGSGSGTDFTLTISSLQPEDFATYFCQHHSDN

PWTFGQGTKVEIKR

Linker region (SEQ ID NO: 11 (amino acids 109-128 of SEQ ID NO: 9))

(SEQ ID NO: 11)
GGGGSGGGGSGGGGSGGGGS

VH chain (SEQ ID NO: 12 (amino acids 129-244 SEQ ID NO: 9))

(SEQ ID NO: 12)
AVQLVQSGAEVKKPGSSVKVSCKASGYSFTGYNMNWVRQAPGQGLEWMGN

IDPYYGGTTYNRKFKGRVTLTVDKSSSTAYMELSSLRSEDTAVYYCARSV

GPMDYWGQGTLVTVSS

Example 9

ITAM Sequences
CD3ζ-ITAM 3 (SEQ ID NO: 13)

(SEQ ID NO: 13)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

CD3ζ-mutITAM 1 (SEQ ID NO: 14). As described herein, certain residues are mutated in CD3ζ-ITAM 3 to inhibit the function of CD3ζ-ITAM 3, namely: Y21 and Y32. The locations of these residues are depicted below with bold type.

(SEQ ID NO: 14)
RVKFSRSADAPAYQQGQNQLFNELNLGRREEFDVLDKRRGRDPEMGGKPR

RKNPQEGLYNELQKDKMAEAYSEIGMKGERRRGKGHDGLYQGLSTATKDT

YDALHMQALPPR

CD3ζ-mutITAM1 and mutITAM2 (SEQ ID NO: 33). As described herein, certain residues are mutated in CD3ζ-ITAM 3 to inhibit the function of CD3ζ-ITAM 3, namely: Y21, Y32, Y59 and Y71. The locations of these residues are depicted below with bold type.

(SEQ ID NO: 33)
RVKFSRSADAPAYQQGQNQLFNELNLGRREEFDVLDKRRGRDPEMGGKPR

RKNPQEGLFNELQKDKMAEAFSEIGMKGERRRGKGHDGLYQGLSTATKDT

YDALHMQALPPR

CD3ζ-mutITAM1 and mutITAM3 (SEQ ID NO: 34). As described herein, certain residues are mutated in CD3ζ-ITAM 3 to inhibit the function of CD3ζ-ITAM 3, namely: Y21, Y32, Y90 and Y100. The locations of these residues are depicted below with bold type.

(SEQ ID NO: 34)
RVKFSRSADAPAYQQGQNQLFNELNLGRREEFDVLDKRRGRDPEMGGKPR

RKNPQEGLYNELQKDKMAEAYSEIGMKGERRRGKGHDGLFQGLSTATKDT

FDALHMQALPPR

Example 10

CAR Sequences
pMGH8-CD8Leader/anti-BCMA/CD8hinge+TM/4-1BB/CD3ζ (SEQ ID NO: 15) comprising CD8 leader sequence (amino acids 1-21 (SEQ ID NO: 16)); anti-BCMA (amino acids 22-270 (SEQ ID NO: 17)); CD8 hinge and TM domain (amino acids 271-339 (SEQ ID NO: 18)); 4-1BB (amino acids 340-381 (SEQ ID NO: 19)); and CD3ζ (amino acids 382-493 (SEQ ID NO: 20)).

(SEQ ID NO: 15)
MALPVTALLLPLALLLHAARPQVQLVQSGAEVKKPGSSVKVSCKASGGTF

SNYWMHWVRQAPGQGLEWMGATYRGHSDTYYNQKFKGRVTITADKSTSTA

YMELSSLRSEDTAVYYCARGAIYNGYDVLDNWGQGTLVTVSSGGGGSGGG

GSGGGGSGGGGSDIQMTQSPSLSASVGDRVTITCSASQDISNYLNWYQQ

KPGKAPKLLIYYTSNLHSGVPSRFSGSGSGTDFTLTISSLQPEDFATYYC

QQYRKLPWTFGQGTKLEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAE

AYSEIGMKGERRRGKGHDGLYQGLSTATKDTYDALHMQALPPR

CD8 leader sequence (SEQ ID NO: 16 (amino acids 1-21 of SEQ ID NO: 15))

(SEQ ID NO: 16)
MALPVTALLLPLALLLHAARP anti-BCMA (SEQ ID NO: 17 (amino acids 22-270 of SEQ ID NO: 15))

(SEQ ID NO: 17)
QVQLVQSGAEVKKPGSSVKVSCKASGGTFSNYWMHWVRQAPGQGLEWMGA

TYRGHSDTYYNQKFKGRVTITADKSTSTAYMELSSLRSEDTAVYYCARGA

IYNGYDVLDNWGQGTLVTVSSGGGGSGGGGSGGGGSGGGGSDIQMTQSPS

SLSASVGDRVTITCSASQDISNYLNWYQQKPGKAPKLLIYYTSNLHSGVP

SRFSGSGSGTDFTLTISSLQPEDFATYYCQQYRKLPWTFGQGTKLEIKR

CD8 hinge and TM domain (SEQ ID NO: 18 (amino acids 271-339 of SEQ ID NO: 15))

(SEQ ID NO: 18)
TTTPAPRPPTPAPTIASQPLSLRPEACRPAAGGAVHTRGLDFACDIYIWA

PLAGTCGVLLLSLVITLYC 4-1BB (SEQ ID NO: 19 (amino acids 340-381 of SEQ ID NO: 15))

(SEQ ID NO: 19)
KRGRKKLLYIFKQPFMRPVQTTQEEDGCSCRFPEEEEGGCEL

CD3ζ (SEQ ID NO: 20 (amino acids 382-493 of SEQ ID NO: 15))

(SEQ ID NO: 20)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR pMGH8-CD8Leader/anti-CD37 H-L/CD8hinge+TM/4-1BB/CD3ζ (SEQ ID NO: 21) comprising CD8 leader sequence (amino acids 1-21 (SEQ ID NO: 22)); anti-CD37 H-L (amino acids 22-265 (SEQ ID NO: 23)); CD8 hinge and TM domain (amino acids 266-334 (SEQ ID NO: 24)); 4-1BB (amino acids 335-376 (SEQ ID NO: 25)); and CD3ζ (amino acids 377-488 (SEQ ID NO: 26)).

(SEQ ID NO: 21)
MALPVTALLLPLALLLHAARPDIQMTQSPSSLSASVGDRVTITCRTSENV

YSYLAWYQQKPGKAPKLLVSSAKTLAEGVPSRFSGSGSGTDFTLTISSLQ

PEDFATYFCQHHSDNPWTFGQGTKVEIKRGGGSGGGGSGGGGSGGGGSA

VQLVQSGAEVKKPGSSVKVSCKASGYSFTGYNMNWVRQAPGQGLEWMGNI

DPYYGGTTYNRKFKGRVTLTVDKSSSTAYMELSSLRSEDTAVYYCARSVG

PMDYWGQGTLVTVSSTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

CD8 leader sequence (SEQ ID NO: 22 (amino acids 1-21 of SEQ ID NO: 21))

(SEQ ID NO: 22)
MALPVTALLLPLALLLHAARP anti-CD37 H-L (SEQ ID NO: 23 (amino acids 22-265 of SEQ ID NO: 21))

(SEQ ID NO: 23)
DIQMTQSPSSLSASVGDRVTITCRTSENVYSYLAWYQQKPGKAPKLLVSS

AKTLAEGVPSRFSGSGSGTDFTLTISSLQPEDFATYFCQHHSDNPWTFGQ

GTKVEIKRGGGSGGGGSGGGGSGGGGSAVQLVQSGAEVKKPGSSVKVSC

KASGYSFTGYNMNWVRQAPGQGLEWMGNIDPYYGGTTYNRKFKGRVTLTV

DKSSSTAYMELSSLRSEDTAVYYCARSVGPMDYWGQGTLVTVSS

CD8 hinge and TM domain SEQ ID NO: 24 ((amino acids 266-334 of SEQ ID NO: 21))

(SEQ ID NO: 24)
TTTPAPRPPTPAPTIASQPLSLRPEACRPAAGGAVHTRGLDFACDIYIWA

PLAGTCGVLLLSLVITLYC 4-1BB (SEQ ID NO: 25 (amino acids 335-376 of SEQ ID NO: 21))

(SEQ ID NO: 25)
KRGRKKLLYIFKQPFMRPVQTTQEEDGCSCRFPEEEEGGCEL

CD3ζ (SEQ ID NO: 26 (amino acids 377-488 of SEQ ID NO: 21))

(SEQ ID NO: 26)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR pMGH8-CD8Leader/anti-CD37 L-H/CD8hinge+TM/4-1BB/CD3ζ (SEQ ID NO: 27) comprising CD8 leader sequence (amino acids 1-21 (SEQ ID NO: 28)); anti-CD37 L-H (amino acids 22-265 (SEQ ID NO: 29)); CD8 hinge and TM domain (amino acids 266-334 (SEQ ID NO: 30)); 4-1BB (amino acids 335-376 (SEQ ID NO: 31)); and CD3ζ (amino acids 377-488 (SEQ ID NO: 32)).

(SEQ ID NO: 27)
MALPVTALLLPLALLLHAARPAVQLVQSGAEVKKPGSSVKVSCKASGYSF

TGYNMNWVRQAPGQGLEWMGNIDPYYGGTTYNRKFKGRVTLTVDKSSSTA

YMELSSLRSEDTAVYYCARSVGPMDYWGQGTLVTVSSGGGGSGGGGSGGG

GSGGGGSDIQMTQSPSSLSASVGDRVTITCRTSENVYSYLAWYQQKPGKA

PKLLVSSAKTLAEGVPSRFSGSGSGTDFTLTISSLQPEDFATYFCQHHSD

NPWTFGQGTKVEIKRTTTPAPRPPTPAPTIASQPLSLRPEACRPAAGGAV

HTRGLDFACDIYIWAPLAGTCGVLLLSLVITLYCKRGRKKLLYIFKQPFM

RPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

CD8 leader sequence (SEQ ID NO: 28 (amino acids 1-21 of SEQ ID NO: 27))

(SEQ ID NO: 28)
MALPVTALLLPLALLLHAARP anti-CD37 L-H (SEQ ID NO: 29 (amino acids 22-265 of SEQ ID NO: 27))

(SEQ ID NO: 29)
AVQLVQSGAEVKKPGSSVKVSCKASGYSFTGYNMNWVRQAPGQGLEWMGN

IDPYYGGTTYNRKFKGRVTLTVDKSSSTAYMELSSLRSEDTAVYYCARSV

GPMDYWGQGTLVTVSSGGGGSGGGGSGGGGSGGGGSDIQMTQSPSSLSAS

VGDRVTITCRTSENVYSYLAWYQQKPGKAPKLLVSSAKTLAEGVPSRFSG

SGSGTDFTLTISSLQPEDFATYFCQHHSDNPWTFGQGTKVEIKR

CD8 hinge and TM domain SEQ ID NO: 30 ((amino acids 266-334 of SEQ ID NO: 27))

```
                                          (SEQ ID NO: 30)
TTTPAPRPPTPAPTIASQPLSLRPEACRPAAGGAVHTRGLDFACDIYIWA

PLAGTCGVLLLSLVITLYC
```

4-1BB (SEQ ID NO: 31 (amino acids 335-376 of SEQ ID NO: 27))

```
                                          (SEQ ID NO: 31)
KRGRKKLLYIFKQPFMRPVQTTQEEDGCSCRFPEEEEGGCEL
```

CD3ζ (SEQ ID NO: 32 (amino acids 377-488 of SEQ ID NO: 27))

```
                                          (SEQ ID NO: 32)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
``` anti-BCMA CAR-mutITAM1 (SEQ ID NO: 35). As described herein, certain residues are mutated in this anti-BCMA CAR to inhibit the function of CD3ζ-ITAM, namely: Y402 and Y413 of SEQ ID NO: 35. The locations of these residues are depicted below with bold type.

```
                                          (SEQ ID NO: 35)
MALPVTALLLPLALLLHAARPQVQLVQSGAEVKKPGSSVKVSCKASGGTF

SNYWMHWVRQAPGQGLEWMGATYRGHSDTYYNQKFKGRVTITADKSTSTA

YMELSSLRSEDTAVYYCARGAIYNGYDVLDNWGQGTLVTVSSGGGGSGGG

GSGGGGSGGGGSDIQMTQSPSSLSASVGDRVTITCSASQDISNYLNWYQQ

KPGKAPKLLIYYTSNLHSGVPSRFSGSGSGTDFTLTISSLQPEDFATYYC

QQYRKLPWTFGQGTKLEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LFNELNLGRREEFDVLDKRRGRDPEMGGKPRRKNPQEGLYNELQKDKMAE

AYSEIGMKGERRRGKGHDGLYQGLSTATKDTYDALHMQALPPR
``` anti-BCMA CAR-mutITAM2 (SEQ ID NO: 36). As described herein, certain residues are mutated in this anti-BCMA CAR to inhibit the function of CD3ζ-ITAM, namely: Y440 and Y452 of SEQ ID NO: 36. The locations of these residues are depicted below with bold type.

```
                                          (SEQ ID NO: 36)
MALPVTALLLPLALLLHAARPQVQLVQSGAEVKKPGSSVKVSCKASGGTF

SNYWMHWVRQAPGQGLEWMGATYRGHSDTYYNQKFKGRVTITADKSTSTA

YMELSSLRSEDTAVYYCARGAIYNGYDVLDNWGQGTLVTVSSGGGGSGGG

GSGGGGSGGGGSDIQMTQSPSSLSASVGDRVTITCSASQDISNYLNWYQQ

KPGKAPKLLIYYTSNLHSGVPSRFSGSGSGTDFTLTISSLQPEDFATYYC

QQYRKLPWTFGQGTKLEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LYNELNLGRREEYDVLDKRRGRDPEMGGKPRRKNPQEGLFNELQKDKMAE

AFSEIGMKGERRRGKGHDGLYQGLSTATKDTYDALHMQALPPR
``` anti-BCMA CAR-mutITAM3 (SEQ ID NO: 37). As described herein, certain residues are mutated in this anti-BCMA CAR to inhibit the function of CD3ζ-ITAM, namely: Y471 and Y482 of SEQ ID NO: 37. The locations of these residues are depicted below with bold type.

```
                                          (SEQ ID NO: 37)
MALPVTALLLPLALLLHAARPQVQLVQSGAEVKKPGSSVKVSCKASGGTF

SNYWMHWVRQAPGQGLEWMGATYRGHSDTYYNQKFKGRVTITADKSTSTA

YMELSSLRSEDTAVYYCARGAIYNGYDVLDNWGQGTLVTVSSGGGGSGGG

GSGGGGSGGGGSDIQMTQSPSSLSASVGDRVTITCSASQDISNYLNWYQQ

KPGKAPKLLIYYTSNLHSGVPSRFSGSGSGTDFTLTISSLQPEDFATYYC

QQYRKLPWTFGQGTKLEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAE

AYSEIGMKGERRRGKGHDGLFQGLSTATKDTFDALHMQALPPR
``` anti-BCMA CAR-mutITAM1 and mutITAM3 (SEQ ID NO: 38). As described herein, certain residues are mutated in this anti-BCMA CAR to inhibit the function of CD3ζ-ITAM, namely: Y402, Y413, Y471 and Y482 of SEQ ID NO: 38. The locations of these residues are depicted below with bold type.

```
                                          (SEQ ID NO: 38)
MALPVTALLLPLALLLHAARPQVQLVQSGAEVKKPGSSVKVSCKASGGTF

SNYWMHWVRQAPGQGLEWMGATYRGHSDTYYNQKFKGRVTITADKSTSTA

YMELSSLRSEDTAVYYCARGAIYNGYDVLDNWGQGTLVTVSSGGGGSGGG

GSGGGGSGGGGSDIQMTQSPSSLSASVGDRVTITCSASQDISNYLNWYQQ

KPGKAPKLLIYYTSNLHSGVPSRFSGSGSGTDFTLTISSLQPEDFATYYC

QQYRKLPWTFGQGTKLEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LFNELNLGRREEFDVLDKRRGRDPEMGGKPRRKNPQEGLYNELQKDKMAE

AYSEIGMKGERRRGKGHDGLFQGLSTATKDTFDALHMQALPPR
```

CD3 eta CAR (SEQ ID NO: 39)

```
                                          (SEQ ID NO: 39)
MALPVTALLLPLALLLHAARPQVQLVQSGAEVKKPGSSVKVSCKASGGTF

SNYWMHWVRQAPGQGLEWMGATYRGHSDTYYNQKFKGRVTITADKSTSTA

YMELSSLRSEDTAVYYCARGAIYNGYDVLDNWGQGTLVTVSSGGGGSGGG

GSGGGGSGGGGSDIQMTQSPSSLSASVGDRVTITCSASQDISNYLNWYQQ

KPGKAPKLLIYYTSNLHSGVPSRFSGSGSGTDFTLTISSLQPEDFATYYC
```

```
-continued
QQYRKLPWTFGQGTKLEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAE

AYSEIGMKGERRRGKGHDGLYQDSHFQAVPVQEKKKRLRRAPWRAFAQPQ

RLKHPAEQPIVRQCLQRPPLCGVLGPVQQQLPPSLGPVLSPHSDPGWCRV

DDGGDGVFSGGGGEGRGSLLTCGDVEENPGPRMVSKGEEDNMAIIKEFMR

FKVHMEGSVNGHEFEIEGEGEGRPYEGTQTAKLKVTKGGPLPFAWDILSP

QFMYGSKAYVKHPADIPDYLKLSFPEGFKWERVMNFEDGGVVTVTQDSSL

QDGEFIYKVKLRGTNFPSDGPVMQKKTMGWEASSERMYPEDGALKGEIKQ

RLKLKDGGHYDAEVKTTYKAKKPVQLPGAYNVNIKLDITSHNEDYTIVEQ

YERAEGRHSTGGMDELYK
```

CD3 theta CAR (SEQ ID NO: 40)

```
                                        (SEQ ID NO: 40)
MALPVTALLLPLALLLHAARPQVQLVQSGAEVKKPGSSVKVSCKASGGTF

SNYWMHWVRQAPGQGLEWMGATYRGHSDTYYNQKFKGRVTITADKSTSTA

YMELSSLRSEDTAVYYCARGAIYNGYDVLDNWGQGTLVTVSSGGGGSGGG

GSGGGGSGGGGSDIQMTQSPSSLSASVGDRVTITCSASQDISNYLNWYQQ

KPGKAPKLLIYYTSNLHSGVPSRFSGSGSGTDFTLTISSLQPEDFATYYC

QQYRKLPWTFGQGTKLEIKRTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYQQGQNQ

LYNELNLGRREEYDVLDKRRGRDPEMGGKPRRKNPQEGLYNELQKDKMAE

AYSEIGMKGERRRGKGHDGLYQDSHFQAVPVQEKKKRLRRAPWRAFAQPQ

RLKHRNNELPDSLEPIYKNIWNKTFIGESGGGGEGRGSLLTCGDVEENPG

PRMVSKGEEDNMAIIKEFMRFKVHMEGSVNGHEFEIEGEGEGRPYEGTQT

AKLKVTKGGPLPFAWDILSPQFMYGSKAYVKHPADIPDYLKLSFPEGFKW

ERVMNFEDGGVVTVTQDSSLQDGEFIYKVKLRGTNFPSDGPVMQKKTMGW

EASSERMYPEDGALKGEIKQRLKLKDGGHYDAEVKTTYKAKKPVQLPGAY

NVNIKLDITSHNEDYTIVEQYERAEGRHSTGGMDELYK
```

Example 11

Anti-CD37 CAR-T Cells Effective Against B Cell Malignancies

CD37 is a tetraspanin expressed on mature B cells but absent on early progenitors or terminally differentiated plasma cells. It is highly expressed on malignant B cells and it represents a promising target for B-cell malignancies, particularly for variants that escape existing therapies targeting the common B-cell antigens CD19 and CD20. We designed the first anti-CD37 CAR (CAR-37) for the treatment of B-cell malignancies. In vitro cytotoxic activity of CART-37 cells was evaluated by co-culturing CART-37 cells with CD 37-expressing human tumor cell lines at different effector to target ratios. CD37-directed CAR T cells demonstrated antigen-specific proliferation, cytokine production, and cytotoxic activity in vitro in multiple models of B-cell malignancy. We assessed the anti-lymphoma efficacy in vivo in a mantle cell lymphoma model. CAR-37 treatment eliminated the tumor cells within 2 weeks, and mice maintained durable remissions. Together these results show that T cells expressing anti-CD37 CAR have substantial activity in vitro and in vivo against B-cell malignancies. These findings indicated that CD37-CAR T cells are a novel potential therapeutic agent for the treatment of patients with CD37-expressing tumors.

Figure 51A:
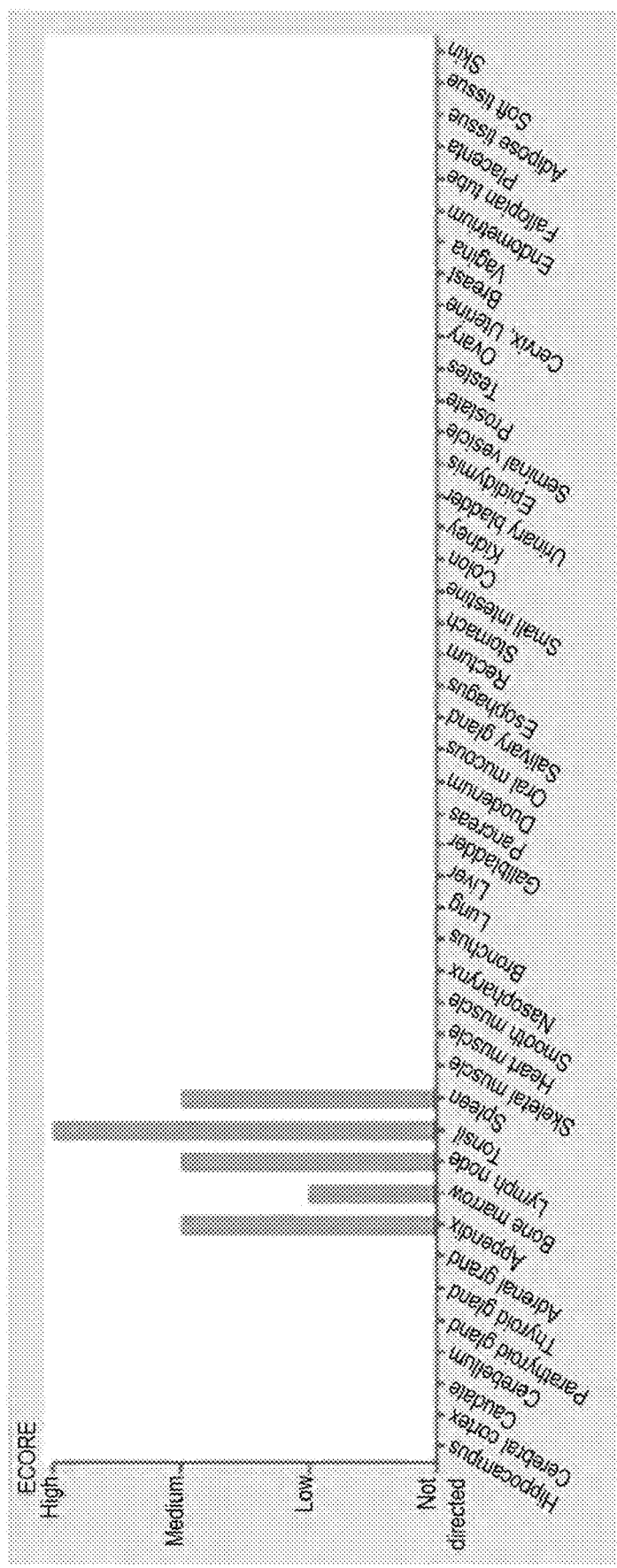
FIGS. 51A and 51B show CD37 protein expression in normal cells (FIG. 51A) and tumor cells (FIG. 51B).
Figure 51B:
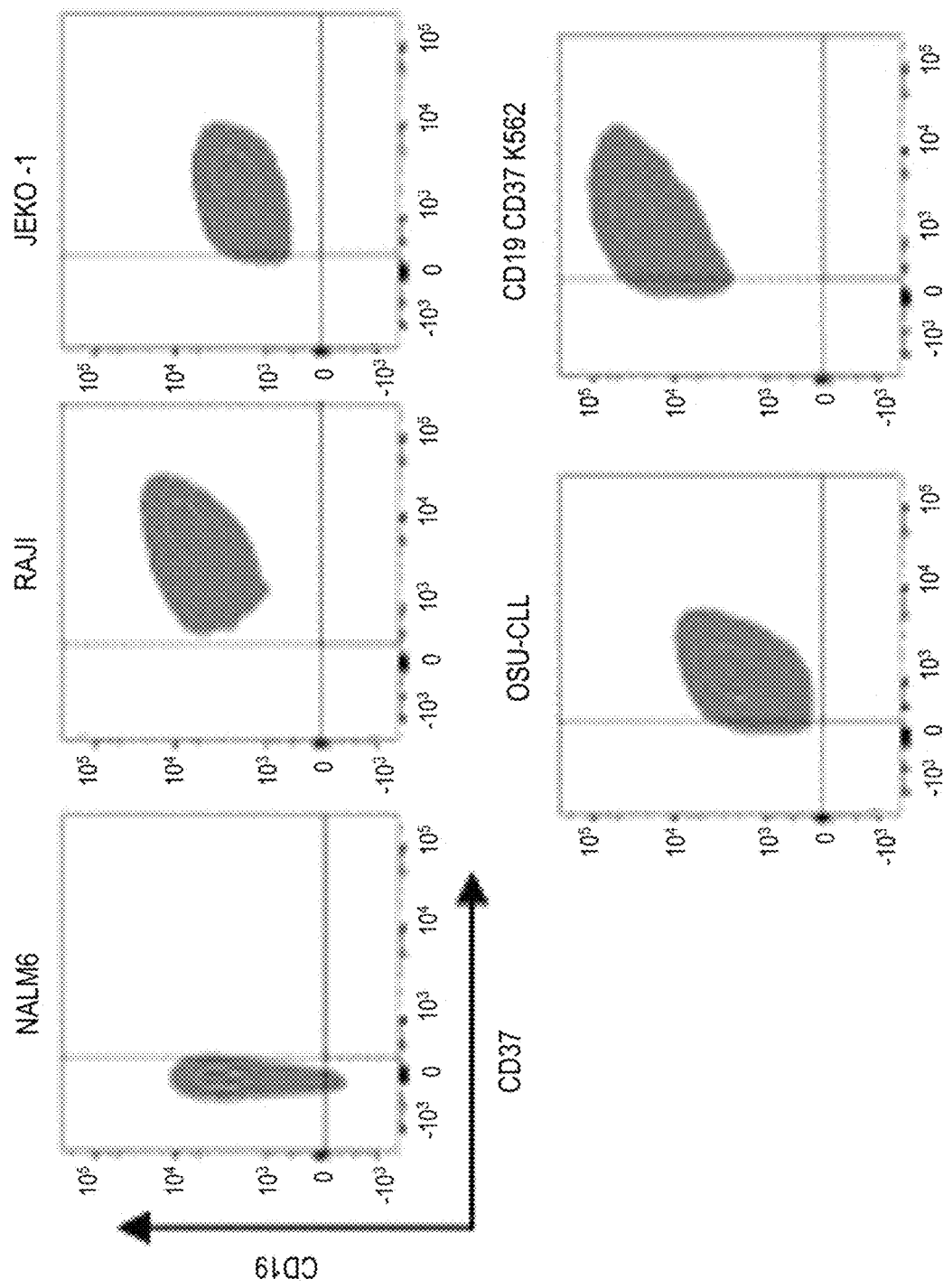
Figure 52:
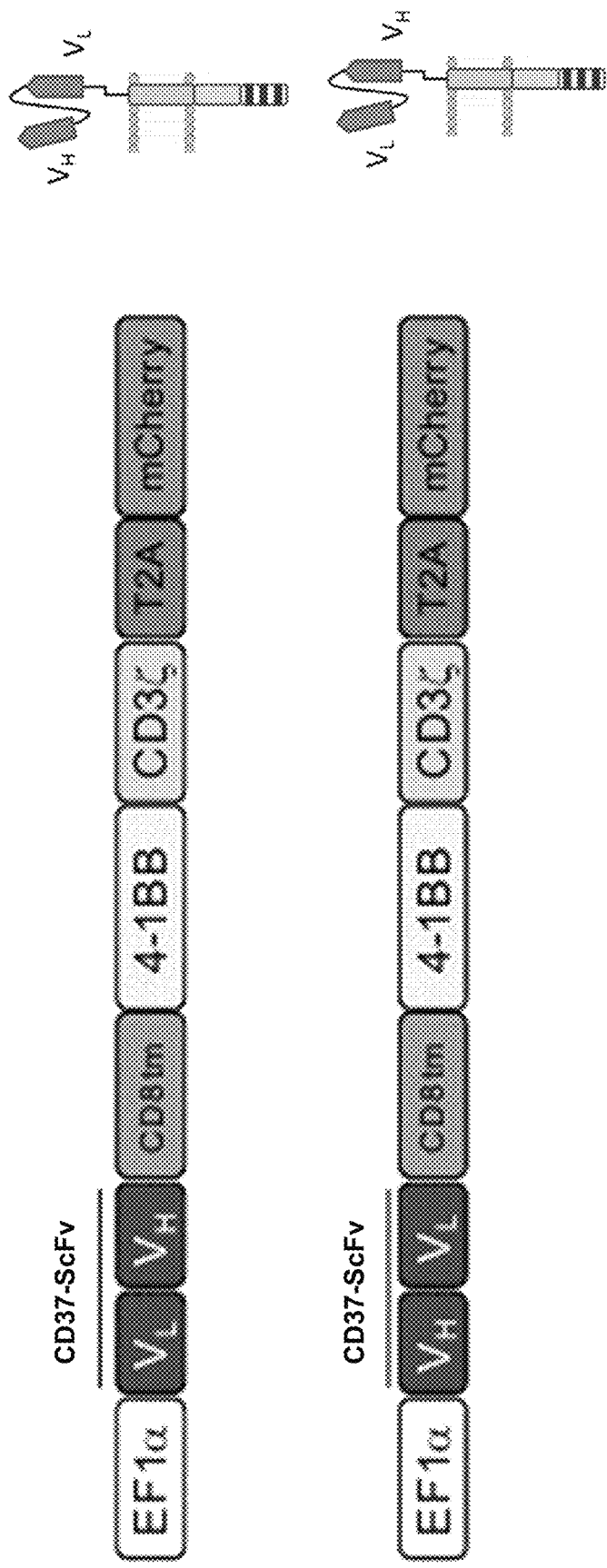
FIG. 52 shows exemplary CAR-37 T cells design.
Figure 53A:
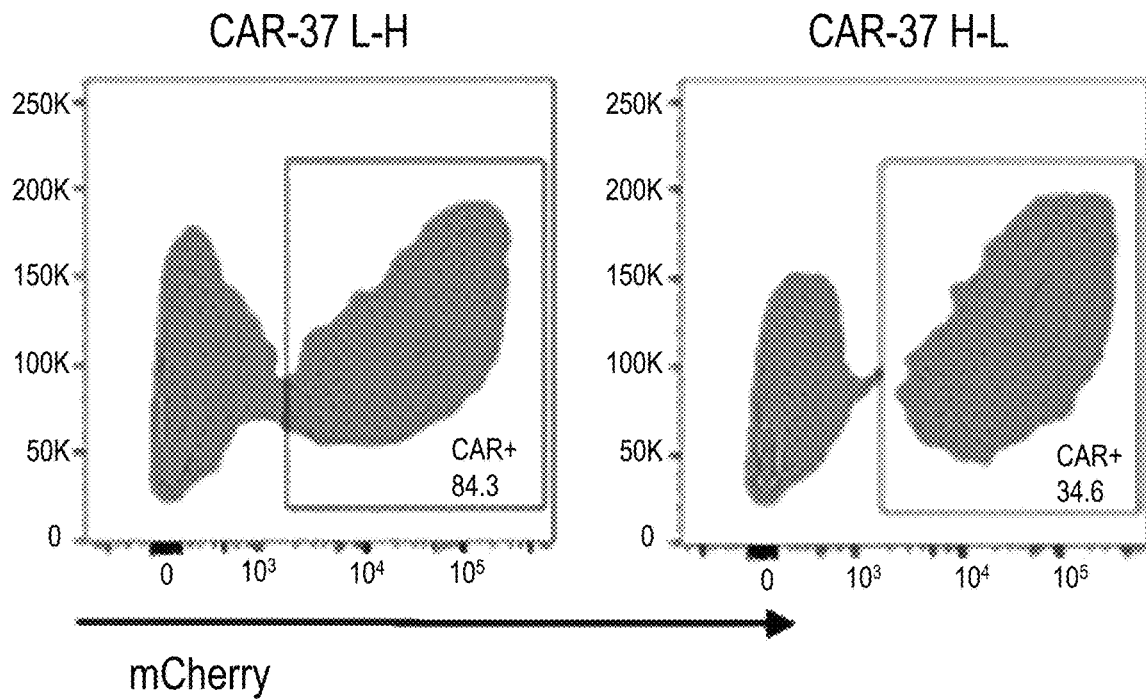
FIGS. 53A-53D show generation and expansion of CAR-37 T cells.
Figure 53B:
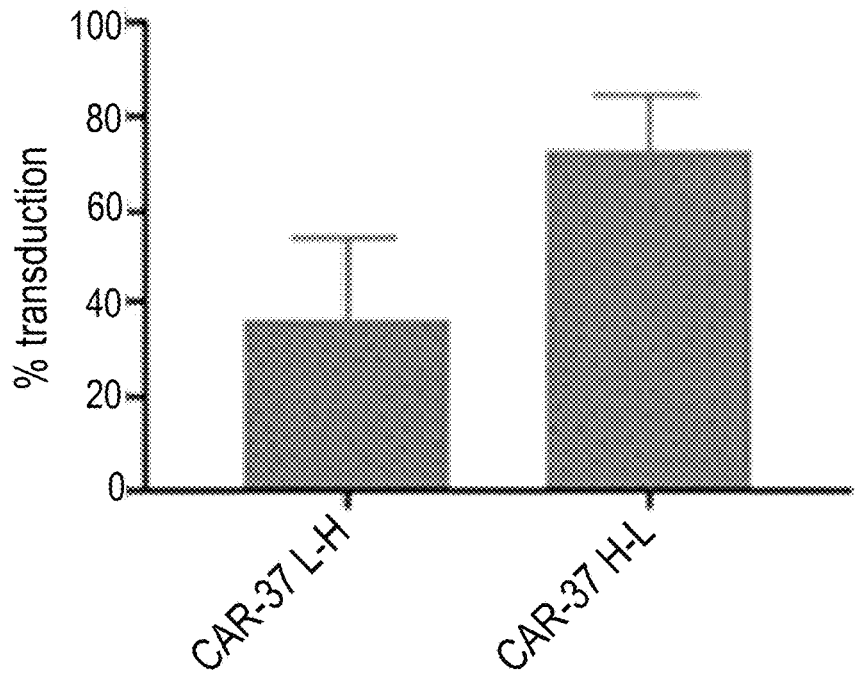
Figure 53C:
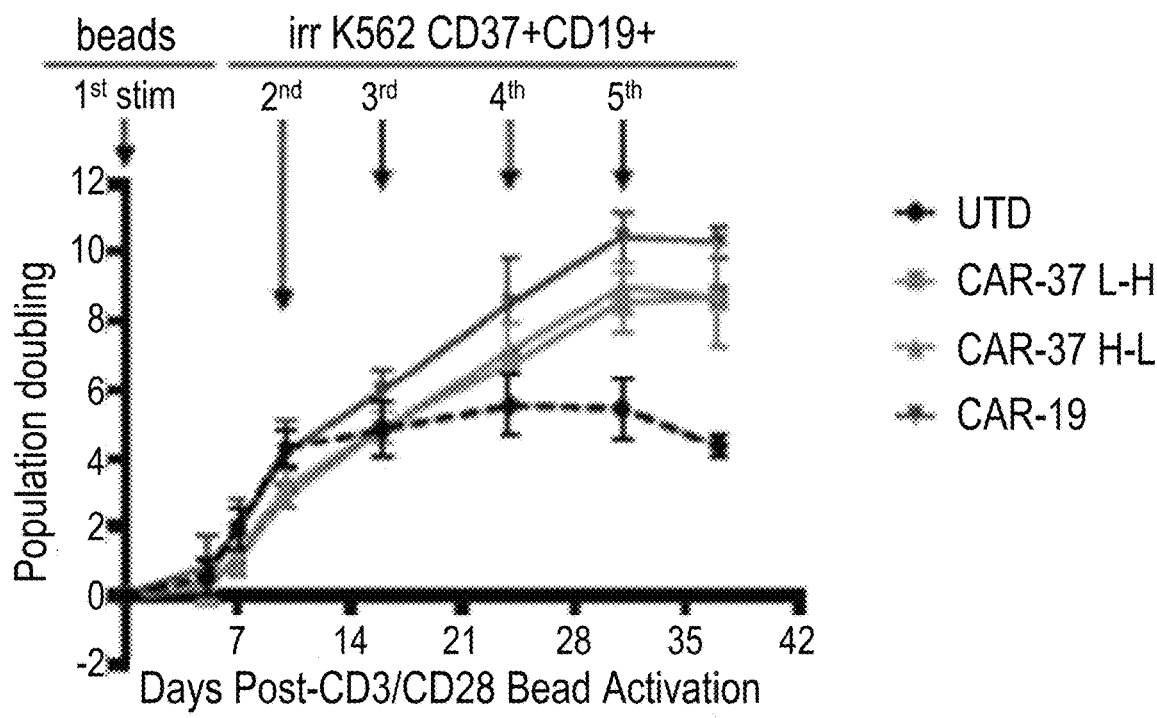
Figure 53D:
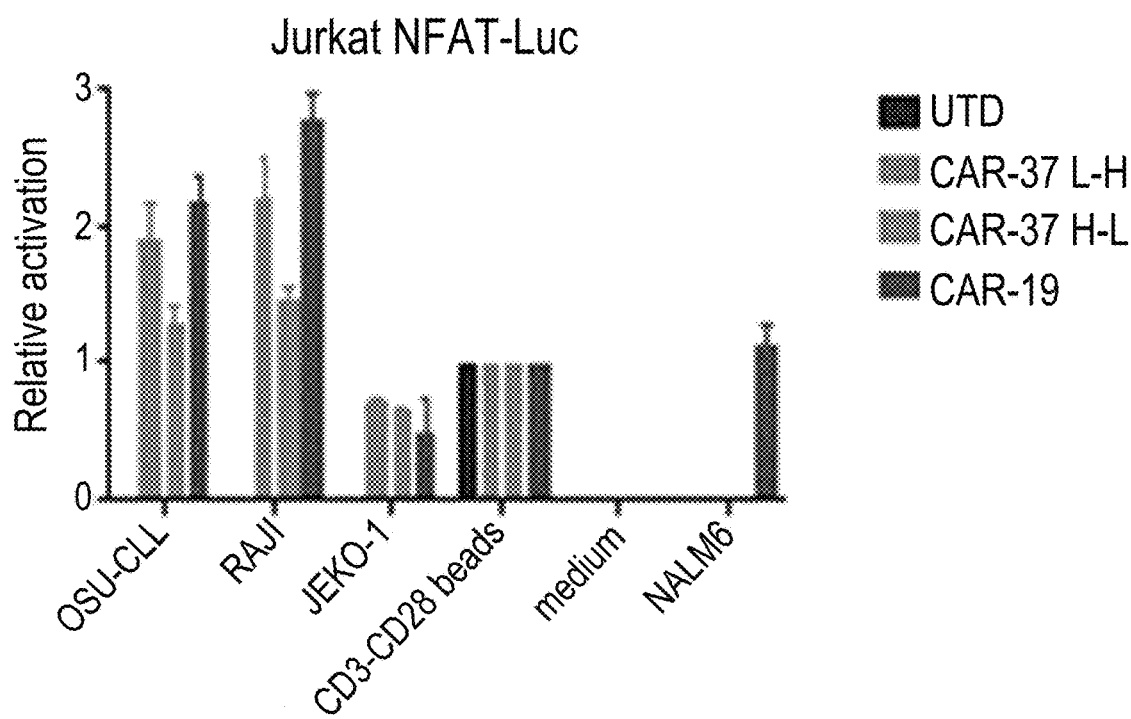
Figure 55A:
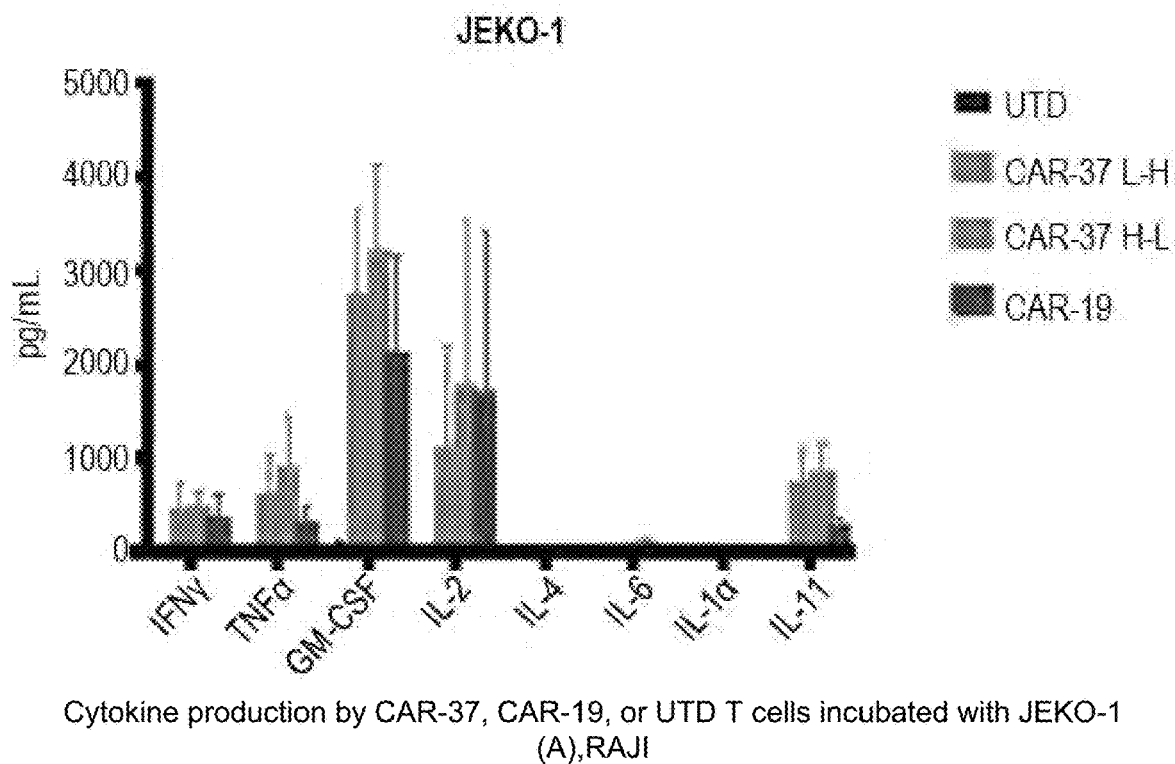
FIGS. 55A-55C show in vitro cytokine production of CAR-37 T cells.
Figure 55B:
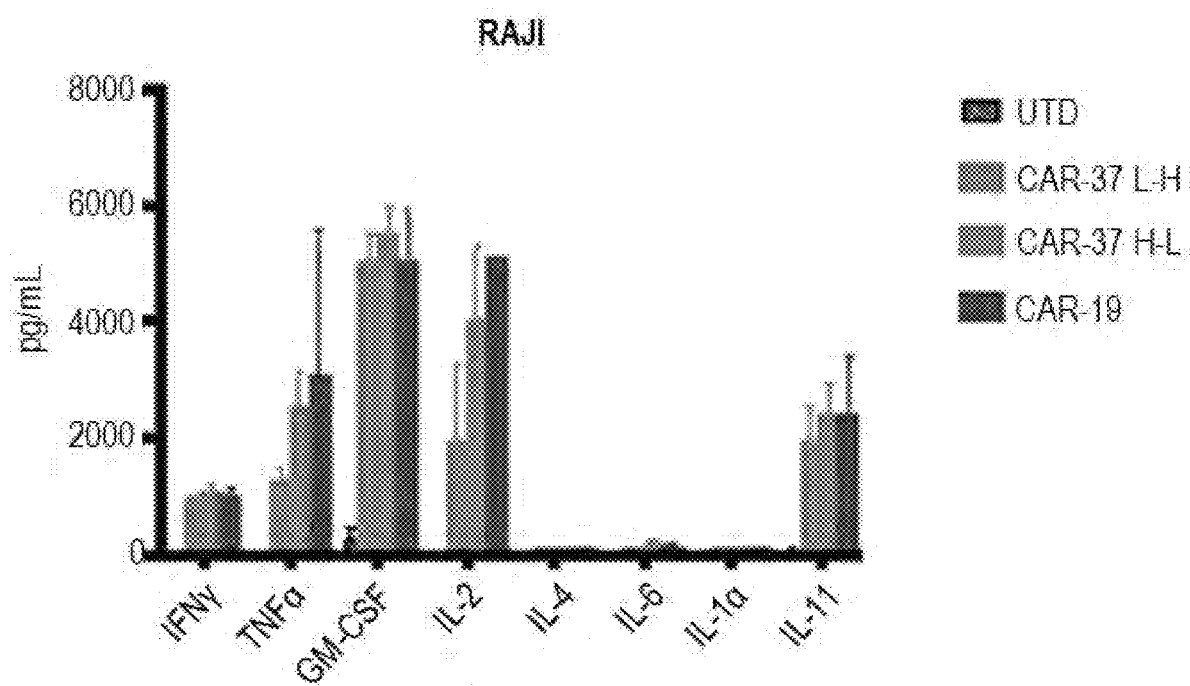
Figure 55C:
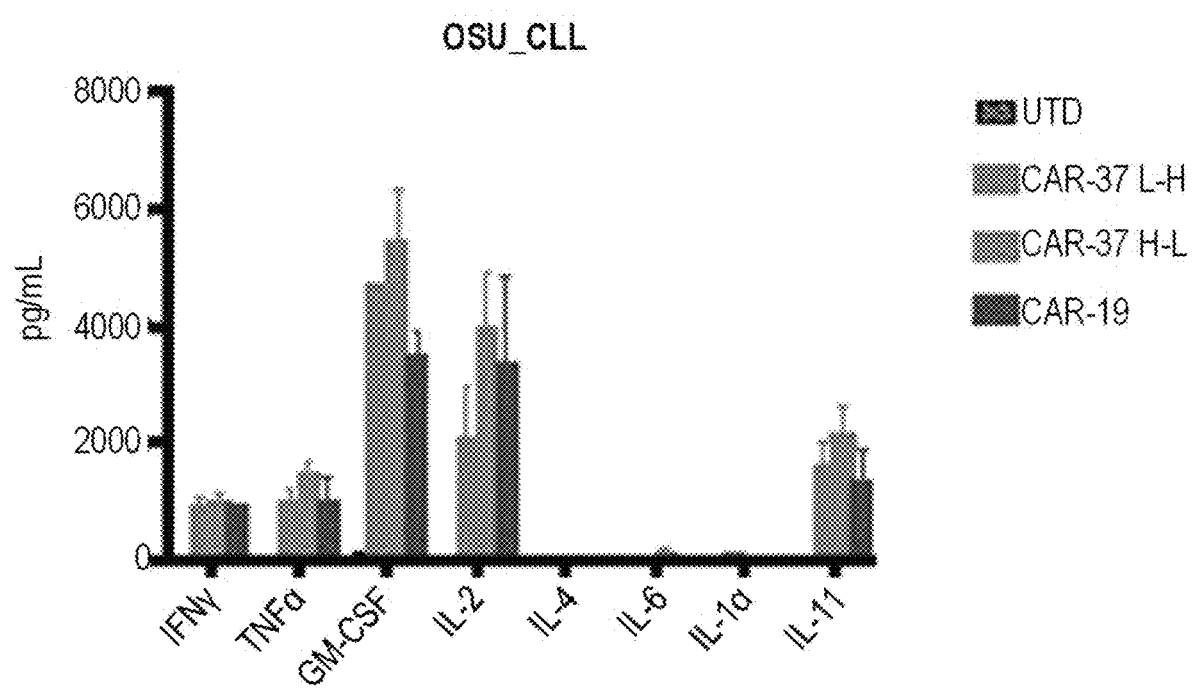

In normal tissues, CD37 expression is restricted to lymphoid organs (FIG. 51A). However, it is highly expressed on B-cell leukemia and lymphoma cells (FIG. 51B).

CAR-37 T cells are able to proliferate and expand ex-vivo (FIGS. 53A-53D).

T cells expressing anti-CD37 CAR have substantial in vitro activity against mantle cell lymphoma, Burkitt lymphoma and B-cell lymphoblastic leukemia tumor cells (FIGS. 54A-54D).

Figure 56A:
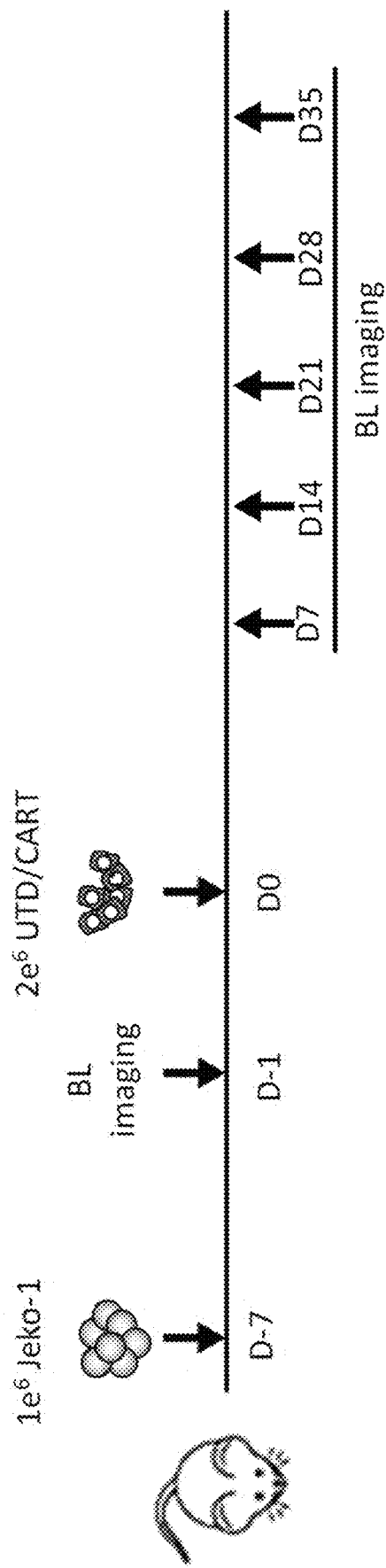
FIGS. 56A-56C show in vitro effector function of CAR-37 T cells.
Figure 56B:
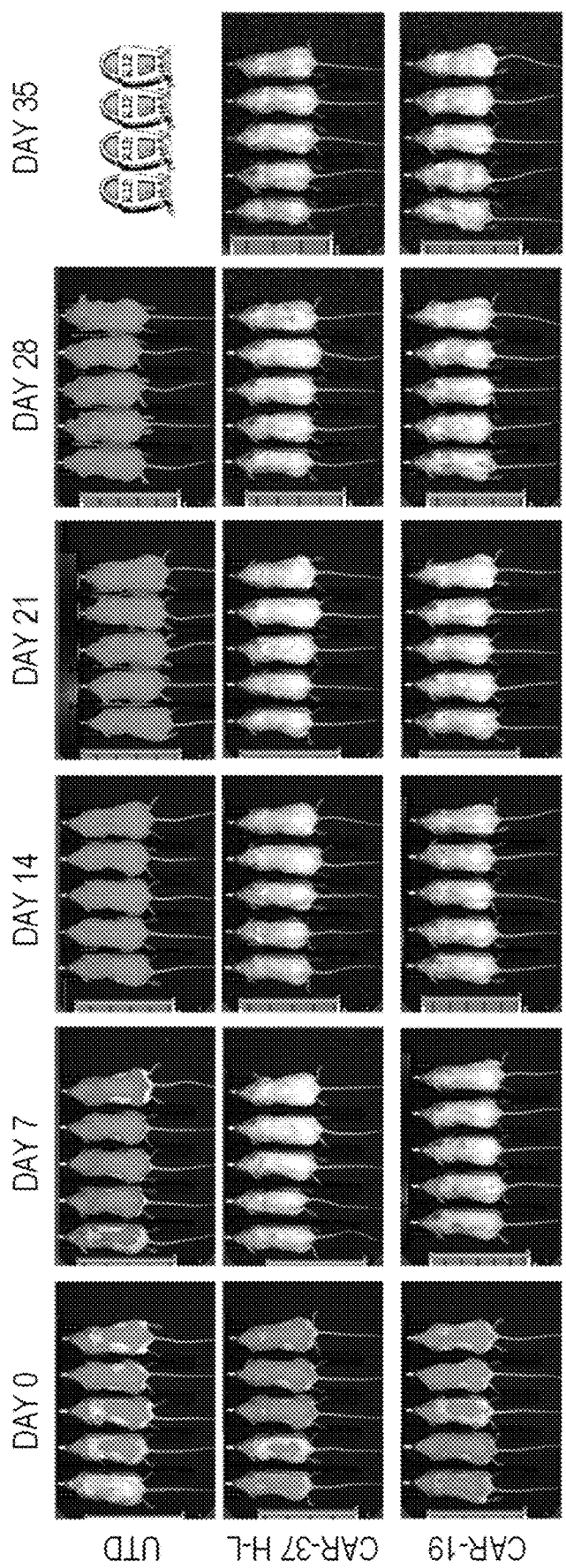
Figure 56C:
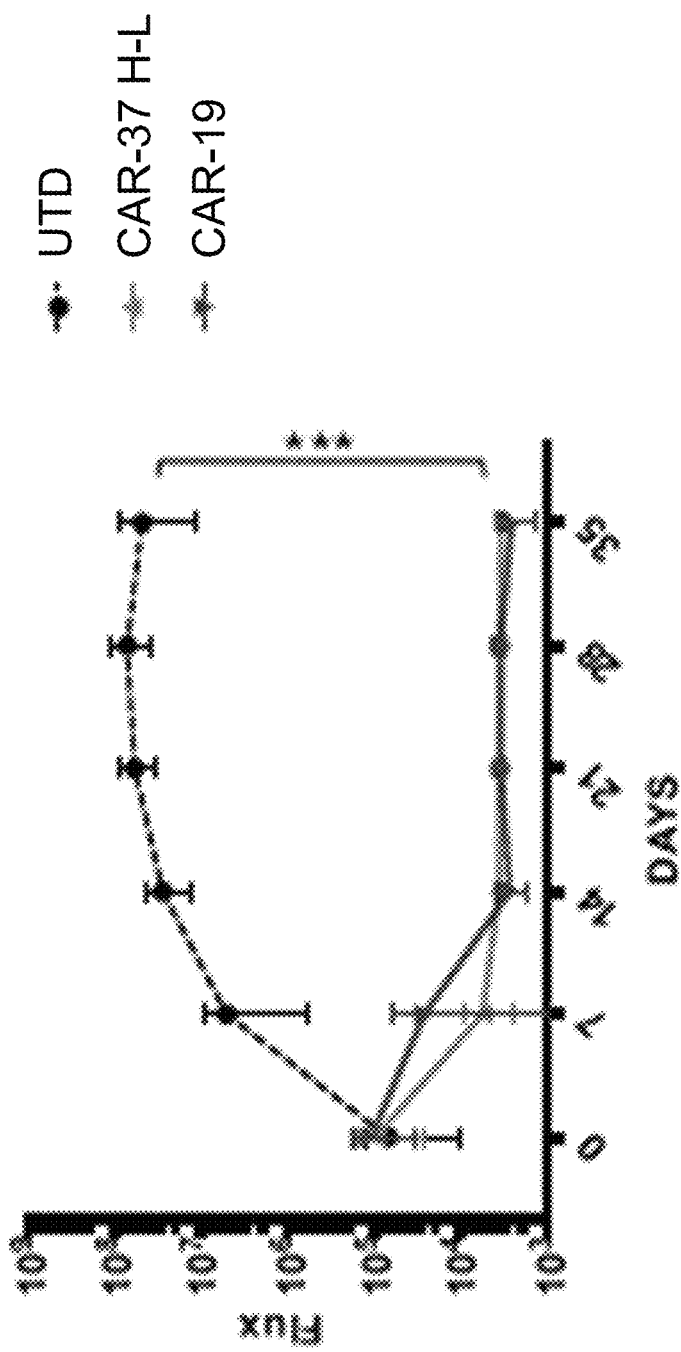

T cells expressing anti-CD37 CAR have a strong anti-tumor activity in a mantle cell lymphoma model in vivo (FIGS. 56A-56C)

Example 12

CD37 and CD19 Expression in Human Tumor Cell Lines

Figure 57:
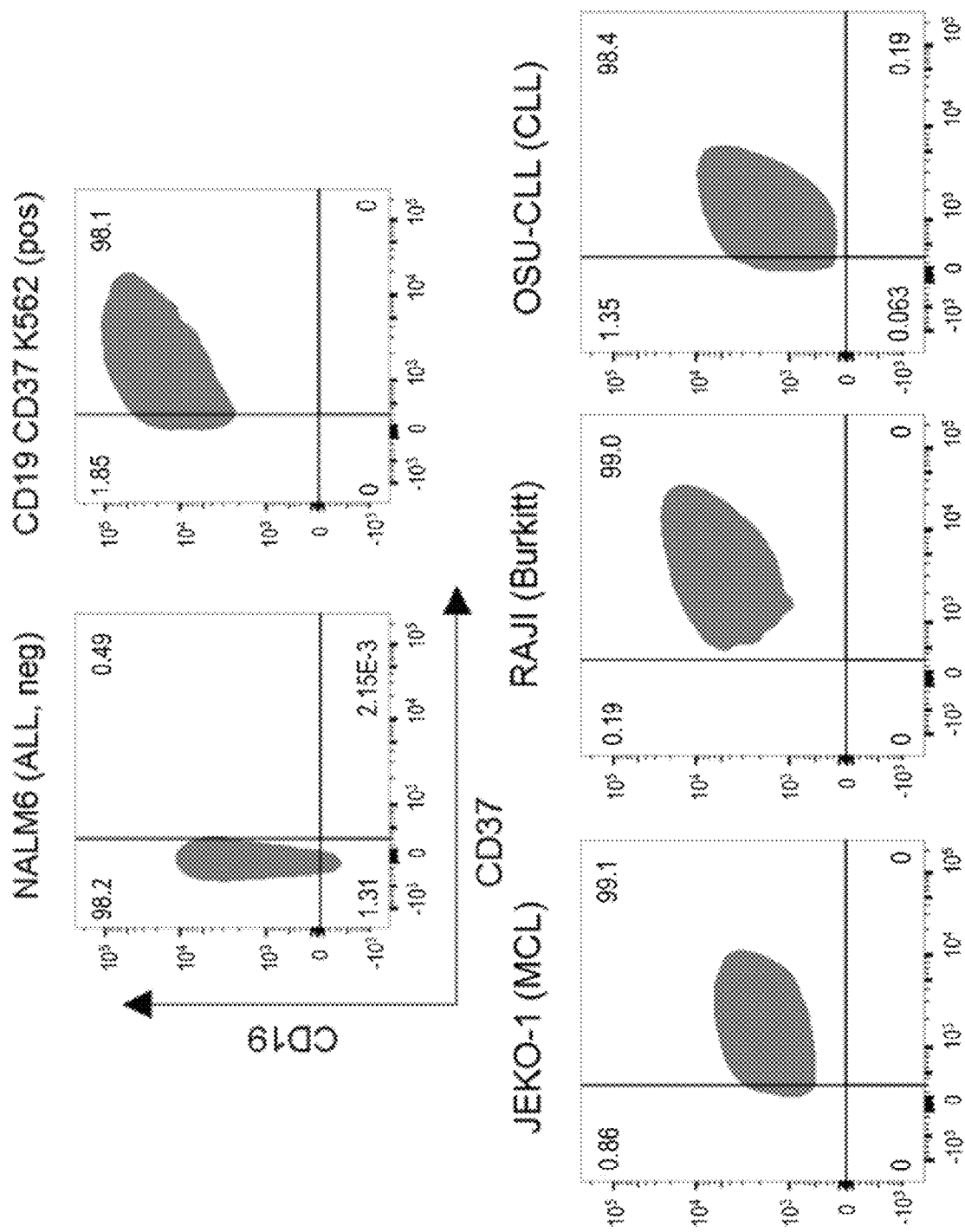
FIG. 57 shows expression of CD37 in tumor cells. The top panel shows expression of CD37 and CD19 in NALM6, CD19 CD38 K562, JEKO-1, RAJI, and OSU-CLL cell lines as assessed by flow cytometry. The bottom panel shows expression of CD37 and CD17 in MCL patient-derived xenograft (PDX) cell lines PDX_44685, PDX_98848, and PDX_96069 as assessed by flow cytometry. The graph on the bottom right panel shows the percent expression of CD19 and CD37 in MCL PDX cell lines.
Figure 57:
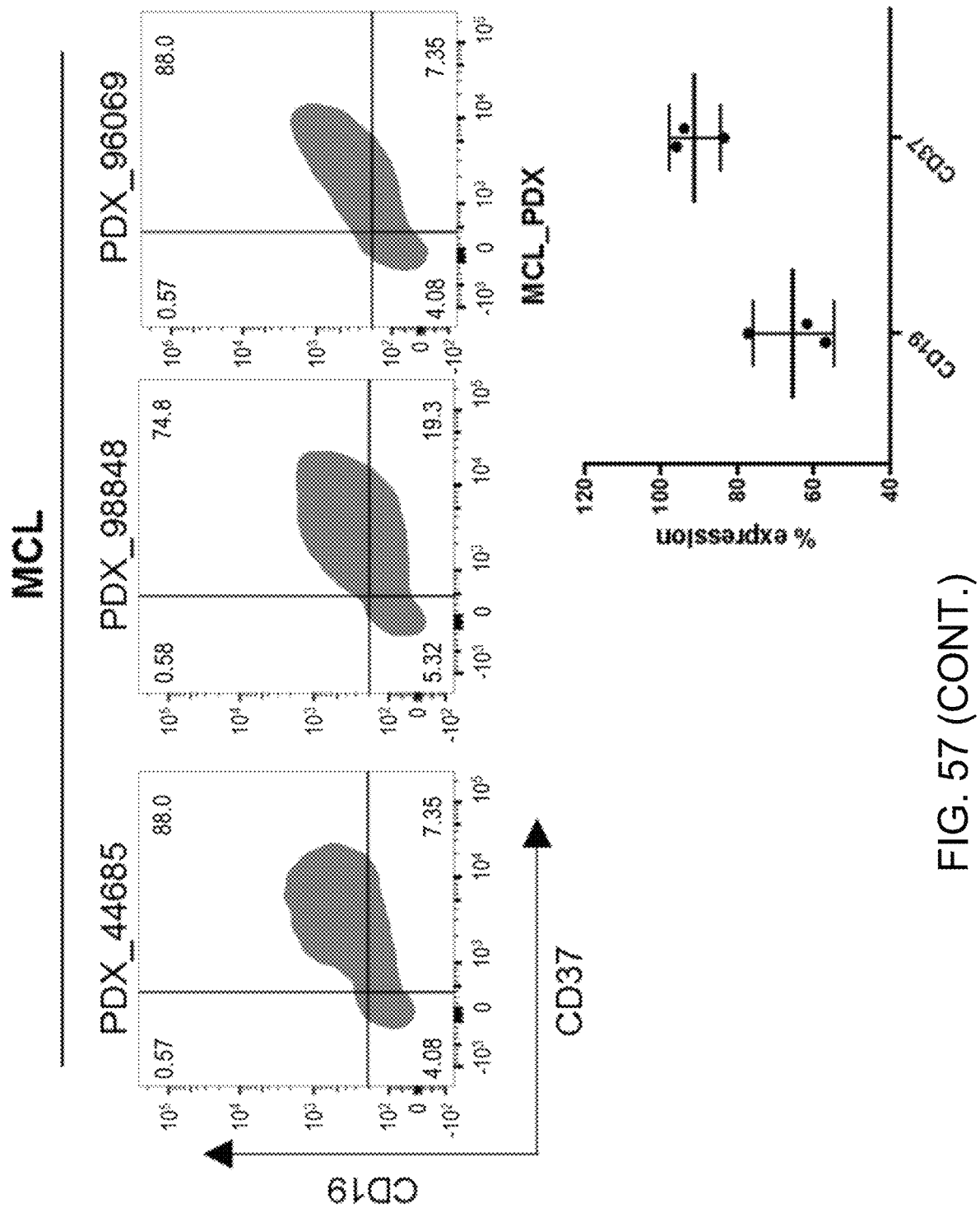

The expression of CD37 and CD19 in human tumor cell lines was evaluated (FIG. 58). The top panel of FIG. 57 reproduces the data shown in FIG. 51A, and shows that CD37 is highly expressed in non-Hodgkin lymphomas including MCL (JEKO-1), Burkitt lymphoma (RAJI), and B-cell chronic lymphocytic leukemia (OSU-CLL), but is absent in the ALL cell line NALM6. The bottom panel of FIG. 57 shows the expression of CD37 and CD19 in the MCL patient-derived xenograft (PDX) lines PDX_44685, PDX_98848, and PDX_96069, as well as the percent expression of CD19 and CD37 in the PDX cell lines. The MCL PDX cell lines expressed both CD37 and CD19.

Example 13

Anti-CD37 CAR-T Cells are Effective Against MCL PDX Tumors

Figure 58A:
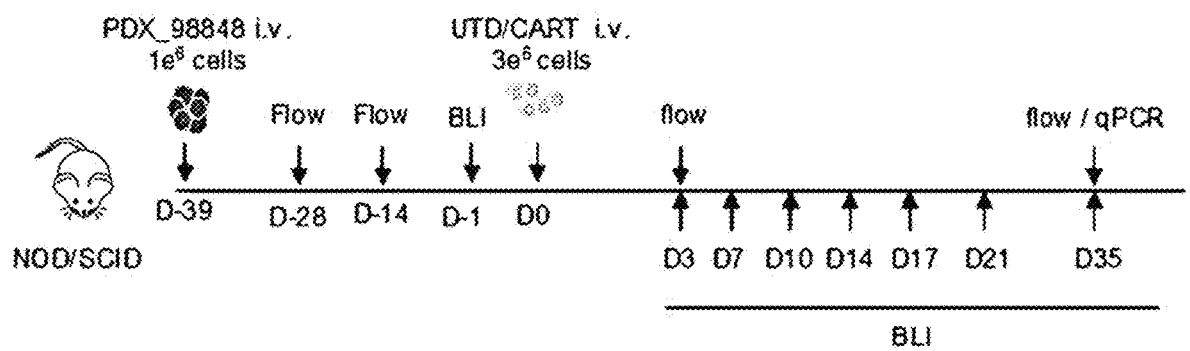
FIGS. 58A-58C demonstrate in vivo efficacy of CAR-37 T cells against MCL PDX tumors.
Figure 58B:
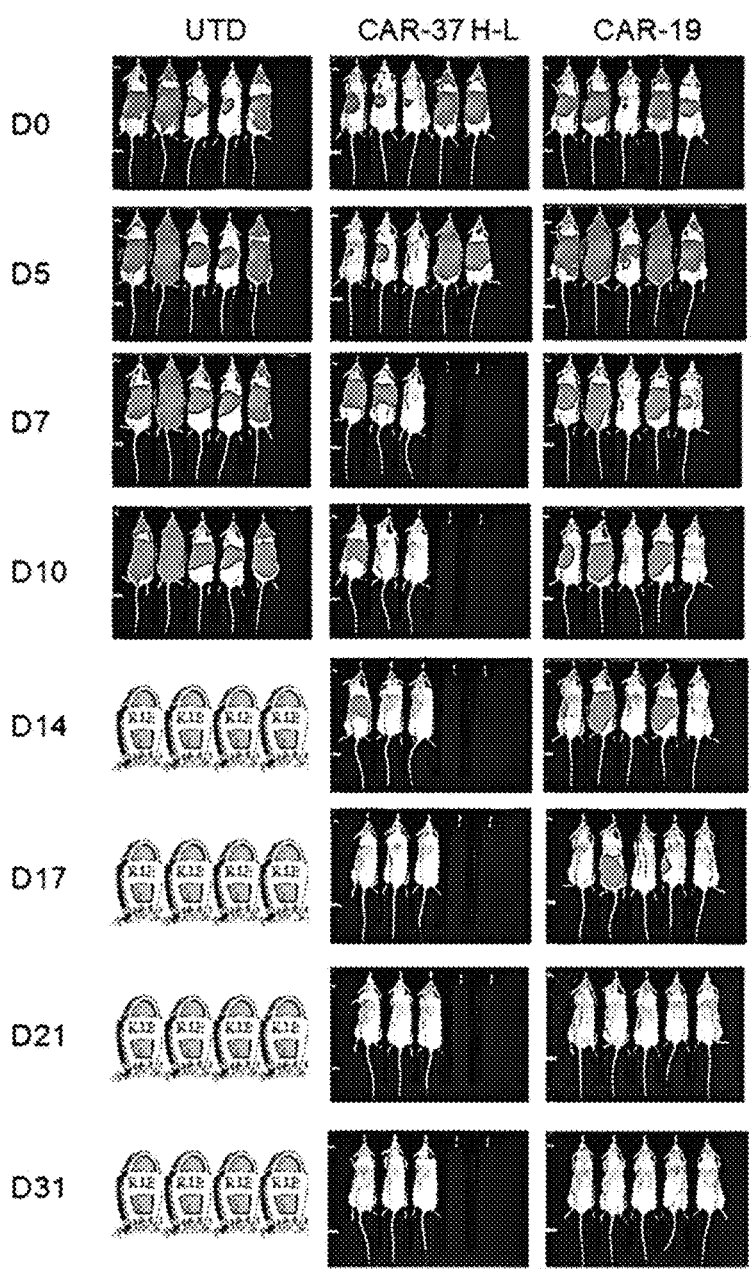
Figure 58C:
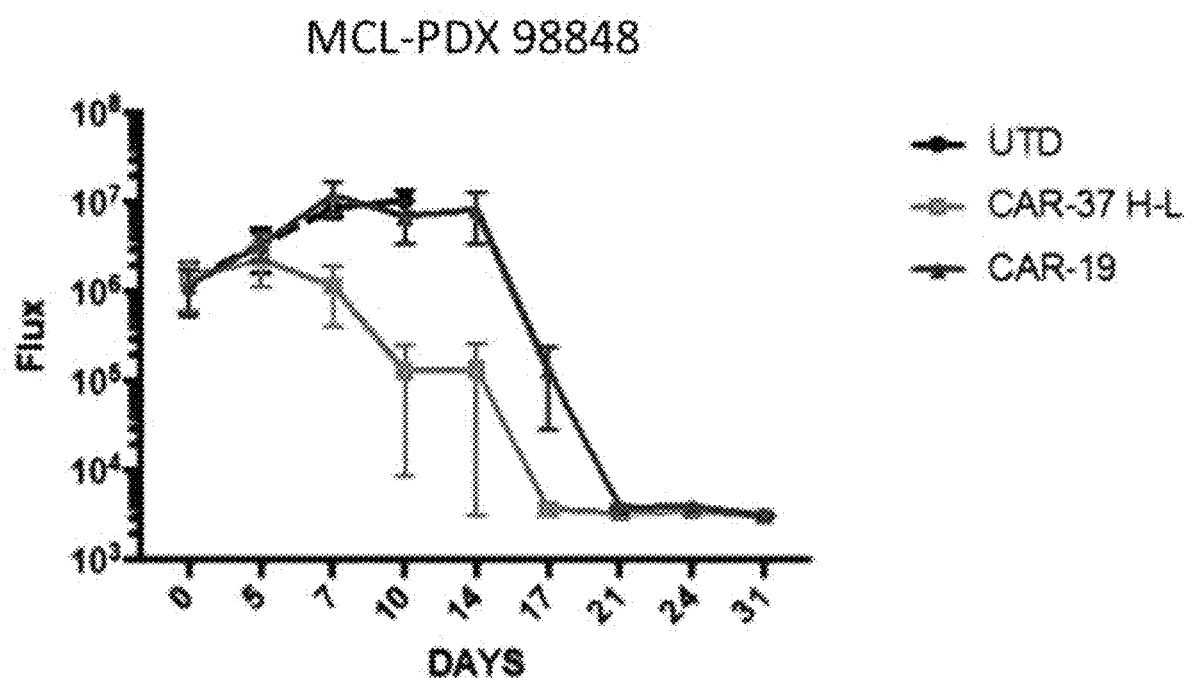

The efficacy of anti-CD37 CAR-T cells against MCL PDX cells was evaluated in vivo. FIG. 58A shows an experimental schematic; NOD/SCID mice were injected i.v. with $1 \times 10^6$ PDX_98848 cells. On day 0, mice received $3 \times 10^6$ control T cells (UTD), CAR-37 H-L, or CAR-19. Tumor growth was evaluated by BLI on day 3, day 7, day 10, day 14, day 17, day 21, and day 35. Representative bioluminescent images of the PDX growth over time is shown in FIG. 58B. T cells expressing anti-CD37 CAR have strong anti-tumor activity against MCL PDX in vivo (FIGS. 58A-58C).

Example 14

CD37 Expression in Peripheral T Cell Lymphoma (PTCL)

Figure 59A:
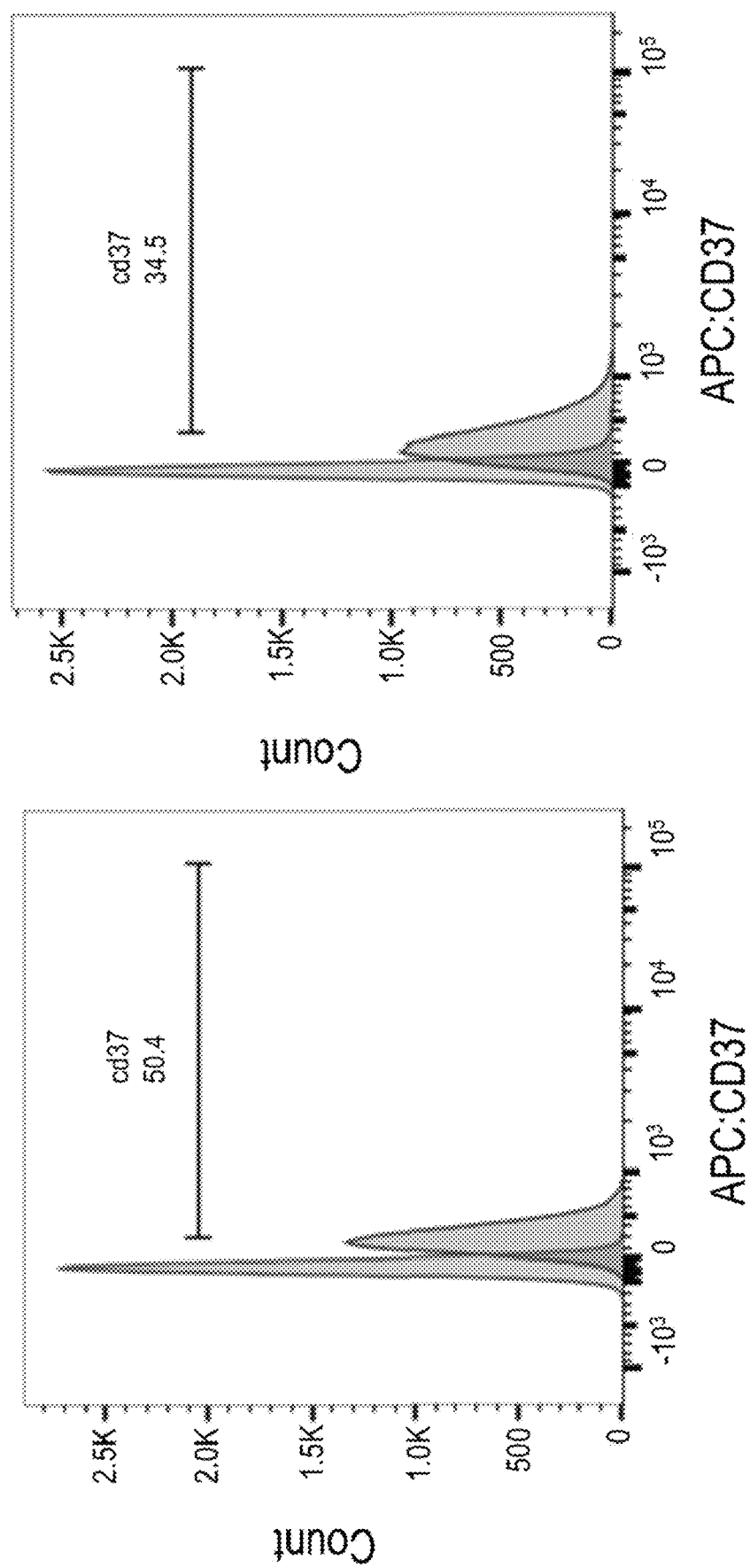
FIG. 59A shows expression of CD37 in the peripheral T cell lymphoma (PTCL) cell lines HUT78 (cutaneous T-cell lymphoma (CTCL)) (left panel) and FEPD (anaplastic large cell lymphoma (ALCL)) (right panel) as assessed by flow cytometry.
Figure 59B:
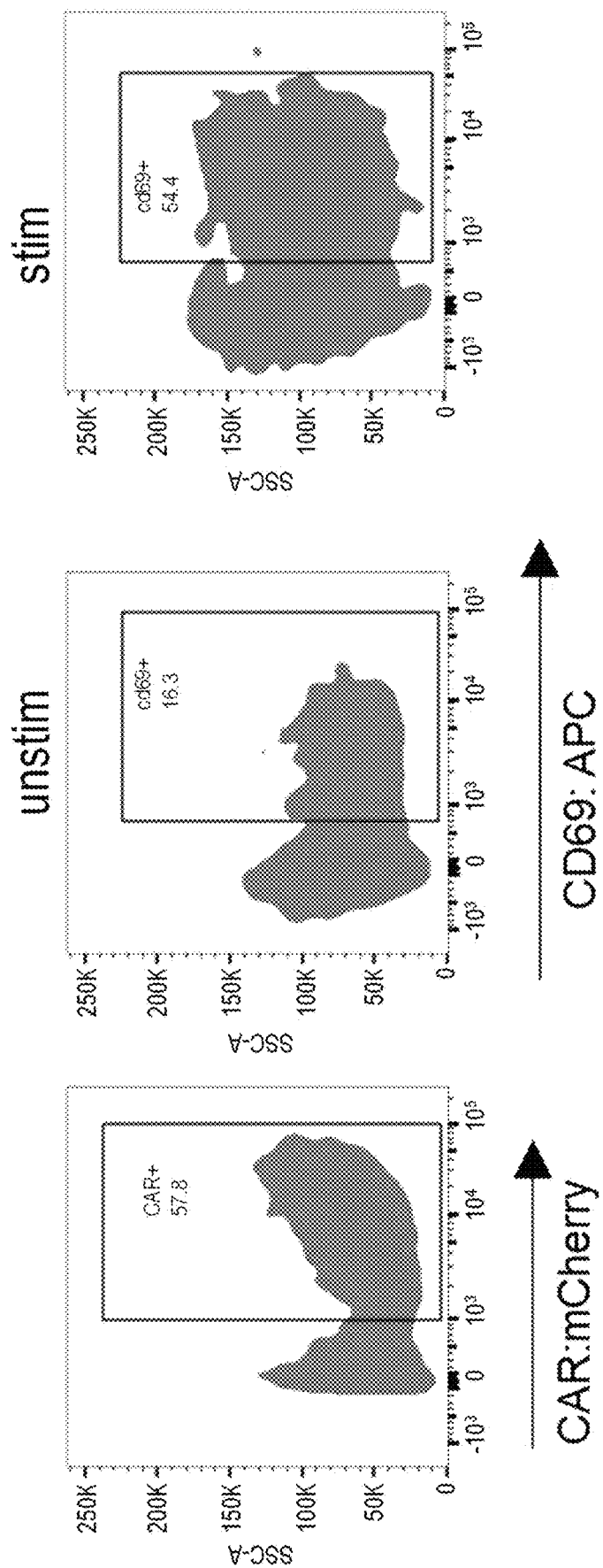
FIG. 59B shows expression of CD69 in unstimulated (unstim) and stimulated (stim) CAR T cells as assessed by flow cytometry. The left panel shows expression of mCherry (CAR+) as assessed by flow cytometry.
Figure 59C:
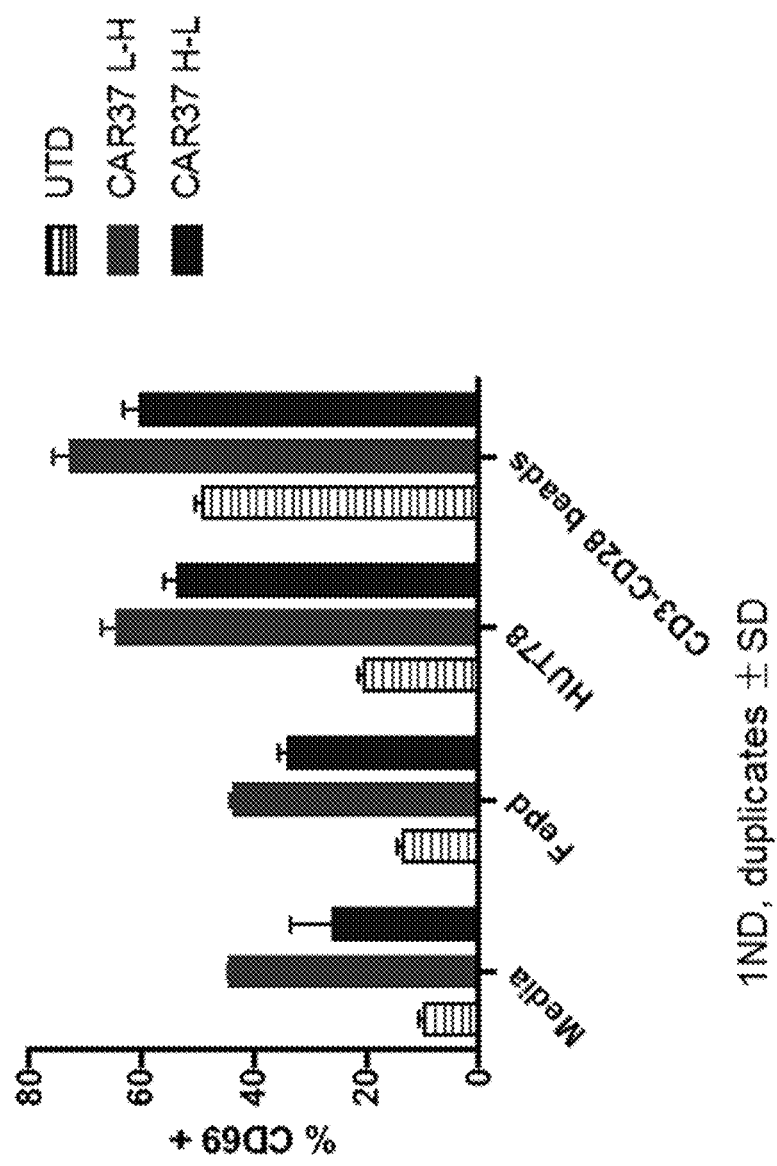
FIG. 59C shows the percentage of CD69+ UTD (control) CAR-37 L-H, and CAR-37 H-L cells stimulated with media, FEPD cells, HUT78 cells, or CDR-CD28 beads.

The expression of CD37 was evaluated in PTCL cell lines, including HUT78 (cutaneous T-cell lymphoma (CTCL)) and FEPD (anaplastic large cell lymphoma (ALCL)) (FIG. 59A). CD37 was expressed in both cell lines. Expression of the early activation marker CD69 was examined after CAR stimulation (FIGS. 59B and 59C).

Example 15

Figure 60:
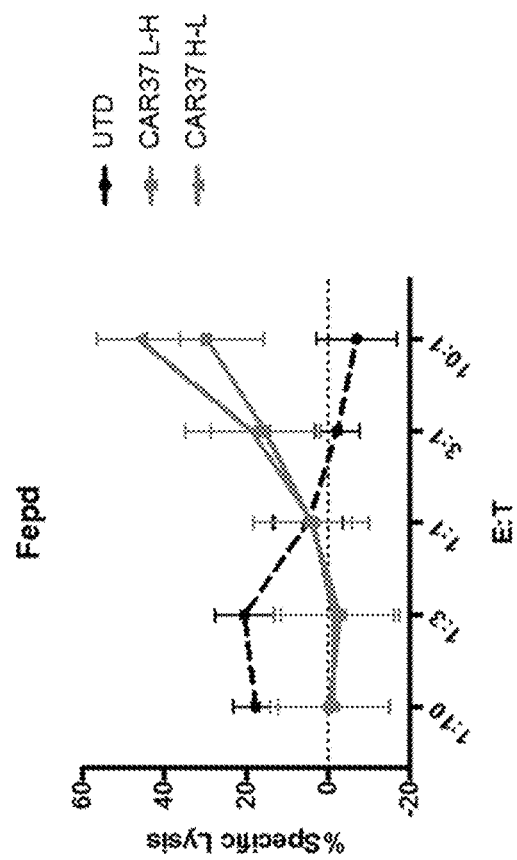
FIG. 60 shows in vitro effector function of UTD (control), CAR-37 L-H, and CAR-37 H-L T cells against HUT78 (CTCL) and FEPD (ALCL) PTCL cell lines. The graphs plot percent specific lysis for the indicated E:T ratios.
Figure 60:
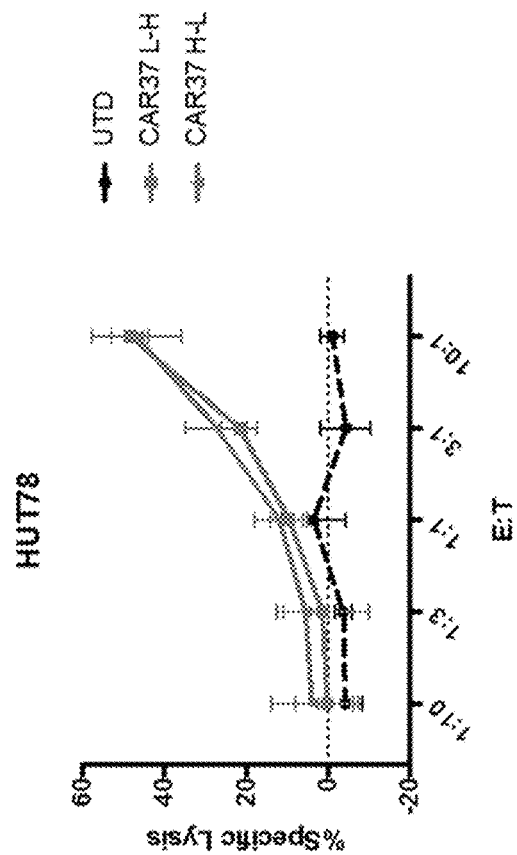

Anti-CD37 CAR-T Cells have In Vitro Cytotoxic Activity Against PTCL Cell Lines The in vitro cytotoxic activity of anti-CD37 CAR-T cells against PTCL lines was evaluated (FIG. 60). T-cells expressing anti-CD37 CAR have substantial in vitro activity against PTCL lines, including CTCL and ALCL tumor models (FIG. 60). These findings demonstrated that CD37-CAR T cells are useful as therapeutic agents for the treatment of patients with PTCL, including CTCL and ALCL.

Example 16

CD37 Expression in AML

Figure 61:
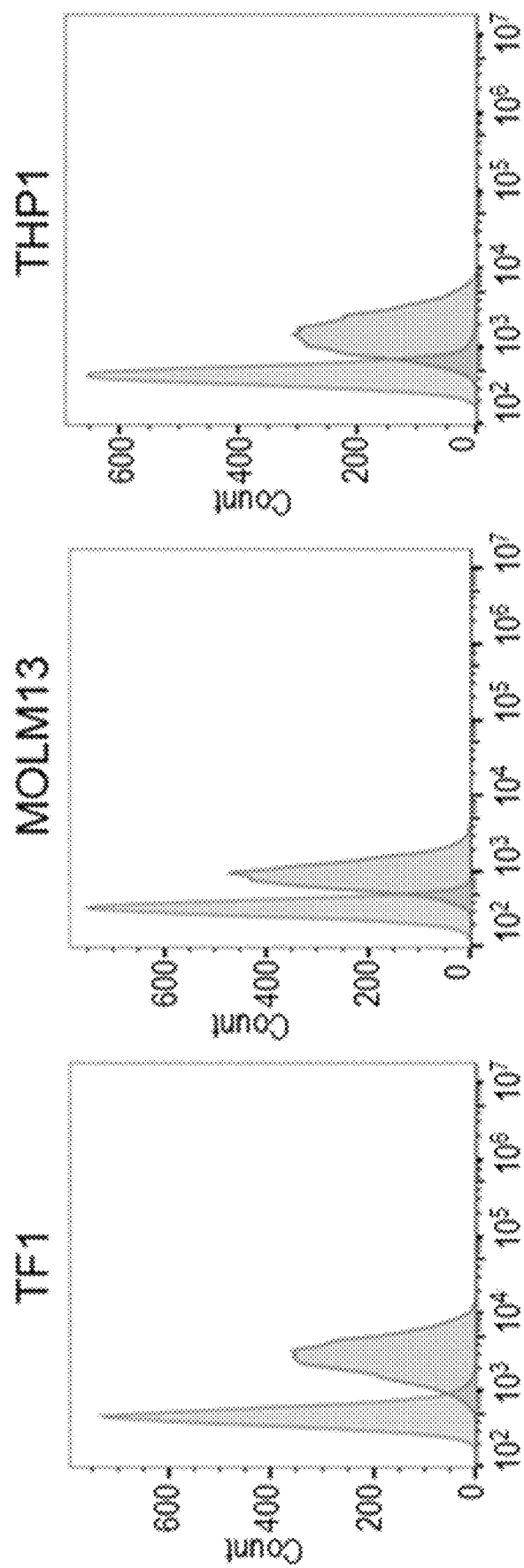
FIG. 61 shows expression of CD37 in the AML cell lines TF1, MOM13, and THP1 as assessed by flow cytometry.

CD37 expression has been detected in AML samples (Pereira et al. *Mol. Cancer Ther.* 14(7):1650-1660, 2015). The expression of CD37 in AML cell lines was evaluated in the AML cell lines TF1, MOLM13, and THP by flow cytometry (FIG. 61). All three AML cell lines expressed CD37 (FIG. 61). These findings demonstrated that CD37-CAR T cells are useful as therapeutic agents for the treatment of patients with AML.

---

What is claimed herein is:

1. A chimeric antigen receptor (CAR) polypeptide comprising:
   a) an extracellular domain comprising a target-binding sequence that binds to BCMA, CD37 or CD19;
   b) a transmembrane domain;
   c) a co-stimulatory domain; and
   d) a T cell intracellular signaling domain, comprising a mutation of a tyrosine residue in an immunoreceptor tyrosine-based activation motif (ITAM) II.

2. The CAR polypeptide of claim 1, wherein the transmembrane domain is the transmembrane domain from CD8 or 4-1BB.

3. The CAR polypeptide of claim 1, wherein the intracellular signaling domain comprises a CD3ζ ITAM3 sequence of SEQ ID NO: 33.

4. The CAR polypeptide of claim 1, wherein the intracellular signaling domain comprises a CD3ζ ITAM3 sequence comprising a mutation of a tyrosine residue in ITAM II relative to the CD3ζ ITAM3 sequence of SEQ ID NO: 13.

5. The CAR polypeptide of claim 1, wherein the T-cell intracellular signaling domain is the intracellular signaling domain of CD3ε or CD3θ.

6. The CAR polypeptide of claim 1, wherein the target-binding sequence comprises a ligand of the target or an antibody reagent that specifically binds the target.

7. The CAR polypeptide of claim 1, wherein the target is B cell maturation antigen (BCMA).

8. The CAR polypeptide of claim 1, wherein the target is CD37.

9. The CAR polypeptide of claim 1, wherein the target-binding sequence has the sequence of SEQ ID NO: 1.

10. A chimeric antigen receptor (CAR) polypeptide comprising:
    a) an extracellular domain comprising a BCMA-binding sequence;
    b) a transmembrane domain of CD8;
    c) a co-stimulatory domain of a 4-1BB; and
    d) a T cell intracellular signaling domain comprising a mutation of a tyrosine residue in an immunoreceptor tyrosine-based activation motif (ITAM) II.

11. The CAR polypeptide of claim 10, wherein the BCMA-binding sequence comprises a ligand of BCMA or an antibody reagent that specifically binds BCMA.

12. The CAR polypeptide of claim 11, wherein the antibody reagent comprises the sequence of SEQ ID NO: 1.

13. The CAR polypeptide of claim 10, wherein the intracellular signaling domain comprises a CD3ζ ITAM3 sequence comprising a mutation of a tyrosine residue in ITAM II relative to the CD3ζ ITAM3 sequence of SEQ ID NO: 13.

14. A chimeric antigen receptor (CAR) polypeptide comprising:
    a) an extracellular domain comprising a CD37-binding sequence;
    b) a transmembrane domain of CD8;
    c) a co-stimulatory domain of a 4-1BB; and
    d) a T cell intracellular signaling domain comprising a mutation of a tyrosine residue in an immunoreceptor tyrosine-based activation motif (ITAM) II.

15. The CAR polypeptide of claim 14, wherein the CD37-binding sequence comprises a ligand of CD37 or an antibody reagent that specifically binds CD37.

16. The CAR polypeptide of claim 15, wherein the antibody reagent comprises a scFv.

17. The CAR polypeptide of claim 14, wherein the intracellular signaling domain comprises a CD3ζ ITAM3 sequence comprising a mutation of a tyrosine residue in ITAM II relative to the CD3ζ ITAM3 sequence of SEQ ID NO: 13.

18. The CAR polypeptide of claim 4, wherein the CD3ζ ITAM3 sequence comprises a substitution mutation at amino acids positions relative to Y59 and Y71 of SEQ ID NO: 13.

19. The CAR polypeptide of claim 18, wherein CD3ζ ITAM3 sequence comprises a phenylalanine at amino acid positions Y59 and Y71 of SEQ ID NO: 13.

20. The CAR polypeptide of claim 18, wherein the CD3ζ ITAM3 sequence comprises a phenylalanine at amino acid positions Y90 and Y100 of SEQ ID NO: 13.

21. The CAR polypeptide of claim 20, wherein the extracellular domain comprises a target-binding sequence that binds to CD19.

22. The CAR polypeptide of claim 21, wherein the transmembrane domain is a CD28 transmembrane domain.

23. A nucleic acid sequence comprising a polynucleotide encoding the CAR polypeptide of claim 1.

24. A mammalian cell comprising the CAR polypeptide of claim 1.

25. The mammalian cell of claim 24, wherein the mammalian cell is a T cell.

26. The mammalian cell of claim 24, wherein the mammalian cell is a human cell.

27. A composition comprising the CAR polypeptide of claim 1.

28. A composition comprising the T cell of claim 25.

* * * * *

UNITED STATES PATENT AND TRADEMARK OFFICE
CERTIFICATE OF CORRECTION

| | |
|---|---|
| PATENT NO. | : 11,578,115 B2 |
| APPLICATION NO. | : 16/476588 |
| DATED | : February 14, 2023 |
| INVENTOR(S) | : Marcela V. Maus et al. |

It is certified that error appears in the above-identified patent and that said Letters Patent is hereby corrected as shown below:

On the Title Page

Column 1, item (72) should read:
(72) Inventors: Marcela V. Maus, Lexington, MA (US);
Mark Cobbold, Winchester, MA (US);
Irene Scarfo, Cambridge, MA (US);
Felipe Bedoya, Eagleville, PA (US);

Signed and Sealed this
Ninth Day of January, 2024

Katherine Kelly Vidal
*Director of the United States Patent and Trademark Office*

```
                        SEQUENCE LISTING

<160> NUMBER OF SEQ ID NOS: 40

<210> SEQ ID NO 1
<211> LENGTH: 249
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Ser Ala Ser Gln Asp Ile Ser Asn Tyr Leu Asn Trp
                165                 170                 175

Tyr Gln Gln Lys Pro Gly Lys Ala Pro Lys Leu Leu Ile Tyr Tyr Thr
            180                 185                 190

Ser Asn Leu His Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Arg Lys Leu Pro Trp Thr Phe Gly
225                 230                 235                 240

Gln Gly Thr Lys Leu Glu Ile Lys Arg
                245

<210> SEQ ID NO 2
<211> LENGTH: 121
<212> TYPE: PRT
```

```
<213> ORGANISM: Artificial Sequence
<220> FEATURE:
<223> OTHER INFORMATION: Synthetic Construct

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser
        115                 120

<210> SEQ ID NO 3
<211> LENGTH: 20
<212> TYPE: PRT
<213> ORGANISM: Artificial Sequence
<220> FEATURE:
<223> OTHER INFORMATION: Synthetic Construct

<400> SEQUENCE: 3

Gly Gly Gly Gly Ser Gly Gly Gly Gly Ser Gly Gly Gly Gly Ser Gly
1               5                   10                  15

Gly Gly Gly Ser
            20

<210> SEQ ID NO 4
<211> LENGTH: 108
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105

<210> SEQ ID NO 5
```

<211> LENGTH: 244
<212> TYPE: PRT
<213> ORGANISM: Artificial Sequence
<220> FEATURE:
<223> OTHER INFORMATION: Synthetic Construct

<400> SEQUENCE: 5

```
Ala Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Gly Tyr
                20                  25                  30
Asn Met Asn Trp Val Arg Gln Ala Pro Gly Gln Gly Leu Glu Trp Met
            35                  40                  45
Gly Asn Ile Asp Pro Tyr Tyr Gly Gly Thr Thr Tyr Asn Arg Lys Phe
        50                  55                  60
Lys Gly Arg Val Thr Leu Thr Val Asp Lys Ser Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Val Gly Pro Met Asp Tyr Trp Gly Gln Gly Thr Leu Val
                100                 105                 110
Thr Val Ser Ser Gly Gly Gly Gly Ser Gly Gly Gly Gly Ser Gly Gly
            115                 120                 125
Gly Gly Ser Gly Gly Gly Ser Asp Ile Gln Met Thr Gln Ser Pro
        130                 135                 140
Ser Ser Leu Ser Ala Ser Val Gly Asp Arg Val Thr Ile Thr Cys Arg
145                 150                 155                 160
Thr Ser Glu Asn Val Tyr Ser Tyr Leu Ala Trp Tyr Gln Gln Lys Pro
                165                 170                 175
Gly Lys Ala Pro Lys Leu Leu Val Ser Ala Lys Thr Leu Ala Glu
                180                 185                 190
Gly Val Pro Ser Arg Phe Ser Gly Ser Gly Ser Gly Thr Asp Phe Thr
            195                 200                 205
Leu Thr Ile Ser Ser Leu Gln Pro Glu Asp Phe Ala Thr Tyr Phe Cys
        210                 215                 220
Gln His His Ser Asp Asn Pro Trp Thr Phe Gly Gln Gly Thr Lys Val
225                 230                 235                 240
Glu Ile Lys Arg
```

<210> SEQ ID NO 6
<211> LENGTH: 116
<212> TYPE: PRT
<213> ORGANISM: Artificial Sequence
<220> FEATURE:
<223> OTHER INFORMATION: Synthetic Construct

<400> SEQUENCE: 6

```
Ala Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Gly Tyr
                20                  25                  30
Asn Met Asn Trp Val Arg Gln Ala Pro Gly Gln Gly Leu Glu Trp Met
            35                  40                  45
Gly Asn Ile Asp Pro Tyr Tyr Gly Gly Thr Thr Tyr Asn Arg Lys Phe
        50                  55                  60
Lys Gly Arg Val Thr Leu Thr Val Asp Lys Ser Ser Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110

Thr Val Ser Ser
        115

<210> SEQ ID NO 7
<211> LENGTH: 20
<212> TYPE: PRT
<213> ORGANISM: Artificial Sequence
<220> FEATURE:
<223> OTHER INFORMATION: Synthetic Construct

<400> SEQUENCE: 7

Gly Gly Gly Gly Ser Gly Gly Gly Ser Gly Gly Gly Ser Gly
1               5                   10                  15

Gly Gly Gly Ser
            20

<210> SEQ ID NO 8
<211> LENGTH: 108
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Tyr
            20                  25                  30

Leu Ala Trp Tyr Gln Gln Lys Pro Gly Lys Ala Pro Lys Leu Leu Val
        35                  40                  45

Ser Ser Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His His Ser Asp Asn Pro Trp
                85                  90                  95

Thr Phe Gly Gln Gly Thr Lys Val Glu Ile Lys Arg
            100                 105

<210> SEQ ID NO 9
<211> LENGTH: 244
<212> TYPE: PRT
<213> ORGANISM: Artificial Sequence
<220> FEATURE:
<223> OTHER INFORMATION: Synthetic Construct

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Tyr
            20                  25                  30

Leu Ala Trp Tyr Gln Gln Lys Pro Gly Lys Ala Pro Lys Leu Leu Val
        35                  40                  45

Ser Ser Ala Lys Thr Leu Ala Glu Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Phe Cys Gln His His Ser Asp Asn Pro Trp
                 85                  90                  95

Thr Phe Gly Gln Gly Thr Lys Val Glu Ile Lys Arg Gly Gly Gly Gly
                100                 105                 110

Ser Gly Gly Gly Gly Ser Gly Gly Gly Ser Gly Gly Gly Gly Ser
            115                 120                 125

Ala Val Gln Leu Val Gln Ser Gly Ala Glu Val Lys Lys Pro Gly Ser
            130                 135                 140

Ser Val Lys Val Ser Cys Lys Ala Ser Gly Tyr Ser Phe Thr Gly Tyr
145                 150                 155                 160

Asn Met Asn Trp Val Arg Gln Ala Pro Gly Gln Gly Leu Glu Trp Met
                165                 170                 175

Gly Asn Ile Asp Pro Tyr Tyr Gly Gly Thr Thr Tyr Asn Arg Lys Phe
                180                 185                 190

Lys Gly Arg Val Thr Leu Thr Val Asp Lys Ser Ser Thr Ala Tyr
            195                 200                 205

Met Glu Leu Ser Ser Leu Arg Ser Glu Asp Thr Ala Val Tyr Tyr Cys
        210                 215                 220

Ala Arg Ser Val Gly Pro Met Asp Tyr Trp Gly Gln Gly Thr Leu Val
225                 230                 235                 240

Thr Val Ser Ser

<210> SEQ ID NO 10
<211> LENGTH: 108
<212> TYPE: PRT
<213> ORGANISM: Artificial Sequence
<220> FEATURE:
<223> OTHER INFORMATION: Synthetic Construct

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Arg Thr Ser Glu Asn Val Tyr Ser Tyr
                20                  25                  30

Leu Ala Trp Tyr Gln Gln Lys Pro Gly Lys Ala Pro Lys Leu Leu Val
            35                  40                  45

Ser Ser Ala Lys Thr Leu Ala Glu Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln His His Ser Asp Asn Pro Trp
                 85                  90                  95

Thr Phe Gly Gln Gly Thr Lys Val Glu Ile Lys Arg
                100                 105

<210> SEQ ID NO 11
<211> LENGTH: 20
<212> TYPE: PRT
<213> ORGANISM: Artificial Sequence
<220> FEATURE:
<223> OTHER INFORMATION: Synthetic Construct

<400> SEQUENCE: 11

Gly Gly Gly Gly Ser Gly Gly Gly Gly Ser Gly Gly Gly Gly Ser Gly
 1               5                  10                  15
```

Gly Gly Gly Ser
        20

<210> SEQ ID NO 12
<211> LENGTH: 116
<212> TYPE: PRT
<213> ORGANISM: Artificial Sequence
<220> FEATURE:
<223> OTHER INFORMATION: Synthetic Construct

<400> SEQUENCE: 12

Ala Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Met
        35                  40                  45

Gly Asn Ile Asp Pro Tyr Tyr Gly Thr Thr Tyr Asn Arg Lys Phe
    50                  55                  60

Lys Gly Arg Val Thr Leu Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110

Thr Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: Synthetic Construct

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Synthetic Construct

<400> SEQUENCE: 14

Arg Val Lys Phe Ser Arg Ser Ala Asp Ala Pro Ala Tyr Gln Gln Gly

```
1               5                   10                  15
Gln Asn Gln Leu Phe Asn Glu Leu Asn Leu Gly Arg Arg Glu Glu Phe
            20                  25                  30

Asp Val Leu Asp Lys Arg Arg Gly Arg Asp Pro Glu Met Gly Gly Lys
            35                  40              45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 15
<211> LENGTH: 493
<212> TYPE: PRT
<213> ORGANISM: Artificial Sequence
<220> FEATURE:
<223> OTHER INFORMATION: Synthetic Construct

<400> SEQUENCE: 15

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
            35                  40                  45

Thr Phe Ser Asn Tyr Trp Met His Trp Val Arg Gln Ala Pro Gly Gln
        50                  55                  60

Gly Leu Glu Trp Met Gly Ala Thr Tyr Arg Gly His Ser Asp Thr Tyr
65                  70                  75                  80

Tyr Asn Gln Lys Phe Lys Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Gly Ala Ile Tyr Asn Gly Tyr Asp Val
            115                 120                 125

Leu Asp Asn Trp Gly Gln Gly Thr Leu Val Thr Val Ser Ser Gly Gly
        130                 135                 140

Gly Gly Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Ser Ala Ser Gln Asp Ile Ser
            180                 185                 190

Asn Tyr Leu Asn Trp Tyr Gln Gln Lys Pro Gly Lys Ala Pro Lys Leu
        195                 200                 205

Leu Ile Tyr Tyr Thr Ser Asn Leu His Ser Gly Val Pro Ser Arg Phe
        210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Tyr Arg Lys Leu
                245                 250                 255

Pro Trp Thr Phe Gly Gln Gly Thr Lys Leu Glu Ile Lys Arg Thr Thr
```

```
                260                 265                 270
Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
        420                 425                 430

Lys Asn Pro Gln Glu Gly Leu Tyr Asn Glu Leu Gln Lys Asp Lys Met
    435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 16
<211> LENGTH: 21
<212> TYPE: PRT
<213> ORGANISM: Artificial Sequence
<220> FEATURE:
<223> OTHER INFORMATION: Synthetic Construct

<400> SEQUENCE: 16

Met Ala Leu Pro Val Thr Ala Leu Leu Leu Pro Leu Ala Leu Leu Leu
1               5                   10                  15

His Ala Ala Arg Pro
            20

<210> SEQ ID NO 17
<211> LENGTH: 249
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45
```

```
Gly Ala Thr Tyr Arg Gly His Ser Asp Thr Tyr Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ala Ile Tyr Asn Gly Tyr Asp Val Leu Asp Asn Trp Gly
                100                 105                 110

Gln Gly Thr Leu Val Thr Val Ser Gly Gly Gly Ser Gly Gly
            115                 120                 125

Gly Gly Ser Gly Gly Gly Ser Gly Gly Gly Ser Asp Ile Gln
        130                 135                 140

Met Thr Gln Ser Pro Ser Ser Leu Ser Ala Ser Val Gly Asp Arg Val
145                 150                 155                 160

Thr Ile Thr Cys Ser Ala Ser Gln Asp Ile Ser Asn Tyr Leu Asn Trp
                165                 170                 175

Tyr Gln Gln Lys Pro Gly Lys Ala Pro Lys Leu Leu Ile Tyr Tyr Thr
            180                 185                 190

Ser Asn Leu His Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Arg Lys Leu Pro Trp Thr Phe Gly
225                 230                 235                 240

Gln Gly Thr Lys Leu Glu Ile Lys Arg
            245

<210> SEQ ID NO 18
<211> LENGTH: 69
<212> TYPE: PRT
<213> ORGANISM: Artificial Sequence
<220> FEATURE:
<223> OTHER INFORMATION: Synthetic Construct

<400> SEQUENCE: 18

Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
 50                  55                  60

Ile Thr Leu Tyr Cys
 65

<210> SEQ ID NO 19
<211> LENGTH: 42
<212> TYPE: PRT
<213> ORGANISM: Artificial Sequence
<220> FEATURE:
<223> OTHER INFORMATION: Synthetic Construct

<400> SEQUENCE: 19

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
                20                  25                  30
```

```
Pro Glu Glu Glu Glu Gly Gly Cys Glu Leu
        35                  40

<210> SEQ ID NO 20
<211> LENGTH: 112
<212> TYPE: PRT
<213> ORGANISM: Artificial Sequence
<220> FEATURE:
<223> OTHER INFORMATION: Synthetic Construct

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 488
<212> TYPE: PRT
<213> ORGANISM: Artificial Sequence
<220> FEATURE:
<223> OTHER INFORMATION: Synthetic Construct

<400> SEQUENCE: 21

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Thr Ser Glu
        35                  40                  45

Asn Val Tyr Ser Tyr Leu Ala Trp Tyr Gln Gln Lys Pro Gly Lys Ala
    50                  55                  60

Pro Lys Leu Leu Val Ser Ser Ala Lys Thr Leu Ala Glu Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Phe Cys Gln His His
            100                 105                 110

Ser Asp Asn Pro Trp Thr Phe Gly Gln Gly Thr Lys Val Glu Ile Lys
        115                 120                 125

Arg Gly Gly Gly Gly Ser Gly Gly Gly Gly Ser Gly Gly Gly Gly Ser
    130                 135                 140

Gly Gly Gly Gly Ser Ala Val Gln Leu Val Gln Ser Gly Ala Glu Val
145                 150                 155                 160

Lys Lys Pro Gly Ser Ser Val Lys Val Ser Cys Lys Ala Ser Gly Tyr
                165                 170                 175

Ser Phe Thr Gly Tyr Asn Met Asn Trp Val Arg Gln Ala Pro Gly Gln
```

```
            180                 185                 190
Gly Leu Glu Trp Met Gly Asn Ile Asp Pro Tyr Tyr Gly Gly Thr Thr
            195                 200                 205

Tyr Asn Arg Lys Phe Lys Gly Arg Val Thr Leu Thr Val Asp Lys Ser
        210                 215                 220

Ser Ser Thr Ala Tyr Met Glu Leu Ser Ser Leu Arg Ser Glu Asp Thr
225                 230                 235                 240

Ala Val Tyr Tyr Cys Ala Arg Ser Val Gly Pro Met Asp Tyr Trp Gly
                245                 250                 255

Gln Gly Thr Leu Val Thr Val Ser Ser Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 22
<211> LENGTH: 21
<212> TYPE: PRT
<213> ORGANISM: Artificial Sequence
<220> FEATURE:
<223> OTHER INFORMATION: Synthetic Construct

<400> SEQUENCE: 22

Met Ala Leu Pro Val Thr Ala Leu Leu Leu Pro Leu Ala Leu Leu Leu
1               5                   10                  15

His Ala Ala Arg Pro
            20

<210> SEQ ID NO 23
<211> LENGTH: 244
<212> TYPE: PRT
```

<213> ORGANISM: Artificial Sequence
<220> FEATURE:
<223> OTHER INFORMATION: Synthetic Construct

<400> SEQUENCE: 23

```
Asp Ile Gln Met Thr Gln Ser Pro Ser Leu Ser Ala Ser Val Gly
1               5                   10                  15

Asp Arg Val Thr Ile Thr Cys Arg Thr Ser Glu Asn Val Tyr Ser Tyr
            20                  25                  30

Leu Ala Trp Tyr Gln Gln Lys Pro Gly Lys Ala Pro Lys Leu Leu Val
        35                  40                  45

Ser Ser Ala Lys Thr Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Ser Asp Asn Pro Trp
                85                  90                  95

Thr Phe Gly Gln Gly Thr Lys Val Glu Ile Lys Arg Gly Gly Gly Gly
                100                 105                 110

Ser Gly Gly Gly Gly Ser Gly Gly Gly Ser Gly Gly Gly Gly Ser
            115                 120                 125

Ala Val Gln Leu Val Gln Ser Gly Ala Glu Val Lys Lys Pro Gly Ser
            130                 135                 140

Ser Val Lys Val Ser Cys Lys Ala Ser Gly Tyr Ser Phe Thr Gly Tyr
145                 150                 155                 160

Asn Met Asn Trp Val Arg Gln Ala Pro Gly Gln Gly Leu Glu Trp Met
                165                 170                 175

Gly Asn Ile Asp Pro Tyr Tyr Gly Gly Thr Thr Tyr Asn Arg Lys Phe
                180                 185                 190

Lys Gly Arg Val Thr Leu Thr Val Asp Lys Ser Ser Thr Ala Tyr
            195                 200                 205

Met Glu Leu Ser Ser Leu Arg Ser Glu Asp Thr Ala Val Tyr Tyr Cys
        210                 215                 220

Ala Arg Ser Val Gly Pro Met Asp Tyr Trp Gly Gln Gly Thr Leu Val
225                 230                 235                 240

Thr Val Ser Ser
```

<210> SEQ ID NO 24
<211> LENGTH: 69
<212> TYPE: PRT
<213> ORGANISM: Artificial Sequence
<220> FEATURE:
<223> OTHER INFORMATION: Synthetic Construct

<400> SEQUENCE: 24

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
        50                  55                  60

Ile Thr Leu Tyr Cys
65
```

<210> SEQ ID NO 25
<211> LENGTH: 42
<212> TYPE: PRT
<213> ORGANISM: Artificial Sequence
<220> FEATURE:
<223> OTHER INFORMATION: Synthetic Construct

<400> SEQUENCE: 25

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 26
<211> LENGTH: 112
<212> TYPE: PRT
<213> ORGANISM: Artificial Sequence
<220> FEATURE:
<223> OTHER INFORMATION: Synthetic Construct

<400> SEQUENCE: 26

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 27
<211> LENGTH: 488
<212> TYPE: PRT
<213> ORGANISM: Artificial Sequence
<220> FEATURE:
<223> OTHER INFORMATION: Synthetic Construct

<400> SEQUENCE: 27

```
Met Ala Leu Pro Val Thr Ala Leu Leu Leu Pro Leu Ala Leu Leu Leu
1               5                   10                  15

His Ala Ala Arg Pro Ala Val Gln Leu Val Gln Ser Gly Ala Glu Val
            20                  25                  30

Lys Lys Pro Gly Ser Ser Val Lys Val Ser Cys Lys Ala Ser Gly Tyr
        35                  40                  45

Ser Phe Thr Gly Tyr Asn Met Asn Trp Val Arg Gln Ala Pro Gly Gln
    50                  55                  60

Gly Leu Glu Trp Met Gly Asn Ile Asp Pro Tyr Tyr Gly Gly Thr Thr
65                  70                  75                  80

Tyr Asn Arg Lys Phe Lys Gly Arg Val Thr Leu Thr Val Asp Lys Ser
                85                  90                  95

Ser Ser Thr Ala Tyr Met Glu Leu Ser Ser Leu Arg Ser Glu Asp Thr
            100                 105                 110
```

```
Ala Val Tyr Tyr Cys Ala Arg Ser Val Gly Pro Met Asp Tyr Trp Gly
            115                 120                 125

Gln Gly Thr Leu Val Thr Val Ser Ser Gly Gly Gly Gly Ser Gly Gly
        130                 135                 140

Gly Gly Ser Gly Gly Gly Ser Gly Gly Gly Ser Asp Ile Gln Met
145                 150                 155                 160

Met Thr Gln Ser Pro Ser Ser Leu Ser Ala Ser Val Gly Asp Arg Val
                165                 170                 175

Thr Ile Thr Cys Arg Thr Ser Glu Asn Val Tyr Ser Tyr Leu Ala Trp
            180                 185                 190

Tyr Gln Gln Lys Pro Gly Lys Ala Pro Lys Leu Leu Val Ser Ser Ala
        195                 200                 205

Lys Thr Leu Ala Glu Gly Val Pro Ser Arg Phe Ser Gly Ser Gly Ser
210                 215                 220

Gly Thr Asp Phe Thr Leu Thr Ile Ser Ser Leu Gln Pro Glu Asp Phe
225                 230                 235                 240

Ala Thr Tyr Phe Cys Gln His His Ser Asp Asn Pro Trp Thr Phe Gly
                245                 250                 255

Gln Gly Thr Lys Val Glu Ile Lys Arg Thr Thr Thr Pro Ala Pro Arg
        260                 265                 270

Pro Pro Thr Pro Ala Pro Thr Ile Ala Ser Gln Pro Leu Ser Leu Arg
    275                 280                 285

Pro Glu Ala Cys Arg Pro Ala Ala Gly Gly Ala Val His Thr Arg Gly
290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 28
<211> LENGTH: 21
<212> TYPE: PRT
<213> ORGANISM: Artificial Sequence
<220> FEATURE:
```

<223> OTHER INFORMATION: Synthetic Construct

<400> SEQUENCE: 28

Met Ala Leu Pro Val Thr Ala Leu Leu Leu Pro Leu Ala Leu Leu Leu
1               5                   10                  15

His Ala Ala Arg Pro
            20

<210> SEQ ID NO 29
<211> LENGTH: 244
<212> TYPE: PRT
<213> ORGANISM: Artificial Sequence
<220> FEATURE:
<223> OTHER INFORMATION: Synthetic Construct

<400> SEQUENCE: 29

Ala Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Met
        35                  40                  45

Gly Asn Ile Asp Pro Tyr Tyr Gly Gly Thr Thr Tyr Asn Arg Lys Phe
    50                  55                  60

Lys Gly Arg Val Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Thr Ser Glu Asn Val Tyr Ser Tyr Leu Ala Trp Tyr Gln Gln Lys Pro
                165                 170                 175

Gly Lys Ala Pro Lys Leu Leu Val Ser Ser Ala Lys Thr Leu Ala Glu
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Phe Cys
    210                 215                 220

Gln His His Ser Asp Asn Pro Trp Thr Phe Gly Gln Gly Thr Lys Val
225                 230                 235                 240

Glu Ile Lys Arg

<210> SEQ ID NO 30
<211> LENGTH: 69
<212> TYPE: PRT
<213> ORGANISM: Artificial Sequence
<220> FEATURE:
<223> OTHER INFORMATION: Synthetic Construct

<400> SEQUENCE: 30

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
50                  55                  60

Ile Thr Leu Tyr Cys
65

<210> SEQ ID NO 31
<211> LENGTH: 42
<212> TYPE: PRT
<213> ORGANISM: Artificial Sequence
<220> FEATURE:
<223> OTHER INFORMATION: Synthetic Construct

<400> SEQUENCE: 31

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 32
<211> LENGTH: 112
<212> TYPE: PRT
<213> ORGANISM: Artificial Sequence
<220> FEATURE:
<223> OTHER INFORMATION: Synthetic Construct

<400> SEQUENCE: 32

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Synthetic Construct

<400> SEQUENCE: 33

Arg Val Lys Phe Ser Arg Ser Ala Asp Ala Pro Ala Tyr Gln Gln Gly
1               5                   10                  15

Gln Asn Gln Leu Phe Asn Glu Leu Asn Leu Gly Arg Arg Glu Glu Phe
            20                  25                  30

```
Asp Val Leu Asp Lys Arg Arg Gly Arg Asp Pro Glu Met Gly Gly Lys
            35                  40                  45

Pro Arg Arg Lys Asn Pro Gln Glu Gly Leu Phe Asn Glu Leu Gln Lys
 50                  55                  60

Asp Lys Met Ala Glu Ala Phe Ser Glu Ile Gly Met Lys Gly Glu Arg
 65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

<210> SEQ ID NO 34
<211> LENGTH: 112
<212> TYPE: PRT
<213> ORGANISM: Artificial Sequence
<220> FEATURE:
<223> OTHER INFORMATION: Synthetic Construct

<400> SEQUENCE: 34

```
Arg Val Lys Phe Ser Arg Ser Ala Asp Ala Pro Ala Tyr Gln Gln Gly
 1               5                  10                  15

Gln Asn Gln Leu Phe Asn Glu Leu Asn Leu Gly Arg Arg Glu Glu Phe
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Phe Gln Gly Leu Ser Thr Ala
                85                  90                  95

Thr Lys Asp Thr Phe Asp Ala Leu His Met Gln Ala Leu Pro Pro Arg
                100                 105                 110
```

<210> SEQ ID NO 35
<211> LENGTH: 493
<212> TYPE: PRT
<213> ORGANISM: Artificial Sequence
<220> FEATURE:
<223> OTHER INFORMATION: Synthetic Construct

<400> SEQUENCE: 35

```
Met Ala Leu Pro Val Thr Ala Leu Leu Leu Pro Leu Ala Leu Leu Leu
 1               5                  10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Gly
            35                  40                  45

Thr Phe Ser Asn Tyr Trp Met His Trp Val Arg Gln Ala Pro Gly Gln
 50                  55                  60

Gly Leu Glu Trp Met Gly Ala Thr Tyr Arg Gly His Ser Asp Thr Tyr
 65                  70                  75                  80

Tyr Asn Gln Lys Phe Lys Gly Arg Val Thr Ile Thr Ala Asp Lys Ser
                85                  90                  95

Thr Ser Thr Ala Tyr Met Glu Leu Ser Ser Leu Arg Ser Glu Asp Thr
                100                 105                 110

Ala Val Tyr Tyr Cys Ala Arg Gly Ala Ile Tyr Asn Gly Tyr Asp Val
                115                 120                 125
```

Leu Asp Asn Trp Gly Gln Gly Thr Leu Val Thr Val Ser Ser Gly Gly
130                 135                 140

Gly Gly Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
        165                 170                 175

Val Gly Asp Arg Val Thr Ile Thr Cys Ser Ala Ser Gln Asp Ile Ser
        180                 185                 190

Asn Tyr Leu Asn Trp Tyr Gln Gln Lys Pro Gly Lys Ala Pro Lys Leu
        195                 200                 205

Leu Ile Tyr Tyr Thr Ser Asn Leu His Ser Gly Val Pro Ser Arg Phe
210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Tyr Arg Lys Leu
            245                 250                 255

Pro Trp Thr Phe Gly Gln Gly Thr Lys Leu Glu Ile Lys Arg Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
            325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
        370                 375                 380

Phe Ser Arg Ser Ala Asp Ala Pro Ala Tyr Gln Gln Gly Gln Asn Gln
385                 390                 395                 400

Leu Phe Asn Glu Leu Asn Leu Gly Arg Arg Glu Glu Phe Asp Val Leu
            405                 410                 415

Asp Lys Arg Arg Gly Arg Asp Pro Glu Met Gly Gly Lys Pro Arg Arg
        420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 36
<211> LENGTH: 493
<212> TYPE: PRT
<213> ORGANISM: Artificial Sequence
<220> FEATURE:
<223> OTHER INFORMATION: Synthetic Construct

<400> SEQUENCE: 36

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Gly
            35                  40                  45

Thr Phe Ser Asn Tyr Trp Met His Trp Val Arg Gln Ala Pro Gly Gln
        50                  55                  60

Gly Leu Glu Trp Met Gly Ala Thr Tyr Arg Gly His Ser Asp Thr Tyr
65                  70                  75                  80

Tyr Asn Gln Lys Phe Lys Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Gly Ala Ile Tyr Asn Gly Tyr Asp Val
        115                 120                 125

Leu Asp Asn Trp Gly Gln Gly Thr Leu Val Thr Val Ser Ser Gly Gly
    130                 135                 140

Gly Gly Ser Gly Gly Gly Ser Gly Gly Gly Ser Gly Gly Ser Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Ser Ala Ser Gln Asp Ile Ser
                180                 185                 190

Asn Tyr Leu Asn Trp Tyr Gln Gln Lys Pro Gly Lys Ala Pro Lys Leu
        195                 200                 205

Leu Ile Tyr Tyr Thr Ser Asn Leu His Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Tyr Arg Lys Leu
                245                 250                 255

Pro Trp Thr Phe Gly Gln Gly Thr Lys Leu Glu Ile Lys Arg Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
            325                 330                 335

Leu Tyr Cys Lys Arg Gly Arg Lys Lys Leu Leu Tyr Ile Phe Lys Gln
        340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415
```

Asp Lys Arg Arg Gly Arg Asp Pro Glu Met Gly Gly Lys Pro Arg Arg
            420                 425                 430

Lys Asn Pro Gln Glu Gly Leu Phe Asn Glu Leu Gln Lys Asp Lys Met
        435                 440                 445

Ala Glu Ala Phe Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 37
<211> LENGTH: 493
<212> TYPE: PRT
<213> ORGANISM: Artificial Sequence
<220> FEATURE:
<223> OTHER INFORMATION: Synthetic Construct

<400> SEQUENCE: 37

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Asn Tyr Trp Met His Trp Val Arg Gln Ala Pro Gly Gln
    50                  55                  60

Gly Leu Glu Trp Met Gly Ala Thr Tyr Arg Gly His Ser Asp Thr Tyr
65                  70                  75                  80

Tyr Asn Gln Lys Phe Lys Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Gly Ala Ile Tyr Asn Gly Tyr Asp Val
        115                 120                 125

Leu Asp Asn Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Ser Ala Ser Gln Asp Ile Ser
            180                 185                 190

Asn Tyr Leu Asn Trp Tyr Gln Gln Lys Pro Gly Lys Ala Pro Lys Leu
        195                 200                 205

Leu Ile Tyr Tyr Thr Ser Asn Leu His Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Tyr Arg Lys Leu
                245                 250                 255

Pro Trp Thr Phe Gly Gln Gly Thr Lys Leu Glu Ile Lys Arg Thr Thr
            260                 265                 270

Thr Pro Ala Pro Arg Pro Pro Thr Pro Ala Pro Thr Ile Ala Ser Gln
        275                 280                 285

```
Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Ser Leu Val Ile Thr
                325                 330                 335

Leu Tyr Cys Lys Arg Gly Arg Lys Leu Leu Tyr Ile Phe Lys Gln
            340                 345                 350

Pro Phe Met Arg Pro Val Gln Thr Thr Gln Glu Asp Gly Cys Ser
        355                 360                 365

Cys Arg Phe Pro Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Phe Gln Gly Leu Ser Thr Ala Thr Lys Asp
465                 470                 475                 480

Thr Phe Asp Ala Leu His Met Gln Ala Leu Pro Pro Arg
                485                 490

<210> SEQ ID NO 38
<211> LENGTH: 493
<212> TYPE: PRT
<213> ORGANISM: Artificial Sequence
<220> FEATURE:
<223> OTHER INFORMATION: Synthetic Construct

<400> SEQUENCE: 38

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Asn Tyr Trp Met His Trp Val Arg Gln Ala Pro Gly Gln
    50                  55                  60

Gly Leu Glu Trp Met Gly Ala Thr Tyr Arg Gly His Ser Asp Thr Tyr
65                  70                  75                  80

Tyr Asn Gln Lys Phe Lys Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Gly Ala Ile Tyr Asn Gly Tyr Asp Val
        115                 120                 125

Leu Asp Asn Trp Gly Gln Gly Thr Leu Val Thr Val Ser Ser Gly Gly
    130                 135                 140

Gly Gly Ser Gly Gly Gly Gly Ser Gly Gly Gly Gly Ser Gly Gly Gly
145                 150                 155                 160
```

Gly Ser Asp Ile Gln Met Thr Gln Ser Pro Ser Ser Leu Ser Ala Ser
              165                 170                 175

Val Gly Asp Arg Val Thr Ile Thr Cys Ser Ala Ser Gln Asp Ile Ser
            180                 185                 190

Asn Tyr Leu Asn Trp Tyr Gln Gln Lys Pro Gly Lys Ala Pro Lys Leu
        195                 200                 205

Leu Ile Tyr Tyr Thr Ser Asn Leu His Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Tyr Arg Lys Leu
                245                 250                 255

Pro Trp Thr Phe Gly Gln Gly Thr Lys Leu Glu Ile Lys Arg Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Phe Asn Glu Leu Asn Leu Gly Arg Arg Glu Glu Phe Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Phe Gln Gly Leu Ser Thr Ala Thr Lys Asp
465                 470                 475                 480

Thr Phe Asp Ala Leu His Met Gln Ala Leu Pro Pro Arg
                485                 490

<210> SEQ ID NO 39
<211> LENGTH: 818
<212> TYPE: PRT
<213> ORGANISM: Artificial Sequence
<220> FEATURE:
<223> OTHER INFORMATION: Synthetic Construct

<400> SEQUENCE: 39

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

```
Lys Lys Pro Gly Ser Ser Val Lys Val Ser Cys Lys Ala Ser Gly Gly
             35                  40                  45

Thr Phe Ser Asn Tyr Trp Met His Trp Val Arg Gln Ala Pro Gly Gln
 50                      55                  60

Gly Leu Glu Trp Met Gly Ala Thr Tyr Arg Gly His Ser Asp Thr Tyr
 65                  70                  75                  80

Tyr Asn Gln Lys Phe Lys Gly Arg Val Thr Ile Thr Ala Asp Lys Ser
                 85                  90                  95

Thr Ser Thr Ala Tyr Met Glu Leu Ser Ser Leu Arg Ser Glu Asp Thr
                100                 105                 110

Ala Val Tyr Tyr Cys Ala Arg Gly Ala Ile Tyr Asn Gly Tyr Asp Val
            115                 120                 125

Leu Asp Asn Trp Gly Gln Gly Thr Leu Val Thr Val Ser Ser Gly Gly
130                 135                 140

Gly Gly Ser Gly Gly Gly Gly Ser Gly Gly Gly Ser Gly Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Ser Ala Ser Gln Asp Ile Ser
            180                 185                 190

Asn Tyr Leu Asn Trp Tyr Gln Gln Lys Pro Gly Lys Ala Pro Lys Leu
            195                 200                 205

Leu Ile Tyr Tyr Thr Ser Asn Leu His Ser Gly Val Pro Ser Arg Phe
            210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Tyr Arg Lys Leu
                245                 250                 255

Pro Trp Thr Phe Gly Gln Gly Thr Lys Leu Glu Ile Lys Arg Thr Thr
            260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
            290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
```

```
            450                 455                 460
Lys Gly His Asp Gly Leu Tyr Gln Asp Ser His Phe Gln Ala Val Pro
465                 470                 475                 480

Val Gln Glu Lys Lys Arg Leu Arg Arg Ala Pro Trp Arg Ala Phe
                485                 490                 495

Ala Gln Pro Gln Arg Leu Lys His Pro Ala Glu Gln Pro Ile Val Arg
                500                 505                 510

Gln Cys Leu Gln Arg Pro Pro Leu Cys Gly Val Leu Gly Pro Val Gln
            515                 520                 525

Gln Gln Leu Pro Pro Ser Leu Gly Pro Val Leu Ser Pro His Ser Asp
            530                 535                 540

Pro Gly Trp Cys Arg Val Asp Asp Gly Gly Asp Gly Val Phe Ser Gly
545                 550                 555                 560

Gly Gly Gly Glu Gly Arg Gly Ser Leu Leu Thr Cys Gly Asp Val Glu
                565                 570                 575

Glu Asn Pro Gly Pro Arg Met Val Ser Lys Gly Glu Glu Asp Asn Met
                580                 585                 590

Ala Ile Ile Lys Glu Phe Met Arg Phe Lys Val His Met Glu Gly Ser
            595                 600                 605

Val Asn Gly His Glu Phe Glu Ile Glu Gly Glu Gly Glu Gly Arg Pro
            610                 615                 620

Tyr Glu Gly Thr Gln Thr Ala Lys Leu Lys Val Thr Lys Gly Gly Pro
625                 630                 635                 640

Leu Pro Phe Ala Trp Asp Ile Leu Ser Pro Gln Phe Met Tyr Gly Ser
                645                 650                 655

Lys Ala Tyr Val Lys His Pro Ala Asp Ile Pro Asp Tyr Leu Lys Leu
                660                 665                 670

Ser Phe Pro Glu Gly Phe Lys Trp Glu Arg Val Met Asn Phe Glu Asp
            675                 680                 685

Gly Gly Val Val Thr Val Thr Gln Asp Ser Ser Leu Gln Asp Gly Glu
            690                 695                 700

Phe Ile Tyr Lys Val Lys Leu Arg Gly Thr Asn Phe Pro Ser Asp Gly
705                 710                 715                 720

Pro Val Met Gln Lys Lys Thr Met Gly Trp Glu Ala Ser Ser Glu Arg
                725                 730                 735

Met Tyr Pro Glu Asp Gly Ala Leu Lys Gly Glu Ile Lys Gln Arg Leu
                740                 745                 750

Lys Leu Lys Asp Gly Gly His Tyr Asp Ala Glu Val Lys Thr Thr Tyr
            755                 760                 765

Lys Ala Lys Lys Pro Val Gln Leu Pro Gly Ala Tyr Asn Val Asn Ile
            770                 775                 780

Lys Leu Asp Ile Thr Ser His Asn Glu Asp Tyr Thr Ile Val Glu Gln
785                 790                 795                 800

Tyr Glu Arg Ala Glu Gly Arg His Ser Thr Gly Gly Met Asp Glu Leu
                805                 810                 815

Tyr Lys

<210> SEQ ID NO 40
<211> LENGTH: 788
<212> TYPE: PRT
<213> ORGANISM: Artificial Sequence
<220> FEATURE:
<223> OTHER INFORMATION: Synthetic Construct

<400> SEQUENCE: 40
```

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Asn Tyr Trp Met His Trp Val Arg Gln Ala Pro Gly Gln
    50                  55                  60

Gly Leu Glu Trp Met Gly Ala Thr Tyr Arg Gly His Ser Asp Thr Tyr
65                  70                  75                  80

Tyr Asn Gln Lys Phe Lys Gly Arg Val Thr Ile Thr Ala Asp Lys Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Gly Ala Ile Tyr Asn Gly Tyr Asp Val
        115                 120                 125

Leu Asp Asn Trp Gly Gln Gly Thr Leu Val Thr Val Ser Ser Gly Gly
    130                 135                 140

Gly Gly Ser Gly Gly Gly Ser Gly Gly Gly Ser Gly Gly Gly Ser Gly
145                 150                 155                 160

Gly Ser Asp Ile Gln Met Thr Gln Ser Pro Ser Ser Leu Ser Ala Ser
            165                 170                 175

Val Gly Asp Arg Val Thr Ile Thr Cys Ser Ala Ser Gln Asp Ile Ser
        180                 185                 190

Asn Tyr Leu Asn Trp Tyr Gln Gln Lys Pro Gly Lys Ala Pro Lys Leu
    195                 200                 205

Leu Ile Tyr Tyr Thr Ser Asn Leu His Ser Gly Val Pro Ser Arg Phe
210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Tyr Arg Lys Leu
            245                 250                 255

Pro Trp Thr Phe Gly Gln Gly Thr Lys Leu Glu Ile Lys Arg Thr Thr
        260                 265                 270

Thr Pro Ala Pro Arg Pro Pro Thr Pro Ala Pro Thr Ile Ala Ser Gln
    275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
            325                 330                 335

Leu Tyr Cys Lys Arg Gly Arg Lys Lys Leu Leu Tyr Ile Phe Lys Gln
        340                 345                 350

Pro Phe Met Arg Pro Val Gln Thr Thr Gln Glu Glu Asp Gly Cys Ser
    355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
            405                 410                 415
```

```
Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Asp Ser His Phe Gln Ala Val Pro
465                 470                 475                 480

Val Gln Glu Lys Lys Arg Leu Arg Arg Ala Pro Trp Arg Ala Phe
            485                 490                 495

Ala Gln Pro Gln Arg Leu Lys His Arg Asn Asn Glu Leu Pro Asp Ser
            500                 505                 510

Leu Glu Pro Ile Tyr Lys Asn Ile Trp Asn Lys Thr Phe Ile Gly Glu
            515                 520                 525

Ser Gly Gly Gly Gly Gly Arg Gly Ser Leu Leu Thr Cys Gly Asp
            530                 535                 540

Val Glu Glu Asn Pro Gly Pro Arg Met Val Ser Lys Gly Glu Glu Asp
545                 550                 555                 560

Asn Met Ala Ile Ile Lys Glu Phe Met Arg Phe Lys Val His Met Glu
            565                 570                 575

Gly Ser Val Asn Gly His Glu Phe Glu Ile Glu Gly Glu Gly Glu Gly
            580                 585                 590

Arg Pro Tyr Glu Gly Thr Gln Thr Ala Lys Leu Lys Val Thr Lys Gly
            595                 600                 605

Gly Pro Leu Pro Phe Ala Trp Asp Ile Leu Ser Pro Gln Phe Met Tyr
            610                 615                 620

Gly Ser Lys Ala Tyr Val Lys His Pro Ala Asp Ile Pro Asp Tyr Leu
625                 630                 635                 640

Lys Leu Ser Phe Pro Glu Gly Phe Lys Trp Glu Arg Val Met Asn Phe
            645                 650                 655

Glu Asp Gly Gly Val Val Thr Val Thr Gln Asp Ser Ser Leu Gln Asp
            660                 665                 670

Gly Glu Phe Ile Tyr Lys Val Lys Leu Arg Gly Thr Asn Phe Pro Ser
            675                 680                 685

Asp Gly Pro Val Met Gln Lys Lys Thr Met Gly Trp Glu Ala Ser Ser
            690                 695                 700

Glu Arg Met Tyr Pro Glu Asp Gly Ala Leu Lys Gly Glu Ile Lys Gln
705                 710                 715                 720

Arg Leu Lys Leu Lys Asp Gly Gly His Tyr Asp Ala Glu Val Lys Thr
            725                 730                 735

Thr Tyr Lys Ala Lys Lys Pro Val Gln Leu Pro Gly Ala Tyr Asn Val
            740                 745                 750

Asn Ile Lys Leu Asp Ile Thr Ser His Asn Glu Asp Tyr Thr Ile Val
            755                 760                 765

Glu Gln Tyr Glu Arg Ala Glu Gly Arg His Ser Thr Gly Gly Met Asp
            770                 775                 780

Glu Leu Tyr Lys
785
```